US010181009B2

(12) United States Patent
Yeatman et al.

(10) Patent No.: US 10,181,009 B2
(45) Date of Patent: Jan. 15, 2019

(54) METHODS AND SYSTEMS FOR PREDICTING CANCER OUTCOME

(75) Inventors: Timothy J. Yeatman, Thonotosassa, FL (US); Steven Eschrich, Lakeland, FL (US); Gregory C. Bloom, Tampa, FL (US)

(73) Assignees: H. Lee Moffitt Cancer Center and Research Institute, Inc., Tampa, FL (US); University of South Florida, Tampa, FL (US)

( * ) Notice: Subject to any disclaimer, the term of this patent is extended or adjusted under 35 U.S.C. 154(b) by 2217 days.

(21) Appl. No.: 11/134,688

(22) Filed: May 19, 2005

(65) Prior Publication Data

US 2006/0195269 A1 Aug. 31, 2006

Related U.S. Application Data

(63) Continuation-in-part of application No. 11/065,794, filed on Feb. 25, 2005, now abandoned.

(60) Provisional application No. 60/547,871, filed on Feb. 25, 2004.

(51) Int. Cl.
*G06F 19/20* (2011.01)
*C12Q 1/6886* (2018.01)
*G06F 19/24* (2011.01)

(52) U.S. Cl.
CPC ............ *G06F 19/20* (2013.01); *C12Q 1/6886* (2013.01); *C12Q 2600/106* (2013.01); *C12Q 2600/118* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 2004/0053317 | A1 | 3/2004 | Glinskii |
| 2004/0146921 | A1 | 7/2004 | Eveleigh et al. |
| 2005/0048542 | A1 | 3/2005 | Baker et al. |
| 2006/0195266 | A1 | 8/2006 | Yeatman et al. |

FOREIGN PATENT DOCUMENTS

| | | |
|---|---|---|
| WO | WO 02/103320 | 12/2002 |
| WO | WO 04/065545 | 8/2004 |

OTHER PUBLICATIONS

Zhan et al., Global gene expression profiling of multiple myeloma, monoclonal gammopathy of undertermined significance, and normal bone marrow plasma cells, Mar. 2002, Blood, vol. 99, pp. 1745-1757.*

Hegde et al., Identification of Tumor Markers in Models of Human Colorectal Cancer Using 19,200 Element Complementary DNA Microarray, Nov. 1, 2001, Cancer Research, No. 61, pp. 7792-7797.*
Chen et al., Discordant Protein and mRNA Expression in Lung Adenocarcinomas, Mar. 12, 2002, Molecular and Cellular Proteomics, vol. 1, pp. 304-313.*
Cole et al., The genetics of cancer—a 3D model, 1999, Nature, vol. 21, pp. 38-41.*
Agrawal et al., 2002, "Osteopontin identified as lead marker of colon cancer progression, using pooled sample expression profiling." J. Natl. Canc. Inst. 94:513-21.
Alizadeh et al., 2000, "Distinct types of diffuse large B-cell lymphoma identified by gene expression profiling." Nature 403:513-11.
Arango et al., 2004, "Molecular Mechanisms of Action and Prediction of Response to Oxaliplatin in Colorectal Cancer Cells." Br. J. Canc. 91:1931-46.
Beer et al., 2002, "Gene-expression profiles predict survival of patients with lung adenocarcinoma." Nat Med. 8:816-24.
Bhattacharjee et al., 2001, "Classification of human lung carcinomas by mRNA expression profiling reveleas distcint adenocarcinoma subclasses." Proc. Natl. Acad. Sci USA 98:13790-5.
Bloom et al., 2004, "Multi-platform, multi-site microarray based human tumor classification." Am J. Pathol 164:9-16.
Carraway et al, 1997, "Neuregulin-2, a new ligand of ErbB3/ErbB4-receptor tyrosine kinases." Nature 387:512-6.
De Hoon et al., 2003, "Open Source Clustering Software." Bioinformatcs 20:1453-1454.
Dukes et al., 1932, "The classifiction of cancer in the rectum." J. Pathol Bacteriol. 35:323.
Dyrskjot et al., 2003, "Identifying distinct classes of bladder carcinoma using microarrays." Nat. Genet 33:90-6.
Fahlman, 1988, "Faster-Learning Variations of Back-Propogation: An Empirical Study." Proceedings of the 1988 Connectionist Model Summer School. Los Altos, CA, Morgan-Kaufmann.
Fedarko et al., 2001, "Elevated serum bone sialoprotein and osteopontin in colon, breast, prostate, and lung cancer." Clin Cancer Res. 7:4060-6.
Frederiksen,2003, "Classification of Dukes' B and C colorectal cancers using expression arrays," J. Cancer Res Clin. Oncol. 129:263-71.
Furey et al., 2000, "Support Vector machine classification and validation of cancer tissue samples using microarray expression data." 16:906-914.
Garber et al., 2001, "Diversity of gene expression in adenocarcinoma of the lung" Proc. Natl. Acad Sci USA 98:13784-9.
Henshall et al., 2003, "Survival analysis of genome-wide gene expression profiles of prostate cancers identifies new prognostic targets of disease relapse" Cancer Res. 63:4196-203.
Kanazawa et al., 2003, "Does early polypoid colorectal cancer with depression have a pathway other than adenoma carcinoma sequence?" Tumori 89(4):408-11.
Khan et al., 2001, "Classification and diagnostic prediction of cancers using gene expression profiling and artificial neural networks." Nat. Med 7:673-9.

(Continued)

*Primary Examiner* — Jason M Sims
(74) *Attorney, Agent, or Firm* — Thomas|Horstemeyer, LLC

(57) ABSTRACT

The invention provides a molecular marker set that can be used for prognosis of colorectal cancer in a colorectal cancer patient. The invention also provides methods and computer systems for evaluating prognosis of colorectal cancer in a colorectal cancer patient based on the molecular marker set. The invention also provides methods and computer systems for determining chemotherapy for a colorectal cancer patient and for enrolling patients in clinical trials.

6 Claims, 6 Drawing Sheets

Specification includes a Sequence Listing.

(56) References Cited

OTHER PUBLICATIONS

Leeman et al., 2003, "New insights into the roles of matrix metalloproteinases in colorectal cancer development and progression." J. Pathol. 201(4):528-34.

Muro et al., 2002, "Identification of expressed genes linked to malignancy of human colorectal carcinoma by parametric clustering of quantitative expression data." Genome Biology 4:R21.

Notarnicola et al., 2003, "Genetic and biochemical changes in colorectal carcinoma in relation to morphologic characteristics." Oncol. Rep. 10(6):1987-91.

Pomeroy et al., 2002, "Prediction of central nervous system embyonal tumour outcome based on gene expression." Nature 415:436-42.

Ramaswamy et al., 2001, "Multiclass cancer diagnosis using tumor gene expression signatures." Proc. Natl. Acad Sci USA 98:15149-54.

Ramaswamy et al., 2003, "A molecular signature of metastasis in primary solid tumors." Nat. Genet 33:49-54.

Resnick et al., 2004, "Epidermal growth factor receptor, c-MET, beta-catenin, and p53 expression as prognostic indicators in stage II colon cancer: a tissue microarray study." Clin. Can. Res. 10:3069-3075.

Sanchez-Carbayo et al., 2003, "Gene Discovery in Bladder Cancer Progression using cDNA Microarrays." Am. J. Pathol. 163:505-16.

Shipp et al., 2002, "Diffuse large B-cell lymphoma outcome prediction by gene-expression profiling and supervised machine learning." Nat. Med. 8:68-74.

Sorlie et al, 2003, "Repeated observation of breast tumor subtypes in independent gene expression data sets." Proc. Natl. Acad. Sci USA 100:8418-23.

Sorlie et al., 2001, "Gene expression patterns of breast carcinomas distinguish tumor subclasses with clinical implications." Proc. Natl. Acad. Sci 98:10869-74.

Su et al., 2001, "Molecular Classification of Human Carcinomas by Use of Gene Expression Signatures" Cancer Res. 61:7388-93.

Takahashi et al., 2001, "Gene expression profiling of clear cell renal cell carcinoma: gene identification and prognostic classification." Proc. Natl. Acad Sci USA 98:9754-9.

Tomida et al., 2004, "Gene expression-based individualized outcome prediction for surgically treated lung cancer patients." Oncogene 23:5360-5370.

Tusher et al., 2001, "Significance analysis of microarrays applied to the ionizing radiation response." 98:5116-21.

Van De Vijver et al., 2002, "A gene-expression signature as a predictor of survival in breast cancer." New Engl. J. Med 347:1999-2009.

Van'T Veer et al., 2002, "The microarray way to tailored cancer treatment." Nat. Med. 8(1):13-14.

Van'T Veer et al., 2002, "Gene expression profiling predicts clinical outcome of breast cancer." Nature 415:530-6.

Vasselli et al., 2003,"Predicting survival in patients with metastatic kidney cancer by gene-expression profiling in the primary tumor." Proc Natl. Acad. Sci USA 100:6958-63.

Wang et al., 2004, "Gene expression profiles and molecular markers to predict recurrence of Dukes B colon cancer." J Clin Oncol 22:1564-71.

Welsh et al., 2001, "Analysis of gene expression profiles in normal and neoplastic ovarian tissue samples identifies candidate molecular markers of epithelial ovarian cancer." Proc. Natl. Acad. Sci 98(3):1176-1181.

Welsh et al., 2003, "Large-scale delineation of secreted protein biomarkers overexpressed in cancer tissue and serum." Proc. Natl. Acad. Sci USA 100(6):3410-15.

Yang et al., 2004, "Molecular Profiling Predicts Colon Cancer Survival Better than Dukes Staging." SSO 57th Annual Cancer Symposium.

Yeatman et al., 2003, "Osteopontin and colon cancer progression." Clin. Exp. Metastasis 20:85-90.

International Search Report (ISR) and Written Opinion for PCT/US05/17988, dated Jun. 19, 2008, 1pg.

Van Erk et al., European Journal Nutrition, 44:143-156, 2004.

Bertucci et al., "Gene expression profiling of colon cancer by DNA microarrays and correlation with histoclinical parameters," *Oncogene*, 23:1377-1391 (2004).

Birkenkamp-Demtroder et al., "Gene Expression in Colorectal Cancer," *Cancer Res.*, 62:4352-4363 (2002).

Eschrich et al., "Molecular Staging for Survival Prediction of Colorectal Cancer Patients," *J. Clin. Oncol.*, 23(15):3526-3535 (2005).

Koehler et al., "Gene expression profiling of colorectal cancer and metastases divides tumours according to their clinicopathological stage," *J. Pathol.*, 204:65-74 (2004).

Supplementary European Search Report issued in EP 05754399.3.

* cited by examiner

A

B

C

SEQUENCE LISTING

<160> NUMBER OF SEQ ID NOS: 218

<210> SEQ ID NO 1
<211> LENGTH: 421
<212> TYPE: DNA
<213> ORGANISM: Homo sapiens

<400> SEQUENCE: 1
cttatgaata atgttagaaa tggaacatga tgttttaaat gtatacataa accttccaat      60
taattatcag gtgatccagt agtagacctg tgacctctga aggctcctgc ttctcatccc     120
ttcccttctg ctgtgatttg ttgtcttccc tctgctcatt ccccttgtgt ctgtttcttc     180
catcctctcc ccatgctccc tctgttgtca tttcccctta ctctccactg cacccagcct     240
ctgttcataa ttttactgc aattccgatg attgaattat aaactggaag ggagcaggga      300
tattgatctt catgtagttg gacatgtact agactcacgg agaacaagga ctgggttgta     360
ggcacaatgc tgtgtgggtt ttgggtaaat ctaactcaca ctcaacttga ttttgttttc     420
c                                                                    421

<210> SEQ ID NO 2
<211> LENGTH: 466
<212> TYPE: DNA
<213> ORGANISM: Homo sapiens

<400> SEQUENCE: 2
gtttgtagca gttccaaaaa gaaagcagaa ctcatttagc aattgtgata aagaaggaa       60 aaatgcatat gttttaaaag tcattaacgc atcgtgaaag cgctcccaat caacctcatt    120
ccctaggatt ttcagctaac taacaatagt gtcttttttaa tttgatgtca tgaaaatctg    180
gtcacagcaa acacaatgtt ttctaaagca gatctggcct ccgagggagg aaagctctcc    240
agggcctcca gtgccttgtt tccatggtaa cgacacaggt caatagctga agtcacacct    300
ttgccagctt tgattctttc tcgcaactgg gagtctgagg caagaggatc acttgagccc    360
aggagtggga ggctgcagta agctatgatt gtgacactgc actccagcct gagcgacaga    420
gcgagaccct atctcttagc atagtccaat cttcctttt cttgag                     466

<210> SEQ ID NO 3
<211> LENGTH: 462
<212> TYPE: DNA
<213> ORGANISM: Homo sapiens

<400> SEQUENCE: 3
cacagcaatt catctttgct tttattaata atttcaacgt atgttttgag cactttacaa      60
tgtaggaaat gctttcatag acattatttc ctatgattct cacaaaacct tcactgaaaa    120
aaaagacttc aaggtcactt gccctatgtt tataaaataa tccgctttaa ataagcagat    180
aggagtccaa aaattcttac aatcataaga aaaaaaagt ctaaccagta cttaattatt     240
tcttgtcatg attactttgt tttaacgcca ctgtttcctt gcttccccca ttttcttcag    300
ataagtttac tccttttggc ttgtcctgca tccttttctg acagctgccc tgtgtacacc    360
tgccttaaac atctatcctt ctactctgga atagactaag ccaaaagcaa ttaagaaata    420
tttcattcta aagaaaacag aatttagtc caaacccaa at                          462

<210> SEQ ID NO 4
<211> LENGTH: 463
<212> TYPE: DNA
<213> ORGANISM: Homo sapiens
<220> FEATURE:
<221> NAME/KEY: misc_feature
<222> LOCATION: 441
<223> OTHER INFORMATION: n = A,T,C or G

<400> SEQUENCE: 4

| | | |
|---|---|---|
| ttgtttttat cttttttta aaggtgcctc tcaaagtgct gggattacag gcgtgacacc | 60 |
| agtgcccaga ccatttttagc cttttttctta ccagaaccac actcagcttg gggcttaaga | 120 |
| tggataggct aagaggggaa ctaagcttgt aactgttgcg gagacaggca ctccaggtga | 180 |
| cagttcacag gccctttcaa gtgactggag ccatgggatc atttctctcc aaggatttgt | 240 |
| gagtagaagt gatgtgtgtc atctcccagg tgaacaggtt cggccttccc tacatgctcc | 300 |
| aagggtacag tgaagagcag agctacaaca gagatggggc ctggatccct gaatcactgt | 360 |
| atggagcaga gtgcaaacca atattataag caacagcaac accaacacag gacaatcgac | 420 |
| tgtttagtaa ataatttttt nttttgagt cagggtcttg ttc | 463 |

<210> SEQ ID NO 5
<211> LENGTH: 557
<212> TYPE: DNA
<213> ORGANISM: Homo sapiens
<220> FEATURE:
<221> NAME/KEY: misc_feature
<222> LOCATION: 233, 406, 420, 500, 543
<223> OTHER INFORMATION: n = A,T,C or G

<400> SEQUENCE: 5

| | | |
|---|---|---|
| gtatttcatt cgttttattt tctccatacc agggttcagc aaagttcttt ctataaaggg | 60 |
| ttagttagta aatatttag gttttgcaga ccattaggtc tctgtcatgg ctactcagca | 120 |
| ctaccacggt aggtgaaagc atcaatagat aaatatgtaaa taaatgagta taattgtgtt | 180 |
| ccagtaaaac tatttacaaa tacttaccat gggctggatt tggcctgtgc atnagtttgc | 240 |
| tcagtctgct ctatagtatt ctgttacatg catgtaccat aacttagcca ttttattgtc | 300 |
| agcattcaaa ttttttccag taagagtatg tgcatagaaa aaaattgtgt atttcacttt | 360 |
| aaatatacta taaaatttat cgcataacat aaattcgacg atagtnttct tagacatcan | 420 |
| caaaccatta ggtctgacag gtcaagaaaa gggctttata agtaggcaag gaacttctca | 480 |
| ggggttctag agatttatan gatccccct taatggaatg tgtgtgtatt gcgattgggt | 540 |
| atntcctgtc acttgaa | 557 |

<210> SEQ ID NO 6
<211> LENGTH: 189
<212> TYPE: DNA
<213> ORGANISM: Homo sapiens
<220> FEATURE:
<221> NAME/KEY: misc_feature
<222> LOCATION: 7
<223> OTHER INFORMATION: n = A,T,C or G

<400> SEQUENCE: 6

| | | |
|---|---|---|
| tttttntttt ttttttttttt tttttttttt tccaggaaag acagatgtta tttaccacca | 60 |
| atgaatttt atcatattta aatgaacttg aaaatgtcat tcaactcaaa tccctcaatc | 120 |
| aacttacttc agcccattct gaaacttcat attgcagcaa accagccatg tgaaagaaat | 180 |
| aaattcaat | 189 |

<210> SEQ ID NO 7
<211> LENGTH: 370
<212> TYPE: DNA

```
<213> ORGANISM: Homo sapiens
<220> FEATURE:
<221> NAME/KEY: misc_feature
<222> LOCATION: 139, 267
<223> OTHER INFORMATION: n = A,T,C or G

<400> SEQUENCE: 7
ctattaatca acactttta atgtagtaca tatatatctt acagttattt aagtcaaata      60
tgtaaaggtt tacaactgat ttacagatga agcaatcaca gattgcagta atatgtgtgt    120
gtgtatatat atatttatnc catatataca cacacgccaa tcaaggggaa aactgcatcc    180
tggcaatttt acagtctgaa gttttgttgg tatatctacc atttcacatc cttttcatct    240
tgcttttctg tacaaaagat atttttngcc ttcttcattc ctgatgagat ttttctgcga    300
taactttaca ttcgtacatt gccagttgtc gaccaatgtt tcccattgtt atgcctccag    360
caaaaaatat                                                            370

<210> SEQ ID NO 8
<211> LENGTH: 375
<212> TYPE: DNA
<213> ORGANISM: Homo sapiens
<220> FEATURE:
<221> NAME/KEY: misc_feature
<222> LOCATION: 298
<223> OTHER INFORMATION: n = A,T,C or G

<400> SEQUENCE: 8
caaggtatag ctaattttat tattatcaaa caaaactagt agatataact tccaggaaat     60
aagttacata aatataacag aataaattca ttttcttaag tttcaaatta agatgatta    120
agaaatacag ctttatgtaa agtttctgct ttttctcaac cacgcctaaa gaggaaagaa   180
ctggcagcag gaacacttgc tcctaggaaa caaatacaac aaaattataa ttaaaaagat   240
cttcaagcta tcaaaatttg tgagagaagg atggtaagaa tgcagtagaa attaccanat   300
gacaaacaaa atcctatcag ttttcaggtt ggtcaaaaag taacttccat gaatatagcc   360
tgtggatccg gccat                                                     375

<210> SEQ ID NO 9
<211> LENGTH: 683
<212> TYPE: DNA
<213> ORGANISM: Homo sapiens
<220> FEATURE:
<221> NAME/KEY: misc_feature
<222> LOCATION: 535, 586, 621, 648, 679
<223> OTHER INFORMATION: n = A,T,C or G

<400> SEQUENCE: 9
gttgttgcca attgttttg ttgtcttcca gaggtaatac aaggctttgc tcctttagca     60
ggattcccag ttggaccctc tccagagagg attcatattt gaattccat ctgaatacca   120
acccaaatgt tgatacagaa cactcctgta ttaaaattaa tatccatccc agataaacct   180
actctgtgac taagacaatt gagatcttct aggtgaagat gctataattc aaaatattac   240
atggaaaacc atgtcttact taaaacgggt acttgttttc cggccataat tattccagtc   300
tcttccacag aactgcttct gcaaacagtt tttttaatgt atcaaagaga gtctctcgcc   360
aacatttaat acagtcaaat ctattccaac ttcagagttc ttatatgtct tatttagcag   420
acactatgat tctatcttct tattctctgg aaatccatca gatgtgtgtt ccaacacaga   480
agtgccttcc ttccttctca tggtggcaaa agcatatcca tcatcccaa ggttntaaca   540
atcccttggt aatcaactct tttctacaag ccctgaagag taaacnttta tcactacagg   600
```

```
gctgaccatt cagggaatt nccataattt tcagcgctga taacaggnaa ctgcggaaat    660
ccccggcgat ttgccgggna atc                                          683

<210> SEQ ID NO 10
<211> LENGTH: 331
<212> TYPE: DNA
<213> ORGANISM: Homo sapiens

<400> SEQUENCE: 10
tttcacagtg aaagaaacaa gtttattgga aactactcct ttacagagta gagtgtcctc    60
agaaagcagg gggagaaacc cacagccctt tgttagtatt tctacttata agaaactata   120
aggaactata gttaaacttg gagtgtgcag ataagctcac taaaggtagg ggctattggt   180
gttatccacg accattaatc ctgcaaccta agcttgctca ttttatgtta tatttaagta   240
atgggggctg cattcttagg acattggaca tctgcaggct tggtggaaca tgttctgtaa   300
tgggccataa atattccgta attaaaattg g                                 331

<210> SEQ ID NO 11
<211> LENGTH: 417
<212> TYPE: DNA
<213> ORGANISM: Homo sapiens
<220> FEATURE:
<221> NAME/KEY: misc_feature
<222> LOCATION: 27, 381, 389, 394
<223> OTHER INFORMATION: n = A,T,C or G

<400> SEQUENCE: 11
tttctgtcaa gctgttcttt atttcangga gagggcaggg gcagagcttt acaggagtag    60
agattttgta tgctattgaa ggtaaattgg tatcagttta aattgattg ttttaagtgt   120 aggatgttaa ctataatccc catagcaacc acaaataaaa catctaacaa atatacacaa   180
aggggagtgg aaagagaatc agactagttc actacaaaaa aacagaaaag aaggccataa   240
agaggaaatg aggggccaaa aaagtatatg acatatagaa gaagtgttaa atggtagaag   300
aaagtccttc cttaattact ttaaatgcaa atggattaaa ttttccaatc caaaaggcag   360
aaattggcag aatggacaga naaaacaana catnaacatg atagtgatat gcctgtc     417

<210> SEQ ID NO 12
<211> LENGTH: 435
<212> TYPE: DNA
<213> ORGANISM: Homo sapiens

<400> SEQUENCE: 12
acgagccatt gacatcaatt tattccttca ataattgtt aggcagtata aatgaaggct     60
aatagaccat ttacaaatgc tgtttgttgg caaccagagc ccctggagc tgcctgtgtg   120 cacggggaca ctagcaggca cagttgggct gcggtggagg aggagtttcc ttgagtctcg   180
tgttctgctt tgcagcagtg atggcaggat cagtctccaa actctctgac attttgtcgc   240
agatgatatc cacaaggcgc tcaaatgtct gcttgacatt aatgttgtcc ttggcacttg   300
tttcaaaaaa ctcaaaccca agctgttctc ctaaatgttg acctcgctca gttgagatga   360
cccgctcgtc ttccatgtca cacttgttcc caaccagaat aacttgggca ttgtccaaga   420
gtatgttttg atttg                                                   435

<210> SEQ ID NO 13
<211> LENGTH: 354
<212> TYPE: DNA
```

<213> ORGANISM: Homo sapiens

<400> SEQUENCE: 13

```
tttttttttt ttttttttgc aagatgaaat aaactgtttt ttttctcca gaaatctcta    60
ctccagtgcc cacagcacac aagagtcaaa acaaataagc aactaagatc ccccgatcac   120
aaatttccaa agaactggag gaggggaaga acagggtgaa aatggtggt atgaaaggga   180
atggatgtta gcagcactgt tcaataactg atctattctg gatgaaatac ccttttttat   240
gtgcagtaaa ttctgaacaa ggctaaattt taggatattc cttgaactga aattagaaaa   300
taccctgaca atggaagcag ctcttttcat ctaagtttac cccgagcctc tttc         354
```

<210> SEQ ID NO 14
<211> LENGTH: 437
<212> TYPE: DNA
<213> ORGANISM: Homo sapiens
<220> FEATURE:
<221> NAME/KEY: misc_feature
<222> LOCATION: 373, 420, 437
<223> OTHER INFORMATION: n = A,T,C or G

<400> SEQUENCE: 14

```
gagacacagt acaacagtct ttaatgtata tataaatatg cctacataac agagtttgat    60
aagagaagtt ttggctatat acaactctgc atgtaatcaa actctagaac atcaaatgca   120
actccactgc atagctgttt tgacagagca acagttaagc ataaaatagc tttgcacctt   180
attattttgg agcaaaataa aaaataacca ccacaaaaaa aatctctaca ataatttaaa   240
ctaaaaatgt tgttgaggat agggtaaaca acaaaaaaga aaataatttg atccatatgt   300
gatatttggc tgaagattaa cagtgttaag tctaaccaac agcgagataa ttttaatttt   360
cccaagcatc ttnctaccgg tttattagcc atatttggat attaagggga agggcatttn   420
gccctttacc aaaaccn                                                  437
```

<210> SEQ ID NO 15
<211> LENGTH: 274
<212> TYPE: DNA
<213> ORGANISM: Homo sapiens

<400> SEQUENCE: 15

```
caagaacatc ccttttaatc acaaaccact catccacaaa tgtggctatg gggtaagcag    60
tctaggctgg gacccttttcc agaggtaagt caaggtcacg tccctgcccc cttcctaggg   120
tggcggtggc tccagccagg ggggcttcca ggttaatacc agagcctcgg ctactctgga   180
ctcctgtgag ctcttcttgg ctggaagaag ggggcattg tgggcctgct ctgtcccaag   240
gctccagaag ctgcccctac ccaggcctgc ctgc                               274
```

<210> SEQ ID NO 16
<211> LENGTH: 319
<212> TYPE: DNA
<213> ORGANISM: Homo sapiens
<220> FEATURE:
<221> NAME/KEY: misc_feature
<222> LOCATION: 203, 210, 289
<223> OTHER INFORMATION: n = A,T,C or G

<400> SEQUENCE: 16

```
gagtatttcc agccataaca acatttatta gttctctggt aaacatttta acatttctga    60
agaaacagca aagtgggcat gtatcttaa tgtggagcac tggggacata tctgagacc   120
tacaactctg aggaacagag acaagtgatt tgggggatat tctccgatta acaagccaaa   180
```

-continued

```
gaatcaggaa aatgggctgg aancgggtan ccacacacct ctctccctgt gtggggcctc    240
taatatgtga ctgatgcctt ccttttctgt gcctttgaaa tctcatgcna gattggctat    300
aggtgaattg tattaccga                                                 319
```

<210> SEQ ID NO 17
<211> LENGTH: 567
<212> TYPE: DNA
<213> ORGANISM: Homo sapiens
<220> FEATURE:
<221> NAME/KEY: misc_feature
<222> LOCATION: 415, 454, 465, 474, 486, 493, 519, 549, 562
<223> OTHER INFORMATION: n = A,T,C or G

<400> SEQUENCE: 17

```
aatatggaca gggagtctca ttgtgtttat catatcaatt aatattacag tacatccttg     60
gtaatacaaa attgtacacc ttcatcaaat aaattaggat aaattaaacc aataaattat    120
gcaaagtctt cagaacaata gacaacaaca aaaattcaca attgaaattg cctctagcta    180
aaaaaaacaa acaaaaatca aaaattgact ttatcagttc agttattgta ctatattcaa    240
atcaaagggt ctttattaca aaaaagagct taataatgct atttacaaca tattgctaaa    300
taatataaag gcagtgtttt gtcacggttt atactatata catatgagaa atggctggga    360
caatattgag ggaagcccat gacctttggg attcttccag gtagcgctga gaccnatccc    420
aatacatttt ttttccttag ttccaaattt gganggcgta atatngcagt tttnagaaat    480
tttccncccc ccnttttag gggggattgg atattttana aaaattccgg atggaatacg    540
gtttccccna aggagggtag cntggtt                                        567
```

<210> SEQ ID NO 18
<211> LENGTH: 516
<212> TYPE: DNA
<213> ORGANISM: Homo sapiens
<220> FEATURE:
<221> NAME/KEY: misc_feature
<222> LOCATION: 18, 47, 94, 123, 125, 128, 132, 270, 324, 513
<223> OTHER INFORMATION: n = A,T,C or G

<400> SEQUENCE: 18

```
ggccggggag ctgcgtantc ccggcccgcg gccatgccca agcggantgc cccttcgcgg     60
acgtggcccc gctacagctc aaggtccgcg tgancagagg gagttgagcc gcggcgtgtg    120
cgnangcnta cntcgcagga ggtcttcgag aagaccaagc gactcctgtt cctcggggcc    180
caggcctacc tggaccacgt gtgggatgaa ggctgtgctg tcgttcacct gccagagtcc    240
ccaaagcctg gccctacagg ggcccgaggn tgcacgtggg cagatgtgat tggaccagac    300
ggccgcctga tcaggagcct tggnaggcct ccgaagctga cccatctggg gtagcgtcca    360
ttgcctgttc ctcatgcgtg cgagccgtgg atgggaaggc ggtctgcggt cagtgtgagc    420
gagccctgtg cgggcagtgt gtgcgacctg ctggggctgc ggctccgtgg ctgtaacctg    480
tgtggcctct gactgcatga catgtacaag aantgc                              516
```

<210> SEQ ID NO 19
<211> LENGTH: 454
<212> TYPE: DNA
<213> ORGANISM: Homo sapiens
<220> FEATURE:
<221> NAME/KEY: misc_feature
<222> LOCATION: 75, 77, 123, 127, 393, 408, 417, 432, 439, 445
<223> OTHER INFORMATION: n = A,T,C or G

<400> SEQUENCE: 19

```
tttatcctta gggggatcct ttatttcatt cacttcctcc ttacaaggtg aaatttcaat    60
ctgtacagga tgtgncngcc agttcagtcc acagctcaga gtatcacctt gtcctcattc   120
canggtnata agctcctgcg aggggacagg tctgcgggtc gtggattcac tggactggat   180
gggacatgat ccagaactcc gctccgtttg gcttcccaag gatcccacca actcattcta   240
atcagtgatc actgaggaaa tgcattgtat tcctattcac tatttcaaag atcaggccta   300
cctcattggc atattaagaa agttttctca agtatattta gtgtttatca ttttactata   360
gttcttcaaa tgtctggaca ttcatctttt ccntacctct aaattccntt ccttttnaca   420
ttaatctttt cntgattgnc ttttnaatag aaaa                               454
```

<210> SEQ ID NO 20
<211> LENGTH: 453
<212> TYPE: DNA
<213> ORGANISM: Homo sapiens
<220> FEATURE:
<221> NAME/KEY: misc_feature
<222> LOCATION: 393, 404
<223> OTHER INFORMATION: n = A,T,C or G

<400> SEQUENCE: 20

```
aggaggaaag cataaattac ccataggtcc acaaattcca catttctctg catctcttct    60
acctcccagt atggtaagta ggtaaatcag ttatgggggt aacgggctga cctccaagga   120
aaaatcgctg ggtgggtggg agctgatggt ggtccacttc tgcttttgct cacaaatagg   180
ttgtgcaagg ccaaaggagt acaaagaaaa aggaatactc aatgtttctt gctgattttg   240
cacccaggct gtagtggcga ttcagtcctt ttcaagaaag cagctcgtag gagaaaggga   300
gagagggaag aaggagtggg ggagtggcaa gaccacaggg ttcttgggga cagtctcaac   360
ttccagccga atggctctct ctgccagagt ctnttgtcca gctnggagtg aaggtgtcca   420
gtccatggta gtggtgggga caatgattat ata                                453
```

<210> SEQ ID NO 21
<211> LENGTH: 426
<212> TYPE: DNA
<213> ORGANISM: Homo sapiens

<400> SEQUENCE: 21

```
ggggccccgt gatctcaacg gtcctgccct cggtctccct cttccccgc cccgccctgg     60
gccaggtgtt cgaatcccga ctccagaact ggcggcgtcc cagtcccgcg ggcgtggagc   120
gctggaggac ccgccctcgg gctcatggcg gccccggtcc gcatgggccg gaagcgcctg   180
ctgcctgcct gtcccaaccc gctcttcgtt cgctggctga ccgagtggcg ggacgaggcg   240
acccgcagca ggcaccgcac gcgcttcgta tttcagaagg cgctgcgttc cctccgacgg   300
tacccactgc cgctgcgcac gggaaggaag ctaagatcct acagcacttc ggagacgggc   360
tctgctggat gctggacgag cggctgcagc ggcaccgaac atcgggcggt gaccatgccc   420
cggact                                                              426
```

<210> SEQ ID NO 22
<211> LENGTH: 415
<212> TYPE: DNA
<213> ORGANISM: Homo sapiens

<400> SEQUENCE: 22

```
ctcggtcaat aatttattag taaaatatac atttctcatt attaaagaat aaaagctttc    60
```

```
agccctgctg aacacacatc tgaggtctca agaaaaccag acaagatagc tgactctccc    120
acatagccct ttccataaag gcgattccta agcttaaaca cacacaaagc tggggctgtc    180
cctcttgaat cccatgggaa acaggcccca agatcagggg acctggagtc gggagcttgg    240
ggtgcagtct gctcactgac accctctcga agagcacgca ggggaacctg gtcctgggat    300
ggagtctttc tggggatgcc ccacgtctgt gctgcctgga accgggtgcc cagggcagcc    360
ggctcagcag gccccagagc aggggcaggt gtggctggga ggggctgtat atgtg         415

<210> SEQ ID NO 23
<211> LENGTH: 385
<212> TYPE: DNA
<213> ORGANISM: Homo sapiens

<400> SEQUENCE: 23
tttcccagac ccatgacaac agagagcatc tagccatgat ggaaaggatc ttgggtccta     60
tcccttcccg gatgatccga aagacaaggt gaaccttgag ggggcactag ttaactcttt    120
tccttttctc tccacagaat tggtctattt cacatcattt tcttttttct ttgatacctc    180 ctctccccc agttactttc agatggggaa ataagggaat tgtaacaagg gtgacctttct   240 gattcctcaa cctccacttc ccctctagaa agcagaaata tttttaccgg ggtcgcctgg    300
attgggatga gaacacatca gctgggcgct atgttcgtga gaactgcaaa ccgctgcggg    360
tgagctgggc tcgggataaa tagtg                                          385

<210> SEQ ID NO 24
<211> LENGTH: 376
<212> TYPE: DNA
<213> ORGANISM: Homo sapiens

<400> SEQUENCE: 24
gtgttaaagt tggatggatt tatttttta aaggcccagt acaaaaaaat ggttgaggaa      60
agtgactctt caacaaaata tacacctgta gaaaaaaatc cctaatatac tgatatttaa    120
ttgaacggaa agtactaaag agaacatact ttaatatcta ggcacaattg gtcaggtact    180
aattataatt tctgttctca tttaaaagtt taaaccaatt cttcaactgg actgatgtgt    240
gtgagtctaa tacagagaag gcacctctct catctctcac tctccttaag gacctttga    300 gagaaactct ttgtaacact ttaagggaca cagacaatgc actatatcta agtatagata    360
tagttattta acatac                                                    376

<210> SEQ ID NO 25
<211> LENGTH: 485
<212> TYPE: DNA
<213> ORGANISM: Homo sapiens

<400> SEQUENCE: 25
tttttttttt tcccaaacaa tacatatcag atttatcca ttttgttttc tacatgttct       60
ttgtgactca gtttgacat tagcatttgc accccaaatg agttccccta caaataaaat      120
ttgttcatgt tgacacaaag aacacaaagc aagtatagat ccctcaggaa gttgtcacaa    180
ctcttgataa gattaactcc accactatca tcacttttg ctttgtcccc tagtttgaag     240
cctgctggct ttataattc aatgagaatg actccacact cttctccaaa gcgcccatta     300 ttttagttt ttcggtgcgc gactcaacat aaagacctgt ggctcttatg agctgcctgt     360
ttttaaatgg tgcagtagtt tcagtttcca tttaataagt tcccagataa caaatggaga    420
```

```
atgggaagaa tcttctcaag gtcacagtga aggtaaaaat aaattatctc catcactgag    480
aggct                                                                485

<210> SEQ ID NO 26
<211> LENGTH: 530
<212> TYPE: DNA
<213> ORGANISM: Homo sapiens

<400> SEQUENCE: 26
ttgttcttgc agcccggcat gccagtgctt cctccacgaa tttgaaagac atattggctg     60
acctgatacc taaggagcag gccagaatta agactttcag gcagcaacat ggcaagacgg    120
tggtgggcca atcactgtg gacatgatgt atggtggcat gagaggcatg aagggattgg    180
tctatgaaac atcagttctt gatcctgatg agggcatccg tttccgaggc tttagtatcc    240
ctgaatgcca gaaactgcta cccaaggcta agggtgggga agaacccctg cctgagggct    300
tattttggct gctggtaact ggacatatcc aacagagga acaggtatct tggctctcaa    360
aagagtgggc aaagagggca gctctgcctt cccatgtggt caccatgctg acaactttc    420 ccaccaatct acaccccatg tctcagctca gtgcagctgt tacagccctc aacagtgaaa    480
gtaactttgc ccgagcatat gcacagggta tcagccgaac caagtactgg                530

<210> SEQ ID NO 27
<211> LENGTH: 566
<212> TYPE: DNA
<213> ORGANISM: Homo sapiens

<400> SEQUENCE: 27
ttacgcatac aaaaaaactt tatttacagt tgaaaactta agacaatct tggattctga     60 atctctgaca cttccatggt ctcttgatca aatggggcag cagcaggcag ggaagcaaag    120 acggggggcca gtccagatta tcttactcaa gaacaccacc aagaagaagg aaggcctga    180 ttcagtctttt gtctggacta catctcccca cactgcgaga tcaccacagg tagcttgggc    240
ttattgttgg ggcctgtggg aacattctca atctttctca tcactagaag tccatcgatg    300
atttttccaa acaccacatg cttcccatcc agccaatcgc acttagagca ggtgataaag    360
aactgacagc catttgtact tggaccactg ttcgccatgg aaagcaggcc tggagctgag    420
tgtctaagtt taaattttc atctgcaaat ggccccccggt aaatactggc gactccagta    480
ccatctccat taacaaaatc tccaccctga atcatgaaat cctttatgac cctgtggaag    540
gtgcttcctt tgtatcctat tggaac                                        566

<210> SEQ ID NO 28
<211> LENGTH: 295
<212> TYPE: DNA
<213> ORGANISM: Homo sapiens

<400> SEQUENCE: 28
tttgagtttc aaaggattta tttgatttcc ccacatgatc acaaccatgg ttttacattg     60
atagagtctg ttgccactga caaacagaat gcagatgaaa acaaacgcac tccttttcctc    120 tcaaaggtac acagtggggg tgccaggctt cttgtgaggg aggtgtcctt gaagtctctg    180
aacagtctgg ggattcagga cctgattcta attgcttaaa acaactcgga ggcaaaagat    240
attttccaag aggagatgca tgctgtgtgc agtctcgatg tgactgcaca cagaa         295

<210> SEQ ID NO 29
<211> LENGTH: 550
```

<212> TYPE: DNA
<213> ORGANISM: Homo sapiens

<400> SEQUENCE: 29

```
ttttcaggtt gtaaatattt atatttctct cacatacaat gttgtatgag acacttgttt      60
taatatgtat ccataggatt aatactcata tggagtataa tgtggaaaag tgcagaacta     120
aagaaataag tctatccgaa aacaaaagca cacatttctc aggatttaaa aatattgcac     180
atagtaaggt tgcacagaaa ttactggctg gttttacaaa cagaatgagg tatcagtcaa     240
tctctagata aagatgagag agaggataaa ctacacacac acaaacacat aaatccatac     300
taagacctaa gagtgccaac aactaagaaa gaaatatgaa aaagctatgt taggtagcca     360
ggatttcaac actacaaaat cattttagg ctggaaccaa acacataaca atctcttggc      420
aatatttcgt taagttttca acttttttcc agcctaaatg actatgggca ataaaaccat     480
ttcctttacc ccagttctac tgtagaaagg cacagcgctg tggtaaatat caaaccattc     540
ctttctcaac                                                            550
```

<210> SEQ ID NO 30
<211> LENGTH: 428
<212> TYPE: DNA
<213> ORGANISM: Homo sapiens

<400> SEQUENCE: 30

```
tttttttagg ccacacatag aatttcagtt ttattaaaat aagcacaatg tataaaagca      60
ccgtggtgtt gtataaacgt ctgcctgaca aatgcaaatc tatttctttt atgtaactca     120
atagttccac ttatctgaat ggctgtacct tcatgcacac gggcagcagg cactgcattg     180
ctcaaacagg gaagtgaggc ttcaccctag tgtggcttca ccttaggcac agagcactat     240
ctaactgccc agatctgtgc cacccacaca agacctgggg acacagcagc agacaccgat     300
gctgtctcta agttcatcac aggaacagct taaaatcaga ataataggga actgctgatt     360
aaaacccaag tgcatggaca ttctagaaag aagagcaagc cgttccactc tctgggaagt     420
tcatgggc                                                              428
```

<210> SEQ ID NO 31
<211> LENGTH: 423
<212> TYPE: DNA
<213> ORGANISM: Homo sapiens

<400> SEQUENCE: 31

```
gccctcgaaa agctgctgtt acgcccagtc cccagagcga agggctggcc tttattctcc      60
atctgagggt gatcactagc gcttcttgag agaacggaga cctggcttct ccatctctgc     120
ctaatcagag aagtacctgg aagcttctct cagtgagaac aaactgagtt ctgcctcccc     180
aagcaccctg tggaatcgag cctgtccatt tatacaggag gacctgctag gcaggagtcc     240
agaggagggg atgtctgaac tgagtctgga aggatggaag ggagttttc aggcagatga      300
gcttctgaag gcatccaggt agagaccaac atgtgctaag gcccagaaac aaaatcaact     360
ggttgtgttc caggagctgt ggttgactcg aggggaaaat gggaatgggg gtgtgtggat     420
ggt                                                                   423
```

<210> SEQ ID NO 32
<211> LENGTH: 452
<212> TYPE: DNA
<213> ORGANISM: Homo sapiens

<400> SEQUENCE: 32

```
tttggtgaat aaactaacag ctttattaat gaaggcaaac atcagatcat tgtatgaata    60
ttatatatat atataaaaag aaatccaaac taacagcatt gtatttcaaa agtactgtac   120
ttctgtttct tttaaagaga cttgtcatct gtttttataa aacaaaatgg gtactcttct   180
cctaaaaaat cctggaaaaa tgaaatagtc aatttcaagc tgatgaattg aacacacctt   240
tctttaaatg cagactattg ctaggaagca aataaagtca agcatcagaa agaagatgta   300
tgagaaatgc atgaaagtca gagaaagggg atgtagtgaa attactgcta atctttcccc   360
cctatattca aagaccatcc aaaactggtc tttcatacaa atataaaata actataaaga   420
gagggaattt gaaaccatac ccatctgaaa tc                                 452
```

<210> SEQ ID NO 33
<211> LENGTH: 363
<212> TYPE: DNA
<213> ORGANISM: Homo sapiens

<400> SEQUENCE: 33

```
tttccagaaa aggatatttt ttttattcaa gtaactgcaa ataggaaacc agagagggag    60
ccccaggctg ggacaaatca tggctacccc tccccaacag aacaggggga ggaggtggcc   120
cctacaccct ttatggtcga ttcgggcccc cttgctcact ctgctgcagc atcctagggg   180
cagggccagc cttccctggg actggggtag tcggtcaccc agcctgccat gcccagccc    240
ctcttcccca caaagagtat cttggggag gggatcgtgg gcagaacagg aggcaatgag    300
gatgaacatt tggcgctggt agcagcagca atgacggatt gtcgaagaat ggaacattga   360
aca                                                                 363
```

<210> SEQ ID NO 34
<211> LENGTH: 408
<212> TYPE: DNA
<213> ORGANISM: Homo sapiens

<400> SEQUENCE: 34

```
agccttagga atggttttta ttcacttgaa cactgtacaa atattacaat ttccttttgc    60
tgcaaaaagt ataaaaataa tctttatata ggaatccatt cgttactgta aatctttcta   120
aatctctgca aatggcccta aatgagggta aatgaaaaag ccgaaatgaa gagagggtta   180
tggggcagca ggaggtgggg ccaatcatca gggctggacc acccagactc ctccccagag   240
acctctgttc cttcttggta gccgccccca ccacctgcag gttctagggc taaaggccca   300
gcagaagtgg gcacgtgaga gggccaggag gagctggagg gtcaggggggt ggggatagc   360
gaaggaagct agaagtggtg ctggcatgtg cccagttcca ccccacca                408
```

<210> SEQ ID NO 35
<211> LENGTH: 300
<212> TYPE: DNA
<213> ORGANISM: Homo sapiens

<400> SEQUENCE: 35

```
aaatgtgtaa aaactgtgaa tcagactttt attggattaa atagcaacgt atgggaactg    60
gaacaaaaat ggcatagagc tatccaagag tttctgctgc gccggttgag aaagatgcca   120
agttaagatc aaggagttga ttgaggtaac tacgggaatc tgaggaaaca tcgttgctta   180
actgtaaaaa ctaaatcaaa ctatttcatc ctcctcaaga ccacagcaac atccatcttg   240
ctcctctgta gcgtggacgg ggcagaaccc aggtgttagg aaacgcacct ggtctgctcc   300
```

<210> SEQ ID NO 36
<211> LENGTH: 409
<212> TYPE: DNA
<213> ORGANISM: Homo sapiens

<400> SEQUENCE: 36

```
tttttgtttt ctttcattat ctttatttta aatttgatat tttagaatag gaaattatct      60
ttcacagcaa tgcctcctgg tctgataata cagtatctca tttctgaatg taaagattta     120
aaataaatca aaatgaacat taaggcgtac aaagctactt taagtctgct cttaagatca     180
gttttttgctc atattcaaaa tacatggaat gttggcacaa aactgaagct gctgtagaaa    240
gatcacagat gttctgtggg ttactcaaac ttccatttct ctaaaaacat acccttacat    300
ggtcttaatt ttatgaattt aagtgttgag aaatatctaa ataataagta acaattaaaa    360
taaaatgttt tatttgtaaa ttatgtacag aatacacttt acgttacgc                409
```

<210> SEQ ID NO 37
<211> LENGTH: 428
<212> TYPE: DNA
<213> ORGANISM: Homo sapiens

<400> SEQUENCE: 37

```
tttgcattaa aaatacggca cttttcctgt attttagcag taagatagaa atactaggga      60
tagaaatata ccaaaaaaca aaattaatgc tttaattaat atccaccctg aaatgtcagt     120
ctctgaagca agatgggcaa ttaaaggagg agcagaaata aaaagggaa atatgataaa     180
ataaactcca tgtgaagttt tacgaagcta tctgcaaaga aaccgatttg tccttttgaag    240
gctattaact caggacaatt aagttatcca gcagccatgc tgaggagttc atagtctagc    300
aatacgttgc acacaggcaa atacacttaa gacgagttgg agatatacag aactatcatt    360
tagaaatgat tttactctgg atggctcaaa aaactttgaa agggctatga agaaaacttg    420
aagtctgt                                                             428
```

<210> SEQ ID NO 38
<211> LENGTH: 424
<212> TYPE: DNA
<213> ORGANISM: Homo sapiens

<400> SEQUENCE: 38

```
ttttcatatt tgacaacttt atttagtttt gctaaaaggg aaaaacaaag tcatgcagcc      60
ttctccaaac acatcttaac atttcaaaaa gctgagcaaa tctcatttga tgaatctaga    120
gttttataaa cactttgaat ggtacacagt gacaagatgc agggaagata tatggaattt    180
tattagtttg attaccttgg taatgttatg ctattaaact catttctcat tgaattagca    240
ttaaggtcat gataaccctc agcttttatc aaggggcctg ggatattata ataacttgaa    300
aattccagtt tggcagtaat gattatactt aaccatgatc tttaccagaa agtcaaatat    360
attctacctt aattcctcag aattcacatt ccttgcattc agctccaagg aaggagtaca    420
ataa                                                                 424
```

<210> SEQ ID NO 39
<211> LENGTH: 318
<212> TYPE: DNA
<213> ORGANISM: Homo sapiens

<400> SEQUENCE: 39

| | |
|---|---:|
| tttggttatt cagtatttat tctgcaatgc aaaggtgaca aactaaaata taaaaaggct | 60 |
| gttatggctt aacattttttg ttgcagatta aatatgcagc attgaaaaat ggaaaggcgt | 120 |
| ggcttcatct ctgaccagca gagttaaaaa gaaaaatctc tccatttttcc ttcatcatca | 180 |
| tgggatacac tgttcaggca atccaaatta ataaagactt gcactttcat atgaacacaa | 240 |
| gatcaagtgt accagttagg ttttcacatt cacagtatat aagaaaatac acatggaagg | 300 |
| aaaagtaaag ggttaact | 318 |

<210> SEQ ID NO 40
<211> LENGTH: 417
<212> TYPE: DNA
<213> ORGANISM: Homo sapiens

<400> SEQUENCE: 40

| | |
|---|---:|
| aacaaatata tttagatata tttaaaagaa ttaaaaaaaa catttcacaa aacatttgtt | 60 |
| gccataggaa ttattttttag caataaatgc ccacatcaaa atttaaacat ttttcaaagt | 120 |
| atgattatct gtactaagta atgcaacaaa ttatgtaaac agagtcagat acatttccct | 180 |
| gtaggagtca cttccttccc gggattaaag ctgtcccaga catcttttcca ggggaccaat | 240 |
| taagaaactg ctattttcag agcaacgaaa ataaaagctt ttatttgttc atttgaatat | 300 |
| aaaacaggcg ttatcacaga tgtacaaagc gtactggtgg tttaacatac aagaaggttg | 360 |
| ctgtcctttg cacataaaaa ttttgtttga aactgtggct ggttgagtac atgagtt | 417 |

<210> SEQ ID NO 41
<211> LENGTH: 380
<212> TYPE: DNA
<213> ORGANISM: Homo sapiens

<400> SEQUENCE: 41

| | |
|---|---:|
| ctcagacaca tctatcttta tttgtttcct gtcagaaaat ttcaagaatt acaccaaaaa | 60 |
| atacttccgc ctctgctacc tactgacaaa aatacaccac aaaattataa agcgctcagc | 120 |
| ggttttgcta gggacaactt gttattccgc tttgaatgac aaatgaattt acaggtgact | 180 |
| cagggtgatt ggaggttggg ggagaaggga ggaaaaatca gatgagagcg tttggcagga | 240 |
| tagtttgagc tatgctagtc ttattaccca gctgttgcat acgatgatct cagcaacaca | 300 |
| gcaagccaca aaaaaatacc ctttacatgg cctgtgggag acttgtgagg aagcagtacc | 360 |
| acatctcaaa taaccaattc | 380 |

<210> SEQ ID NO 42
<211> LENGTH: 418
<212> TYPE: DNA
<213> ORGANISM: Homo sapiens

<400> SEQUENCE: 42

| | |
|---|---:|
| aaaagaatga gttacattta ttgatatggt ttgtcatatg ctttataaat ggtcaccctt | 60 |
| tgaaacatgt attattacta tttgcgggag aggggggactg ttcattttac aggggacaag | 120 |
| caagacaggc tcaaggaggg aaaggacagg ctcaaagtca tcacagtgtg ggtgctggaa | 180 |
| tgcagttgcc cttccttctt tcttttttgca catcttccgt tctagggtg aggaggggtg | 240 |
| taggcacagg cacccaagac agctgcggtc cagccccggc cccacctgtg gtctcagtga | 300 |
| cgccccagag gccccatctt ccccacataa tgaggctgct ccatcctcct caaagcccag | 360 |
| acctatttca taagccccag accccacctt caccaggggc cccaagagaa cagagctg | 418 |

<210> SEQ ID NO 43
<211> LENGTH: 436
<212> TYPE: DNA
<213> ORGANISM: Homo sapiens

<400> SEQUENCE: 43
ttgagtatgt tatacatcca agagccttat atttcactcc acataaacag taaacataaa      60
agaaaaaaga aacactttgt ctccctatag agcattttat agtataggaa gggattcaaa     120
ttctcttttt aacaaaattc ttgtttctat atagaggaga ttttatattc ttaatgttta     180
caacaaagcc tatttccacc aaaaaagcaa gaagaaatta ataaatgaaa tcctgaactc     240
taaaaaccta agaaataaaa ctgtgaacaa ttctgaaacg gagtgttttt tctaaaggct     300
aatacaaaca taccaaaata gaatttctga gcacgaacta tgtgatttca tttcaatcgt     360
atcactttca tctgattgaa ataatttaga aacaataagg atgatcttaa tctcactatt     420
ttctgcatga gactat                                                    436

<210> SEQ ID NO 44
<211> LENGTH: 439
<212> TYPE: DNA
<213> ORGANISM: Homo sapiens

<400> SEQUENCE: 44 ttttttttt gacagttttt aattgtgcct ttattcaact tagttcatta aaaatgtttt      60
aaagatccta taaataaagt gaccactcac atgggatata ggtcacccct cagcatgtta    120
ttttttttct taaaaagcag tatttcttac aggaatctta ctgatcacac ggtagttaca    180
ataatgtcag atatgatgta tacagtctaa acgagacagt ccagttaaga atatacataa    240
tgtaaaaata cacatattaa aagttagcca agtggacaga cgcatgcggg ggtgggggga    300
gcaggtgaca ggaactccct taacaatcag tagagggccc agatgcaaag aatctggttt    360
tccccgttac agtaaacagc tttcactaac gtatacaggt atttcataca catctaaaca    420
cacaagggta agttgtgac                                                 439

<210> SEQ ID NO 45
<211> LENGTH: 426
<212> TYPE: DNA
<213> ORGANISM: Homo sapiens

<400> SEQUENCE: 45
tccagagaca gtagagcttt attgtgtaaa agctgagttg gtagaagtat gaaacggcaa      60
caatgtttag cccagcccat ctatttacaa tatataggggttggggtttc ccatacacat     120 ctgtaccacc cgccctcagc ctcaagattt atccctatca gcaacattca tttcctggat     180
ttgtcactgg ccacaaaaga cacaactctt cagggtgata tcccatcaca taaacctaca    240
tacacattat ctcctagtcc ctctagctct cttcccagtc ttttttttt ttttttgaga     300 cagggtctag ctgtcaccca ggctggagtg cagggtgtg actgcaactc actgcaacct     360
ccgcctcctg ggatcaagtg atcctcctta gcctccccaa tagttgagac tacaggtgtg    420
caccac                                                                426

<210> SEQ ID NO 46
<211> LENGTH: 223
<212> TYPE: DNA
<213> ORGANISM: Homo sapiens

<400> SEQUENCE: 46

```
ggaaaacaaa aggaaaactt atttattctt agaggtggga atgtggggag tggggcagaa      60
caggtggtgg ccctgggaga gggtcccaag gggcagaggt tggggatgtc tcagtaaaga     120
ggggcaggtc atgaatagag cctccacccc cagcaggggt tccttgggcc cgcccaagca     180
ctgggctaaa acgtggaaac tgggcattga caaagtacag cgg                      223
```

<210> SEQ ID NO 47
<211> LENGTH: 352
<212> TYPE: DNA
<213> ORGANISM: Homo sapiens

<400> SEQUENCE: 47

```
tttcccagcc ctcaggccac tttattgctc aagagtggtc agtctggggt atctgcatgc      60
ctgaactcca tgatgatgtc gcctgtgtcg gggtgaaact ccactgcata gctgacagtc     120
cgtgggccac ccagcagtgc tctgggatct ggggcagggc tgaagaagta gacggcctgc     180
ttgcagtggg ggttccagca gcagcccccc tcgggatctg caggctccag gaggccagtg     240
ctgagcgtgc actccggggt caggtggtac tccatccata gcaccgctgc gtggctctgc     300
acgggccttc tgagctccac ggtgccctcg gcacacaggg gctgcagggg ca             352
```

<210> SEQ ID NO 48
<211> LENGTH: 317
<212> TYPE: DNA
<213> ORGANISM: Homo sapiens

<400> SEQUENCE: 48

```
ctctgaattc atttatttag aggtaaaaca cagccattca aaattgtgga atacaatgtc      60
tacacacaga ataaggttgg ggaattaagc tgaattgtta tattccattc acattaataa     120 atattttaa agaagaaatt gtagatttta aaagcttcat tagacactag tgacacatac     180
aaataactaa actctcatac tgcttgattt tcaggttgaa aggttacaat aatctatata     240
tttcaattac atggcagtaa atacaaaagc attttaaaca tcttttgaac tgtgtagtat     300
actataagca ggagttt                                                    317
```

<210> SEQ ID NO 49
<211> LENGTH: 414
<212> TYPE: DNA
<213> ORGANISM: Homo sapiens

<400> SEQUENCE: 49

```
aacagtctgg ctgttgtttg aattaaactc ttaaacagga tgtttagtta gagggtaatt      60
gttgagtaat gatgcataca acagcatact tcccttttctt gctgggggtg cagcttttca    120
gttttcttgt tttactttga cagtgcaagg ggaactgaaa ataatttcca ttgtattatt     180
tatcttagtt cagctgaggg ctttatgaga cagtggatgg ggaggcagta agacggtgat     240
gagataaaat gtgtgtgttg cactgactgt ctataaagtt atcctttctt catgaaaaag     300 tagcattta  atctggatga gtttataaag gattacaaaa tgctgattta tagagtaaac     360
tttaaaatat taaagactaa agactaaaag aagagtaata atgaagtaat gtag          414
```

<210> SEQ ID NO 50
<211> LENGTH: 593
<212> TYPE: DNA
<213> ORGANISM: Homo sapiens

<400> SEQUENCE: 50

```
tttttttttt ttactggagc aaaatgaatt tttttttattg tacttcaggg caacaagtca      60
```

```
acagctgcag gaaaacaaaa ccaggtccaa tctatgatct aagaggaagt caggaaaggc      120
ttggaagaga gatccaaagg ccggcctggc aaggggaatc ccacatgaga attcctggga      180
gagagcaggc cccaggcagc aaggtcatct tgcctgcttc tctgtaagtt aatccttcac      240
agggagccaa ggcttctctt gactgcttgg acaagagggt aagggccctg gttgcaggat      300
ttgccagtga agtcatccat gtcaatagac cagatcatgg ctcctcccag gtttaaattc      360
tttaagaact gaaccttggt ctccatactc ttcacatcat catagcccac ccactggttc      420
cccttgactg cgtagggaac ctgctgatcc tggagccgcg tgatcttggc tcctttcagg      480
aactggcaga tctcataata ggccaggaag cctgaagact ctgtgatggg tccagcagct      540
ccagggccag aggcaggggg ccccacggtg ggttctgcag aggccagtgt gaa            593
```

`<210>` SEQ ID NO 51
`<211>` LENGTH: 407
`<212>` TYPE: DNA
`<213>` ORGANISM: Homo sapiens
`<220>` FEATURE:
`<221>` NAME/KEY: misc_feature
`<222>` LOCATION: 126, 129, 130
`<223>` OTHER INFORMATION: n = A,T,C or G

`<400>` SEQUENCE: 51

```
tttttatttt atttacatat gtacattatc ctttattaaa agtatggcac tttatataac       60
agcagaaata attacatgat ttacacatcc agaagcaata aaatgtgaag gtgcaaacat      120
tacctnttnn aaattcccaa taaaagtaaa aaaagtttca acatgttctg taagccctta     180
attgcataaa gtatatttag catcatttac agccagtaca cttatataaa ctaattatca      240
ttacctttta cattctgcaa agaaatatg ttaaagtaaa gaagcatggc gagacaaaca       300
tgaattaaat gtcagttctg atcattcatg gggaaatata agccgataat ataaactact      360
agataacaca atgattttaa caattttttga tgttttttaaa gttaaaa                   407
```

`<210>` SEQ ID NO 52
`<211>` LENGTH: 368
`<212>` TYPE: DNA
`<213>` ORGANISM: Homo sapiens

`<400>` SEQUENCE: 52

```
atgtcaagat atgcagcaag tttaatacct gaaggttaac ataaatgaca acaggacaca       60
gatgcaatgc tacagtcaaa tgtggttggg gatggaaggg ggcagaggga cactggatat      120
catcacagca accagtgagt gagtcctctg gtgccctgag gaggttgtga gccacttgac      180
tcgtgtcaca aagaatggag taaactaaca actctgaaag acaagagggt ggcagcattg      240
ctgagatgag actcaaggca ggggtctgca gctctgtcac agagtgttaa tgctcaacga      300
tgcctgggct caagagcgtt ctggtcagca ttttaacatc agaagaaggg cttcttcagg      360
gcacactc                                                                368
```

`<210>` SEQ ID NO 53
`<211>` LENGTH: 192
`<212>` TYPE: DNA
`<213>` ORGANISM: Homo sapiens

`<400>` SEQUENCE: 53

```
ggaggtagtg actgacaaga taataaagcc caaagcatta tgctgactag gaccattgaa       60
gttggcaaaa aaaggccaca acaacagcaa gaaggcccag gattttcaac agaaaagaaa      120
```

```
ctgagaaatt agatgaatcc ttcagggccc gagtcttgag tggcttcagt attctttgtt    180
tctgggtgaa ga                                                        192

<210> SEQ ID NO 54
<211> LENGTH: 306
<212> TYPE: DNA
<213> ORGANISM: Homo sapiens

<400> SEQUENCE: 54
ttcggcagca actcctttcc tttatttctt ccccttgtaa agggaaattc aagttcagca     60
gcattccttt cctgcccaa gtcctcaacc agacaagagg ctgcaggcac caaatcttgg    120
gctggataat ggcaaaggcc tcagaagctc acctccagct ctgagcttca acagctgttt   180
gtaccagtga gtcagcatta aatccaccag aaaagaacag caccacccaa agactggggg   240
gcagctgggc ctgaagctgt agggtaaatc agaggcaggc ttctgagtga tgagagtcct   300
gagaca                                                              306

<210> SEQ ID NO 55
<211> LENGTH: 267
<212> TYPE: DNA
<213> ORGANISM: Homo sapiens

<400> SEQUENCE: 55
ttcagtttgg aaaaaatgtt ttattcctct ttgcacagag cagtttatga aggtggtttt     60
ctcctgactc catgcatctt ttacacaaag atgccccctt aaatatgccc agttatctgc   120
cccacctcag tgctggagaa ctggcagtta gtaagtgggg cagaatgctt aagtctcagg   180
aaggttttta aaggcatttt tgtggggagg aagttctggg tcaaggggaa agattagacc   240
caagagtgag tattccattc tccatct                                       267

<210> SEQ ID NO 56
<211> LENGTH: 537
<212> TYPE: DNA
<213> ORGANISM: Homo sapiens

<400> SEQUENCE: 56
caaattgaat attttattaa catggtagtt gcctttgtaa catgtgcaca cacactcgca     60
cactcagaat gatctgcctg ggggaaaaat actaaatatg cctaagggga aaatgaaaaa   120
taaaaaaatt cctgtaggtt ttcattattg taggcaatta tgtccacatc acttacaaag   180
ctattgccaa atctgtccaa ggaagcgag tttgaagtga gggctaggga caggaatctt    240
gggaaaaatt caacagtggc atagcagagc tctcaatatg agaaagctga cataatgtgg   300
acttttgctg tgaattacct ctttgcaaaa tatggggaga ggtttatcaa tgggcagaaa   360
ataagagaag gcggtgtgaa gtaggcttct gcagtcaatt ttcctcacag tattgtgcag   420
ggtcatcaag aaaatgctta gtctttctct ggaaccagtt tcagaacttt ccaattgca    480 atggtcttac cctcatctct taagggtgaa cgacccacct aagggaagtc tttaaag      537

<210> SEQ ID NO 57
<211> LENGTH: 327
<212> TYPE: DNA
<213> ORGANISM: Homo sapiens

<400> SEQUENCE: 57
tattactgca tatgttatat taaatttaca caatgatata taaaaacaca tactgtttat     60
attatatagt aatttaacat caacaggagt atcaacacaa gtactactca tgcacaaaac   120
```

```
atgcatatat tggtatacaa aaagcaattt tacacaatac tgtttaccaa aaattttttc    180
ttaaaaaaca gcccttccac ataggatcaa aggtccaatc tggactggat tgcactaata    240
tgttcaggtc aacgcttcgg tggcatagcg ctcagtgagc aattctggga ttggagtcat    300
gcccaagggc tacttcatta atagtga                                        327

<210> SEQ ID NO 58
<211> LENGTH: 566
<212> TYPE: DNA
<213> ORGANISM: Homo sapiens

<400> SEQUENCE: 58
tttttttttt tttgcaacgc aagggctctt tattgtcagc gagacgagca ggccaaacgg     60
gcactgaggc tccacggggc ccaggcctct ttccgtggaa gagaggcaag aggggtttca    120
ggattcagag gggtcctccg ctcacgcagc accatgcaaa tatagagcta aaactttct    180 gaatgtctct ggcttgaaac caactgggcc aacaggttcc acaaccactc tcttttgat    240 cactgggaga caccaaaaat gctgatagag agctggtct gagtccaccc aggccaaatt    300
cttgacaccc tcgttagagt ccaggtctgt ggtattcagt tgaaacacta ggaaatggaa    360
gacacgtcca tccgtgccca ggctctgcac caccacgggc tgctccaaga ccttggcatc    420
attcccatag aggagccggg cctgagcagg gcactgcaaa agcaaacagg atcatcttgg    480
cccgcagctg atctggttga aggcggtgtg gtcgtaaatt ggctttgtcc agtaagtaca    540
gggtatgggg atagggtaa ggatag                                          566

<210> SEQ ID NO 59
<211> LENGTH: 263
<212> TYPE: DNA
<213> ORGANISM: Homo sapiens

<400> SEQUENCE: 59
tctttattga cttattgtaa ttttttggca tacaaattac ttaagtatat ttacaattct     60
tacataatgt acattttaga agataatgta ctttgctcca tttacaatga caaactactg    120
taaaactaca ttcatgaatt agatacaaat cctctacata ctaataaaaa gtaaatggac    180
tgttggttat acattctta aaatatacct tttcacaggt agcaagaaat agtacatgta    240
ataagtcttt atgactggaa tga                                            263

<210> SEQ ID NO 60
<211> LENGTH: 416
<212> TYPE: DNA
<213> ORGANISM: Homo sapiens

<400> SEQUENCE: 60
tttttttttt tgagagataa ttctactta gttgttacac agggttgttg ggtagagaag     60
gaaggtgatg ccttggaaca gactttaaca actgtgaggc aggataaaaa acaagtcctg    120
aaagccatca cttttgacc atagtgagct cttctttgt aacggttcag gcttctaacc    180
ttatttcctc ctttggcaac tgaccagctc acgcacacat actagtgatg aaatccacat    240
aactccatat cttttcctct acatggccaa gagtttcagt gcaacaggaa agtgctgtca    300
cggatccatc gtgcaacaca tacagtgctg taaagcaaag gcctcgtctg cctgcaggca    360
gcaggaactg cacgcattac ccttctgtct gatgtacagc taactgcttt cgtgct        416

<210> SEQ ID NO 61
```

-continued

<211> LENGTH: 571
<212> TYPE: DNA
<213> ORGANISM: Homo sapiens

<400> SEQUENCE: 61

```
tttttttttt ttatatatata tataaattt tatttaaaat ttagatccct attcccacac      60
tctaataagc tgtataattt ttgtttagaa ttttctgca aacatactac aataagcttc     120
ttttatttgg agacaaaata cagtggcatt actggaagga atatcacaac attacatttt     180
tatcttaaag gacaagcaaa ctttcagggt tgataatggg ataagcatgt ttgagactgg     240
ttaccttctg gcagttcact gcatctggat atttctgaaa agtatagaga agctcttgga     300
ttttaaaaat atcttaaaat acttttagat gaaaaaattg taaagttct gcttataagt     360
ttacttttct ccacaattac aatatttaaa acaaagtttt gttgattgac gttttaagca     420
tttaaattta gaatgctaaa aacaattcta tcctacactt tcttcagggt aggggaataa     480
atacatcctt aacattgttt tctggatgta aacagaaatc cagcagaggt catcattatt     540
tagtacaacc agtaaataaa tgtaagagaa t                                    571
```

<210> SEQ ID NO 62
<211> LENGTH: 545
<212> TYPE: DNA
<213> ORGANISM: Homo sapiens

<400> SEQUENCE: 62

```
tttttttttt tttttttttt tttttttttt cattttcact tgcctcatct tttattaaga      60
ataaatact tttaagatgt aaacaaaggg aaccatgacc aaggattaag tcaacgtatc     120
tattttatt atgaaacatt aaattttgac acattgcctc atttgctttt ttaaaatcta     180
ttatctgact taaacctatt cagcaaaaat gccaataaat tatattaatc atactttggg     240
tcttttaaa actaggaaca taatatgttt tatgataaac aataatacta aatctgagtt     300
gtatgaactg ttaacttgaa atttgtttta gatgtttagc ttaaaacaaa aagaaaacca     360
atcacattaa tacactgttg caaaagtttc tccggaatgc cctccacatc actgtgtgtc     420
agcatccttc ggcttcttca ctgaggtatg gaatgcagcc atatgtaggt gtcaaggcac     480
tcattctaag ctgtcctatc ctgcacatct tagcaatcac attagatgga gggctgatga     540
tatgc                                                                 545
```

<210> SEQ ID NO 63
<211> LENGTH: 410
<212> TYPE: DNA
<213> ORGANISM: Homo sapiens

<400> SEQUENCE: 63

```
tttttttttt tttttttttt tttttttttt tatgtcataa ttttttattg atggcattta      60
tcccatgatt tagcatgtta attaaactgg ataaaacatg gctttaatat taaacttttc     120
cttattatcc aaagtcacca cagtccattt tagtaaatat aaaaatatat gcttaatact     180
ttgtacaata ctggttttg gtccaaacaa aactggatca gaaaagccaa taaattcaac     240
tttaagaatc cccaattttt tttttaaga tttccaaatg gatttaggca actttgaata     300
atgggattta cataataaaa tctgagacaa gactaaacaa acaacaaaaa aatctctaac     360
acaaaattca aatttcaagt tcacagattt atgttatgcc aaaaagtaca                410
```

<210> SEQ ID NO 64
<211> LENGTH: 600

<210> SEQ ID NO 64
<211> LENGTH: 600 (implied)
<212> TYPE: DNA
<213> ORGANISM: Homo sapiens

<400> SEQUENCE: 64

```
tttttttttt gacttttcaa cattttattc ttatatttgt acagctatat tttacaacgc     60
ggtaatgcag tttagacaca gccaaaccct gtctccggag tagttataac acaagcatga    120
cgcagaatgg gatgagacaa acattcccaa agagagttta gttagtaaca acttcaagtc    180
cctgtgtctg cctacacttc aaaaagggat ggtgcacgct cgcccatcat tgaaaacttc    240
cgtgaaaaaa ggcaccgtga ggacacgttg tacgggtata tacaaactga aaactagaac    300
aaaattacac attttttcctt ctgcagattt ttttggtctt tttgtgtttt ttaatacaca    360
ctttgtaaat tgtaaacctt cacttgcaaa aaaatacaaa tacactgagg catttaggc     420
aaatattttc ctacttgtac agatgcgata ctttaaatat tctcctaagt gggcgtgcgc    480
ttttaaggtc tcaggggcgg ggggatgatt tttgttttta tttttttttt gttttttttat   540
ttttgtggtg tggtgtgtgg gtccgtgtta tgtttgtgtt tgtttgtatt gctttcgccc    600
```

<210> SEQ ID NO 65
<211> LENGTH: 410
<212> TYPE: DNA
<213> ORGANISM: Homo sapiens

<400> SEQUENCE: 65

```
caggttacat tatgacttta ttgtgcctta gaactaggtc tagagaatca ggtccctcat     60
gctcccagtt ccatggtttc tgctttttttc taggccaggg caaaaggaga tcttggtaac   120
aagatgatgg gccccatgtt tgctgatgtt tatgagggct tgtgtggtaa tctggtgcct   180
gttcccctc tctgttcaca tgggtctcat ttactcccag aaatgccttg aagagaagaa    240
cgaaatcctt cagggaaaac tttcacagct ggaagaacac ttgtcccagc tgcaggataa    300
cccacccccag gagaagggcg aggtgctggg tgatgtcttg caggtaggaa tgcacagaaa   360
gacctgtgtg ctgctggttg gtgtggactc acattcagta catttgggtt              410
```

<210> SEQ ID NO 66
<211> LENGTH: 243
<212> TYPE: DNA
<213> ORGANISM: Homo sapiens

<400> SEQUENCE: 66

```
ttggcatatt attattagtt tattatttat accgtgctct gttccaaaaa ggatgtaagg     60
aggcagcatg gcttgagtac caccttactt gatgagttaa ggagttcaca tccatctaga   120
gacacttgtc tgagagactg tattagaaga ctacgggatg gtttagggga gggaagagtg   180
ctaagaaaag cagtggcatc ttgtccaacc tcatcttctc cccacgcgtc cgcccacgcg   240
tcc                                                                  243
```

<210> SEQ ID NO 67
<211> LENGTH: 323
<212> TYPE: DNA
<213> ORGANISM: Homo sapiens

<400> SEQUENCE: 67

```
tttttttttt tttttttttt tttttttttt ctggttggtt tgggttttat tctcaggaaa     60
tcagaaagcc tctggagggc tttaagcagg caggcaacac agtctgactt gagtttctaa   120
aaactctctc tggctgagat gtggagaata aacctcagtg ggtcgaggat ggaatcactc   180
```

```
tccaatgagt ggttaggaag ccactgctgg aattcaaatg agagctggtg cttggaatta    240 agggtggct atgacggtgg agaaaaggga ccagttctgg atgttctgga ggtaggtcca     300
gcaagacctg ggagctgcag aaa                                            323

<210> SEQ ID NO 68
<211> LENGTH: 291
<212> TYPE: DNA
<213> ORGANISM: Homo sapiens

<400> SEQUENCE: 68
agcttggcaa accttttta ttttgtgata aaaatgcttt catataaatt tcatcttaac      60
tacctttaga atgaaacgga aaagtaaaaa caaagtgtgc attttcctta ctacgtttag    120
tcaggaatat gcggtcattt tattggttac tgggtttctc atacaaacag atataatatc    180
acttttaaga gaaatgtaca caaggaagta accatagtac cacttattag tgggggcctc    240
tgggtacata aatgtgtcct cccaaatagt catcatacat tcaatggtat t             291

<210> SEQ ID NO 69
<211> LENGTH: 350
<212> TYPE: DNA
<213> ORGANISM: Homo sapiens

<400> SEQUENCE: 69
gtttttaaaa gtcagggttt tttgttgttg cttgtgtgtt ttataattaa catagtttat     60
ttttaatact ggcatccaag aatcctggtt tactcaggtg cagaaagact ctctaactaa    120
gcagccaaaa aaattttttgg tatgcaagtt ttatcatttt ttaatttgca tatgacttga    180
acgtgtcttc aagtataggt ctacataata acttttttaag aaaattataa agctcaatac    240
aataaatcta atacataaat gctgcttgta agtcaaatat ttaagagact ataaaaatgg    300
gtaattttgt gataaaattt agaatcattt gacaagagat caatgaattg                350

<210> SEQ ID NO 70
<211> LENGTH: 543
<212> TYPE: DNA
<213> ORGANISM: Homo sapiens

<400> SEQUENCE: 70
atagtgaaaa tatactttat tttttaatac aatagctgcc agcaatatac tggtgctgat     60
gttccaaaga taaagaaaaa tacatgcatt ctataataag ctttcatttg cctgttcaag    120
aaattataaa gaaaatactc caattctgtt caacattacg gcttgaggag ttgaaatttt    180
tccatgataa aaatatactt tgtgtggccc aaaccttgac tatttataaa ggatggagtt    240
tttaaaagcc cacatgtatc aataatggat gctcccctct ctttgaatta aatgcctaaa    300
ttcaaattaa tgcaagaaat tggtgaatca ttaaatgatg aaatttgtat caaaatgttc    360
atgaaaaaat acatttctat ttcctctaca tttttacttt gtagttattt tctaaatggg    420
tttaagggca cagaaataaa tgctatctac atgcaactct ggagagattc aaaacacaac    480
agaagttaac atgcctaaat cctagagttg atccatttag tgtaagaata aatgtcagaa    540
atc                                                                 543

<210> SEQ ID NO 71
<211> LENGTH: 435
<212> TYPE: DNA
<213> ORGANISM: Homo sapiens

<400> SEQUENCE: 71
```

```
tgtgataggg ttccactttt tctctcatac tggtgtgcag ttgctgattc atggctcact    60
gcatcttcag tctcccatgt taaaggaatc ctttcacctc agcctactga gtgtgcacca   120
ccaggtccag ctaattgttt ttttaacttt ttttttttt tttttttctt ggtagagaca   180
gggtcccctc tgttgcccag gatggtttgg aactcctggg ctcaagcaat cctcccactt   240
tggcttccca aagtgctgag attacaggca tgagcactat gcccaacctg agcaggatga   300
cttaaacctg atcaattcta ctccaaaaca gcaactatca ttaagtcagg ggtgtcaagg   360
aggactctgt gaaggcaaag actagactgg gatgtgtgcg agagtgggat aagaaggccc   420
atccctagca gactg                                                    435

<210> SEQ ID NO 72
<211> LENGTH: 528
<212> TYPE: DNA
<213> ORGANISM: Homo sapiens

<400> SEQUENCE: 72
aataccttct gttttaagtt tttcttttgt tttcatcttg gaaaaaagga aatttagaaa    60
taagacagga aaagaatggc ccagaaaattc agcacaaaga gaggtgtaca cattgacgcc   120
atctgtgggt cacatacgaa cgcctctggg acagagctct aaaacgagtc acgtgtcgta   180
gggagtgggc ctgtggcaag gcagtcctcg cagtgtgcag ggacgcaggc ccccttacca   240
tggaagcccc acccagaagg aagtgggtgc cccatgcagg ccgaggtgga tgagggggaca  300 gtggtgtgct cacagctgtc agctccccac tgaagcccca aaccagcaga tgtgggcagg   360
ggctcaagtg gtgtctgact acccaggtca cacgtgcctt aagcgtgaaa gctgtcagct   420
cccggcacgg gctctggtgg ggctgggaac accaggacac acatgggctg aagcttccag   480
agacagtgag acacggaagg gacagagagg tgccctccac acagtgtg                528

<210> SEQ ID NO 73
<211> LENGTH: 390
<212> TYPE: DNA
<213> ORGANISM: Homo sapiens

<400> SEQUENCE: 73
attcctttaa tgtttgcaga catagattag taataggacc tagattagta atgtttgcag    60
acatagacct tagtaatggt ctgcacatct gaccaaagtg acaggtttga ggattccagg   120
cagcttgaga aaaggcagga aaggccagaa ccagtgtcaa agggtcaggg ttgagcacag   180
gatacatgga agctcatctt ccccagcaag agggaactca acagctcaca tctacaggca   240
gcaatggggg ctgcttgtcc ctgagagtaa ggcataagcc cagtgttcag actcctgagg   300
ggatgaggga gtagtggctc aagcctgagc cccagaatga gtatgaggat aatcagggct   360
caggagaaca agcagagggc aggcggtgca                                    390

<210> SEQ ID NO 74
<211> LENGTH: 368
<212> TYPE: DNA
<213> ORGANISM: Homo sapiens
<220> FEATURE:
<221> NAME/KEY: misc_feature
<222> LOCATION: 19
<223> OTHER INFORMATION: n = A,T,C or G

<400> SEQUENCE: 74
ttaaagttcc tattttttang tttcttttatt ttttttcct cctgcggcct ctatgttttg    60
```

| | |
|---|---|
| ggcttgctga ggttctgtgt ctcagattct ggctgtcctg tgctctcttc ctagcacatt | 120 |
| ctggttttca gcctgggccc tatataagtc attgatctcc tgtacgtgga agaggtagaa | 180 |
| tgcacctgcc cacagcacca gccctacact gggggtccag agcagtatgg cagcttcccc | 240 |
| ggcccctcct ccagccgcca gacacacagc agtgccagga gaagcagccc caggccaatc | 300 |
| acatagctag cgaaggtggc ccaccagcga gcctgagcca tgcccagacc cagctccgtc | 360 |
| caggcctc | 368 |

<210> SEQ ID NO 75
<211> LENGTH: 467
<212> TYPE: DNA
<213> ORGANISM: Homo sapiens

<400> SEQUENCE: 75

| | |
|---|---|
| cctgtgggct atattttcct gtatgttttg tatttttttg ttggaaactg aacattccaa | 60 |
| gttttacact ggggaagctc tggaaactga attattttac tcctccagga ttgtttattt | 120 |
| ttaaaatttt gctggcttat gataaagggt atttcgagga aacagataaa gggatgtata | 180 |
| gggcgaggta tgggggaagg ggtgcagagc ttccatgccc tccgtaggtg caccactctc | 240 |
| caggaacctg caggtgttca gctatgtgga ggctccctga atgcggtcct cttgggtttt | 300 |
| tatggaagct tcataatgtc agcattcctt cccccaaggt atagggcaag actctctctg | 360 |
| gggaaggtct taggaccaca atcagaaaag tgggcagaca ttagagtcct gccttggggc | 420 |
| agatgaaagg agggcaggag aaggtcagag aaattgtttt tcttgag | 467 |

<210> SEQ ID NO 76
<211> LENGTH: 454
<212> TYPE: DNA
<213> ORGANISM: Homo sapiens

<400> SEQUENCE: 76

| | |
|---|---|
| gaatcatttt attagaacac attcaagaaa gtgacatacg gaaaaaagac agcagcaatt | 60 |
| ctcagtcatg caaatgcccg tgttaaagtt ctccattgga tttaaattca agtacaaaga | 120 |
| cagtcctttc ctgagccagg tgcaattcca gagaatgaca ctttgcattg agagcacgat | 180 |
| tccttcgaaa agttcagaac actgaacaag tcacatcctc acaataagat tgtgagatac | 240 |
| atagaagtgt aaacttttt aaggatccct ttaccctgcc ctcccccata acccagccag | 300 |
| ggaaataagc ccaacttcag gacctctcag aaatcaggtt taatctattg aaaataaagc | 360 |
| agtgggcctt taaaaaaagt tagaaaatga gtgtatatat gaaatggaat catcatctct | 420 |
| gcctcttgcc ttggtgtggg gtttccatga aact | 454 |

<210> SEQ ID NO 77
<211> LENGTH: 337
<212> TYPE: DNA
<213> ORGANISM: Homo sapiens

<400> SEQUENCE: 77

| | |
|---|---|
| tttgacagaa gaaacatttt taattgttct tgtcctgccc catcaccagg ggagtcccgg | 60 |
| cattgctcag gctcactgcg cttgctttcc cctgggatgt cgaggacact ttgacctcat | 120 |
| ctatgtcata gcccatgtgt ttctcagatg ccaccgccat aagatctagt gcccctggt | 180 |
| gccattggga taggcaggcc agagaggcat gggagctggg tgtgcaccag gccacagggc | 240 |
| tgtggggcat gcagccgatg gtgcagcttc aggtggatgt gctgggtgaa gcgactccgg | 300 |
| cagacactgc actggaaggg ccgggtccgg aggtgca | 337 |

<210> SEQ ID NO 78
<211> LENGTH: 390
<212> TYPE: DNA
<213> ORGANISM: Homo sapiens

<400> SEQUENCE: 78

```
taacagtctt aatattcatg tatttattct cagaacatac aaacttatct tctcagagaa      60
tagaaaacag agatttcact cagtgacaaa gatggacaca gccagttcac cgtgtccccc     120
catctactta gaaaatcccc tgggggaggg gatgcctaga gcatacagca ccccttggtg     180
gccggctgtg cacaggtcta aagactctca acttccttta ccatccaaaa aggaaaacag     240
ctgtccagat gacagtaaga ttccactgtc tgtaatcctc atggtgccag gtctcctggg     300
gcatctaggg caatgatgct actgcagttt atgcagttac acagtcaagt ctgtgccaaa     360
ggaggtccca tccggcggcc aggtttctgt                                      390
```

<210> SEQ ID NO 79
<211> LENGTH: 382
<212> TYPE: DNA
<213> ORGANISM: Homo sapiens

<400> SEQUENCE: 79

```
ggtagaggca aagtttcgct atgttgccca ggctggtgtc gaattccagg cctcaggtga      60
tcttcccacc ttggcctccc aaagtgctgg gattacaggc gtgaaccacc gtgccaaacc     120
tacattttta gatttattat ggtgttctga ttaacaataa agctaggtta ttagctgcct     180
gggaagagga ggaagtagat ttttacagtc acttttatag aaactgttaa attcacatga     240
gaaattccac cttacgagaa ttggctccct gacatgtctt tggactacct ctgtttctct     300
aagtttttgt ttttttctgg tgtctgaatt aagttggtga cagatttggg ggatatttga     360
gtagcacttt atctagagtt gc                                              382
```

<210> SEQ ID NO 80
<211> LENGTH: 563
<212> TYPE: DNA
<213> ORGANISM: Homo sapiens

<400> SEQUENCE: 80

```
catcttcagc attaagaagt gctgacacaa tatcattaac tgttttatag ttctctccag      60
ttgtcaggat tttactttga actgtttgtt tcaccaggtc tctattaaag cccatttcca     120
aggcagattt aaccacaggt gtattcatca tgacagcatc ttctgaagaa ctttctccag     180
gtccaaaatg aataattggt gggtcagcat tttcttctcc agtggtatct gaagttgaca     240
acagctgttc aagaagatga ggatatctac cttgaatctc atcaacaaac tcttggcctt     300
tcattcgtat caagaactca caccttggaa accacttggc atgttctacc catggatcat     360
ctccagattc ccaacacctc aagccaccat cacaacaaaa gcatttgaca tcatcattgc     420
gacccacata ataaaaacca gcacttgcaa gctgctcagg ctgaactgga acactagatg     480
gccagtacat aaatgttctc attcgagctg catgtgtctg catgctcaga tttgaaatgc     540
taaacctcag agtttctaga gaa                                             563
```

<210> SEQ ID NO 81
<211> LENGTH: 541
<212> TYPE: DNA
<213> ORGANISM: Homo sapiens -continued

<400> SEQUENCE: 81

| aaatgtcttt aattgctgaa tgcctctttg gctaatattt ggaagatcat tatttagtcc | 60 |
| tacaacagac gcattgttcc actttcccat cattttgttt gcaaaccgct aaaagtctta | 120 |
| tttcctcatc tctttgacac attaccaaag tggaccctat gctgtaatca cacaggataa | 180 |
| tgttggaaag tatgaatatc taaattattt tttaaggta ttattttttt ccttctgttt | 240 |
| tcaaatcatt tctgacagtt tctaaagaca tggtcacagc tgcctgaagc atgtcttctt | 300 |
| cactcatagc atcacctaga tcactcccaa gtgctcctga actggtggct ggccttttcac | 360 |
| atggatgtga actctgtcct gataggtccc cctgctgctg ctgctgctgc tgctgctgct | 420 |
| gctgctgctg ctgttgctgc ttttgctgct gtttttcaaa gtaggcttct cgtctcttcc | 480 |
| gaagctcttc tgaagtaaga tttgtacctg atgtctgtgt catatcttga gaaatgtttc | 540 |
| g | 541 |

<210> SEQ ID NO 82
<211> LENGTH: 463
<212> TYPE: DNA
<213> ORGANISM: Homo sapiens

<400> SEQUENCE: 82

| ggcatttcag taaatttttt taatgacttt aatgattctt atttaagaaa agcccttaa | 60 |
| ataaatgcta ccaaggcagt aatatttgac catatgaacc agaccaaata cccctttaatt | 120 |
| ttagtatatt aacctctgct gtaaatgctc ttttaacatt gccacatgta caaatttgtc | 180 |
| tagaacttca cgacacaaaa gtgtgcaaat atgagtctaa gattgtgctg aaatagggaa | 240 |
| aggctaacac tgatgtgcaa agtaaaaaag aaagataacc gcttctgcaa caggtaataa | 300 |
| aacaaggaaa aaacgagtta ggtcctgcat gtgtctccac ttcattgctt ccatgtttga | 360 |
| aaaagggagt ctgttctttt gctaggccat gaggctggaa tccacttggc atactgtgtt | 420 |
| gagaggtcta agttcagtgg tgctctcagc agcagccggg agg | 463 |

<210> SEQ ID NO 83
<211> LENGTH: 330
<212> TYPE: DNA
<213> ORGANISM: Homo sapiens

<400> SEQUENCE: 83

| ctaaatcaag tagtgctact gaaatccagt gcctaatgga gcagatggtg gaggtcttag | 60 |
| actctggaac atttatagtg atgcttctga atgcaaaaca ccaagagtgg atttcacagg | 120 |
| ctgtgaatct gatttgattt tgatgggagt aaagcttcca ttttcactgt acttgaacca | 180 |
| caaaagaaaa aaagcatgtg tgactgacac aagctagtta agaaaaagga acatgttaaa | 240 |
| tattagtccc ataaagggaa gcagtttaaa caagtgatta tttgtttgta tcatttaaca | 300 |
| tgattatgtt tgtatacaat accaccgttt | 330 |

<210> SEQ ID NO 84
<211> LENGTH: 497
<212> TYPE: DNA
<213> ORGANISM: Homo sapiens
<220> FEATURE:
<221> NAME/KEY: misc_feature
<222> LOCATION: 283
<223> OTHER INFORMATION: n = A,T,C or G

<400> SEQUENCE: 84

| ttcaggattt tatttaaaat ttattgtaat ggggtccgcg caacacgaag gggtggaggg | 60 |

```
tggggtacat gcaggggaca caggaacacg atgacatggc cagggcaaca acttcttctg    120
tcgtggggaa gagggatgaa aagacaagac cagggctgga gctggggtgg aagaggggag    180
ggggacactg gctgcattcc cccgccccca ggaagcacct ctaggccctg acccctcgc     240 tcaccctggc ccctaagact ccatctcttc tctgcctctg gcnctcctgg ctcttcctcc    300
tgctcccctt gactttttcc cctgacagat tctcaagtag gacgatgttc agggcctgac    360 gccaacccc cataccacct tatgaaggta caacctttgc cggccctgct ctgcccctc      420 ctcaaacctc agcgctttcc ctctttggga cagctctgat cccctcgttc taaacgtccc    480
ttcccctgga agaaaaa                                                   497

<210> SEQ ID NO 85
<211> LENGTH: 349
<212> TYPE: DNA
<213> ORGANISM: Homo sapiens

<400> SEQUENCE: 85
gtagagtcgc ggtctcactg tgttgcccag actcgtctca aaaaactcct gggctcaagc    60
aatcctcctg cctcagcctc ccaaagtgct gggagtctag gggtgagcca tcatgcccag    120
ccaagcctga ttttaaatca ggtctctgcc actagcagct gagagctcct cactgataaa    180 tccttttgcag ctggaagtat tcaatggtat ccagtatatt cccaatggct cattcctctt    240
ggacagagaa actcaagtta aatgaactct tttggctgtt tttctccctc ccctttgttt    300
cctccctctc ccttgcctgt gtctctctgt ccactctctc aggcccttc                349

<210> SEQ ID NO 86
<211> LENGTH: 391
<212> TYPE: DNA
<213> ORGANISM: Homo sapiens

<400> SEQUENCE: 86
cgctgagctg cttatttatt gaaataaaac gacggaaaag tctggccttg ctcctgtgca    60
agcttggagg cctgggtcgc cgctgtggac aagcgtctta gtgtcatgca gaccagaagg    120
cagctgctgt cccagggccg gggccacctc actgcctctg atggggactc ccagccccca    180
tggctccgct gtgccctggg caggggacgg gctgggggca ggggagggct ggagcccagg    240
aggcagcaca gcagccagaa agccgcacgc tgagcctgca cctatggttc cgggaggggc    300
ttgggccgtc acccaagtgt gatccctaag aacaggaggc ccagcaccct ggaaggaggc    360
gctggaaggc ggggcggtgg tggccccgtc a                                   391

<210> SEQ ID NO 87
<211> LENGTH: 549
<212> TYPE: DNA
<213> ORGANISM: Homo sapiens
<220> FEATURE:
<221> NAME/KEY: misc_feature
<222> LOCATION: 355
<223> OTHER INFORMATION: n = A,T,C or G

<400> SEQUENCE: 87
atcccgggga gaaagccacc cggcccaagt tgaagaagat gaagagccag acgggacagg    60
tgggtgagaa gcaatcgctg aagtgtgagg cagcagcggg taatcccag ccttcctacc     120 gttggttcaa ggatggcaag gagctcaacc gcagccgaga cattcgcatc aaatatggca    180
acggcagaaa gaactcacga ctacagttca acaaggtgaa ggtggaggac gctggggagt    240
```

```
atgtctgcga ggccgagaac atcctgggga aggacaccgt cggaggccgg ctttacgtca    300
acagcgtgac gaccaccctg tcatcctggt cggggcacgc ccggaagtgc aacgngacag    360
ccaagtccta ttgcgtcaat ggaggcgtct gctactacat cgagggcatc aaccagctct    420
cctgcaaggc acctgggctg cactgcttag aacttggtac ccagagccac cacttcccca    480
tctcagcctc ccctggttcc agccaaggtt cctggaacca acttcccaa cacccttgt     540 cagccctcg                                                             549
```

<210> SEQ ID NO 88
<211> LENGTH: 423
<212> TYPE: DNA
<213> ORGANISM: Homo sapiens

<400> SEQUENCE: 88

```
ttttttttcct tcaactccct ccaagttgtt tatttaataa taataaaaaa gaaatgcaca    60
cacataaacc tgaactcccc cccaccccac cctcccttac tcccagtaac tagctccaaa   120
atgaaaaaac ttcccttgtc ccacctgggg actaaattcc cacctccact gccataacac   180
tagagaaaca aaataaaaaa tatgcagcag ctcaccaccc accccacaac tgaacctcac   240
acaatcccct caaacaaaga agccaggact gggggttcac aggaatgaga ggagccctat   300
attctgaaaa gggatgagaa gagaggtgaa cacccccacc tcaaataagt gcttaacccc   360
cacacctgct ctttccttta ccaattgccc caagcctggg gaatcaggga aatttgaaac   420
agt                                                                  423
```

<210> SEQ ID NO 89
<211> LENGTH: 474
<212> TYPE: DNA
<213> ORGANISM: Homo sapiens
<220> FEATURE:
<221> NAME/KEY: misc_feature
<222> LOCATION: 80, 82
<223> OTHER INFORMATION: n = A,T,C or G

<400> SEQUENCE: 89

```
ttatacacac attttttaat tgaggaacca aaggagaaga ggaaaggaga gaaaatctta    60
aaactcagcc ctgggtgagn anggcgccac acagcactga gtctgccaca gagggcgatg   120
gggtgactgg ccaggaactc ctagagcagc ttctggtaac agtgggtgca aagcaatgaa   180
agacatactg gccactggaa acatgtttct tcttactttg ggggtggggc agaggcagga   240
aatacaaaag cccctgcctc gtgggcacag cgccaccaac actacactct gagtatctcc   300
aggcagttgt tgtagcagat ggcgatccag tcgggctgag ttgatgccca ctgcacattg   360
ttgatctctc cttcagctgt gtaggccagg atagggtcct caatggctcg ggcatttgc    420 tggatgtccc agatgagagc ctggtggtca tccgctgcag tgcagatgtg gcag          474
```

<210> SEQ ID NO 90
<211> LENGTH: 299
<212> TYPE: DNA
<213> ORGANISM: Homo sapiens

<400> SEQUENCE: 90

```
gagttaattt tatggaaatg gcgtgtgctt tgagaagccc agttttattc tgtcttatga    60
aactaatttc cactttgaaa attgttcttc tgttgtttat ggtataaatg aatggaatat   120
aatgatatcc tccttctagg aagcaaagca tttccttaaa atgtttgcta ggttaagcta   180
tgctgttcta ctgatgattg ttttaaatta ataatgagag ctataattta gataatatttt  240
```
ctttgttaga cattatagtg ttaaactgag agactagatt ctgcaagtac tatatgata      299

<210> SEQ ID NO 91
<211> LENGTH: 284
<212> TYPE: DNA
<213> ORGANISM: Homo sapiens

<400> SEQUENCE: 91
ccatgaacac agtagtgaga tattcctttt ccactcctac actatcttct gcttaaaacc      60
ctctgagggg tcccatctct ctcagggtga tgtctagact tcttctgagg ctagaccagg     120
tggtgcggcc ccatgtgcca cgcacccaag ccccctgcct cagtgtcccc catatcccac     180
accacagggg ggtggctgcg ttctgtatgg taggtggtgc tgaccactgg gcctctgcac     240
acgctgctct cagttccctg gccaactctc cttcaggcct cagc                     284

<210> SEQ ID NO 92
<211> LENGTH: 543
<212> TYPE: DNA
<213> ORGANISM: Homo sapiens

<400> SEQUENCE: 92
tttttacatt caagataaaa gatttattca caccacaaaa agataatcac aacaaaatat      60
acactaactt aaaaaacaaa agattatagt gacataaaat gttatattct cttttttaagt    120
gggtaaaagt attttgtttg cgtctacata aatttctatt catgagagaa taacaaatat     180
taaaatacag tgatagtttg catttcttct atagaatgaa catagacata accctgaagc     240
ttttagttta cagggagttt ccatgaagcc acaaactaaa ctaattatca aacacatcag     300
ttatttccag actcaaatag atacacattc aaccaataaa ctgagaaaga agcatttcat     360
gttctctttc attttgctat aaagcatttt ttcttttgac taaatgcaaa gtgagagatt     420
gtattttttc tccttttaat tgacctcaga agatgcacta tctaattcat gagaaatacg     480
aaatttcagg tgtttatctt cttccttact tttggggtct acaccagcat atcttcatgg     540
ctg                                                                   543

<210> SEQ ID NO 93
<211> LENGTH: 581
<212> TYPE: DNA
<213> ORGANISM: Homo sapiens

<400> SEQUENCE: 93
tctaaaaaag gaagatcaaa ttgccatctg tctggcttat tttgtgtgtg catgtatata      60
taggaacagc ttgaggggaa gggttatgtc atgcaatgaa gcaaaaacaa gacgacctcc     120
tctgacagag gagccttagt gttgtagaag agaagcaagg ctgaggtcac tggaaaggct     180
tagaatgaag ctgctcttgc ctgttcctcc tgagaaccca gagcagcagt ggtccagggc     240
acaaagcata atgatctctc atgaggattc ctatctgaac acatcagaag tcctatgaac     300
atagataggt ctgttttaga atataaatgg tagtgacttc ctgcgctcct gaggcgggc     360
aaaataatcc ataaacacat aatccttctg ggcaataatg tttctggact cgccagcaga     420
gggctctagg aacagaggtg ggggtagagt cggggagaaa aaaggttcta gagatggcat     480
gtcttcaggg gaactttgag aaatgtcctt tgttccagca ttcctaagtg acggcaccgg     540
tgagcctggt ctgaattgtc atcagtgtca ctgccgaggc c                        581

<210> SEQ ID NO 94

```
<211> LENGTH: 403
<212> TYPE: DNA
<213> ORGANISM: Homo sapiens

<400> SEQUENCE: 94
aaatatttaa tttgagaaaa aatgatgtta cctttttataa taaaagtgca actggaatag        60
ctttatgtta tatattaaat tcacataaac ctaggctttc caaaaaccat actaagaaat       120
tctgccaaac attatttaca taattttgag acttatataa acatggggtg ctcataaatt       180
tgtatcatac ctcacacctg aaaataagaa tttatattca gtactggaaa agattaaaat      240
gaccatcctt cctgtcttag ctttccaatc tgaagaagac aattgatgag tgattactga      300
agaataataa gtctaatttg tattgtattt tactttctca aagtgttttc acgtctgtta      360
tctaggagaa gtttggggtc tgttgaaaaa gagaagaggt ttg                        403

<210> SEQ ID NO 95
<211> LENGTH: 141
<212> TYPE: DNA
<213> ORGANISM: Homo sapiens

<400> SEQUENCE: 95
ttttgtagag ctgggatctc actatgttgc ccaaggtggt ctcaaactcc tggcctcaac       60
tgattctcag gcctcagctc cggaagtgct ggaatcacag gcaggagcac ggtaacccgg      120
gccccacagg ggtttggggt c                                                141

<210> SEQ ID NO 96
<211> LENGTH: 330
<212> TYPE: DNA
<213> ORGANISM: Homo sapiens

<400> SEQUENCE: 96
actctctgtt catgggagct gctgccccca cctccagtct gaccgcttcc atttatttaa      60
gaaaaatccg acacagtggt gggtagaacc cgagagaaaa atggctgtgg gatgggtag     120 gggcgacact ggctcccttc tgcatttgcc caccctgaag tccctcacag cattccctgg    180
tgccctctac tcccctcccg ggttccgtct tgtggggcat aggtggctgc ctgccctgtg    240
ctgcagaggg aagtcgcagt cagcagggtg acgggtggct aaggcgtagt agtgttgacc   300
ttgctgtggg ggacggggaa ggcaaggagg                                     330

<210> SEQ ID NO 97
<211> LENGTH: 396
<212> TYPE: DNA
<213> ORGANISM: Homo sapiens

<400> SEQUENCE: 97
tcatggaatc tggtgtttat tacactcggg ggagagagga ggtcactcgg tccagcggtg     60
gccgcagtgt ggggctgtgc acacgtagta aaggcgcatg gcgtcctcgg cccgcgcact   120
gtgtgactgg aagaacacag cctccttgtg gccgcacttt tggcacgggt ggtcctcggt   180
ccgcggcaac gtggggtcct gggacacgtc ggcgataatc tgggtcagtt cgtccacttc   240
gtgcgtgatc ttgttgacat agatgcagct gttgtcggcc tcctgctggt aatcacagtt   300
ccggcacgcg tagagcagaa tgcggttctc cttgtcttcc ttggggtaca gcatgttgtt   360
acattcctgg cagaagcgaa tacccacgaa gcccgg                              396

<210> SEQ ID NO 98
<211> LENGTH: 637
```

<212> TYPE: DNA
<213> ORGANISM: Homo sapiens
<220> FEATURE:
<221> NAME/KEY: misc_feature
<222> LOCATION: 374, 375, 391
<223> OTHER INFORMATION: n = A,T,C or G

<400> SEQUENCE: 98

```
cagcttgcat cataagttttt attcccgatg cgggacagat ctttccatcc ctcaaatgta    60
ttacatgtcg ccacggaagg gcttaggatg ctgctcccat ctccaggaaa gatgagaaaa   120
aggtacagac tgggagccag tccaggacca ttctgcagtt cctggctctc ttaccctccc   180
ttctcagcag aggaattatc tctcatccat tcagttaaaa agaaaaaaaa aaaaatcatt   240
aacaaaacaa aacacacctt aagtattggg caggggtgtt cttgtcctca gtaggacgtc   300
aagttctggg tcaccaatgg tgattttttt tgttttttgtt ttttgtcatt tttgtttgtt   360
attttttttt tttnnatttg ttagttatgg ntagcagttg tgtgtccacc tcatctgcag   420
gcagctgcac atagcggacg actgagcccc tgatgaagca gttcttgact gataacatgt   480
gagggtattt ctcagggtct gtgacactga tgtcggttag tttgatattg aggtactggt   540
ccacagagtg gagggttcca cagatgctca ggtcattctt gagttccacg actacatacc   600
ttgccacaag agacttgaaa aaggagtaga agagcat                            637
```

<210> SEQ ID NO 99
<211> LENGTH: 468
<212> TYPE: DNA
<213> ORGANISM: Homo sapiens
<220> FEATURE:
<221> NAME/KEY: misc_feature
<222> LOCATION: 399
<223> OTHER INFORMATION: n = A,T,C or G

<400> SEQUENCE: 99

```
aaagatgaga accagaatgc ttatatttta ttagtatcca agactgggga gagggatggg    60
gtgggagaga tcaagaattg gggagcagat gggaggcgct acctcactca ggagacacga   120
gttcttatcc aagttcaagg tgaaagaagt gagggcagga agagaaatct ccctgctagc   180
aacagcgact caggagaaaa ctctgggccc atagctagct ggaggcaggg tgacattgct   240
cccaccaatg ggccatcttc ttagctacac cttgtagct gtggtgccag gcagaagaac   300
cacctggaaa ctgagctaag gcaggttcct tcttccaaca gaagacacag ctgggcaggg   360
actgtgcaga ctcaacaggg ccaggccagc tagtggcang tcagtgttca tgtctctcac   420
cagtgcctgg agggtcccca gccaaggaaa gaactggtca gttcctgc                468
```

<210> SEQ ID NO 100
<211> LENGTH: 494
<212> TYPE: DNA
<213> ORGANISM: Homo sapiens

<400> SEQUENCE: 100

```
ttttttttaa aaataagttt gtttttattt ttcagggctc tagagactga gacaggtgaa    60
ggtactgaag atcagcgatg caaactcatt agggaggaga tggtctgaac tgagttggag   120
acatagtcta gtttaatttt tgacttcata gtaattgcag gaccagttct agacatccat   180
ttttcagctt cctctagttt ttgaacttgc aaacaaagga gaacttcttc tcacaagatt   240
catccttcca tttcttgaat cctgagcatg aagtcaggct tgcacagtag ccagcattag   300
cactgctcgg ggatccagtg tcccaggact tgtaggagac cagggaccca ctactccagt   360
```

```
gccagcggcg gttctttttt gggtcatgga ggccaatcca gacattgctg tcatcagtgc    420
tactctcctt aatcagtgag gccagaaggc accctccgcc tggtgagcac gacaccagtt    480
gcctaattca tgtt                                                      494
```

<210> SEQ ID NO 101
<211> LENGTH: 578
<212> TYPE: DNA
<213> ORGANISM: Homo sapiens

<400> SEQUENCE: 101

```
tttatgctag gcaaggaggg atgattattt attagcttct acagattaga caatggggtg     60
ggggtgggct caaggtgaga tgattttttg ggtccaagtc tactcaagac aggcatccca    120
gtcttcggtc tccaaatcca cctcctgtct gtcccccac actgctcctc aggccttgtg    180
gatccattga ctgtgatttc tgtggttcag ctccacatc aggcaggaag gcagctact    240 gggtctgaga tcccacattg cctccaaccc ttgcttccta gctggcctcc cagggcacca    300 cgagggctg ggccaggctg ctgtgctgca cgtggcagga gtagggggct gtgtcctgcg    360
ggggcactgc accaccaccc aggactggta agtgccattt ccattgtgaa gaacatctcc    420
cgtactcagg ctcctgcacc tcgcggcccg agtccagtgc acatcaattt ccctgggtag    480
aagtcgtagg ccagcacttc agtttcttct tttctcctgg gggctggtgg ctggtgacac    540
cacagaggga ggatctgccg gtccaggata ttttgct                             578
```

<210> SEQ ID NO 102
<211> LENGTH: 360
<212> TYPE: DNA
<213> ORGANISM: Homo sapiens

<400> SEQUENCE: 102

```
tttctgtagg atttttattg gtggcacctg ggccacatg gagggagtcc tcagcacagg      60
cgctggggtg tgggaaattt cagaggcccc tcctgggatg tcacccttca ggtcctcatg    120
agtcaatctt gagttctcc ttcactttct gaaatggctc tggaaaacca ctcccgcatc    180
ttggcagaaa gttcactctg tttgatgcgg ctgatgagtt cccgagcctt gtcctccagt    240
gtgtttccaa actccttcag cttatccaag gcactggaga cgtctggggt cccctgggct    300
ggggctgggc cttccaagac gatcgacaga accaccacca ggaccgggag cgacaggaag    360
```

<210> SEQ ID NO 103
<211> LENGTH: 444
<212> TYPE: DNA
<213> ORGANISM: Homo sapiens

<400> SEQUENCE: 103

```
cagtaggatc atagcccctg ggaaaatgcc ataaatttta tcttaatctc tagtgccaga     60
aactgcctgg gcgtaaacac tagcttgaac atctgaacta aagatagca tagtattgga    120 attagaaact taaattctat ttaggtgaaa ggatgtttcc tcaaattatg aacaaacttt    180
aatgtgtttg aaacggggta ttttatttt ttaaatgtat gctgttaata catactttgg    240
gaaaaggaac tatatgtact taaggctgtg cttcagtctt agcttttggc ttccagagaa    300
gggctaagaa aacttccaag ggttaaataa tgtgttcagg tttcagtcat aggatctcag    360
tcgcaactat ttaactctgt tgtttaacc caacagcagc cagatgaatg agttggggcc    420
ctattccaat aaaagattat tttg                                           444
```

<210> SEQ ID NO 104
<211> LENGTH: 474
<212> TYPE: DNA
<213> ORGANISM: Homo sapiens

<400> SEQUENCE: 104

| | | | | | | |
|---|---|---|---|---|---|---|
| gtctgtgact | cttggttagg | gcaaatttca | aatccattat | aatacataca | ttgcagcaac | 60 |
| actgagtttc | ttataatagg | tactatccaa | agctttcttt | tttttacatg | tatcacttaa | 120 |
| tcctcacaac | cacctgagga | ttaataccat | ttacctgttt | tacagataag | gaaaacaatc | 180 |
| attttcaat | tatgactatg | cccccaaaca | ctggtttgga | tggagccttc | actggtatag | 240 |
| agaatgacct | tcttcccttaa | gactagactc | tggctataat | aaaggatggt | ttaatcatcc | 300 |
| cctgaagcaa | tgcataagat | aatctgcaat | gtatcttcac | atactgtacc | ttatttgata | 360 |
| ggcaagagac | cctaaaagga | agctgagcat | ggattatcag | cttcatcaca | aatctgaaga | 420 |
| aactgacatt | tatgttatgt | tgccttaccc | aagttgggac | atcagagcag | caac | 474 |

<210> SEQ ID NO 105
<211> LENGTH: 555
<212> TYPE: DNA
<213> ORGANISM: Homo sapiens

<400> SEQUENCE: 105

| | | | | | | |
|---|---|---|---|---|---|---|
| taacttcctt | cctataaaca | ccttcagtca | agaaagcca | gaggagatgc | actgagactg | 60 |
| aaataacatc | tgttgactac | cagacttcac | tgaaatcggc | cgtctgctct | cctgagttgg | 120 |
| cattgttgct | aagataaagc | aaatgaaatt | gaagctgtac | tcttgatatt | tacaccatac | 180 |
| aagactaggc | tgttagggtt | gtcctgtgtg | gtctgcagcc | agaggttaca | ctgtaactac | 240 |
| catatgcagg | ccagacattc | attctgtgct | tagggactga | attacactat | aaggtgtaac | 300 |
| actggaccga | agacttttcc | attaaaaaaa | agtgctgctt | ttctaattct | ttatattttc | 360 |
| caatactcat | tcctaaaatg | tcatgaaatg | gtacctaaaa | gcaaagtact | ggaagataat | 420 |
| cacatcatgt | cacatttggt | cttaatataa | gacatcagaa | cacatcttta | acagtgagtc | 480 |
| ctcccttagt | ttgattcttg | gcatccttca | gaagaatcaa | agcctgcctc | agtttaaaaa | 540 |
| tcagatgaaa | tgtga | | | | | 555 |

<210> SEQ ID NO 106
<211> LENGTH: 342
<212> TYPE: DNA
<213> ORGANISM: Homo sapiens

<400> SEQUENCE: 106

| | | | | | | |
|---|---|---|---|---|---|---|
| ttttaatggg | caaaagaaca | agttgcagtc | aatggctgca | gaggggtgtc | tggggtccaa | 60 |
| tgtgggctgc | actttgtggg | tactgaggaa | atggaagat | gctgcttcta | ggtcagctgg | 120 |
| tgggttggag | gttgggggct | gtaattagca | gcagccttag | aactgggatg | cctttcaatc | 180 |
| cctcctggcc | cctttatctct | gtggggcagt | cacaggacat | catctgtttt | attcaaagtt | 240 |
| gggacttgca | gcaggagacc | ctgtcctgca | tggagtaggg | gtcctctgtt | gacaaacttc | 300 |
| ttggtttcca | gctcttcccc | atctgcagca | ggcctctgga | ta | | 342 |

<210> SEQ ID NO 107
<211> LENGTH: 375
<212> TYPE: DNA
<213> ORGANISM: Homo sapiens

<400> SEQUENCE: 107

```
ttttgttgta gaaatatatt tattaacata agcagttcac aatttactgt aagaaaaaaa      60
gcaagctaca aaacagtgat tccatgttta tattaaaata aacatacaca aattaaaaat     120
ttccttagat atccatttaa tctctgggat cataagcaat gtttaggtat ttttgctca     180 tttattgcct aggttttaca caatgagcat atatgttaat tgtgtaattt aaaattatgg     240
aattaagtgc aagagttcct aaccacctt tacaaaactg ttatgagaaa atacattcta     300
gattcaaaca aaactaagc aatatatccc ttattctaac agctctaaaa tctgttcttc      360
tcattatact cccac                                                      375

<210> SEQ ID NO 108
<211> LENGTH: 416
<212> TYPE: DNA
<213> ORGANISM: Homo sapiens

<400> SEQUENCE: 108
ggtattataa agacatttat ttaatctatg aaaataatgt acaataaata ctttccccctt     60 ttcctattat taaagaattt taataaataa tctacagtct aaaacataaa aaagaggaaa    120
ataggtccct ctagttattt ttaagaaagt cccctagag tttaattat cctgagattt      180 cattggaagg agtctaccaa acggaatttt tctgtgtgaa ttttaaaaga taaccgagtg     240
cccaatattt tagaagaaga agaaaggaag tggattaaac gctaattcag taatacctga    300
attttagcaa aacacataag tctatgcgac tgagggtggg agaggctcga ttttttccagt    360 agacggccaa ggagcgcggg ggtcgaaagg accgggagca ggaaacaggt taggga        416

<210> SEQ ID NO 109
<211> LENGTH: 472
<212> TYPE: DNA
<213> ORGANISM: Homo sapiens

<400> SEQUENCE: 109
ttggtttaaa caaagaggga tttattttat ttacaagaat tctggagaag gatggcggct     60
ggtattggct tggtgaaata atgatagggt caatgactct gtgattctct tggcctttt     120 gtcatggtag caaagtggct gctgtggctc caggcatcac accctcaatc aaggtaggaa    180
gaagaggccc agggaggtgt tagccatgcc tgtgtctttt attggaaaag ctttcccaga    240
agcccaggta gacttcctct tcaattcat tggccacacc tgatcacata gccatcctaa    300
gctgcaaagg agactggaac agtgaaaatc tggatttaca gcctccacag ttggagtggc    360
tggagataca gagttgggac gaccccctgaa aagtgaacca aggtcgtctg cacggctgcc    420
ctggagggcg tggtgcttga ggtccttct acctctgggg cttcatggaa tg            472

<210> SEQ ID NO 110
<211> LENGTH: 372
<212> TYPE: DNA
<213> ORGANISM: Homo sapiens

<400> SEQUENCE: 110
atctgtcagt aaattacatg tatcctggct gtttatttca aaaatgcttc agtatgtatt     60
tcctaaaata gggatattct cctttgtaat cacagcaggg tagatactgc tctttagttg    120
tcatgtctct tagccttctt taatgtggaa cacgtccaca ccctttcttt atcttctgtc     180
ttttaaacat cttttctgtt gtccaatttt taacaacaaa gatgttaaaa atcagaaaac    240
tcagaaaagc acatggtgta ttaaaattcc acctaggaat aactgccatt aaagttttgg     300
tgtctccctt tctgtctctt cagatgcaac ttactagtct agacaaagca ggtttctcag    360
```

```
tgaataaaac at                                                             372
```

<210> SEQ ID NO 111
<211> LENGTH: 357
<212> TYPE: DNA
<213> ORGANISM: Homo sapiens

<400> SEQUENCE: 111

```
gaacgtttgc aaaggtttat taactgtcag tgactgatac aggggaatcg gatgagggga         60
gtacatgctg aacaggaaac agagtgaggg gggcttgacc aggacgcatg gcaatgggaa        120
aagcagatgg gagatgctta tactggtact tggtgtgtgt gtgtgcgtgt gtgtgtgtgt        180
gtgtgtgtaa atgcagagga aaaagtctga aattaaacac tcagaactgc cctcagtagt        240
cacatctggg gagagatgag gatagtgctg ttctatggag agaatacctg acaatacttg        300
ttttctgacg taggtgcatg gatacacaaa ccgaaatatg cattcagtat gtcttgc          357
```

<210> SEQ ID NO 112
<211> LENGTH: 391
<212> TYPE: DNA
<213> ORGANISM: Homo sapiens

<400> SEQUENCE: 112

```
ctaatcctgc gaatatgggt agtgcttcgt tccatggacg ttacgcccg ggagtctctc          60 agtatcttgg tagtggctgg gtccggtggg cataccactg agatcctgag gctgcttggg        120
agcttgtcca atgcctactc acctagacat tatgtcattg ctgacactga tgaaatgagt        180
gccaataaaa taaattcttt tgaactagat cgagctgata gagaccctag taacatgtat        240
accaaatact acattcaccg aattccaaga agccgggagg ttcagcagtc ctggccctcc        300
accgttttca ccaccttgca ctccatgtgg ctctcctttc ccctaattca cagggtgaag        360
ccagatttgg tgttgtgtaa cggaccagga a                                      391
```

<210> SEQ ID NO 113
<211> LENGTH: 369
<212> TYPE: DNA
<213> ORGANISM: Homo sapiens

<400> SEQUENCE: 113

```
tttttttttt tttttcact tcttcaacaa gtatttattg aacgccaact atggaccagg          60
ccctgtgctc aatgctgggt acagagtgga gactgaacca ggcatggcac ctggcctcat        120
gagcttacac tcgagtggga ggcacagtca accaacaagt aaattacaca atggatatg        180 cagtggcaaa ttctccatga agggaaagaa cagaggcctt gtgatagagg aactccacaa        240
gtaaagtagt cgaggaaggc ctcttggacg aggcaacgtt gaagccaagg cctgagggtc        300
tgcagaactc agccatgcac agggtagggg aagagcattc ttggcaaagg gaacagcata        360
tgcaaagtg                                                              369
```

<210> SEQ ID NO 114
<211> LENGTH: 462
<212> TYPE: DNA
<213> ORGANISM: Homo sapiens

<400> SEQUENCE: 114

```
tttttttctac accaacctgc ttccacttta ttcttgttta cacattctcc tgctcccaga         60
tttggagtca gaacactatg tgagctcaac agtcctgctc agagccatgt tccatatccc        120
```

```
accagtttcc cttttcccaa cccccaccca cccccactca gtaagtcccc ttgcccaggt    180
tttgctcttg gagggaagaa agcagaagaa aagatgcagg actgagatga ttgtcctgac    240
cccgctaccc tcaagtgtaa gagaagtcct ggatggaatg ggtggtgatt ccaatgaggg    300 atggaacct  ctttccaagg cacaaggggc catcttctca acatgctgct ttttcagatt    360
tgggtagtat gttggccagg agctgggggc tgcagccctc cagctgactg aggaggagag    420
gaatgtgagg acgctgatgc gggtccacgg tcatcatcga gt                     462
```

<210> SEQ ID NO 115
<211> LENGTH: 483
<212> TYPE: DNA
<213> ORGANISM: Homo sapiens

<400> SEQUENCE: 115

```
cattagtcat tggaccacag ccattcagga actacccct  gccccacaaa gaaatgaaca     60
gttgtaggga gacccagcag cacctttcct ccacacacct tcattttgat gttcgggttt    120
ttgtgttaag ttaatctgta cattctgttt gccattgtta cttgtactat acatctgtat    180
atagtgtacg gcaaaagagt attaatccac tatctctagt gcttgacttt aaatcagtac    240
agtacctgta cctgcacggt cacccgctcc gtgtgtcgcc ctatattgag ggctcaagct    300
ttcccttgtt ttttgaaagg ggtttatgta taaatatatt ttatgccttt ttattacaag    360
tcttgtactc aatgactttt gtcatgacat tttgttctac ttatactgta aattatgcat    420
tatacagagt tcatttaagg aaaattactt ggtacaataa ttattgtaat taagagatgt    480
agc                                                                  483
```

<210> SEQ ID NO 116
<211> LENGTH: 426
<212> TYPE: DNA
<213> ORGANISM: Homo sapiens

<400> SEQUENCE: 116

```
tttggcattg taattatgca gaagaaaatc tttattctta gggatcatgc tgggaactga     60
gggatgaagt atatgcatat tccaaatggt tcaggaaaaa tcctgtctat aaagcataca    120
tgataaaatg tcaacaataa gacaaactag aggaaggata tacaggtgct tactgtcaaa    180
tttcaaattt tctgtaggtt tgagagattc aagatgaaaa cttgggggaa aattatatat    240
tctgataata aaacagatgg gaaacaaaga gggcccataa gacagtcact gattaagatg    300 cttttctacat ggatgggcct catccttttg tccaaaggga ctacctggca tctgttccat    360
gttagtgaca gtgactcacc ccaggttgct gcacagatat gagaggcttt agatcatagc    420
acagtc                                                               426
```

<210> SEQ ID NO 117
<211> LENGTH: 443
<212> TYPE: DNA
<213> ORGANISM: Homo sapiens

<400> SEQUENCE: 117

```
gggtagatag ctagaagtga tagtgctagg tcatatggta aatatatctt caacatttta     60
agatactgcc aaactggttt ccaacgtgac tgcatgtccc atcaacaatg cgtgagtgtt    120
ttagtttttc cacgtcatta tttcacttcc cccaggtgtt actgtccttt tttattatag    180
cattctagtg ggtaagaagt ggtgtctcac tgtagttttg atttgcatgt ccctgctgac    240
tgatgatgct gaccatcttt tcatgtattt tattgtctat tcctacacct ttttgatgaa    300
```

```
atggttattc aaatattttg cctattttaa aaatggggta attatcattt tgttgcgtag    360
ttgtaagtgt atttcatatt ctggatatga gtcctgtatt aaatatatga tttgaatttt    420
taaaaaaaaa aaaaaaacct cgt                                            443
```

<210> SEQ ID NO 118
<211> LENGTH: 475
<212> TYPE: DNA
<213> ORGANISM: Homo sapiens

<400> SEQUENCE: 118

```
cataattatc ttgtttaatc tcttttttt tttcacactt gactttcagg tcaacttttg     60
aatctcattg tacagatgag aaaattgagg ctcagaagga agtgacttgt gcaaggtcat    120
acagcaaacc agatgctaac gcagaataag aggcgcccta ggatcctgcc tggtgccctg    180
cagtgcccga ccatctgctt agtaaaacct actgcttgct gaagttcctg cacatccaac    240
cagcacacct aacgcaaagt atgacttctt tgtggaagtt aatgattaaa acctagtctg    300
atctaaagca tcttatccat ggttactaat taagccaatt tcagtgacag aaagcatttc    360
aaacagaaga gtgttctctt aagctaaatc tataggcctc aaattatggt ggcataaact    420
gtacaattat gatattttga gtacacttaa aatattttat aatacaatac attaa         475
```

<210> SEQ ID NO 119
<211> LENGTH: 430
<212> TYPE: DNA
<213> ORGANISM: Homo sapiens

<400> SEQUENCE: 119

```
tttttccaga ttctatgctt tattcatttt gcattaagat gaccaaagaa ataaaaccta     60
aataaaataa acataaaatc attttttccct atttaaatac tgataatttc tattaaccct    120 attttttaatt tagggagttt tatattcata ttgtcaagat atccagtgca caagtttctg    180
cagaatcact aatttttatta taaagcttcc tctccccaca ccttagggga caatgtattt    240
tcactctgac ttgtttaaaa gacacaagga ggttggcata ttttaaagtt aacacatttt    300
ttcattataa aaacaggctt aggttaatgg tcactctcta gcatttggtt accgactgac    360
tgattatcat atgtgtgcgt gtgtgtgtgt gtgtgtgtgt gtgtttgtgt gtatatatat    420
atatatatac                                                           430
```

<210> SEQ ID NO 120
<211> LENGTH: 296
<212> TYPE: DNA
<213> ORGANISM: Homo sapiens

<400> SEQUENCE: 120

```
tttaattgcg tttattttt ccatcctta gatacacaca gaatgtaaaa gggagcatgg      60
ggctggggga cgggaagcaa gaagcagcag ccaggcgctt tggtaacacg cgagtgttag    120
gttttttggc tccctaaggc cccttttgtgt ccgctgctgg gaaggcggag tgtcaggagg   180
tcacgcaacc acagggttag tccagaccca cagtccacaa atacagcatt aaagatggct    240
tacaaaactg caagattta caaagacctt acaatagcaa catagaaaag gggagg         296
```

<210> SEQ ID NO 121
<211> LENGTH: 403
<212> TYPE: DNA
<213> ORGANISM: Homo sapiens

<400> SEQUENCE: 121

```
tttttttttt tttttttttt tttttttttt ttttcacaat tcttaagtct tgttaagaaa      60
gtaaaaaacg tttgggtata ttttgatcca tgggtggcat tttcaaatgt gcaaaaacaa     120
agtcttggaa gagattcctt gtcactagaa agttcgccct tccttttgct gtcagttgta     180
cgtaagagaa attcgtccac attaaggaat ccaaaaaggg taaactaaag ggatttaaaa     240
agagtacatt acaaagaata agaagccctg taacatctat ctgagaatac tagataaatc     300
tgtgagtaga tgtggcacct ggagctactc actacattac taaaaacaga aacaagaaat     360
ctataatggc aggatcacaa catttgcgcg caaatagcta acc                       403
```

<210> SEQ ID NO 122
<211> LENGTH: 282
<212> TYPE: DNA
<213> ORGANISM: Homo sapiens

<400> SEQUENCE: 122

```
tttttttttt ttctaaaact acctttattg tggttggctc gacataagat gccgccatca      60
gcagaattat aaaactgtac aggaggcaca aaataggct gtttaactta gataatgacc      120
ctcatgtctt caagctttaa aaatgcacat aaaagttgta caatctggca gtttataaaa     180
tataaagcta aaagaggat tttgggttcc acaagaaga ctgtatcaca caattaacac       240
gtactaatta aacaattaac catccacaca gaagacataa tg                        282
```

<210> SEQ ID NO 123
<211> LENGTH: 502
<212> TYPE: DNA
<213> ORGANISM: Homo sapiens

<400> SEQUENCE: 123

```
tttttcatct tgagccagat gtgtataata tatacagctt aattatgttg gctaacaaaa      60
tcttatttta aggtgacaag agagaatttg aaaatagcat tcattttcat ggtcatataa     120
ttctgtactt ggaatacatg ccattatctc tgcattttac aaataagaaa tcatcacttt     180
gatggattgt gggtttggct tataatcatg ctgctcaatt aattgttca gaaataaaac      240
ctgcttggct cctttttgttg atacactgta ggatccaact ccgaggtcaa ccagttatgg    300
gaagggttgg cctgttgaag ctgtagctct ttgaacttct gtccttctca tccctcacct     360
ctccatcttt ggattccagt tcagctctg tcctgcaggt ggcttccata ttgccagctt      420
ctgcattgat ttccactcct tttggggcct ccatcactag gaccgggtt ggggactcca      480
accttagttc tttgaagggg tc                                               502
```

<210> SEQ ID NO 124
<211> LENGTH: 404
<212> TYPE: DNA
<213> ORGANISM: Homo sapiens

<400> SEQUENCE: 124

```
cattgatttt ttttaatag agaaagatgt ggaaataaat taaagatca tttccctgta        60
aaggtggttt cagcacagtc ttcagcaaac ctgtgcccta aaattcctct cagttacttc     120
aattctcttc ttacagaatt gcccaagatt tcttcccact gatcttctcc tggaggtctt     180
tctgtttctg ttgctcctcc tcttcatcca gatgggacct gcaagtcatt gacagcttct     240
tgatcagcct ttccatctcc cggcactgct cctccctctg ctctgtctcc aactgcttga     300
agcggcgcca gtcattgatc acacctttg ggcctgtgtt aactgagatg ccttcgcctg      360
```
ccagctcagc ctctgcaggc acagaactgc tggctggggc acat            404

<210> SEQ ID NO 125
<211> LENGTH: 170
<212> TYPE: DNA
<213> ORGANISM: Homo sapiens

<400> SEQUENCE: 125 tttttttgagt ttggcatgtt aattttatc agcgacttct ggggcctagc accattcccg    60
gaagaaggga gttgtcgggc agggtcctta atggggttg caattcttgt cttggttggg   120
aaagagccta gctgggaaca ggggtcgttt gtgtagtaac tgtattaagc              170

<210> SEQ ID NO 126
<211> LENGTH: 443
<212> TYPE: DNA
<213> ORGANISM: Homo sapiens

<400> SEQUENCE: 126
tcggttaaga tttttattat tccagagaaa aattagaatg tatcggtaaa agaaatagga    60
atgcatattt caactcactg tcacaaacag gtgttttatt atcccaaatg acagtgttgc   120
ctgagatgat gcatgtggca gacgaggaac caatgagtcg gtatccttta ggacaagaat   180
atttaatttg ggatccgaac tggatgtctt tgatcacatg tgccatgcca ttcacaggat   240
ctggaggatt acgacatgat ttacgttttgc acttgtcctt agcacttgtc cagactgagt   300
tttttaggca gatgatagaa aacggtcttc cggaataacc agggcggcat tcatagttca   360
gatatgtccc aatgggaaac tcagagtcat cagttaggtt ggtaggcctg gcaaatggaa   420
gcccattccg gacattgcat tga                                           443

<210> SEQ ID NO 127
<211> LENGTH: 469
<212> TYPE: DNA
<213> ORGANISM: Homo sapiens
<220> FEATURE:
<221> NAME/KEY: misc_feature
<222> LOCATION: 391, 423
<223> OTHER INFORMATION: n = A,T,C or G

<400> SEQUENCE: 127 atccagggggc gcaggcagcg gcttcacctg cttcacaggc ggcggctcct gccacttgtc    60
gaatttgcgc tcgatctcat ccttcagttc gtagcccacc ttcccttctg tgctctcgtg   120
gaaactgtcc acacgggctg ccagtgtgca cttggcggcc accagccggg ccgctttccg   180
ccgcagatcc tggagcaacg gaaaacgggg gtggaatcgg tggcagggac tgcacgatgt   240
cactgtggta gatgtagccg gtgtggggca gcactgaggg agacgagaag cccgacagcg   300
tcttgcgctg ggccccgagc agcatgatgt tgcaggcggg catcttggag aggttggtca   360
ggccgccggc cacacccatg atcttggcgg ncgtggatgc cccgataatg atggacaggt   420
tgngtgcgat gaatgacatc ccggactcca catactcgta gatgcgcct               469

<210> SEQ ID NO 128
<211> LENGTH: 336
<212> TYPE: DNA
<213> ORGANISM: Homo sapiens

<400> SEQUENCE: 128
cactgttaaa aatacattta tcattaaaat atattacaca tggagacagg atgcatcata    60

| | |
|---|---|
| tacagtttgg aagacttgct ggcccagaaa atcccacttg tttcaccgaa cactcatttt | 120 |
| ttcagggatt ttacatttta ttttagaga cggggtctcc ctctctcacc cgggctggcg | 180 |
| tacagtgatg tggtcatagg tcactgcagc ctcaaactcc tgtgctcaag tgagccaccc | 240 |
| acgtcagcct cccaagtaac tgggaccaca ggcacgcatc accacgccca gccaattttt | 300 |
| taaaaatgtt tttgtagaga gggggtctcc ccgtgt | 336 |

<210> SEQ ID NO 129
<211> LENGTH: 369
<212> TYPE: DNA
<213> ORGANISM: Homo sapiens

<400> SEQUENCE: 129

| | |
|---|---|
| tttttagatg tttaaaata catttatttc atgtcgtttg tccccagggt ttggagtttg | 60 |
| atgttctgga ccaagcgtag gctctgagca aatgctacca gggctggaga atcagttctg | 120 |
| ccacttccta gttaagtgat cttagacaaa tttccgcgcc ttagttttct tctcagagaa | 180 |
| atgagactag tcctatccac actatggaca agtggtagga ggcgaaggag ctcacgtttg | 240 |
| taaagagcct tgcacggtgc ctgagacaaa ttcagtgctt agcaaatgtt agctcacctc | 300 |
| tcccttttct tcctgtatcc gattttgtat acaaatgtgt agaaaattta catgaaataa | 360 |
| tgcagaaag | 369 |

<210> SEQ ID NO 130
<211> LENGTH: 437
<212> TYPE: DNA
<213> ORGANISM: Homo sapiens

<400> SEQUENCE: 130

| | |
|---|---|
| gcggccgcgc cggctccagg gccatttagc ccccaggagg agaatcgagc aatcttttg | 60 |
| gaagtccaga agaagctact ccttccagca ggcctaatag gatggcatct aatatttttg | 120 |
| gaccaacaga agaaccctcag aacatacccca agaggacaaa tccccagggg ggtaaaggaa | 180 |
| gtggtatctt tgacgaatca accccgtgc agactcgaca gcacctgaac ccacctggag | 240 |
| ggaagaccag cgacattttt gggtctccgg tcactgccac ttcacgcttg gcacacccaa | 300 |
| acaaacccaa ggatcatgtt ttcttatgtg aaggagaaga accaaaatcg gatcttaaag | 360 |
| ctgcaaggag catcccggct ggagcagagc caggtgagaa aggcagcgcc agaaaagcag | 420 |
| gccccgccaa ggagcag | 437 |

<210> SEQ ID NO 131
<211> LENGTH: 460
<212> TYPE: DNA
<213> ORGANISM: Homo sapiens

<400> SEQUENCE: 131

| | |
|---|---|
| ttttttttt ttttttgca agggctgcgc ggcattttat tttctgaacc ccccacagca | 60 |
| ggggcggcca gtcctgctgc aggcagagtt tcagtcttcg gagtttgacc ttctggccca | 120 |
| aggtcatcac agccacaggc ggaggctctg gggaaaggtc cagttcctgg gatgctggcc | 180 |
| cctaatgatg ggcccatctt tccagtgccg cccttccctc ccgcctggca caggagttct | 240 |
| ggagccacgg tcctgagtct acagaacagc ccggtcagcc tcgtcccgcg gtgcaagcga | 300 |
| ggcctggcct ccctccctgc ctgtcctggg cccggccaca tcactccctg cgtttcttct | 360 |
| tcttctccgg ctcctggaca ttggccggct ttgctcgggc actggtcagg ggccgaggtg | 420 |
| tcctccttct ttggcgagcc ccttttggc cacgggccct | 460 |

<210> SEQ ID NO 132
<211> LENGTH: 403
<212> TYPE: DNA
<213> ORGANISM: Homo sapiens
<220> FEATURE:
<221> NAME/KEY: misc_feature
<222> LOCATION: 331, 332, 333, 361
<223> OTHER INFORMATION: n = A,T,C or G

<400> SEQUENCE: 132
tgagagagta cccccttat tgtgcacccc tggtgcaggc acttgacacc caggcttccc    60
tgggccctc gaggcaagag gtcaccccct ttccagggca gagccacacc cccaactcag   120
ctctgggcag ggtcccgtct ccgaggttac tggatcagct ccatcctggg acaaggaaag   180
aggactgacc cacagaccag agcacctcag atctccggct gcagggccac aacggtgggc   240
agaggtagag agcgggccag ggtgcagggc agaagtgtcc gagtccaagt ccacatccag   300
gtgtgctgcc tgccctagcg tcctcaaggg nnngcacacc acccaccccac cccagcctt   360
nagaatgctg ctgtgggtcc cacatccaag gagaaagccc ctg                    403

<210> SEQ ID NO 133
<211> LENGTH: 383
<212> TYPE: DNA
<213> ORGANISM: Homo sapiens
<220> FEATURE:
<221> NAME/KEY: misc_feature
<222> LOCATION: 247, 373
<223> OTHER INFORMATION: n = A,T,C or G

<400> SEQUENCE: 133
tttttttttt ttacatgaag tagaacttt atttggaaag ttgaatttca tgtataatga    60
aaatatttc aaaccataca tagtcataag cataatacaa acaccaccta caatacaaac   120
acgttttata aagttctact atgaatatta atccaagcca aaagaaaaag gtaatcacgt   180
gaacctgttc tacatacctt tcatctcttt tgatgacgta atcgaacaat ttaaggtaca   240
aaacaangaa agctttgggc tgaaccctac ttatttcact ataggaacac taggatatat   300
actaccacag gtaaccaaac ccaatcccat tataattaat ttaacattgt tacatggatc   360
ctatcttaat ggnatgtaaa cat                                          383

<210> SEQ ID NO 134
<211> LENGTH: 513
<212> TYPE: DNA
<213> ORGANISM: Homo sapiens
<220> FEATURE:
<221> NAME/KEY: misc_feature
<222> LOCATION: 24, 56, 451, 466, 495
<223> OTHER INFORMATION: n = A,T,C or G

<400> SEQUENCE: 134
tttttacttg aaattaaatt tggnctctaa agttggtgta gcagcagttg atcagnactg    60
aaaaacggtt tttagtctcg gaaaaagact gattttgctt tttataaat attattagat   120
ttattaattt ttcgtgctca atgtgtaaat tgtattataa ttcattgtga tttatttcac   180
ttttaatttg ctggtgtttt aataaatggg ggtgttactg aatctttctt cccacttcca   240
tttcttttga ccacccctta accctcaact gtgacggtag tagtattatc atttatacca   300
aagttttgca tagtccctgt tgactttgta atgttaacgg agtcataaaa gcactaggca   360
agagaaagat agaaatttgc ttttaatctt tttgcctttt attttgcaca ttatgcaaaa   420

```
gggaaaacat taaaggacac tttttttaag ngagtgaaac atgggnaagg catccagtgc    480
tttatgcaca ttgtnagcta atcaggccat tat                                513

<210> SEQ ID NO 135
<211> LENGTH: 489
<212> TYPE: DNA
<213> ORGANISM: Homo sapiens
<220> FEATURE:
<221> NAME/KEY: misc_feature
<222> LOCATION: 434, 448, 458
<223> OTHER INFORMATION: n = A,T,C or G

<400> SEQUENCE: 135
tttttttttt tttaacctct tgctcatttt tattccagaa cctaggaaga actagtacac     60
tgaaggcatt tgatgtttgt tatgaaaagg aaacaacaaa aaaatcaagt tcaggctggg    120
catggtgcct catacccgta atcccaagca ctttgggagg ctgaggcagg agggatgctt    180
gagcccaggg agtttgagat cagcctaggc cacatattca gaccccattg ctaccaaaaa    240 attttttaaat taaaaaatgg ctaggcatgg tgggcataca actgtaattc aagctacttg    300
aggaggctga ggtggggagg atcacttgaa cccgggggt tgagggccac agcgagctgt    360
gattcacaac actacactcc accctggggc gacgaagcaa gatttcgttt tcaaaaaaca    420 attttttgttt caantcccat cttcaccnta aaaacctngc tacattcccc agggaaaaac    480
caattttca                                                            489

<210> SEQ ID NO 136
<211> LENGTH: 310
<212> TYPE: DNA
<213> ORGANISM: Homo sapiens
<220> FEATURE:
<221> NAME/KEY: misc_feature
<222> LOCATION: 134, 176, 276
<223> OTHER INFORMATION: n = A,T,C or G

<400> SEQUENCE: 136 ttttttttttg ggcagatgag aaacagaatt atcatcagag tcttgctaca aacagggaaa     60
aacacaaacc aagatgacac acggacatgg tagattaaac attcctcccc accttcagga    120
tacatttaca ttgnaataaa tactgcaatc tcagcagcgg caaacaagga ggaatntagg    180
aaatgcccac ctcctcccct ctgtcttatc tgtgtgctct cttccttggg tagcaccgat    240
ctccccaggg tgctgggtga gaaacaggac aggggngaag aggtccgtgc atgctcactt    300
gccctttgc                                                            310

<210> SEQ ID NO 137
<211> LENGTH: 311
<212> TYPE: DNA
<213> ORGANISM: Homo sapiens
<220> FEATURE:
<221> NAME/KEY: misc_feature
<222> LOCATION: 151, 267
<223> OTHER INFORMATION: n = A,T,C or G

<400> SEQUENCE: 137
tttttttttc caaaaaatcg ctttcctctt taataccaac ccaccccagg agacagctgt     60 ccaccccag ttgggggaagg ggccacactg cccccacctc cttgttccag ggaacactca    120
tttccctaca ggtgatcttg gggagagact nttcccaggc aaccctggga gtctggctca    180
gcgcacaaat ctgtccaggg cagatggccg ggccccgtg ggcttggcct tcgcctcctt    240
atgatgctgc tgctgaaggc tctgcgnacc ttgtcctggg ggaccggaga cgggaggaca    300
```

-continued

```
caggcacaga g                                                          311

<210> SEQ ID NO 138
<211> LENGTH: 337
<212> TYPE: DNA
<213> ORGANISM: Homo sapiens
<220> FEATURE:
<221> NAME/KEY: misc_feature
<222> LOCATION: 54, 217, 278
<223> OTHER INFORMATION: n = A,T,C or G

<400> SEQUENCE: 138
tttttttttt ttgcttattc tctgctctct gacgtgaaga tattgttgga attntcagaa      60
agtcctgcag atatccctgt gggtaaaaca ataagaaaa agggaaagca ttactagcaa     120
agaaagtcaa gctgttggaa aaactgacag tgatgtctga aatgtcttac agaagagtat    180
gttgttggaa tgaccactgt atatatgacc tgaaaantac agtaggataa attattaaag    240
ttctaggttg aaagtgatgg gcagaagtta gtaaaaanta gaaaggcac tgcatgaagg     300 ctgaaaatga ccttgattag gatcttgaaa ggggtag                             337

<210> SEQ ID NO 139
<211> LENGTH: 461
<212> TYPE: DNA
<213> ORGANISM: Homo sapiens
<220> FEATURE:
<221> NAME/KEY: misc_feature
<222> LOCATION: 46, 285, 357, 366, 400, 414, 426, 457
<223> OTHER INFORMATION: n = A,T,C or G

<400> SEQUENCE: 139
tttttttttt ttttttttac atgtaagaag tggttttatt ccaggngtgt gtttcataaa     60
gacgaggtcc tcaaggacag ctagtggcac atgctttggt caagaagagg aaaagcaaaa    120
acagaacagg gctgcgttgc cacaaaggac cggctgataa gtgcagagcc tgatctgacc    180
acagcaaagg acagagagac cctcttgaag gccctctggt cagcagtcct cttacattca    240
acaggcgcac ccggctcccc agccccaaag gtccatgccc gagtntggcc cgggcttcta    300
gtccatcctc tggggagag gccttttgccc tggggcccag ttttgtccta aggttttnggc    360 agggangggtt tcccagatgg aacagggga ttttttagggn tgcacttggg tttncggaag    420
gaaacntcac gacagaggga caggcaaagc ttggccntgg g                        461

<210> SEQ ID NO 140
<211> LENGTH: 457
<212> TYPE: DNA
<213> ORGANISM: Homo sapiens
<220> FEATURE:
<221> NAME/KEY: misc_feature
<222> LOCATION: 10, 237, 280, 357, 382, 410, 420, 456
<223> OTHER INFORMATION: n = A,T,C or G

<400> SEQUENCE: 140
gaagtcatan tatgataaac attttattac actaaaaaag tcatctgtta actgactgaa     60 ctgcagggg accacatgtg aggttacttc agaaaaatgg catcagataa catatataga    120
tttctggcat tataaaatgg ctagattctc ccctaccttc cctcattaaa tattaatcag    180
tggcttaggt cagttctagt gggaacactt aattgctgac ttcacataaa accaggntta    240
gcctaatgtg ccaatggtat gagtccattc ctgggccatn ttcccaacag ccagaccgct    300
gtggcttgga caccggaggc aacatctggg gggcctcagt tccactcctc tgtggtnagc    360
```

```
ttgctttccc aataactggc tntggagtca catcaacaat ggtggcattn catctggggn      420
ccacatgagc cctttggggg tgctgcatcc ctactng                               457
```

```
<210> SEQ ID NO 141
<211> LENGTH: 531
<212> TYPE: DNA
<213> ORGANISM: Homo sapiens
<220> FEATURE:
<221> NAME/KEY: misc_feature
<222> LOCATION: 23, 66, 94, 482, 524
<223> OTHER INFORMATION: n = A,T,C or G

<400> SEQUENCE: 141
```

```
tttttttta tgcacactaa ggnatatttt attgtggcat taattagatg aaagttagta        60
atatgncatt gaccaaaaca tttgattgac aagnaccata aaggttaact gagagttttc      120
tttaatataa ttgttgtaca gacaaggatt cctgctgtat agagtatata gaaggatgac      180
atactctagg aattaggaac aatatatatt caatacaata acaaaactat atagtactttt     240 aagaactctt tcacatatat gaacactctt acttaggaac ttcagctgtt taaagtaagc      300
aatatgcaaa cctataaagt acacaccaaa aaaatctaac ctacaaaaca cccaaagcaa      360
atgttagcat atctctatta tcaagaatat cttctcacca tcgtttcttt caaaaatatg      420
tgaaaaagtt ctttctttcc ttatgagtgg caatttttaa aggcccctct tctgaaatta      480
gntatgttcc aatccactat cactcttaag ggaaaatgga accnctctgg g               531
```

```
<210> SEQ ID NO 142
<211> LENGTH: 423
<212> TYPE: DNA
<213> ORGANISM: Homo sapiens
<220> FEATURE:
<221> NAME/KEY: misc_feature
<222> LOCATION: 394, 416
<223> OTHER INFORMATION: n = A,T,C or G

<400> SEQUENCE: 142
```

```
tttttttttt tctataaatc tctaatgtta tttaggtttt ttaaggtttt ggaagtaaca       60
gagggataca tacagcaaga tccacttaca tagttttaaa acatgcaaaa caagattata      120
tatcgtccat atgtaattat atctgtggta aaatataaag atatgcattt tggggacata      180
gtcaccagat tattagtagc tcaaggaaag gcaggaggaa gagtgctctg ggtgggggga      240
ggttcacagg gtgcttggac tgtacctatg atttcttcaa ataaaaattt caagcaagta      300
taaaatatgg gatataggaa tgtaaaggat ttgggcaaag ctgggctggg tgggtatcca      360
atgttcctta tcaccatctc tgtacttctc tgantgcttt aaataggtca caatcnttgt      420
aag                                                                    423
```

```
<210> SEQ ID NO 143
<211> LENGTH: 267
<212> TYPE: DNA
<213> ORGANISM: Homo sapiens
<220> FEATURE:
<221> NAME/KEY: misc_feature
<222> LOCATION: 11, 94, 192, 196, 220, 226, 245
<223> OTHER INFORMATION: n = A,T,C or G

<400> SEQUENCE: 143
```

```
acactcaaag ngccattcat ttatattcat tccatagtcc agaaggttac ttattagagt       60
aagcctttgc accacaatct ttcaaaaaaa tgancatgta agaaaagca gttttcattg       120 tgctaattat tgcaggcctt catgcacgta aacctcaaca aaatgtgtgc caacaatata     180
```

```
caaatttcca tntaancaaa gtcattgatc actaacaaan tataancatg gtttctttta      240
tattnggatt ttttttaaaa aaaagct                                          267
```

<210> SEQ ID NO 144
<211> LENGTH: 311
<212> TYPE: DNA
<213> ORGANISM: Homo sapiens
<220> FEATURE:
<221> NAME/KEY: misc_feature
<222> LOCATION: 27, 42, 124, 141, 149, 240, 280
<223> OTHER INFORMATION: n = A,T,C or G

<400> SEQUENCE: 144

```
atacaacatc tttatttggc attgganatc ctgacatttg tncattacag ttccttaaaa       60
aacaaaccaa aaaatcagaa caaattaatc aaaaataaag atccaatggc tctatttaca      120
tatngcaaag acagcccagg natcttccnt gcacacacac accccgcccc gatacagtta      180
aggggttaat aagctttggg gagcgcagga ggcaggttcc acagttcatc aatcccaagn      240
cacccccatg aggtaggggt gcctcacaca gccagacggn tatcaagagt atgattggta      300 gcttttcct c                                                            311
```

<210> SEQ ID NO 145
<211> LENGTH: 414
<212> TYPE: DNA
<213> ORGANISM: Homo sapiens
<220> FEATURE:
<221> NAME/KEY: misc_feature
<222> LOCATION: 314, 390
<223> OTHER INFORMATION: n = A,T,C or G

<400> SEQUENCE: 145

```
aatgatatca gaaccttta aatgatctag tatctgtgat gttagcgccc ttgggattca        60
gaaagtggtg tgcatagtaa aagctttcat tgtaactcac cctgcctaga tatgcagaaa      120
gcaaattcag tgataagatc tttcctggga gaccaatcag cagcctcagg ctctgttggg      180
gtctatcaca atgatgttat ctaaatttag ggcaaggaac cctttcccca tcttttagag      240
ggcagtgagt gttctaatca cttcaagata ggtatctgat aaaagtcttg gggccaactt      300
tttcatactt aggnagggca caactaaaat ggatatactt aaaatggtat caaggagggg      360
ttaggtgtac actctactag gtgtaaggtn tatttcatta caaaatggct ttgg             414
```

<210> SEQ ID NO 146
<211> LENGTH: 417
<212> TYPE: DNA
<213> ORGANISM: Homo sapiens
<220> FEATURE:
<221> NAME/KEY: misc_feature
<222> LOCATION: 52, 152, 222, 346, 368, 374, 383, 401, 415
<223> OTHER INFORMATION: n = A,T,C or G

<400> SEQUENCE: 146

```
aaattttatt aattttattc aggaaagaca ttgactgtta agtttttttt tnggggggg        60 ggtgatgtct tgctattttt taaaaattat atccagacta tgaatttaat atttactacg      120
gctaatcaac tgctcatgtc agtaatcaaa gncagaaatg agccttatac gtacatctac      180
attaaacaca cacaccccc tttaaggggt gctcagtgta gnttctaatg tcagtctgtc      240
cattcaaccc agggcccaag gttgcatcac atcaccaagt tggaatcatg aagacagccc      300
agatttgact gacatgggca cagcagggct ccctcaccac agcccntggc accagttaac      360
```
tatttctngc tcgngccgaa ttnttgggcc tcgagggcaa ntttccctat tagtnag    417

<210> SEQ ID NO 147
<211> LENGTH: 316
<212> TYPE: DNA
<213> ORGANISM: Homo sapiens
<220> FEATURE:
<221> NAME/KEY: misc_feature
<222> LOCATION: 232
<223> OTHER INFORMATION: n = A,T,C or G

<400> SEQUENCE: 147
agcttcagcc tttattaaac aaaggaggag gtagaaaaca gataagggaa cagttaggga    60
tcccttcttt ccccctataca tacacagaca tacaaacaca cgcacccgag tgaatgacag   120
ggaccatcag gcgacagatt gaagggcaga gggaggcagc accctccgag agttggcccg   180
gacccaaggg tgggctgaga cctgggccag gggcagccgt tccgaggggt tntgcctgag   240
cagtttggag atgaggtcct gggctcccgt ggggcacaga agcggggaac tttaggtcca   300
ccttggacga tggcgg                                                   316

<210> SEQ ID NO 148
<211> LENGTH: 275
<212> TYPE: DNA
<213> ORGANISM: Homo sapiens
<220> FEATURE:
<221> NAME/KEY: misc_feature
<222> LOCATION: 60, 61, 249, 254, 270
<223> OTHER INFORMATION: n = A,T,C or G

<400> SEQUENCE: 148
cacccaggct acagtgcagt agagcaatca caactcactg cagcctcaac ctccctgggn    60
ncatgcaatc ctcccacctc agcctcgcaa gtagctcgga ccatggccac acgccaccac   120
acccggccaa ctttcgtact tcttgcagag agagggattt gccatgttgc ccaggccggt   180
cttgaatttc cgggctcgag tgatccactc acctcagcct cccaaagtac tgtgattaca   240
ggcatgagnc actntgccca gccaataaan tcttt                              275

<210> SEQ ID NO 149
<211> LENGTH: 379
<212> TYPE: DNA
<213> ORGANISM: Homo sapiens
<220> FEATURE:
<221> NAME/KEY: misc_feature
<222> LOCATION: 47, 53, 202, 301, 350, 367, 374
<223> OTHER INFORMATION: n = A,T,C or G

<400> SEQUENCE: 149
gttctcttca attataaaaa taaaagaatc ttatttcact gcctggncct ggnaacatgt    60
actgcaatat acattgtgac aactttttac ctgtcatgtt tttagctttt acctgtgaat   120
ttcttatcat tgttcttatg tgaaggatag atagttgcta caataataat aggatgatgt   180
gtatggtttt tgagcctaaa angtgtagtt ttatctgttg tacctataca agcaggagaa   240
atataacttg ttaataattt tagggtatgg gcaggctgcc atcctaaata tggaagtggg   300
nctttggtat ttgccacttt aatgtgttgg aaatcatagc tttcagtgan ccggggtta    360 gggcagnctc tttnatggc                                                379

<210> SEQ ID NO 150
<211> LENGTH: 337
<212> TYPE: DNA
<213> ORGANISM: Homo sapiens

```
<220> FEATURE:
<221> NAME/KEY: misc_feature
<222> LOCATION: 127, 168, 188, 197, 211, 257, 299, 309, 325, 331, 336
<223> OTHER INFORMATION: n = A,T,C or G

<400> SEQUENCE: 150
aacatcattt aacaagaaaa aacattcaac caaattaaaa agaactaggt tggattaatt      60
tacaataaaa taatcaactt aaaatatcgg cccttccatt tagggccaag gaggcaatag     120
ttcctgntta aacagcagaa ttgcacaatt atttttacct atatttgntg gcacaaaaaa    180
ataaaagnct tacaacntcc acggacatcc nccctccct ccagagcaga gttcatacaa     240
ttccatctta ggtcagnact cagggctttt aaaaatcatc ttacgttttg aaatataana    300
caacgactnc gggtaacaag gaatnctttt naaaana                              337

<210> SEQ ID NO 151
<211> LENGTH: 418
<212> TYPE: DNA
<213> ORGANISM: Homo sapiens
<220> FEATURE:
<221> NAME/KEY: misc_feature
<222> LOCATION: 4, 266, 326, 337, 409
<223> OTHER INFORMATION: n = A,T,C or G

<400> SEQUENCE: 151
gcgnccgccg cccccgcctg ggccgcgctc ccctctccc gctccctccc tccctgctcc      60
aactcctcct ccttctccat gcctctgttc ctcctgctct tacttgtcct gctcctgctg    120
ctcgaggacg ctggagccca gcaaggtgat ggatgtggac acactgtact aggccctgag    180
agtggaaccc ttacatccat aaactaccca cagacctatc ccaacagcac tgtttgtgaa    240
tgggagatcc gtgtaaagat tgggangag gagttcgcat caaatttggt gactttgaca    300
tttgaagatt ctgattcttg tcactntaat tacttgnaga atttataatg ggaattggga    360
gtcagcggaa cttgaaaata aggcaaaata cttggtaggt ctgggggtnt ggcaaaat     418

<210> SEQ ID NO 152
<211> LENGTH: 621
<212> TYPE: DNA
<213> ORGANISM: Homo sapiens
<220> FEATURE:
<221> NAME/KEY: misc_feature
<222> LOCATION: 520, 564
<223> OTHER INFORMATION: n = A,T,C or G

<400> SEQUENCE: 152
gaacagacta aatttgtttt aacaatccca tttacaattc aaattccttt aaacaactta     60
atagcattta tacatttaaa aaaatgattc ttttaagcag cattgcaaat gcttgacccc    120
attagcataa accttcccaa gtgcttaact ctcataaaca taataaatta acatatggt    180 gactttccaa gttctctgaa acatttcagt acttttgcag acttagtaac attttaaaat   240
acctttcaac tgaaactcat aagtctaaaa gtctgttaag cattttaaat tagaatctta   300
aggccagtgt cacatattgt aatatgccaa ttatgtttaa atacttcaaa cagcaaatac   360
tacagtttat ctcaatgaat ataataacca ttcctgctgg gcgcagtggc tcatgccttt   420
aatcccagtc attaaggagg ctgaggtggg aagattgctt gaaaccagga gattgcctca   480
ggcctgggca acatggtgag acctcctatc tcaaaaatcn aataaaaaat tagctgggca   540
ggtggctcat cctgtagccc agcntctcag gaggctgagg tgggaggata gcctcgccta   600
ggagacggag ctgcagtgag c                                              621
```

<210> SEQ ID NO 153
<211> LENGTH: 454
<212> TYPE: DNA
<213> ORGANISM: Homo sapiens
<220> FEATURE:
<221> NAME/KEY: misc_feature
<222> LOCATION: 171, 179, 182, 186, 189, 190, 191, 193, 195, 197, 200
<223> OTHER INFORMATION: n = A,T,C or G

<400> SEQUENCE: 153

```
aataaagaca agtgttcaga tttatttgga aattcacagt ttctaatggc actacagctc      60
cgtagttaca tattgaaaat tctcttccca caacacacag atcacataat ttctcactgt     120
atctctgctc tcatctggac ctcttttcaa ggggcttcta taaaatcagg ncctcttgnt     180
cngganagnn nantngngcn gacaggaaag aaatttaaat cttctaaaac acgctgttaa     240
cctaaagcag caacttaaac aaacaaaaaa ggcgttaaat aagtcacatt acaaacaata     300
cccaagaaag gtattaggca agtttaaaaa cagttatcac tactaaaagt gctcaataag     360
ttataactta aacatcacaa caataaatgg tcaattctct ccctttcaaa aagaaacatg     420
ttccactttc attcactact gtacaatcat acta                                454
```

<210> SEQ ID NO 154
<211> LENGTH: 396
<212> TYPE: DNA
<213> ORGANISM: Homo sapiens
<220> FEATURE:
<221> NAME/KEY: misc_feature
<222> LOCATION: 333
<223> OTHER INFORMATION: n = A,T,C or G

<400> SEQUENCE: 154

```
catggtacaa aaatgtttat ttaaattaaa tatttgcaac aaattaatat tgacaactgt      60
tccaaagtat gagttgttct ttcaaaaaaa cgaaacagtt tagcttaatg tctgtgatac     120
tgttttatga gattattcat acatgctctg gactgcgcat cagtcaatca tatcatcaac     180
aatttactat ttattaccaa atggcatata aagtaatagc ataagagta atcatacctt      240
ataagtgatt ttacaatagg acatcttaga aggacaaaaa ggatttatca acaatacaaa     300
acataagata aaaataatag gagattatat aancatatt tcatacagga aataatatgg     360
ctaaaatcca aaaaccaac caactggtct ttcagc                               396
```

<210> SEQ ID NO 155
<211> LENGTH: 468
<212> TYPE: DNA
<213> ORGANISM: Homo sapiens

<400> SEQUENCE: 155

```
gatacgaaaa ttgagagatt tatgttgttt tcatagtagc aaaaagaaaa aaaaaacctc      60
cagagaggac cccaaaatga taacttggtg caaatacaaa gtgaagagtt atttgtggct     120
tgagataagt tggaaattgc tcctttgatt aggagatggt tgctcagtt tgcaacggaa     180
tgttattgtc tttcttcttt tcctttcttt tctttagtat ctgttgagag agtttatgaa     240
gaaaccagcc aacatcctgg agatcctcag gccacctcaa atactgctgt ttctgtacaa     300
agcctctgat ggattgatgt ttcatcaact ggtactggga caaggaccca accaccacca     360
tgatgagagc actgttaagg tcagataagc acctgccctg gcataactg aaggcttcaa     420
ggcaccagcc atctctaagg aagtgtctgc tcacaagaca aacgatct                 468
```

```
<210> SEQ ID NO 156
<211> LENGTH: 455
<212> TYPE: DNA
<213> ORGANISM: Homo sapiens
<220> FEATURE:
<221> NAME/KEY: misc_feature
<222> LOCATION: 379, 388, 417, 422, 447
<223> OTHER INFORMATION: n = A,T,C or G

<400> SEQUENCE: 156
tttttttttt ttgcaagtcc agagcagttt taatgggggt ggaggctgtc atatcatcta    60
ggcctgacat gtagtcttgt gctccatcaa gcaattctcc ctgaaatcct tgtttccgct   120
ggtactttct cctttgctgc atatcagcaa agtagctgc tccagttggg taggtgtagg    180
ccatatgtgg taggaagctc atctgatcca gtcctgggta tggtcgtagc ccaggaatac   240
tggtctggac tggtggcatg aaagtagcag ggggaaatgc gctttgaggt ggaagagctg   300
tgtataaagg tttgggcact aaatgggttc atgctgaaca ctgggttagt gcttttgttg   360
tccagattat ttgaatttna aaattccntc ctggataaaa gtcaagttca gagggcncat   420
cngaggtttt cagatgagga agaaacnccg ttatg                              455

<210> SEQ ID NO 157
<211> LENGTH: 394
<212> TYPE: DNA
<213> ORGANISM: Homo sapiens
<220> FEATURE:
<221> NAME/KEY: misc_feature
<222> LOCATION: 303, 382
<223> OTHER INFORMATION: n = A,T,C or G

<400> SEQUENCE: 157
ctaggcataa cataaattgt tataattgat cagaatatct tgaatatatt tttacagata    60
actagtggtt tctactagca gattaaaacc aagagaaaat taaaagtaag ttcacattta   120
aaaaaaatta taagcaataa atacagcact acagccacca ctaattctat atacattgga   180
ttacatttaa acaaacactg cattccagaa tgaatatttt atgaataaat gcattggaaa   240
ttaactttag gaaataaaat gacaaattac gaatttagaa aattaaaata tgactttcac   300
aangtaatca cagtaaaatg cagatctaca ttttaaaagc tagaaatttc cccaaattta   360 ttttttttgga cagccaagaa gnttgcctta aaaa                              394

<210> SEQ ID NO 158
<211> LENGTH: 451
<212> TYPE: DNA
<213> ORGANISM: Homo sapiens
<220> FEATURE:
<221> NAME/KEY: misc_feature
<222> LOCATION: 429
<223> OTHER INFORMATION: n = A,T,C or G

<400> SEQUENCE: 158
gtgtctcaaa tagctttatt gttcctttgt ggatctgtcg gcatctgtat ggctaccttc    60
agggtgcaga ggttttaagc tgactctgaa atggaggaca ttcagttact attgcaagaa   120
gttcaagaaa aatttaaaaa gctccaactt ctgtcccca gggtcggtaa ggtttattgt    180
ttgttccact gctggtctgc tgaggactgg acgtggctga tactgacaag gcgggctga    240 tggctgtggc gcggcactgc tgctgctgcg tttgggggaa gcatgggaa tgccccgcg    300 aaggacagag ggaagctgtg tgcagccgcg gtggctgttg cggctgcggc gttgacggt    360 ggcagagagg gacaagagag aggtggagag aagtggcacg caggggggcga cgctgcccgt   420
```
ggaatggcna ttcggagggc tgaatccgca t 451

<210> SEQ ID NO 159
<211> LENGTH: 424
<212> TYPE: DNA
<213> ORGANISM: Homo sapiens

<400> SEQUENCE: 159
tttgcacctt gaaacaattt aataatgtat tacattatag tagcatcaca gcagcagtca 60
ataatgccac tttagacaaa atcagtatt tccattatgc attctgtgta taagaattca 120
taaatcggta aaagtcattc taagaaaact tggcaaatac agctttggac tggaattggc 180
atttctttgt ctacttttcc ttcccctaga ttctttgttt taaactacag tattcatatt 240
ttaaaatgtt ttaaattatt ttaagacgtt aatatagcag ttcatttttt gaatagttat 300
ttgaaagtga ctgtaagata aagttttaga gaatctatta atgggatagg gttgatttac 360
attttcacat ttttcctaaa aatcagcttt ggttttagaa ctgattggtt tttcattttg 420
ggaa 424

<210> SEQ ID NO 160
<211> LENGTH: 502
<212> TYPE: DNA
<213> ORGANISM: Homo sapiens
<220> FEATURE:
<221> NAME/KEY: misc_feature
<222> LOCATION: 119, 296, 341
<223> OTHER INFORMATION: n = A,T,C or G

<400> SEQUENCE: 160
tgaaattttc aggtactctt tctacatgct gacgtgcatt gacatggatt ggaaggtgct 60
cacatggctt cgttacactc tgtggattcc cttatatcca ctgggatgtt tggcggaant 120
gtctcagtga ttcagtccat tccaatattc aatgagaccg gacgattcag tttcacattg 180
ccatatccag tgaaaatcaa agttagattt tcctttttc ttcagattta tcttataatg 240 atattttag gtttatacat aaattttcgt caccttttata aacagcgcag acggcntaat 300
ggacaaaaaa agaaaaagat ccactaaaaa gaaagattta ngatggcttc ttgccagttt 360
gagcctaatc tgattcttac agttttttacc ttcttgaaac caatgtaaaa gttttttaa 420 tgttaaatga ttaaattctc agtgaggcta tcttccttttt ccccagtaac attcctgaat 480
ttactggtat cctaatgtag ta 502

<210> SEQ ID NO 161
<211> LENGTH: 484
<212> TYPE: DNA
<213> ORGANISM: Homo sapiens
<220> FEATURE:
<221> NAME/KEY: misc_feature
<222> LOCATION: 395, 401, 440
<223> OTHER INFORMATION: n = A,T,C or G

<400> SEQUENCE: 161
acgattaatg tttattatt catattttga caaagatagc atattatatt ccaggacatg 60
gtagttacca tgtggggaaa cctatcaaag catttttaat gactgcttag aataactgta 120
gaaagtactt tctcaatgat ttttgtatgc aagaaaaaaa atacctgaaa gtaaccaaaa 180
gtttcagact ggaaaatatg ccaggaagat tttcttctct cattctcagg tgaggttata 240
atccagtttt agcaaatgtt tgacaattta aaatactttt gaaaactgga gatttaaaaa 300
atgtaaacaa ttggtaggca cagcaaaatc gtagttttcc cttctgatat tatacatttt 360

```
ggcatctctc tacagttatg attaaccatt aaatnaaggg nagctaaaac gttccaaaaa    420
taggttttac caacattcan tttttaaaat tttccattca agctggtaat ccttttgggt    480
ttcc                                                                 484
```

<210> SEQ ID NO 162
<211> LENGTH: 347
<212> TYPE: DNA
<213> ORGANISM: Homo sapiens
<220> FEATURE:
<221> NAME/KEY: misc_feature
<222> LOCATION: 77, 340
<223> OTHER INFORMATION: n = A,T,C or G

<400> SEQUENCE: 162

```
cttttaactt aaaagtcttt tattaacatt aacttagcaa cttgataatt tattaaaata     60
accattatag acaaganaaa tctcaaacat ccttcaaaag tatagtctaa aaaattacaa    120
aactgggtac tgaccgaaaa tgccaatttt tccaaaaagt gagcaattcc actaaggtat    180
ttcgcttcat atctcgatcc tgaattgata agaactagta gtaaaagaa aattgacagg     240 ttacatcaga tattcaaaat aagatttaat caaggcgaaa catttaaga tgtcaatatg    300 acatgataat cagatttaat tacatgaggg tggttgtgcn gatgggt                  347
```

<210> SEQ ID NO 163
<211> LENGTH: 266
<212> TYPE: DNA
<213> ORGANISM: Homo sapiens

<400> SEQUENCE: 163

```
ttaggaaaca aaatcttta ttaaaaaaaa ataacttaca aattgagaga actctctgaa     60
atgcaactgt tcgttgtgtg tgcagatttg cagtccagaa cagttttttg tttattttaa    120
aatgtaactt tacaatacta ttaatgtcac aaactgcatt acaaagcagt tttcgttcca   180
tatcccgtgc cggtacaaaa caccacacag atataaaact atggtaaata aaacatttca    240
gccaagactg gcatatattt atatat                                         266
```

<210> SEQ ID NO 164
<211> LENGTH: 446
<212> TYPE: DNA
<213> ORGANISM: Homo sapiens

<400> SEQUENCE: 164

```
aaaatcactt caagaagcat ttattgagaa tctaagacaa acaccctata ttcaaagagc     60
ttacagttta tggaaaggcc agccaatcaa tatgcaatat ttaagtcttt tcattgaggc    120
aagtgttgat tttgagagca gagagatgat gatcgttttc gagctgagtt accaaggttg    180
gagcttacta aactcacaag ggcagtttca ggaaaggaaa ataccatctg caaaggtata    240
tggctcattc aggggctctc tgaattgtgg ctggagcaaa aggtttgaaa tcttttttct    300
tcccaagaag atgaaagagc tcctggagga cagaaactgc ttttattcc ctttgtatct    360 ctcacagcac ctggatactt aagactaaac tattctttca ctcatatggc ccattatcaa    420
tgtcagcatt gtaaggccct gatggg                                         446
```

<210> SEQ ID NO 165
<211> LENGTH: 411
<212> TYPE: DNA
<213> ORGANISM: Homo sapiens
<220> FEATURE:

<221> NAME/KEY: misc_feature
<222> LOCATION: 353, 368
<223> OTHER INFORMATION: n = A,T,C or G

<400> SEQUENCE: 165

```
gccatcatcc cacacatcag caccaagacc atagacagct ggatgagcat catggtgccc      60
aagagggtgc aggtgatcct gcccaagttc acagctgtag cacaaacaga tttgaaggag    120
ccgctgaaag ttcttggcat tactgacatg tttgattcat caaaggcaaa ttttttgcaaa   180
aataacaagg tcagaaaacc tccatgtttc tcatatcttg caaaaagcaa aaattgaagt    240
cagtgaagat ggaaccaaag cttcagcagc aacaactgca attctcattg ccaagatcat    300
cgccttccct gggtttatag tagacagaac cttttttctgg ttttccatcc ggncattaat   360
ccctacangg tggctgtgtt attcatgggg caggttaaac aaacccctgg a             411
```

<210> SEQ ID NO 166
<211> LENGTH: 358
<212> TYPE: DNA
<213> ORGANISM: Homo sapiens

<400> SEQUENCE: 166

```
aacacaagtc aagttttaat tgcatggctt ctcagacaaa tcaggtggca ctgctaactt      60
gagtattggt tgtgtagagg gtgcagtaat gggggggaact gctgcacatt cagtcaccca   120
cctctttttct caacagcttc aatgcattgc tttacaaacc acggaactgt ggaattttca   180
cgttcacaca ctttgtgcag atgagagcca aaaatttgat ctttaataag tccttttttct   240
tgcagagttt tcagggaagg tcttcgggta ataaacttct ttaatctgct tttaactcga    300
tttttgtcgc ttgtatcgga agcactgtga tgcagtctga acattaaaga ttttctgt     358
```

<210> SEQ ID NO 167
<211> LENGTH: 368
<212> TYPE: DNA
<213> ORGANISM: Homo sapiens
<220> FEATURE:
<221> NAME/KEY: misc_feature
<222> LOCATION: 363
<223> OTHER INFORMATION: n = A,T,C or G

<400> SEQUENCE: 167

```
tttaagattt tattttgttt tattgttaat tattttctgg tacagttaag cagttatcca      60
aaagagagaa tagtagttta ctgcatataa atagggaaaa gtcgcacatt gtagttaaga   120
aacttttttct tctaaatgtc agatatgata aactacaaat acttcagaac ctaataggtt   180
aattccatat gtctttattc aaaacgagaa cctatattaa attttttttc ttttatggtt   240
cattatttt ttaagaatca gctaaatttc tttgatattt taaatgtttt tcttgtacat    300
tatacaaaat atattcacta ttctctgact ttatacctgg tacccatggg aggaaaaccc    360
ccntttca                                                             368
```

<210> SEQ ID NO 168
<211> LENGTH: 223
<212> TYPE: DNA
<213> ORGANISM: Homo sapiens
<220> FEATURE:
<221> NAME/KEY: misc_feature
<222> LOCATION: 197
<223> OTHER INFORMATION: n = A,T,C or G

<400> SEQUENCE: 168

```
aaccatcaat gattatttat tgaaatctga ccagttgtac agaagaaaaa aaatggcatt      60
```

```
atcatgcctc tcttaatagt actgtggaaa tgcctatttt tcccttt cta atcacagttt      120 ttcccacttg tatgcttctt cctctgatat cccatcccaa cacccaacag gcaaatccac      180
agacctggca atatgcngga ttttgggtcc tacaaaatat tta                        223
```

```
<210> SEQ ID NO 169
<211> LENGTH: 425
<212> TYPE: DNA
<213> ORGANISM: Homo sapiens
<220> FEATURE:
<221> NAME/KEY: misc_feature
<222> LOCATION: 419
<223> OTHER INFORMATION: n = A,T,C or G

<400> SEQUENCE: 169
```

```
attgttactc tagttttaat ggtttcacaa atacaaaagt tgctagataa gcagtaccaa       60
catatctaaa tctccaatga tgttcaatta aaatttt att tatagactca tacactcagc      120
aaaaccactc atttaataag tccaactgaa ataaattctt attaataaaa tacctatatt      180
gaaagtaata tattgtaaga actctaccttt aaattgacca tggggatgaa ctacaatgtc     240
ataaaatatg agccaaaatg ttcactcaat aatttaatt acatcacaat taagcccaga      300
actatgcctt tttttggtg taaggctgaa taaggaccga aactggatgg agagaaaatt      360
gctttctaaa gcctcattta ctggcaataa cttaccttat gcaataacca acatcacgng      420
actgg                                                                  425
```

```
<210> SEQ ID NO 170
<211> LENGTH: 493
<212> TYPE: DNA
<213> ORGANISM: Homo sapiens
<220> FEATURE:
<221> NAME/KEY: misc_feature
<222> LOCATION: 119
<223> OTHER INFORMATION: n = A,T,C or G

<400> SEQUENCE: 170
```

```
aaacgtggca cagtgtgtgt agtgtatgtg actactatca tttgtgtaag agaaagaaaa       60
gtttactatc agagactgta tctggaggga taaacagact ggcaagggtt gcctctggna      120
agaaaccggg gaatagagag cgggagtaga aagactgtat tagctgggtg tggcagcaca      180
cactgtaggc ccagctactc cagaggctga ggggaagact tgctcaagcc caggagttca     240
ggtccagcct gggcaacaca gcaagactaa aaaaaaacaa ctttcttttc caagaatacc      300 cttttttgtaa cttttgaatt ccgtatttt taatggtcta tggtctacaa acactcatgt      360
gcaaacacat tacacgcaga ataagggatc acctgcacga agctatgaac tatttcctca      420
tcccttctag ccccttccta gaggcgaacc ctccgccccc aacccaggc actatctgtc      480 ctgcttgcac cca                                                         493
```

```
<210> SEQ ID NO 171
<211> LENGTH: 280
<212> TYPE: DNA
<213> ORGANISM: Homo sapiens
<220> FEATURE:
<221> NAME/KEY: misc_feature
<222> LOCATION: 237, 261
<223> OTHER INFORMATION: n = A,T,C or G

<400> SEQUENCE: 171
```

```
tcaagtcata agataaagtt taatcatttg atcatgttaa aagacacaaa acacagccaa       60
```

```
tctaaccaaa tttcaggcat gcatttacat aaatatatta aattaagaaa agaaattgta    120
cacttaaacg tccttttcac ctagaaatca ttaaatccac agatcaacaa taaaaccaat    180
tctctgcatt taccacttca agatacaatt gttctatttt aaagataaca caaactncac    240
tagtctggtt aggaatttat ntgcattata catatattat                         280
```

<210> SEQ ID NO 172
<211> LENGTH: 303
<212> TYPE: DNA
<213> ORGANISM: Homo sapiens
<220> FEATURE:
<221> NAME/KEY: misc_feature
<222> LOCATION: 287, 301
<223> OTHER INFORMATION: n = A,T,C or G

<400> SEQUENCE: 172

```
agagtataat tcagtggaag tgtgtctttg tccccagagg tttctgcatg tgcaagcatt     60
ttaatctaca ctgccagaac ccccaggctt tttagtgaag tttgcagagg aagacttatc    120
tgtattgact tatatgttgc acagaacaaa tgaaagtctc agacagtcct tttttaccca    180
acaaaggctt attttttttcc atcctttgct tgggctcaag cactcctgcc ctgcgtgcct    240
ccactttaaa catgatcaga actgtgcttc attgcaaata caactnacc aacaaatggg    300 ncc                                                                  303
```

<210> SEQ ID NO 173
<211> LENGTH: 534
<212> TYPE: DNA
<213> ORGANISM: Homo sapiens
<220> FEATURE:
<221> NAME/KEY: misc_feature
<222> LOCATION: 277, 373, 396, 410, 421, 453, 459, 492, 503, 518
<223> OTHER INFORMATION: n = A,T,C or G

<400> SEQUENCE: 173

```
tttttttttaa ctcttaaaaa aaatcatttt attgatcctt taccatacaa aatttattca     60
aattcacccc atttgaagtg gtaagatcac agctagagaa caggtcaccc tgtaacaaat    120
ctatttacaa aatccatcat aaaagctttt ttttgttttt ttttacatta tattacatat    180
tttctttttt aaaagcatac aacacaaagc taaactgatt agtagtttgc ctactcccaa    240
ttttgggaga aatacttcct ttttacaaaa tcacgtnccc cgtaggaaaa gaaattccca    300
caccctgaca attggccaac cgacttactc tgcaagccat cttcttcaaa tccctccttc    360
tcatacacac gangttgtca tgcacacact gaatcntaat ttcttttccn ggaagcttaa    420 nccttaaat accgggaatt attttcagat ctncacgtnc caacaaaaat ggaaacaagg    480
gccccaccaa gnccgggaaa acnaaaccca atacccntnt aaaaatttca aggc         534
```

<210> SEQ ID NO 174
<211> LENGTH: 610
<212> TYPE: DNA
<213> ORGANISM: Homo sapiens
<220> FEATURE:
<221> NAME/KEY: misc_feature
<222> LOCATION: 408, 442, 467, 493, 555, 562, 583, 593, 598, 606
<223> OTHER INFORMATION: n = A,T,C or G

<400> SEQUENCE: 174

```
tccctttctc cctgtttccc tcccttcttt ccttccttcc ttccttcctt ccttcttaga     60
attcactgaa gtatttccta ggtagccttt tacttactac tttaatcaaa gcttatcttt    120
gtgcccaatg tgtaaaaagt gaaaatgtct cttcgaaatt ctatattaca atatagacag    180
```

| | |
|---|---|
| agaagttggg ccttgagggc ttgagtttca cttaaatact atacacatgt ggtatcacac | 240 |
| aaggtggagg gggagggaac aaacagaaac ataacaatta tttttattct gtctttacaa | 300 |
| aagaaagcct cttctctatg aaaaagtctt tttggcatct gctcccggaa acctgccccg | 360 |
| agaacacgtt ccccattgct ttgcaagcat ctcttttta aagcacanca ctgtccccgg | 420 |
| gagtcacgta ggttggatta anctgtctta gttgaccaac gaagaancac tggatgagtt | 480 |
| ttccagggat gantggttgt ctggggtgga acatatagtc ctgtctacaa caaatgtaac | 540 |
| tcctgatatg ggacnatgaa cncagtgtgt gacccaggag tgnttgatct gtnaacantc | 600 |
| gcatgnaatt | 610 |

<210> SEQ ID NO 175
<211> LENGTH: 335
<212> TYPE: DNA
<213> ORGANISM: Homo sapiens
<220> FEATURE:
<221> NAME/KEY: misc_feature
<222> LOCATION: 295, 308, 318
<223> OTHER INFORMATION: n = A,T,C or G

<400> SEQUENCE: 175

| | |
|---|---|
| ctgtcctgat tagaattaat tttcataaag agaacaagaa tcttgactgg ttcacccttc | 60 |
| aattccttgt gcccgcaaca gtgaccggca catggaaagc attcagggaa taaaagcaca | 120 |
| atggaaaatt aaaacatact cactgcatgc ctgccaccta taggaaccaa attaaatcac | 180 |
| tgccaatatg gcatgggggg aaaaccttcc cattttctg ggataatgt ttacaaaggg | 240 |
| tgggaaaata aggtggcaca ttcacctggg gtggggcatt ttaatttaaa cgctngttga | 300 |
| ccccagtngg ttgttacntt tttcaggtgg aatta | 335 |

<210> SEQ ID NO 176
<211> LENGTH: 161
<212> TYPE: DNA
<213> ORGANISM: Homo sapiens
<220> FEATURE:
<221> NAME/KEY: misc_feature
<222> LOCATION: 98, 107, 113, 150
<223> OTHER INFORMATION: n = A,T,C or G

<400> SEQUENCE: 176

| | |
|---|---|
| tagaatgaat tgcagaggaa agttttatga atatggtgat gagttagtaa aagtggccat | 60 |
| tattgggctt attctctgct ttatagttgt gaaatganga gtaaaancaa ttngtttgac | 120 |
| tattttaaaa ttatattaga ccttaagctn ttttagcaag c | 161 |

<210> SEQ ID NO 177
<211> LENGTH: 337
<212> TYPE: DNA
<213> ORGANISM: Homo sapiens
<220> FEATURE:
<221> NAME/KEY: misc_feature
<222> LOCATION: 8, 48, 251, 258, 264, 314
<223> OTHER INFORMATION: n = A,T,C or G

<400> SEQUENCE: 177

| | |
|---|---|
| taaacatnaa actctgctat aacaaacatt taggttaatt atgatggnac tttcactgtc | 60 |
| tcttctttat taagtgtggt tatctccaat agtaaacaag ttcatttcac aaaggctgtt | 120 |
| actaaatgac ttatgtatga tgttatctac aattctcaaa ctgtaacagt acagacttga | 180 |
| acttttaaat tgtctgtaaa tcatcatcta tgccatgaat gtttaaatat aatatatatt | 240 |

-continued

| taatatgaaa nagctaangc acangtgctt tcacccaccc ctaaattctg ttttgggccc | 300 |
| tcacagattc ggantgcatt ttcatccacc cttttc | 337 |

<210> SEQ ID NO 178
<211> LENGTH: 487
<212> TYPE: DNA
<213> ORGANISM: Homo sapiens
<220> FEATURE:
<221> NAME/KEY: misc_feature
<222> LOCATION: 383, 397, 408, 459, 467, 476
<223> OTHER INFORMATION: n = A,T,C or G

<400> SEQUENCE: 178

| agaaatggga gaatgggacc tttcctggat ggccgaaaga gacaagcagt gccctgaccc | 60 |
| atgctggagc ccatcttgac ctctctgcat tctcctcctg ggaggagttg gcttctctgg | 120 |
| gtttggacag attgaaatct gctctcttag ctttaggctt gaaatgtggc gggaccctag | 180 |
| aagagcgagc ccagagacta ttcagtacca aggaaagtc cctggagtca cttgatacct | 240 |
| ctttgtttgc caaaatccc aagtcaaagg gcaccaagcg agacactgaa aggaacaaag | 300 |
| acattgcttt tctagaagcc cagatctatg gaatatgtag gagattcttc gggggaacag | 360 |
| cgacattctt cactcatgga aantgttaca gcgcaanaag gccagggnca gggagaagga | 420 |
| gcgaggaagg aaggagggag gaaggggcag ttccagttna ggagttnagg atttanggtt | 480 |
| gaaggag | 487 |

<210> SEQ ID NO 179
<211> LENGTH: 416
<212> TYPE: DNA
<213> ORGANISM: Homo sapiens
<220> FEATURE:
<221> NAME/KEY: misc_feature
<222> LOCATION: 163, 285, 287, 414
<223> OTHER INFORMATION: n = A,T,C or G

<400> SEQUENCE: 179

| tttttttaaca taaggtttt attgaataaa tacatgcact gtcacgtgaa attagttgaa | 60 |
| cagaaaggag gttctctact ttttaacccc catcccccac cgctgttctc tatttgcagt | 120 |
| gggggggtcca gctggaggtg gaataaatgc ggcaaccaca ganaaaacac acagctacac | 180 |
| acaggcctgc atttggctta tgtgcctgaa aaagaagggc cgacctcttg ataaagaatg | 240 |
| tctgtaaaag gaattcttac cgtgcagaat atattatcat gggcnantac agttacaagg | 300 |
| ctgcttctat tttatttatt ttttgagacg gagttcacct ctgttgccca gggtgggagt | 360 |
| gcagtggtgc gatcttgggc tcactggcaa cctccgcctc ctgggttcaa gcantt | 416 |

<210> SEQ ID NO 180
<211> LENGTH: 364
<212> TYPE: DNA
<213> ORGANISM: Homo sapiens
<220> FEATURE:
<221> NAME/KEY: misc_feature
<222> LOCATION: 7, 9, 33, 344, 355
<223> OTHER INFORMATION: n = A,T,C or G

<400> SEQUENCE: 180

| ttttancna tttgtaaata agtttaattt ttnagttttt caatgacatt cagtagagat | 60 |
| agttatattg gctatataac acaagtaaag tggtgtttgg aaagtggagg actaggtttt | 120 |
| ggcacggggc taggacgggg tgaccgccgc ctcaccacca cagactggag ggggcttttg | 180 |
| agagctgggc ttcgctcccg aggactcagc tcagaaactg ctgaggcccg tgatgcagaa | 240 |

```
ccagtgccgt aggtgggcat ctggccatgg cttcgagctc tcaggatgct tttgtatctt      300
gagagggtgc ctccagagaa tgtctgctcc ttgggcctca tctncccggg ttatncccg       360 gcag                                                                  364
```

<210> SEQ ID NO 181
<211> LENGTH: 330
<212> TYPE: DNA
<213> ORGANISM: Homo sapiens
<220> FEATURE:
<221> NAME/KEY: misc_feature
<222> LOCATION: 247, 254, 299, 314, 323
<223> OTHER INFORMATION: n = A,T,C or G

<400> SEQUENCE: 181

```
tgtaaaaaaa atatgtttat ttactctcat gtataaaaat aaggttttg gggccatcct        60 ctcctggggg tgcccatgcc cttcttttgg agaggggggcc gaggggtgac cttttaggcc     120
ttacccgtaa gctattttaa tacacctgct caccccctc ttcctccact acctgctgta      180
gcccattcct tccttctggg tgtaaagcta cagaaggaag tcgtgggaac aaaattatac     240 cgagggntt tttngttttg ttttatactt ttatcaaact ccccaggcaa acttgctgna      300
ctgcatttcc acanattacc aanacctgcc                                     330
```

<210> SEQ ID NO 182
<211> LENGTH: 163
<212> TYPE: DNA
<213> ORGANISM: Homo sapiens
<220> FEATURE:
<221> NAME/KEY: misc_feature
<222> LOCATION: 11, 12, 14, 77, 119, 157
<223> OTHER INFORMATION: n = A,T,C or G

<400> SEQUENCE: 182

```
atttttgaag nngnttcgat gtcttactgt tatgaccata aaaccaataa agctactttg      60
aaaagttaaa gccaggngta attaaacaac tcatacttga ttgttaaagt cagtctctna    120
aaagtgtaat tttaaaaagg taataaaaaa ggtatancat tat                      163
```

<210> SEQ ID NO 183
<211> LENGTH: 354
<212> TYPE: DNA
<213> ORGANISM: Homo sapiens
<220> FEATURE:
<221> NAME/KEY: misc_feature
<222> LOCATION: 222, 298, 312, 330
<223> OTHER INFORMATION: n = A,T,C or G

<400> SEQUENCE: 183

```
tttttttct ctaagtgata atgatatccc agctagaata attgtgctct ccagaagcaa       60
ttaatctgat ttgcaagcac tgattttttc ttttgcaaaa actaataata ttagcctgac    120
caattatgaa ataattccta aatttacaaa ttcccaaatt tgtgctttca tggcttcctt    180
ctattttaaa tctatattat tttaaacaaa ttttccttaa gnaaaatga cttaacttca     240 taaaaatcta cccatttatg gtaaataaaa cattaaccaa aaaccaaaat taagggntt      300 actataaatg gnaacattta cattgctggn tattaaatcc ctttccttgg catt           354
```

<210> SEQ ID NO 184
<211> LENGTH: 432
<212> TYPE: DNA
<213> ORGANISM: Homo sapiens
<220> FEATURE:

```
<221> NAME/KEY: misc_feature
<222> LOCATION: 355, 365, 390, 415, 421, 430
<223> OTHER INFORMATION: n = A,T,C or G

<400> SEQUENCE: 184
tttttttttt atcttttaaa tgggatttat ttatgtttac ataaaaggta gcaaatgtta      60
cataagttgt ttccttaaga acatttattt tgtacaatca cattgttatc aagcaagact     120
tatgaaaat  ttcctgggtc cacaacactg aactttgaaa ctactgtagc attctctttt    180
ccaagtttaa acatgactt  gtgcactgaa gaagtatggc ttcgcattgc acagtgggtc    240
acatgtgaca acctgacacc aagcgagaag ccttttgatg aaggaatgtt ttatcttttg    300
ttgaggttac caaaatgggg actttcatgt gtggtggatt atccaaaccc catantttt     360
ttttncggtt ccatttctgg cttccaattn aaattaaccc ggtttaaact aggcnggttt    420
nggccaatgn ta                                                        432

<210> SEQ ID NO 185
<211> LENGTH: 354
<212> TYPE: DNA
<213> ORGANISM: Homo sapiens
<220> FEATURE:
<221> NAME/KEY: misc_feature
<222> LOCATION: 74, 158, 159, 164, 165, 175, 184, 243, 312, 318, 331,
      341
<223> OTHER INFORMATION: n = A,T,C or G

<400> SEQUENCE: 185
tttttttttt ttcaaaaatg tcaaacttta ttcaagtgtt atggtaagaa atttgaaatt     60
cttaggtaag ctantgaata aatccttggg caggtgcagg catacagatt ctggggtgca    120
gctgctgagt ttaaaagctt cctttggaga tgccccgnng gggnnacacc ccctntcccg    180
cctntcaaga ggaggccatc ctgggcagc  acgttagggg caaatggccc agatgcccag    240
ctnagggaaa cctccatgcc tagaggagga ggtcgctctg ggagcaggag gaccttcttg    300
gaacccctgt tnacaggntc cttttcttg  nttttccag  nacctcctgc aggg          354

<210> SEQ ID NO 186
<211> LENGTH: 438
<212> TYPE: DNA
<213> ORGANISM: Homo sapiens
<220> FEATURE:
<221> NAME/KEY: misc_feature
<222> LOCATION: 59, 250, 292, 337, 344, 349, 375, 382, 387, 403, 411,
      422, 430
<223> OTHER INFORMATION: n = A,T,C or G

<400> SEQUENCE: 186
tttttttttt tttttttgac tttgaaaata tttatttga  atagtaaata gttatacang     60
ttgaaacagt tctattgaag ctttctataa atagctaaca attaagaaaa taatgtatgt    120
agaaaagaga ttgcatttaa aagtaagagc tgtcggttgt acaagggccc tggggaccct    180
cgaagcagaa taaatgatag gttgtctgta attcactcag ataggtataa aagttaaaac    240
tttaagcagn tccctttaga aaaaggctct cttctaaaac gcacagtggg antgtcaaga    300
gtggcagggt ggggaggggg cagcgcgccc aaaaaantct gcantcaant aatatcataa    360
tcttcataat taatntaatt anttaanggt taattaccat ttnctcctta nttcaccatt    420
tnccttggn  gggggccc                                                  438

<210> SEQ ID NO 187
<211> LENGTH: 297
```

<212> TYPE: DNA
<213> ORGANISM: Homo sapiens
<220> FEATURE:
<221> NAME/KEY: misc_feature
<222> LOCATION: 189, 211, 240
<223> OTHER INFORMATION: n = A,T,C or G

<400> SEQUENCE: 187

| | | | | | |
|---|---|---|---|---|---|
| tttttttttt | ttttggaaa | acactgttta | tttgaaaaca | atgagacctc | aaatatgaaa | 60
| tatagttaac | aatgacattg | acactgttgc | tagcactttc | ccctaaacca | cccgtaagtc | 120
| ttggacgcat | gtgcatgcag | cacacacaca | cacacacaaa | aaccaaaaac | aaagccaaaa | 180
| aaaaaaaant | cccaaacaca | acattccatg | nttgttcatt | gaactcctga | tgccgggagn | 240
| acaggactgt | taaaagattt | tgtctcccac | attatctctg | ggagtggggc | acaaagc | 297

<210> SEQ ID NO 188
<211> LENGTH: 405
<212> TYPE: DNA
<213> ORGANISM: Homo sapiens
<220> FEATURE:
<221> NAME/KEY: misc_feature
<222> LOCATION: 277, 349, 359, 390
<223> OTHER INFORMATION: n = A,T,C or G

<400> SEQUENCE: 188

| | | | | | |
|---|---|---|---|---|---|
| tttttttttt | tttttcagg | attcactgcc | tggggtatcc | cactatatat | atctcaccta | 60
| tgatgtagtg | gtgcttgaaa | tactcatctc | attagctcga | ttttattatt | ctaatctaag | 120
| gttttttata | ttattcatac | tatgatattt | ttagggacaa | tcagtaatat | ttggggcaga | 180
| gtactgaggg | acctcttgaa | gtctgcaaca | gcatgcattt | tctttgtttt | tgtggggagt | 240
| gcttccctgt | aggctgtctt | tgttctagga | acactgnctc | caaatttatt | tccatgggga | 300
| tgtaggggc | tagtaggccc | atggtggaaa | ggtcttctgt | aaatctccnt | gggggggtnt | 360
| gagttattgg | gggttatttc | taacagggan | ttttcccaaa | ggggg | | 405

<210> SEQ ID NO 189
<211> LENGTH: 426
<212> TYPE: DNA
<213> ORGANISM: Homo sapiens
<220> FEATURE:
<221> NAME/KEY: misc_feature
<222> LOCATION: 180, 259, 330, 355, 373, 401
<223> OTHER INFORMATION: n = A,T,C or G

<400> SEQUENCE: 189

| | | | | | |
|---|---|---|---|---|---|
| tttttttttt | ttttcattca | aaatatata | atttattgag | tacttgctag | acacaatgga | 60
| tacaatgatt | atatagtccc | aatcctccag | gagaacaata | gacagacacc | tttataatat | 120
| gtatgtggag | tgctctgaca | gggaaaagca | caaggtccat | gggggtggga | gtggccagn | 180
| agctaaggaa | ctcttccccc | atgaagtggt | tacttacttt | ctaatcttta | atttaggatt | 240
| ctctcatgga | acatttgant | ggtgaaattt | tactacataa | aggttctcaa | ccctaggagg | 300
| tttatccctg | ccccctggg | aacatttggn | caatgtctga | acaacaagtt | tattntcaca | 360
| actggggagg | ggngaaggaa | gttagcagag | gccaaggatg | nctggctaaa | ccttaaattc | 420
| ctacat | | | | | | 426

<210> SEQ ID NO 190
<211> LENGTH: 473
<212> TYPE: DNA
<213> ORGANISM: Homo sapiens
<220> FEATURE:

<221> NAME/KEY: misc_feature
<222> LOCATION: 185, 229, 324, 358, 396, 406
<223> OTHER INFORMATION: n = A,T,C or G

<400> SEQUENCE: 190

| | | |
|---|---|---|
| tttttttttg atgtgctaat tttatttttc taatacttac caaaataaat gccaccactt | 60 |
| aacatagaaa aaattgttcc catgtgacct aaaatcattc ctcagtcacc cctgaactgg | 120 |
| ctagtagcga gcatatgtgg agcggtggtg agggcaggat agcctggtta taggaaacct | 180 |
| cagantagga aagacctggg ttcaaatccc cactctgcca cttactagnc tgtgtgactt | 240 |
| tgggacaagt tgtgaaacct ctctgaggat ttatttcttc atgtaaaatg tcaccgataa | 300 |
| tggataactc agtgggtgta agantgatct attttaagga ttctagggca gagtcccngg | 360 |
| gcagggcagt taaggcactt aaataggatg gacagnctat tcattnaatt attaggcagt | 420 |
| tttttcctta atggagggtc cttgttggaa ggacccctt tttcttaacc tcc | 473 |

<210> SEQ ID NO 191
<211> LENGTH: 320
<212> TYPE: DNA
<213> ORGANISM: Homo sapiens
<220> FEATURE:
<221> NAME/KEY: misc_feature
<222> LOCATION: 265, 288
<223> OTHER INFORMATION: n = A,T,C or G

<400> SEQUENCE: 191

| | | |
|---|---|---|
| ttttttttta agagaagatg gcctttattg cagcacgaac tgaggggggac tgcatgtcca | 60 |
| cagctctcca gggagctgcc aaaggaacgg gcccgccctg cccctgcaac aggccctcca | 120 |
| ggggcttaga gcatggctcc cctcaggaag ggtaacgcgt gcttgtaaac aagggcccag | 180 |
| acaacacaga gagggagagg gcagcatcat catgtgcagc tttgctacaa gaaagatagt | 240 |
| tcttaatttt caaagaggga gacancgcta cacctaggcc ctgccctncc atgcactgga | 300 |
| agggcttttg gaagtaggtt | 320 |

<210> SEQ ID NO 192
<211> LENGTH: 453
<212> TYPE: DNA
<213> ORGANISM: Homo sapiens
<220> FEATURE:
<221> NAME/KEY: misc_feature
<222> LOCATION: 221, 386, 407, 424, 439
<223> OTHER INFORMATION: n = A,T,C or G

<400> SEQUENCE: 192

| | | |
|---|---|---|
| aaagcatggc atggcagcat atacacctaa acacatgcat gtgagcatga gaggcctcgc | 60 |
| tctccaagat cagaagctgg gaggggaagg accttgacgt gctctggaga ccagcggtgc | 120 |
| ccatggggat ggcaggtgga ggttctgtcc tcacaacccc tggggttatc gttccagcca | 180 |
| gaaagcgaag agaccactca cagggaagca agggcaccgt nccggtcctc ggcgtggtgt | 240 |
| gaccagagct ctcatgcttc aggcctccac cataacttgc tcttcgggca ttcatggggg | 300 |
| catctcttct tcttgcccaa acaagcaggt ttctgggaaa gagggagtgg gggatgccat | 360 |
| ttaggcacca tttaggccct tgtttnggct tgttgggggg tttgaanttg accacaagtt | 420 |
| gggnaaaggg cagagattnc ggccagaaaa aca | 453 |

<210> SEQ ID NO 193
<211> LENGTH: 433
<212> TYPE: DNA
<213> ORGANISM: Homo sapiens

```
<220> FEATURE:
<221> NAME/KEY: misc_feature
<222> LOCATION: 88, 91, 148, 224, 268, 272, 315, 316, 397, 417
<223> OTHER INFORMATION: n = A,T,C or G

<400> SEQUENCE: 193
tttttttttt ttttcaaaaa ctttattctt ttctaataaa aatgatatat gttcattata    60
aaaagtttca aacacacatg agtctganga ntgtaaagat cacccaaata ccacagccca   120
gaaaaaaaaa tccttaacat ttggtganga tctctctatg aaacatacat tatcttaaaa   180
tattcaatgt tataaatgag ctcatattca acatatatcc tgtngtctac ttttgattc    240 aataatattt tgggaacata tatccatngc antaaacata tatctaaata tttttaaatg   300
acaactggca tgggnnttta tttaatccat cttttactga gggatgtttc agttgtttcc   360
aatgttttaa tcataaaac atcatggaaa tataccnttg gggctccatg tttggangg    420 ttggggcaac ctt                                                      433

<210> SEQ ID NO 194
<211> LENGTH: 375
<212> TYPE: DNA
<213> ORGANISM: Homo sapiens

<400> SEQUENCE: 194 tttttttgg ttttattttc tcctgaagct gaaaatgttt cacccatata aatgtggcat    60
tttagactct agctataaac ctcatcgacc agtatgtttt cagagttgtt cacaacaaaa   120
tattattcgt ttctaaaatc agttttcact tttggtgat agtattccag gctggactgc    180
ttgaatttta gatgcagaga tcattttata tatatctgtc aatgtaatac agaaaaatta   240
catgtgaatt gtttatgtgc cccctctacg tagggacaca gtatcaatca ctcaataagg   300
cactgtaaca tcaggtgggt gtttgggat aaataacctc ttcggggttt ctttcaatcc   360
cactaccata tggct                                                    375

<210> SEQ ID NO 195
<211> LENGTH: 440
<212> TYPE: DNA
<213> ORGANISM: Homo sapiens
<220> FEATURE:
<221> NAME/KEY: misc_feature
<222> LOCATION: 383, 392, 417
<223> OTHER INFORMATION: n = A,T,C or G

<400> SEQUENCE: 195
tttttttttc tatttgatat ttattaaact tagtttctcc aactatggtt tggcattgta    60
caaagcatct taatgacaca gtagagttaa aaagatcttt acaaattgaa atgtgatacc   120
cttgtctcca aatattttaa ttgccataaa tttgtttaaa aatacacatt aaacgcatgt   180
ttgacactct aaactttcta tactctcaat accacaaaat acatataata tactatacag   240
atgtggaaaa atctagttag tatataatac tttgctcacc attaacaggc tttatcgtgt   300
gaaatgcaca tactggactt aggaaatcct aggcttttga ggccccaaag gtacctctgg   360
aaattgtaat gtattggcaa canataaaaa tncacaggta ttataattgg aaattcnggg   420
ttggaaaatg tccggtggcc                                               440

<210> SEQ ID NO 196
<211> LENGTH: 391
<212> TYPE: DNA
<213> ORGANISM: Homo sapiens
<220> FEATURE:
```

<221> NAME/KEY: misc_feature
<222> LOCATION: 7, 8, 12, 278, 309, 371, 386
<223> OTHER INFORMATION: n = A,T,C or G

<400> SEQUENCE: 196

```
aagtcannga tntttactta atttctttca ttgtatactt gtatctcatt ttctcttaac    60
actgaaaatc ctgacttcta aagaaatgta actacttgtt ttcttacaac atagtattct   120
agatacaata ggttcaaaat aacaccagta ttaccattaa caatgagact actaaatgca   180
ttttcacagt gcactaaaat ctcaggaatt cactggcaat ataattcatc catgtaataa   240
aaaaccactt ggtaactcca aaactattca aataaaangg taataacaaa tttaaaaatg   300
gcatttgng ggtttcttcg gaattttttc acccttata ttcccccaaa gggccttctc    360
ctattaattg nggaggggcc ttgggnattg g                                  391
```

<210> SEQ ID NO 197
<211> LENGTH: 441
<212> TYPE: DNA
<213> ORGANISM: Homo sapiens
<220> FEATURE:
<221> NAME/KEY: misc_feature
<222> LOCATION: 18, 19, 20, 307, 388, 418
<223> OTHER INFORMATION: n = A,T,C or G

<400> SEQUENCE: 197

```
tttttatcc ttcttaannn ttattacatg ttttattatc ctgtccccag aggtgggttt    60
atccagaaac caagaaaaaa atcaatcag aataaactca aaaaaaaag gtaggggag     120
caaaaccatc aaccaccagg gcagccaggc catcagccca cctccacctc tggagggtcc   180
ccagagaccc acgcccgacg cagacccgga ggaggcatca gcaaggggc ccgggcagag   240
aatcggctat gtctttcatt atgaggaggc agggagagac gggcagagat atgtttgcta   300
gggtgantat atattttata ttaattaaat ccgtaagttt aattaaagta aataggtatt   360
tctctggaag ttttttaat ttcttctt ttatagtt tttggttt tttgtggntt          420
ttttttttt ttttgggtt t                                               441
```

<210> SEQ ID NO 198
<211> LENGTH: 441
<212> TYPE: DNA
<213> ORGANISM: Homo sapiens
<220> FEATURE:
<221> NAME/KEY: misc_feature
<222> LOCATION: 1, 33, 403, 410, 436
<223> OTHER INFORMATION: n = A,T,C or G

<400> SEQUENCE: 198

```
nataattttt ttattataaa agtaatatat ganctttata gaaaaataaa gaaaataaaa    60
atcatcaata attttatcac ccagaaacaa tcacttttaa tgtgctggta gaggttagtc   120
tattttaaca tttctgaaat catatagatt tacatgattg ttctcacgta acctgtaaca   180
taagcatttc ccaagttgct attatctgtt aataacagtg gtttgattaa ttggattggc   240
tgtgtggatg tggaacggaa gagccttgat gtcaagaaga gctgaagcac agaaggtgca   300
ggtcggtcat ttggggacca tattgtctgt gggctttcag ggacagggga gcttcaggga   360
ctcagggtag gatgactctg ggaggaaacc ttctcttttg ggnactggcn gcatctcccc   420
gtccccccca gggganttta g                                             441
```

<210> SEQ ID NO 199
<211> LENGTH: 481

```
<212> TYPE: DNA
<213> ORGANISM: Homo sapiens
<220> FEATURE:
<221> NAME/KEY: misc_feature
<222> LOCATION: 348, 392, 403, 417, 423, 442
<223> OTHER INFORMATION: n = A,T,C or G

<400> SEQUENCE: 199
ttaaaagctt agagcaaatc ctgttaaatg ggacaaagtc tcaattcttt tttaataaga      60
caaaaacact ttatgtagtc tcttttcttt ttcagtgttt ctcgaaattt caattttatt    120
ccatgctgct acagaataca aacttaccca ataaaaatag cagctccatt gaaagagctt    180
tcccacaaat tgaaatattt aaagcacagt tacaggcttg tgtactgttg gtgcatacat    240
tgtttgattt gttcagttcc tcagttttgc agggaaagat gtcaacatta tctgattttt    300
caagctatct attcaatgat tctaattctc taaaagactt gggaaggngg ggttgttttt    360
tgttctgggc ccctcagttt gttgaggagc cnattttaaa ggnttccggt gggattnaca    420
aanggaacaa atttaggggg gntcatttat ttcccccaac caggtcagtg gcctagtggg    480
g                                                                    481

<210> SEQ ID NO 200
<211> LENGTH: 291
<212> TYPE: DNA
<213> ORGANISM: Homo sapiens
<220> FEATURE:
<221> NAME/KEY: misc_feature
<222> LOCATION: 43, 174, 240
<223> OTHER INFORMATION: n = A,T,C or G

<400> SEQUENCE: 200
gcatttgtat tagttgctat tcctaccacc atgtctatac atntatatta tatgcaaaag     60
atccacataa tttaccatttt gtgtatgttt cactattcga acaggccgca gcaactgtaa   120
cagctgcaaa agtaattaaa atattacttg gggtattact aattgttctg tagncaaagg    180
taaaatctga aggtcattag gcaaatacat tacctttaag ctgaggttgc taatatgggn    240
acccttacat atatacccaa tactaaaata aaggctaact ctgttttaag g              291

<210> SEQ ID NO 201
<211> LENGTH: 328
<212> TYPE: DNA
<213> ORGANISM: Homo sapiens
<220> FEATURE:
<221> NAME/KEY: misc_feature
<222> LOCATION: 104, 161, 178, 183, 191, 289, 324
<223> OTHER INFORMATION: n = A,T,C or G

<400> SEQUENCE: 201
tgagccaaaa tatatatact taattttagt tatgccagaa gtaagtataa tttctcagtc     60
caaggatgtt aggaagcaac ttacagagca tgcttcaaat aganttctct tggcctttga   120
aggtaactat tttcaaactt aatagtagag tcaagcaaga ntggacaatt agagtttnca   180
aanttgaaaa ntattatgta ttttatataa tcattaccta tggtttacag attttatttt   240
tatgatacat atctctaagg taggtgggta cactgaggac ataggcaant atgccaataa   300
atacttattt aagctggaag tganctaa                                        328

<210> SEQ ID NO 202
<211> LENGTH: 351
<212> TYPE: DNA
<213> ORGANISM: Homo sapiens
<220> FEATURE:
```

<221> NAME/KEY: misc_feature
<222> LOCATION: 206, 346
<223> OTHER INFORMATION: n = A,T,C or G

<400> SEQUENCE: 202

| | | | | |
|---|---|---|---|---|
| ggaccaaaga actttatatt tattttaaat atcaaagtaa cacaaagaac tagttcaata | | | | 60 |
| tacagtacac ttcctactct tcacagagaa ctgaaatttt ctataaagac atttatactt | | | | 120 |
| aggaaacatc agacaaccaa agtatgtata aaactcacaa gatattttac acacagttca | | | | 180 |
| caataattaa ttctgatatt ttaggntttt tctgtcattg cttttaaagc atccttaatt | | | | 240 |
| taaaaacaaa aattattatt tgaggactgg aaaacaggtg gcaaaggcat ttctacttt | | | | 300 |
| aattatacac tggtaaatcc ccccttaatc caaaacattt tacttncaca t | | | | 351 |

<210> SEQ ID NO 203
<211> LENGTH: 448
<212> TYPE: DNA
<213> ORGANISM: Homo sapiens
<220> FEATURE:
<221> NAME/KEY: misc_feature
<222> LOCATION: 409, 416, 422
<223> OTHER INFORMATION: n = A,T,C or G

<400> SEQUENCE: 203

| | | | | |
|---|---|---|---|---|
| gcagctgttg tcttccaact cagcggcagg tttgctttcc ccacggacac tctggacctt | | | | 60 |
| gtagctcctc aagcttccct gtctattgag cagataggaa gccgtgtcaa atatgtggca | | | | 120 |
| ccttgaggaa atgcctagtg aatgacagta tgtcctattg tgctctaact ttatttcagc | | | | 180 |
| cttatttctt ttctgaatat tatttttcat ttatcttcat ttccttacct attttctttt | | | | 240 |
| cttctaaagt atgtatcttt gttagctcca tcatcctttt tgggaatgag gcaagtataa | | | | 300 |
| aaataaggta aataaataag gaccccatcc ctaggtattt ttaaggaaac cacccttttg | | | | 360 |
| cggggcacac ttggctacct tggggtcttt agggctctgg ggggctttng ggtgtnccctc | | | | 420 |
| tngggcaggt cctggctggc attggcct | | | | 448 |

<210> SEQ ID NO 204
<211> LENGTH: 299
<212> TYPE: DNA
<213> ORGANISM: Homo sapiens
<220> FEATURE:
<221> NAME/KEY: misc_feature
<222> LOCATION: 110, 125, 128, 196
<223> OTHER INFORMATION: n = A,T,C or G

<400> SEQUENCE: 204

| | | | | |
|---|---|---|---|---|
| ttcatccgct gcatgtggaa aactggcccg atacctcgca ctacgagttt ctcgccgaca | | | | 60 |
| ctatgtggag cgattttgcc tacggtcgca atgccgtata cccggaagcn atcacggcaa | | | | 120 |
| cgcanctngt cgcgttatcc cattgaacat tatgagaatc gcgatgtttc ggtcgatggt | | | | 180 |
| gcggaaaagc gcggcntgct tcttacttgc cgcattgtgc cgccgattga ccgggaaaag | | | | 240 |
| cgattcatgt tgatgttgcg tacatcttgg ggccttgcgt tgagggcgca ccgttcagg | | | | 299 |

<210> SEQ ID NO 205
<211> LENGTH: 470
<212> TYPE: DNA
<213> ORGANISM: Homo sapiens
<220> FEATURE:
<221> NAME/KEY: misc_feature
<222> LOCATION: 6, 10, 13, 49, 51, 73, 94, 130, 232, 235, 256, 328, 412, 432, 454
<223> OTHER INFORMATION: n = A,T,C or G

<400> SEQUENCE: 205

```
caggtntatn ttntttaatt atcactcaca tatttcacag gaaaaggant ntagcaaatg    60
ggtcaaggtg gtntaaaaaa aaaatccagg tttntacatg tctctctgtt tacatctggg   120
agaaaggttn tcctggcatc agtcgcagca gctgcacttc tctgacgccc ctttgcaaac   180
acagccctgg gcacacttgc tacagcccac ggggaggcag gagcagcagc tnttnttgca   240
ggagggtgca tttgcnctct ttgcacttgc agggaaccag cgcagggtgc agggagacac   300
cagcgggcgc agggagcagt tgggggggncc cattgcaagc ccgagggaga gactgggact   360
tttcccaagg agagaagcga aggaagccag tgggggggcag ctcgtgcccg anttccttca   420
gccccggggg gntccccta gttctaggag cggncccccac cgggtgggat              470
```

<210> SEQ ID NO 206
<211> LENGTH: 399
<212> TYPE: DNA
<213> ORGANISM: Homo sapiens
<220> FEATURE:
<221> NAME/KEY: misc_feature
<222> LOCATION: 10, 392
<223> OTHER INFORMATION: n = A,T,C or G

<400> SEQUENCE: 206

```
tgagacggan ttgctctgtc gcttaggctg gagagagact ctgtctcaaa aataaaaata    60
aaaataaaat aggagtaatt cacgaggaaa agattacata ggctgctttc ctgcttttct   120
tatccacagg cagttctttg caatgactat ttaaaaacta aaacaacatc acaagtcatg   180
aagtttgtgc taccccctgaa cttgacaaat tgtctgattc aagtgggcaa agcacaatga   240
ttggatgcat ctgaacagaa cctcctctgg aatgggggcc tcactagagt gagctcttca   300
tgagccttgc caccagggggc aggggattat tctgttattt tggcctgttg tagccaagtc   360
tgcaccccta ggcacccaaa acaaactggg gngagttgg                           399
```

<210> SEQ ID NO 207
<211> LENGTH: 514
<212> TYPE: DNA
<213> ORGANISM: Homo sapiens
<220> FEATURE:
<221> NAME/KEY: misc_feature
<222> LOCATION: 52, 65, 182, 210, 215, 228, 242, 255, 339, 418, 470,
     482, 491, 503
<223> OTHER INFORMATION: n = A,T,C or G

<400> SEQUENCE: 207

```
tttttctagg attgaaaaat tatctttatt atctttgagt gggagctgga gntggaagtc    60
cccantttct tccctccaac aactcagctc ccattgtacc catctgggga cttagatgaa   120
gttacaggtc agttattgga cagctcacag gcctcttgat tcctaggagt caataagaag   180
gntttggagt ccaggcagga agtcagggan ttganttcct ccacacantt tcgggagga    240
tntggtgagc gattntagag gagaaagcgc tggtaaccct gggcctgtct cattcagcat   300
gattccacct ggggcatgag ctgggaaaag agctcagtnt tcatggtcag ggcggccttc   360
agttctgaga tctgtgctcc cttcagtcag ggtgggtagg atccatttcc gggggcanac   420
agagcccatc tttcatggcg ggatgggtag gcacgaaggg tgggaagctn gcatccgggg   480
gnagagccag nccagccatt ttngaaggac aatt                               514
```

<210> SEQ ID NO 208
<211> LENGTH: 295
<212> TYPE: DNA

```
<213> ORGANISM: Homo sapiens
<220> FEATURE:
<221> NAME/KEY: misc_feature
<222> LOCATION: 31, 272, 294
<223> OTHER INFORMATION: n = A,T,C or G

<400> SEQUENCE: 208
atgacctctg caaagagaag gtcagctata ngtagggaga aaaggaagaa ggcaagaaaa    60
ggagactcga gatgagttta catccaagag aagcacagat gtttgtaatc tacctagaat   120
aatgtgaagt acctgtccag catgtatgct cagatcctcc attcattagc acaagctgaa   180
aacatgaact gcaaattcta caccagcatc ctttgcttcc tccatggcag tgggaggtag   240 caagggagt ccaacacttc tccatgacgt angaaaggca gggaaaaata ctgnt          295

<210> SEQ ID NO 209
<211> LENGTH: 405
<212> TYPE: DNA
<213> ORGANISM: Homo sapiens
<220> FEATURE:
<221> NAME/KEY: misc_feature
<222> LOCATION: 6, 7, 287, 316, 364, 367, 399
<223> OTHER INFORMATION: n = A,T,C or G

<400> SEQUENCE: 209
taaagnnatg aggtcttgct ctgtcaccca ggctggagtg cagtggcaat tgtccctcct    60
cagtaagtgc aagccaccat accaggccct ttgaacatat tttaaatggc tgatttaaag   120
tctttgccta atactaaagt ctaacatttg gcttcctca gggaacattt tctaatttac    180
tgctttctct cctatgtgtg gaccatactt aagtggtttt ttgcatgctt tgtaataaca   240
gtctcttgaa aactaaacat tttaaataag gtaatgtgac aactcgnaaa aatcaggatt   300
cttcccctac cagggnattt gttgttatta ctgtttactg ttggttactg gtttattgtt   360
gttnctntta ggtgactttc ctggaactaa ttatctaana tatta                    405

<210> SEQ ID NO 210
<211> LENGTH: 538
<212> TYPE: DNA
<213> ORGANISM: Homo sapiens
<220> FEATURE:
<221> NAME/KEY: misc_feature
<222> LOCATION: 313, 370, 389, 523, 538
<223> OTHER INFORMATION: n = A,T,C or G

<400> SEQUENCE: 210
tgaaaatatt gatctttgtt taatatacat catttaataa aaccgcaggg agggagctgt    60
acaatgcagt tttaagatat ttttattgga ctggattaaa acatcactct gagaacactt   120
agtcccctca catgctagat ttcctttca aaatgtaatc ttgatgatat aataatgcat    180
aacttaaact tcccttccct tcaaaacatc cttggttcta ctcaaggacc tctaattcca   240
tagtatcttt tgtagacaca gaaagtatgc gttttctttg tctttgtgat gtattacacc   300
tcccagtgca ganttttaat atattccaca tatcatatct tcctgttcg gttacaaaac    360 aggtacagan ttgggatcag gcaacacant tttaaacttg gttaatggca accgtgattc   420
tatacattgt ggtaaggttc gcttcccagg attgctgtgg ggcttcggag gttcacagca   480
gctctaaaat gcagcggatc aggcaacatc acctggaagg ggnggtaagg catagggn    538

<210> SEQ ID NO 211
<211> LENGTH: 450
<212> TYPE: DNA
<213> ORGANISM: Homo sapiens
```

```
<220> FEATURE:
<221> NAME/KEY: misc_feature
<222> LOCATION: 4, 6, 10, 69, 235, 284, 383, 390, 414
<223> OTHER INFORMATION: n = A,T,C or G

<400> SEQUENCE: 211
ttantnggtn ggcgtgggga caggagaacg gggagggaag ggagctggca caggcccgga      60
gaaggcaang accctgtgca gcggggacag aggctgacaa cctgtcggag agaatgagca     120
acgggaccca ctccactggc acgggctggc cgcagacgca gctagaacgt gccgctgtct     180
cctcaggacg ctgcttgcag taagatgggc tggggagggg cgcggggagg gtctnttgca     240
gcaggctggc atcaagaagg caaaagccag agcaggacgg ggtntgcggc cgggtagagc     300
aatatacact atgtacagac tctgcgaatc agtccgctcg gcggcaagcg tccttcgcca     360
gggtccaggg cgcctttgcc cgnggaggan ggggcaccag ttagggaaag ggcnggcttg     420
tccaacaact ttttggcac ttcgaggaag                                      450

<210> SEQ ID NO 212
<211> LENGTH: 459
<212> TYPE: DNA
<213> ORGANISM: Homo sapiens
<220> FEATURE:
<221> NAME/KEY: misc_feature
<222> LOCATION: 430, 449
<223> OTHER INFORMATION: n = A,T,C or G

<400> SEQUENCE: 212 tttttttgaaa ttactaaaa ttttattaaa attaaaattt attaaaatgt cacaatttcc      60
cgtttgagcc ttatcctcta ccatgaagta taacctccca aaaagaacc tgagaaacaa     120 cctgacttga catacctttg tagtgttaaa ccttcaacac ttaagaattc atttactcta     180
ttaccacaat accagaaatt ctccaatgac aagaaaataa aactggtaaa aatgagacaa     240
aggtgagtta tgatttatag agaatataga attgaacatt aatgtagcct ggaacagcca     300
taaagacact gatggtactg ggaatgtgtc aaaaaataaa aagatcatt ctacttccaa     360 gctagctttt ctattcatgt gatatcaatt tgctcaacag ataacaagca gaaaggaact     420
caatgactcn ttcttaccat agttttcnc agctctctg                            459

<210> SEQ ID NO 213
<211> LENGTH: 135
<212> TYPE: DNA
<213> ORGANISM: Homo sapiens
<220> FEATURE:
<221> NAME/KEY: misc_feature
<222> LOCATION: 25, 51
<223> OTHER INFORMATION: n = A,T,C or G

<400> SEQUENCE: 213
gtttgtgaaa aggaacaaaa tgaanttgaa ttggacatgt gctttaagca ngccaacaga      60
caacacacca ctagagacac acatcaaaag caatcacagt gctatgatca aatgatgggt     120
acatgtgaac acatc                                                     135

<210> SEQ ID NO 214
<211> LENGTH: 124
<212> TYPE: DNA
<213> ORGANISM: Homo sapiens
<220> FEATURE:
<221> NAME/KEY: misc_feature
<222> LOCATION: 82, 99, 106, 123
<223> OTHER INFORMATION: n = A,T,C or G
```

<400> SEQUENCE: 214

```
tatttcaaaa aaagtctttt aattgttcaa aatagcacaa aacgacatcg cactatggta      60
atattgagtc acaggggtta cnctacaata gtgaacggng tactcncctc agaaacaaat     120 cant                                                                  124
```

<210> SEQ ID NO 215
<211> LENGTH: 403
<212> TYPE: DNA
<213> ORGANISM: Homo sapiens
<220> FEATURE:
<221> NAME/KEY: misc_feature
<222> LOCATION: 128, 333
<223> OTHER INFORMATION: n = A,T,C or G

<400> SEQUENCE: 215

```
cattgattta ttttccaatc ataacggtct gcattttaat attaatattt gttgtaaatg      60
actaatgctt aaatcaaact atatagagag ggaaaagtaa ttttttaaaac atcatctagt     120 taaaaatngg gagggcagaa aaagtagatt tttaaaacac aagctaaatg ggtacatgag     180
cactcagggg cggtggcttg tgtcagtaat cccagcaact tgggaggcca agatgtgttg     240
atttcttgag ctcaggagtt caagaccagc ctggtcaaca tgatgaaacc ccgtctaatg     300
attcttgaag atccacactg ggtctggata atnaagtcca cgtaacatgt agcattgcac     360
agttacgttc agcatgatct gagtctttta tctcatgttt gaa                       403
```

<210> SEQ ID NO 216
<211> LENGTH: 362
<212> TYPE: DNA
<213> ORGANISM: Homo sapiens

<400> SEQUENCE: 216

```
tttttttgga tttcataaaa tgattttaat agaaaagtac aagatatgaa caaaataaa       60 taatctttat ctcatttcta gcccagcaaa ttgtacactg catataaaaa tggtctaaga     120
tgcaattttc ctccattcct tttttgcttt taaaatactg agacagcatt ttaattcaat     180
attctaggtt caaactgata cattaaaaaa aaatcatacc aacctttaat cattctacat     240
ccatttttta agttagctta acaagatgat gtttcactaa aataaaatat ccaatcatca     300
gattaaagtg taaagtttgt gtgaacaggg aaattagatt catttctcta agttttaatt     360
cc                                                                    362
```

<210> SEQ ID NO 217
<211> LENGTH: 490
<212> TYPE: DNA
<213> ORGANISM: Homo sapiens
<220> FEATURE:
<221> NAME/KEY: misc_feature
<222> LOCATION: 437
<223> OTHER INFORMATION: n = A,T,C or G

<400> SEQUENCE: 217

```
tgaatgaggc aacaaaagca gagatttatt gaaaatgaag gtacacttca cagggtggga      60
gtggcttgag caagtggttc aagagcctgg ttaccgaatt ttttgggggt taaatatcct     120
ctagaggttt cccattggtt acttgatgta caccccttgta aatgaagtag tgcccacaat     180
cagtctgatt ggttgaggga ggggacctat cagaggctga agcaagtttc aaagttacac     240
cctatgcaaa tctctgattg attgggaaaa ggctgaagtg aagttacaaa gttatactcc     300
tatgcaaatg aagacttggg cccatgacca gcctcattgg gttgtggaaa gggaccaatc     360
```

```
agaggtactt tcaatttttc catctaccat gcagaaaaag gttcgggggt gggggggttgc    420 caaagggaag ttagccnaac aaactcctga cctaccaaca gagggtccca gttgggtagg    480
ggggcctggg                                                            490
```

<210> SEQ ID NO 218
<211> LENGTH: 441
<212> TYPE: DNA
<213> ORGANISM: Homo sapiens
<220> FEATURE:
<221> NAME/KEY: misc_feature
<222> LOCATION: 153, 237, 252, 266, 290, 319
<223> OTHER INFORMATION: n = A,T,C or G

<400> SEQUENCE: 218

```
tctcaggagg tagaagcttt attatgacat cttcaaaaga caatcaaatc aatagacatt     60
tgctgagcac ctgctgtgtg caagcccgtg tagacagtag ggtccagtgt cccacgcatg    120
gctctcgaat ccccggggag aaaaatcaca tcngggggtca gggagttttg cgtggctgag    180
aacaaagtgg gtttctgaac atcaaagtgc aattcgcttt acggggcaaa ctccgangcc    240
cagccccgcg tnggggaagcc gcagcnggggc gggcccgctt cctggggctn gcggccgggg    300
tttctctaag ccgcacgcnt tgcgtggtgt tgcgggggcct ctcaagcaag cccggaagca    360
gcatccttga gctccggttg ttggagcgct gggacctctg gctgccgccc ccgcagcagc    420
agcaaccact actccgctgt c                                              441
```

METHODS AND SYSTEMS FOR PREDICTING CANCER OUTCOME

This application is a continuation-in-part of U.S. patent application Ser. No. 11/065,794, filed on Feb. 25, 2005 now abandoned, which in turn claims the benefit under 35 U.S.C. § 119(e) of U.S. Provisional Application No. 60/547,871, filed Feb. 25, 2004, each of which is incorporated by reference herein in its entirety.

GOVERNMENT SUPPORT

This invention was made with government support U01CA085052 and DAMD17-12-2-0051 awarded by the National Institutes of Health and the Army Research Office. The government has certain rights in this invention.

1. FIELD OF THE INVENTION

The invention relates to molecular markers that can be used for prognosis of colorectal cancer. The invention also relates to methods and computer systems for determining a prognosis of colorectal cancer in a colorectal cancer patient based on the molecular markers. The invention also relates to methods and computer systems for determining chemotherapy for a colorectal cancer patient and for enrolling patients in clinical trials.

2. BACKGROUND OF THE INVENTION

Ranked as the third most commonly diagnosed cancer and the second leading cause of cancer deaths in the United States (American Cancer Society, "Cancer facts and figures," Washington, D.C.: American Cancer Society (2000)), colon cancer is a deadly disease afflicting nearly 130,000 new patients yearly in the United States. Colon cancer is the only cancer that occurs with approximately equal frequency in men and women. There are several potential risk factors for the development of colon and/or rectal cancer. Known factors for the disease include older age, excessive alcohol consumption, sedentary lifestyle (Reddy, *Cancer Res.*, 41:3700-3705 (1981)), and genetic predisposition (Potter *J Natl Cancer Institute*, 91:916-932 (1999)).

Several molecular pathways have been linked to the development of colon cancer (see, for example, Leeman et al., *J Pathol.*, 201(4):528-34 (2003); Kanazawa et al., *Tumori.*, 89(4):408-11 (2003); and Notarnicola et al., *Oncol Rep.*, 10(6): 1987-91 (2003)), and the expression of key genes in any of these pathways may be affected by inherited or acquired mutation or by hypermethylation. A great deal of research has been performed with regard to identifying genes for which changes in expression may provide an early indicator of colon cancer or a predisposition for the development of colon cancer. Unfortunately, no research has yet been conducted on identifying specific genes associated with colorectal cancer and specific outcomes to provide an accurate prediction of prognosis.

Survival of patients with colon and/or rectal cancer depends to a large extent on the stage of the disease at diagnosis. Devised nearly seventy years ago (Dukes, 1932, J Pathol Bacteriol 35:323), the modified Dukes' staging system for colon cancer, discriminates four stages (A, B, C, and D), primarily based on clinicopathologic features such as the presence or absence of lymph node or distant metastases. Specifically, colonic tumors are classified by four Dukes' stages: A, tumor within the intestinal mucosa; B, tumor into muscularis mucosa; C, metastasis to lymph nodes and D, metastasis to other tissues. Of the systems available, the Dukes' staging system, based on the pathological spread of disease through the bowel wall, to lymph nodes, and to distant organ sites such as the liver, has remained the most popular. Despite providing only a relative estimate for cure for any individual patient, the Dukes' staging system remains the standard for predicting colon cancer prognosis, and is the primary means for directing adjuvant therapy.

The Dukes' staging system, however, has only been found useful in predicting the behavior of a population of patients, rather than an individual. For this reason, any patient with a Dukes A, B, or C lesion would be predicted to be alive at 36 months while a patient staged as Dukes D would be predicted to be dead. Unfortunately, application of this staging system results in the potential over-treatment or under-treatment of a significant number of patients. Further, Dukes' staging can only be applied after complete surgical resection rather than after a pre-surgical biopsy.

DNA array technologies have made it possible to monitor the expression level of a large number of genetic transcripts at any one time (see, e.g., Schena et al., 1995, *Science* 270:467-470; Lockhart et al., 1996, *Nature Biotechnology* 14:1675-1680; Blanchard et al., 1996, *Nature Biotechnology* 14:1649; Ashby et al., U.S. Pat. No. 5,569,588, issued Oct. 29, 1996). Of the two main formats of DNA arrays, spotted cDNA arrays are prepared by depositing PCR products of cDNA fragments with sizes ranging from about 0.6 to 2.4 kb, from full length cDNAs, ESTs, etc., onto a suitable surface (see, e.g., DeRisi et al., 1996, *Nature Genetics* 14:457-460; Shalon et al., 1996, *Genome Res.* 6:689-645; Schena et al., 1995, *Proc. Natl. Acad. Sci. U.S.A.* 93:10539-11286; and Duggan et al., *Nature Genetics Supplement* 21:10-14). Alternatively, high-density oligonucleotide arrays containing thousands of oligonucleotides complementary to defined sequences, at defined locations on a surface are synthesized in situ on the surface by, for example, photolithographic techniques (see, e.g., Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; McGall et al., 1996, *Proc. Natl. Acad. Sci U.S.A.* 93:13555-13560; U.S. Pat. Nos. 5,578,832; 5,556,752; 5,510,270; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123).

By simultaneously monitoring tens of thousands of genes, microarrays have permitted identification of biomarkers of cancer (Welsh et al., *PNAS*, 100(6):3410-3415 (March 2003)), creating gene expression-based classifications of cancers (Alzadeh et al., *Nature*, 403:513-11 (2000); and Garber et al., *Proc Natl Acad Sci USA*, 98:13784-9 (2001); development of gene based multi-organ cancer classifiers (Bloom et al, Am J Pathol 164:9-16, 2004; Giordano et al., *Am J Pathol*, 159:1231-8 (2001); Ramaswamy et al., *Proc Natl Acad Sci USA*, 98:15149-54 (2001); and Su et al., *Cancer Res*, 61:7388-93 (2001)), identification of tumor subclasses (Dyrskjot et al., *Nat Genet*, 33:90-6 (2003); Bhattacharjee et al., *Proc Natl Acad Sci USA*, 98:13790-5 (2001); Garber et al., *Proc Natl Acad Sci USA*, 98:13784-9. (2001); and Sorlie et al., *Proc Natl Acad Sci USA*, 98:10869-74 (2001)), discovery of progression markers (Sanchez-Carbayo et al., *Am J Pathol*, 163:505-16 (2003); and Frederiksen et al., *J Cancer Res Clin Oncol*, 129:263-71 (2003));

and prediction of disease outcome (Henshall et al., *Cancer Res*, 63:4196-203 (2003); Shipp et al., *Nat Med*, 8:68-74 (2002); Beer et al., *Nat Med*, 8:816-24 (2002); Pomeroy et al., *Nature*, 415:436-42 (2002); van't Veer et al., *Nature*, 415:530-6 (2002); Vasselli et al., *Proc Natl Acad Sci USA*, 100:6958-63 (2003); Takahashi et al., *Proc Natl Acad Sci USA*, 98:9754-9 (2001); WO 2004/065545 A2; WO 02/103320 A2)); and in drug discovery (Marton et al., *Nat Med*, 4(11):1293-301 (1998); and Gray et al., *Science*, 281:533-538 (1998)).

One tool that has been applied to microarrays to decipher and compare genome expression patterns in biological systems is Significance Analysis of Microarrays, or SAM (Tusher et al., 2001, *Proc. Natl. Acad. Sci.* 98:5116-5121). This statistical method was developed as a cluster tool for use in identifying genes with statistically significant changes in expression. SAM has been used for a variety of purposes, including identifying potential drugs that would be effective in treating various conditions associated with specific gene expressions (Bunney et al., *Am J Psychiatry*, 160(4):657-66 (April 2003)).

Sophisticated and powerful machine learning algorithms have been applied to transcriptional profiling analysis. For example, a modified "Fisher classification" approach has been applied to distinguish patients with good prognosis from those who do not have a good prognosis, based on their expression profiles (van't Veer et al., 2002, Nature 415: 530-6). A similar study has been reported using an artificial neural network (Bloom et al, Am J Pathol 164:9-16, 2004; Khan et al., 2001, Nat Med 7: 673-9). Support Vector Machine (SVM) (see, e.g., Brown et al., *Proc. Natl. Acad. Sci.* 97(1):262-67 (2000); Zien et al., *Bioinformatics*, 16(9): 799-807 (2000); Furey et al., *Bioinformatics*, 16(10):906-914 (2000)) is a correlation tool shown to perform well in multiple areas of biological analysis, including evaluating microarray expression data (Brown et al, *Proc Natl Acad Sci USA*, 97:262-267 (2000)), detecting remote protein homologies (Jaakkola et al., *Proceedings of the 7th International Conference on Intelligent Systems for Molecular Biology*, AAAI Press, Menlo Park, Calif. (1999)), and classification of cancer tissues (Furey et al., *Bioinformatics*, 16(10):906-914 (2000)). Furey describes using SVM to classify colon cancer tissues based on expression levels of a set of 2000 genes or a set of 1000 genes having the highest minimal intensity across 60 colon tissue samples (40 tumors and 22 normal tissues) on an Affymetrix® oligonucleotide microarray.

Wang et al. (Wang et al., 2004, J. Clinical Oncology 22:1564-1571) reported identification of a 60-gene and a 23-gene signature for prediction of cancer recurrence in Dukes' B patients using an Affymetrix® U133a GeneChip. This signature was validated in 36 independent patients. Two supervised class prediction approaches were used to identify gene markers that could best discriminate between patients who would experience relapse and patients who would remain disease-free. A multivariate Cox model was built to predict recurrence. The overall performance accuracy was reported as 78%.

Resnick et al. (Resnick et al., 2004, Clin. Can. Res. 10:3069-3075) reported a study of the prognostic value of epidermal growth factor receptor, c-MET, b-catenin, and p53 protein expression in TNM stage II colon cancer using tissue microarray technology.

Muro et al. (Muro et al., 2003, Genome Biology 4:R21) describes identification and analysis of the expression levels of 1,536 genes in colorectal cancer and normal tissues using a parametric clustering method. Three groups of genes were discovered. Some of the genes were shown to not only correlate with the differences between tumor and normal tissues but also the presence and absence of distant metastasis.

U.S. Patent Application Publication No. 2005/0048542A1, published on Mar. 3, 2005, describes a noninvasive, quantitative test for prognosis determination in cancer patients. The test makes use of measurements of the tumor levels of certain messenger RNAs (mRNAs). These mRNA levels are inserted into a polynomial formula (algorithm) that yields a numerical recurrence score, which indicates recurrence risk.

Discussion or citation of a reference herein shall not be construed as an admission that such reference is prior art to the present invention.

3. SUMMARY OF THE INVENTION

The invention provides a method for determining a prognosis of colorectal cancer in a colorectal cancer patient, comprising classifying said patient as having a good prognosis or a poor prognosis using measurements of a plurality of gene products in a cell sample taken from said patient, said gene products being respectively products of at least 5 of the genes listed in Table 1, or in any of Tables 2-5, 7, and 8 or any subset of these tables, or respective functional equivalents thereof, wherein said good prognosis predicts survival of a patient within a predetermined time period from obtaining a tumor sample from said patient by surgery or from diagnosis of colorectal cancer, and said poor prognosis predicts non-survival of a patient within said time period. In a specific embodiment, the predetermined time period is not 3 years. For example, in one embodiment, the predetermined time period is longer than 3 years. In other embodiments, the time period is 4 or 5 years or is between 3 and 5 years. In another particular embodiment, measurements of gene products of all or in the range of 8 to 19, in the range of 21 to 25, in the range of 27 to 42, in the range of 44 to 52, or in the range of 54 to 130 of the genes listed in Table 1 are used. In yet another embodiment, both the predetermined time period and the number of genes is as described in these embodiments.

The invention also provides a method for evaluating whether a colorectal cancer patient should be treated with chemotherapy, comprising (a) classifying said patient as having a good prognosis or a poor prognosis using any one of the prognosis methods of the invention; and (b) determining that said patient's predicted survival time favors treatment of the patient with chemotherapy if said patient is classified as having a poor prognosis.

The invention also provides a method for enrolling colorectal cancer patients for a clinical trial of a chemotherapeutic agent for colorectal cancer, comprising (a) classifying each patient as having a good prognosis or a poor prognosis using any one of the prognosis methods of the invention; and (b) assigning each patient having a good prognosis to one patient group and each patient having a poor prognosis to another patient group, at least one of said patient group being enrolled in said clinical trial.

The invention also provides a method for identifying a set of genes for prognosis of colorectal cancer, comprising: (a) determining for each of a plurality of genes a metric of correlation between abundance level of a gene product of said gene and survival outcome in a plurality of colorectal cancer patients having known outcomes at a predetermined time after obtaining tumor samples; and (b) selecting one or more genes based on said metric of correlation.

In another embodiment, the invention provides a method for identifying a set of genes for prognosis of colorectal cancer, comprising: (a) generating a subset of patients by leaving out one or more patients in a plurality of patients having known outcomes at a predetermined time after obtaining tumor samples; (b) determining for each of a plurality of genes a metric of correlation between abundance level of said gene and survival outcome in said subset of colorectal cancer patients having known outcomes at a predetermined time after obtaining tumor samples; (c) selecting one or more genes based on said metric of correlation; (d) repeating steps (a)-(c) for a plurality of iterations, each with a different subset of patients by leaving out one or more patients in said plurality, wherein said one or more patients are different from any previous iteration; and (e) selecting one or more genes that are selected in at least a predetermined percentage of all iterations.

Also provided is a method of identifying genes that discriminate between colorectal cancer patients that have a poor prognosis and colorectal patients that have a good prognosis comprising analyzing survival data and RNA levels of colorectal patients using SAM, clustering analysis, or a neural network to select genes whose RNA levels correlate with a selected survival time.

The invention further provides a method for constructing a prognosis predictor for prognosis of colorectal cancer, comprising: (a) generating a subset of patients by leaving out one or more patients in a plurality of patients having known outcomes at a predetermined time after obtaining tumor samples; (b) determining for each of a plurality of genes a metric of correlation between expression level of said gene and survival outcome in a plurality of colorectal cancer patients having known outcomes at a predetermined time after obtaining tumor samples from a plurality of colorectal cancer patients having known outcomes at a predetermined time after obtaining tumor samples; (c) selecting one or more genes based on said metric of correlation; (d) training a prognosis predictor, wherein said prognosis predictor receives an input comprising a marker profile comprising expression levels of said one or more genes selected in step (c) and provides an output comprising data indicating a good prognosis or a poor prognosis, with training data from said subset of patients, wherein said training data comprise for each of said subset of patients a marker profile comprising measurements of said one or more genes in a tumor cell sample taken from said patient and prognosis information; (e) determining a prognosis for at least one of said one or more patients who are left out in step (a); (f) repeating steps (a)-(e) for a plurality of iterations, each with a different subset of patients by leaving out one or more patients in said plurality, wherein said one or more patients are different from any previous iteration; (g) selecting one or more genes that are selected in at least a predetermined percentage of all iterations; and (h) training a prognosis predictor, wherein said prognosis predictor receives an input comprising a marker profile comprising expression levels of said one or more genes selected in step (g) and provides an output comprising data indicating a good prognosis or a poor prognosis, with training data from said subset of patients, wherein said training data comprise for each of said plurality of patients a marker profile comprising measurements of said one or more genes in a tumor cell sample taken from said patient and prognosis information.

The invention also provides a computer system comprising a processor, and a memory coupled to said processor and encoding one or more programs, wherein said one or more programs cause the processor to carry out any of the methods of the invention.

The invention further provides a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out any of the methods of the invention.

In another embodiment, the invention provides a microarray comprising for each of a plurality of genes, said genes being at least 5 of the genes listed in Table 1, one or more polynucleotide probes complementary and hybridizable to a sequence in said gene, wherein polynucleotide probes complementary and hybridizable to said genes constitute at least 50% of the probes on said microarray. In one embodiment, the invention provides a kit comprising the microarray of the invention in a sealed container.

4. BRIEF DESCRIPTION OF THE DRAWINGS

FIG. 1A shows cluster analysis of the 53 SAM selected genes. Darker levels represent over-expressed genes relative to (lighter levels) under-expressed genes. The data suggest that genes can be identified that discriminate good from poor prognosis. FIG. 1B shows that cluster analysis of SAM selected genes, grouped by Dukes' stage B and C, does not demonstrate a discriminating pattern.

Figure 4:
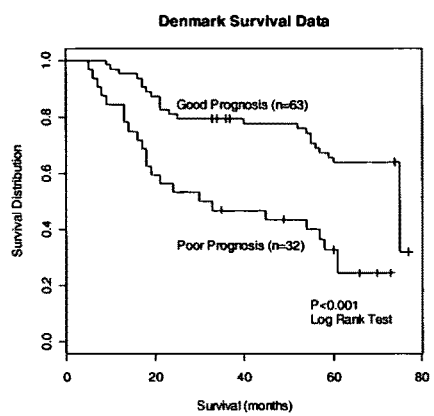
Figure 4:
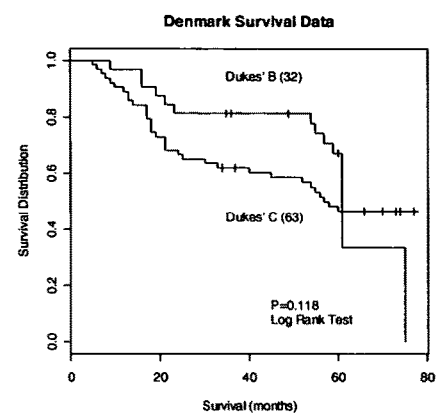
Figure 4:
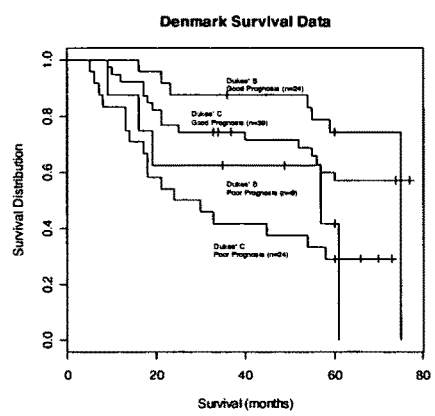

FIGS. 4A-4C show an independent Test Set Evaluation (Denmark Test Set) using the U133A data set. A) Survival curves generated using probe sets corresponding to 26 of the Molecular Classifier genes. Using these translated probe sets, 95 tumors were clustered and censored survivorship was evaluated (P<0.001). B) Survival curves using Dukes' staging criteria show no significant difference in outcome. C) Survival curves grouped by both Dukes' stage and molecular signature show that both Dukes' B and C cases can be further subdivided into good and poor prognosis groups.

Figure 5:
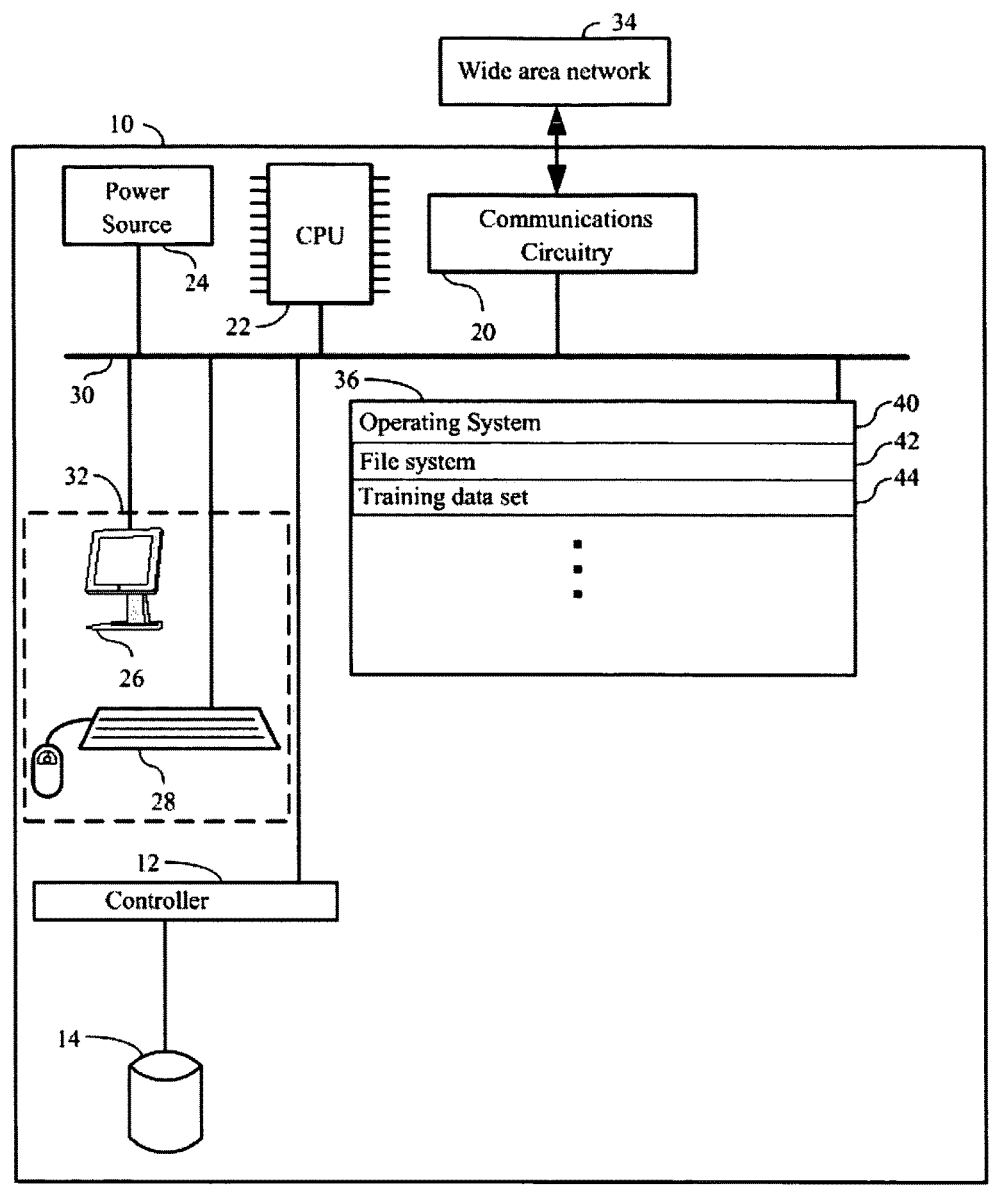

FIG. 5 details an exemplary computer system that supports the functionality described herein.

5. DETAILED DESCRIPTION OF THE INVENTION

The invention provides markers, i.e., genes, the expression levels of which discriminate between a good prognosis and a poor prognosis for colorectal cancer. The identities of these markers and the measurements of their respective gene products, e.g., measurements of levels (abundances) of their encoded mRNAs or proteins, can be used by application of a pattern recognition algorithm to develop a prognosis predictor that discriminates between a good and poor prognosis in colorectal cancer using measurements of such gene products in a sample from a patient. Colorectal cancer includes colon cancer and rectal cancer. Such molecular markers, the expression levels of which can be used for prognosis of colorectal cancer in a colorectal cancer patient, are listed in Table 1, infra. Measurements of gene products of these molecular markers, as well as of their functional equivalents, can be used for prognosis of colorectal cancer. A functional equivalent with respect to a gene, designated as gene A, refers to a gene that encodes a protein or mRNA that at least partially overlaps in physiological function in the cell to that of the protein or mRNA encoded by gene A. In particular, prognosis of colorectal cancer in a colorectal cancer patient is carried out by a method comprising classifying the patient as having a good or poor prognosis based on a profile of measurements (e.g., of the levels) of gene products of (i.e., encoded by) at least 5, 10, 20, 30, 40, 50, 60, 70, 80, or 100 of the genes in Table 1 or in any of Tables 2-5, 7, and 8 or any subset of Tables 2-5, 7, and 8, or functional equivalents of such genes; or of at least 2%, 5%, 10%, 20%, 30%, 40%, 50%, 60%, 70%, 80%, or 90% of the genes in Table 1 or in any of Tables 2-5, 7, and 8 or any subset of Tables 2-5, 7, and 8, or functional equivalents of such genes; or all or in the range of 8 to 19, in the range of 21 to 25, in the range of 27 to 42, in the range of 44 to 52, or in the range of 54 to 130 of the genes listed in Table 1 or in any of Tables 2-5, 7, and 8 or any subset of Tables 2-5, 7, and 8, or functional equivalents of such genes, in an appropriate cell sample from the patient, e.g., a tumor cell sample obtained from biopsy or after surgical resection. Preferably, the tumor sample is contaminated with less than 50%, 40%, 30%, 20%, or 10% of normal cells. Such a profile of measurements is also referred to herein as an "expression profile." In some embodiments, "at least some of the genes listed" in a table refers to at least 5, 10, 20, 40, 50, 70 or 100 of the genes listed in the table. In other embodiments, 26, 43, or 53 genes from Table 1 are used. In still another embodiment, all or in the range of 8 to 19, in the range of 21 to 26, in the range of 27 to 42, in the range of 44 to 52, or in the range of 54 to 130 of the genes listed in Table 1 are used. Different subcombination of genes from Table 1 may be used as the marker set to carry out the prognosis methods of the invention. For example, in various embodiments, the markers that are the genes listed in Table 2, 3, 4, 5, 7 or 8 are used.

In a preferred embodiment, the plurality of gene products for which measurements are used according to the invention comprises gene products of osteopontin and neuregulin 2 isoform 4, respectively.

In a specific embodiment, the classifying of the patient as having good or poor prognosis is carried out using measurements of gene products of less than 30, 40, 50, 70, 100, 200, 300, 400, or 500 total genes, in which all or at least 20%, 30%, 40%, 50%, 60%, 70%, 80%, or 90% of the genes are from Table 1 or any of Tables 2-5, 7, and 8 their functional equivalents, or at least 5, 10, 20, 30, 40, 50, 60, 70, 80, or 100 of the genes are from Table 1 or any of the Tables 2-5, 7, and 8 or their functional equivalents, or in the range of 8 to 19, or in the range of 21 to 25, in the range of 27 to 42, in the range of 44 to 52, or in the range of 54 to 130 of the genes listed in Table 1 or any of the Tables 2-5, 7, and 8 or their functional equivalents.

The measurements in the profiles of the gene products that are used can be any suitable measured values representative of the expression levels of the respective genes. The measurement of the expression level of a gene can be direct or indirect, e.g., directly of abundance levels of RNAs or proteins or indirectly, by measuring abundance levels of cDNAs, amplified RNAs or DNAs, proteins, or activity levels of RNAs or proteins, or other molecules (e.g., a metabolite) that are indicative of the foregoing. In one embodiment, the profile comprises measurements of abundances of the transcripts of the marker genes. The measurement of abundance can be a measurement of the absolute abundance of a gene product. The measurement of abundance can also be a value representative of the absolute abundance, e.g., a normalized abundance value (e.g., an abundance normalized against the abundance of a reference gene product) or an averaged abundance value (e.g., average of abundances obtained at different time points or from different tumor cell samples from the patients, or average of abundances obtained using different probes, etc.), or a combination of both. As an example, the measurement of abundance of a gene transcript can be a value obtained using an Affymetrix® GeneChip® to measure hybridization to the transcript.

In another embodiment, the expression profile is a differential expression profile comprising differential measurements of a plurality of transcripts in a sample derived from the patient versus measurements of the plurality of transcripts in a reference sample, e.g., a cell sample of normal cells. Each differential measurement in the profile can be but is not limited to an arithmetic difference, a ratio, or a log(ratio). As an example, the measurement of abundance of a gene transcript can be a value for the transcript obtained using a cDNA array in a two-color measurement.

The invention also provides methods and systems for predicting prognosis of colorectal cancer in a colorectal cancer patient based on a measured marker profile comprising measurements of the markers of the present invention, e.g., an expression profile comprising measurements of transcripts of at least some of the genes listed in Table 1, e.g., at least 5, 10, 20, 30, 40, 50, 60, 70, 80, or 100 or in the range of 8 to 19, in the range of 21 to 25, in the range of 27 to 42, in the range of 44 to 52, or in the range of 54 to 130 of the genes in Table 1 or funtional equivalents of such genes. The methods and systems of the invention use a prognosis predictor (also termed herein a "classifier") for predicting prognosis. The prognosis predictor can be based on any appropriate pattern recognition method (such as those described in Section 5.4) that receives an input comprising a marker profile and provides an output comprising data indicating a good prognosis or a poor prognosis. The prognosis predictor is trained with training data from a plurality of colorectal cancer patients for whom marker profiles and prognosis outcomes are known. The plurality of patients used for training the prognosis predictor is also referred to herein as the training population. The training data comprise for each patient in the training population (a) a marker profile comprising measurements of gene products of a plurality of genes, respectively, in an appropriate cell sample, e.g., a tumor cell sample, taken from the patient; and (b) prognosis outcome information (i.e., information regarding whether or not survival occurred over a predetermined time period, for example, from diagnosis or from surgical resection of the cancer). Various prognosis predictors that can be used in conjunction with the present invention are described in Section 5.3., infra. In preferred embodiments, an artificial neural network or a support vector machine is used as the prognosis predictor. In some embodiments, additional patients having known marker profiles and prognosis outcomes can be used to test the accuracy of the prognosis predictor obtained using the training population. Such additional patients are also called "the testing population."

The markers in the marker sets are selected based on their ability to discriminate prognosis of colorectal cancer in a plurality of colorectal cancer patients for whom the prognosis outcomes are known. Various methods can be used to evaluate the correlation between marker levels and cancer prognosis. For example, genes whose expression levels are significantly different in tumor samples from patients who exhibit good prognosis and in tumor samples from patients who exhibit poor prognosis can be identified using an appropriate statistical method, e.g., t-test or significance analysis of microarray (SAM).

As used herein, a good prognosis predicts survival of a patient within a predetermined time period from surgical removal of tumor or from diagnosis of colorectal cancer, and a poor prognosis predicts non-survival of a patient within the time period. The predetermined time period is preferably 2, 3, 4, or 5 years. In a specific embodiment, the predetermined time period is not 3 years. For example, in one embodiment, the predetermined time period is longer than 3 years. In other embodiments, the time period is 4 or 5 years or is between 3 and 5 years.

5.1. Diagnostic and Prognostic Marker Sets

The invention provides molecular marker sets (of genes) that can be used for prognosis of colorectal cancer in a colorectal cancer patient based on a profile of the markers in the marker set (containing measurements of marker gene products). Table 1 lists markers that can be used to discriminate between good and poor prognosis of colorectal cancer according to the method of the invention.

TABLE 1

Marker genes that can be used for prognosis of colorectal cancer

| GenBank ID | UNIGENE ID | Description | SEQ ID NO |
|---|---|---|---|
| AA001604 | Hs.204840 | null | 1 |
| AA007421 | Hs.113992 | candidate tumor suppressor protein {Homo sapiens} | 2 |
| AA016210 | Hs.24920 | null | 3 |
| AA017301 | Hs.60796 | artifact-warning sequence (translated ALU class C) - human | 4 |
| AA036727 | Hs.180236 | null | 5 |
| AA045075 | Hs.62751 | syntaxin 7 | 6 |
| AA045308 | Hs.7089 | insulin induced protein 2; INSIG-2 membrane protein | 7 |
| AA045793 | Hs.6790 | hypothetical protein; MDG1; similar to putative microvascular endothelial differentiation gene 1; similar to X98993 (PID:g1771560); microvascular endothelial differentiation gene 1 product; microvascular endothelial differentiation gene 1; DKFZP564F1862 p | 8 |
| AA046406 | Hs.100134 | unnamed protein product [Homo sapiens]; hypothetical protein FLJ12787 [Homo sapiens] | 9 |
| AA071075 | Hs.25523 | Alu subfamily SP sequence contamination warning entry. [Human] {Homo sapiens} | 10 |
| AA121778 | Hs.95685 | null | 11 |
| AA121806 | Hs.84564 | Rab3c; hypothetical protein BC013033 | 12 |
| AA130669 | Hs.16420 | SH3 domain-binding protein SNP70; Npw38-binding protein NpwBP; Npw38-binding protein NpwBP [Homo sapiens]; Unknown (protein for IMAGE:3448162) [Homo sapiens]; WW domain binding protein 11; SH3 domain-binding protein SNP70; Npw38-binding protein NpwBP [Hom | 13 |
| AA132065 | Hs.109144 | unknown; SMAP-5; Similar to hypothetical protein AF140225 | 14 |
| AA133215 | Hs.32989 | Receptor activity-modifying protein 1 precursor (CRLR activity-modifying-protein 1) | 15 |

TABLE 1-continued

Marker genes that can be used for prognosis of colorectal cancer

| GenBank ID | UNIGENE ID | Description | SEQ ID NO |
|---|---|---|---|
| AA148578 | Hs.110956 | KOX 13 protein (56 AA) | 16 |
| AA149253 | Hs.107987 | N/A | 17 |
| AA167823 | Hs.112058 | CD27BP {Homo sapiens} | 18 |
| AA181643 | Hs.167791 | reticulocalbin 1, EF-hand calcium binding domain; reticulocalbin 1, EF-hand calcium binding domain [Homo sapiens] | 19 |
| AA256304 | Hs.172648 | Unknown (protein for MGC:9448) [Homo sapiens]; distal-less homeo box 7 [Homo sapiens]; distal-less homeobox 4, isoform a; beta protein 1 [Homo sapiens] | 20 |
| AA258031 | Hs.125104 | unnamed protein product; MUS81 endonuclease | 21 |
| AA279188 | Hs.86947 | disintegrin and metalloprotease domain 8 precursor | 22 |
| AA283062 | Hs.73986 | Similar to CDC-like kinase 2 {Homo sapiens} | 23 |
| AA284172 | Hs.89385 | NPAT; predicted amino acids have three regions which share similarity to annotated domains of transcriptional factor oct-1, nucleoluscytoplasm shuttle phosphoprotein and protein kinases; NPAT; nuclear protein, ataxia-telangiectasia locus; Similar to nuc | 24 |
| AA411324 | Hs.67878 | interleukin- 13 receptor; interleukin-13 receptor; interleukin 13 receptor,alpha 1 [Homo sapiens]; Similar to interleukin 13 receptor, alpha 1 [Homo sapiens]; bB12804.2.1 (interleukin 13 receptor, alpha 1) [Homo sapiens]; interleukin 13 receptor, alpha 1 | 25 |
| AA416759 | Hs.239760 | Unknown (protein for MGC:2503) [Homo sapiens]; unnamed protein product [Homo sapiens] | 26 |
| AA418410 | Hs.9880 | cyclophilin; U-snRNP-associated cyclophilin; peptidyl prolyl isomerase H (cyclophilin H) [Homo sapiens] | 27 |
| AA418726 | Hs.4764 | null | 28 |
| AA425320 | Hs.250461 | hypothetical protein; MDG1; similar to putative microvascular endothelial differentiation gene 1; similar to X98993 (PID:g1771560); microvascular endothelial differentiation gene 1 product; microvascularendothelial differentiation gene 1; DKFZP564F1862 p | 29 |
| AA431885 | Hs.5591 | MAP kinase-interacting serine/threonine kinase 1; MAP kinase interacting kinase 1 [Homo sapiens] | 30 |
| AA432030 | Hs.179972 | Interferon-induced protein 6-16 precursor (Ifi-6-16). [Human] {Homo sapiens} | 31 |

TABLE 1-continued

Marker genes that can be used for prognosis of colorectal cancer

| GenBank ID | UNIGENE ID | Description | SEQ ID NO |
|---|---|---|---|
| AA437223 | Hs.46640 | adult retina protein | 32 |
| AA448261 | Hs.139800 | high mobility group AT-hook 1 isoform b; nonhistone chromosomal high-mobility group protein HMG-I/HMG-Y [Homo sapiens] | 33 |
| AA448641 | Hs.108371 | transcription factor; E2F transcription factor 4; p107/p130-binding protein | 34 |
| AA449359 | Hs.178100 | null | 35 |
| AA450205 | Hs.8146 | translocation protein-1; Sec62; translocation protein 1; Dtrp1 protein; membrane protein SEC62, S. cerevisiae, homolog of [Homo sapiens]; | 36 |
| AA451865 | Hs.174139 | unnamed protein product {Homo sapiens} | 37 |
| AA452130 | Hs.28219 | Alu subfamily SX sequence contamination warning entry. [Human] {Homo sapiens} | 38 |
| AA453508 | Hs.168075 | transportin; karyopherin (importin) beta 2; M9 region interaction protein | 39 |
| AA453790 | Hs.255585 | null | 40 |
| AA457267 | Hs.70669 | P19 protein; HMP19 protein | 41 |
| AA457528 | Hs.22979 | unnamed protein product [Homo sapiens]; hypothetical protein FLJ13993 [Homo sapiens]; FLJ00167 protein [Homo sapiens] | 42 |
| AA458926 | Hs.163724 | HSPC019 protein; Unknown (protein for MGC:27309) [Homo sapiens]; unnamed protein product [Homo sapiens]; grey-lethal osteopetrosis [Homo sapiens]; | 43 |
| AA460542 | Hs.121849 | microtubule-associated proteins 1A/1B light chain 3; microtubuleassociated proteins 1A/1B light chain 3; microtubule-associated proteins 1A/1B light chain 3 [Homo sapiens]; microtubule-associated proteins 1A/1B light chain 3 [Homo sapiens] | 44 |
| AA464612 | Hs.190161 | PTD017;HSPC183;PTD017 protein [Homo sapiens]; mitochondrial ribosomal protein S18B; mitochondrial ribosomal protein S18-2; mitochondrial 28S ribosomal protein S18-2 [Homo sapiens] | 45 |
| AA477404 | Hs.125262 | hypothetical protein; unnamed protein product; GL003; AAAS protein; adracalin; aladin | 46 |
| AA478952 | Hs.91753 | unnamed protein product; hypothetical protein [Homo sapiens];unnamed protein product [Homo sapiens]; hypothetical protein [Homo sapiens] | 47 |
| AA479270 | Hs.250802 | Diff33 protein homolog; KIAA1253 protein | 48 |

TABLE 1-continued

Marker genes that can be used for prognosis of colorectal cancer

| GenBank ID | UNIGENE ID | Description | SEQ ID NO |
|---|---|---|---|
| AA479952 | Hs.154145 | Alu subfamily SX sequence contamination warning entry. [Human] {Homo sapiens} | 49 |
| AA481250 | Hs.154138 | chitinase precursor; chitinase 3-like 2; chondrocyte protein 39; chitinase 3-like 2 [Homo sapiens] | 50 |
| AA481507 | Hs.159492 | unnamed protein product [Homo sapiens] | 51 |
| AA482110 | Hs.4900 | Unknown gene product; PRO0915; CUA001; hypothetical protein [Homo sapiens]; hypothetical protein [Homo sapiens] | 52 |
| AA485450 | Hs.132821 | flavin containing monooxygenase 2; flavin containing monooxygenase 2 [Homo sapiens] | 53 |
| AA485752 | Hs.9573 | ATP-binding cassette, sub-family F, member 1; ATP-binding cassette 50; ATP-binding cassette, sub-family F (GCN20), member 1 [Homo sapiens]; | 54 |
| AA486228 | Hs.181271 | HSPC181; CGI-120 protein; zeta1-COP; CGI-120 protein [Homo sapiens] | 55 |
| AA486233 | Hs.2707 | G1 to S phase transition 1 | 56 |
| AA487274 | Hs.48950 | heptacellular carcinoma novel gene-3 protein; DAPPER 1 | 57 |
| AA488652 | Hs.4209 | HSPC235; ribosomal protein L2; Similar to ribosomal protein, mitochondrial, L2 [Homo sapiens]; mitochondrial ribosomal protein L37; ribosomal protein, mitochondrial, L2 [Homo sapiens] | 58 |
| AA490493 | Hs.24340 | null | 59 |
| AA490925 | Hs.22464 | LAFPTPase; laforin; epilepsy, progressive myoclonus type 2, Lafora disease (laforin); epilepsy, progressive myoclonic epilepsy, type 2 gene; Lafora disease gene (laforin); Laforin [Homo sapiens] | 60 |
| AA504266 | Hs.8217 | nuclear protein SA-2; bA517O1.1 (similar to SA2 nuclear protein); hypothetical protein [Homo sapiens]; stromal antigen 2 [Homo sapiens] | 61 |
| AA504342 | Hs.7763 | null | 62 |
| AA504785 | Hs.211608 | nuclear pore complex protein hnup153; nucleoporin 153 kDa; nuclear pore complex protein hnup153 [Homo sapiens] | 63 |
| AA521434 | Hs.155024 | B-cell lymphoma 6 protein; B-cell CLL/lymphoma-6; cys-his2 zinc finger transcription factor BCL5; zinc finger protein 51; lymphoma-associated zinc finger gene on chromosome 3 [Homo sapiens] | 64 |

TABLE 1-continued

Marker genes that can be used for prognosis of colorectal cancer

| GenBank ID | UNIGENE ID | Description | SEQ ID NO |
|---|---|---|---|
| AA598659 | Hs.168516 | NuMA protein {Homo sapiens} | 65 |
| AA598970 | Hs.7918 | unnamed protein product; hypothetical protein; dJ453C12.6.2 (uncharacterized hypothalamus protein (isoform 2)); hypothetical protein [Homo sapiens]; uncharacterized hypothalamus protein HSMNP1 [Homo sapiens] | 66 |
| AA626316 | Hs.90020 | unnamed protein product {Homo sapiens} | 67 |
| AA630376 | Hs.8121 | null | 68 |
| AA633845 | Hs.192156 | null | 69 |
| AA634261 | Hs.25035 | null | 70 |
| AA664240 | Hs.8454 | artifact-warning sequence (translated ALU class C) - human | 71 |
| AA676797 | Hs.1973 | cyclin F | 72 |
| AA677254 | Hs.52002 | CT-2; CD5 antigen-like (scavenger receptor cysteine rich family); bA120D12.1 (CD5 antigen-like (scavenger receptor cysteine rich family)) [Homo sapiens]; CD5 antigen-like (scavenger receptor cysteine rich family) [Homo sapiens] | 73 |
| AA680132 | Hs.55235 | sphingomyelin phosphodiesterase 2, neutral membrane (neutral sphingomyelinase); Unknown (protein for MGC:1617) [Homo sapiens] | 74 |
| AA682585 | Hs.193822 | null | 75 |
| AA682905 | Hs.8004 | huntingtin-associated protein interacting protein | 76 |
| AA694500 | Hs.116328 | hypothetical protein MGC33414; Similar to PR domain containing 1, with ZNF domain | 77 |
| AA699408 | Hs.168103 | prp28, U5 snRNP 100 kd protein; prp28, U5 snRNP 100 kd protein [Homo sapiens] | 78 |
| AA701167 | Hs.191919 | Alu subfamily SB sequence contamination warning entry. [Human] {Homo sapiens} | 79 |
| AA702174 | Hs.75263 | pRb-interacting protein RbBP-36 | 80 |
| AA702422 | Hs.66521 | josephin MJD1; super cysteine rich protein; SCRP | 81 |
| AA703019 | Hs.114159 | small GTP-binding protein; RAB-8b protein; Unknown (protein for MGC:22321) [Homo sapiens] | 82 |
| AA704270 | Hs.189002 | Null | 83 |
| AA704613 | Hs.7647 | Similar to MYC-associated zinc finger protein (purine-binding transcription factor) [Homo sapiens] | 84 |
| AA705040 | Hs.119646 | Alu subfamily J sequence contamination warning entry. [Human] {Homo sapiens} | 85 |

TABLE 1-continued

Marker genes that can be used for prognosis of colorectal cancer

| GenBank ID | UNIGENE ID | Description | SEQ ID NO |
|---|---|---|---|
| AA706041 | Hs.170253 | unnamed protein product [Homo sapiens]; hypothetical protein FLJ23282 [Homo sapiens];; | 86 |
| AA706226 | Hs.113264 | neuregulin 2 isoform 4 | 87 |
| AA709158 | Hs.42853 | put. DNA binding protein; put. DNA binding protein; cAMP responsive element binding protein-like 1; Creb-related protein | 88 |
| AA725641 | Hs.154397 | WD-repeat protein | 89 |
| AA757564 | Hs.13214 | Probable G protein-coupled receptor GPR27 (Super conserved receptor expressed in brain 1). [Human] | 90 |
| AA773139 | Hs.66103 | null | 91 |
| AA775616 | Hs.313 | OPN-b; osteopontin; secreted phosphoprotein 1 (osteopontin, bone sialoprotein I, early T-lymphocyte activation 1) | 92 |
| AA775865 | Hs.7579 | KIAAL192 protein; HSPC273; unnamed protein product; hypothetical protein FLJ10402 [Homo sapiens]; unnamed protein product [Homo sapiens]; hypothetical protein FL110402 [Homo sapiens]; hypothetical protein [Homo sapiens]; unnamed protein product [Homo sapiens] | 93 |
| AA775888 | Hs.163151 | null | 94 |
| AA776813 | Hs.191987 | hypothetical protein {Macaca fascicularis | 95 |
| AA777050 | Hs.186566 | Unknown (protein for IMAGE:4154275) [Homo sapiens]; Unknown (protein for IMAGE:4421249) [Homo sapiens] | 96 |
| AA777192 | Hs.47062 | RNA Polymerase II subunit 14.5 kD; DNA directed RNA polymerase II polypeptide I; DNA directed RNA polymerase II 14.5 kda polypeptide [Homo sapiens]; polymerase (RNA) II (DNA directed) polypeptide I (14.5 kD) [Homo sapiens] | 97 |
| AA777892 | Hs.121939 | Null | 98 |
| AA826237 | Hs.3426 | Era GTPase A protein; conserved ERA-like GTPase [Homo sapiens]; ERA-W [Homo sapiens]; Era G-protein-like 1; GTPase, human homolog of E. coli essential cell cycle protein Era; era (E. coli Gprotein homolog)-like 1 [Homo sapiens] | 99 |
| AA844864 | Hs.4158 | regenerating protein I beta; regenerating islet-derived 1 beta precursor; lithostathine 1 beta; regenerating protein I beta; secretory pancreatic stone protein 2 [Homo sapiens] | 100 |
| AA862465 | Hs.71 | zinc-alpha2-glycoprotein precursor; Zn-alpha2-glycoprotein; Znalpha2-glycoprotein; alpha-2-glycoprotein 1, zinc; alpha-2-glycoprotein 1, zinc [Homo sapiens];; | 101 |

TABLE 1-continued

Marker genes that can be used for prognosis of colorectal cancer

| GenBank ID | UNIGENE ID | Description | SEQ ID NO |
|---|---|---|---|
| AA873159 | Hs.182778 | apolipoprotein CI; apolipoprotein C-I variant II; apolipoprotein C-I variant I | 102 |
| AA883496 | Hs.125778 | Null | 103 |
| AA885096 | Hs.43948 | Alu subfamily SQ sequence contamination warning entry. | 104 |
| AA885478 | Hs.125741 | unnamed protein product [Homo sapiens]; hypothetical protein FLJ12505 [Homo sapiens]; Unknown (protein for MGC:39884) [Homo sapiens] | 105 |
| AA909959 | Hs.130719 | NESH; hypothetical protein; NESH protein [Homo sapiens]; NESH protein; new molecule including SH3 [Homo sapiens] | 106 |
| AA910771 | Hs.130421 | null | 107 |
| AA911661 | Hs.2733 | Hox2H protein (AA 1-356); K8 homeo protein; HOX2.8 gene product; HOXB2 protein; HOX-2.8 protein (77 AA); homeo box B2; homeo box 2H; homeobox protein Hox-B2; K8 home protein [Homo sapiens]; | 108 |
| AA932696 | Hs.8022 | TU3A protein; TU3A protein [Homo sapiens] | 109 |
| AA953396 | Hs.127557 | null | 110 |
| AA954482 | Hs.222677 | SSXL; synovial sarcoma, X breakpoint 1 [Homo sapiens]; synovial sarcoma, X breakpoint 8 [Homo sapiens]; synovial sarcoma, X breakpoint 1; sarcoma, synovial, X-chromosome-related 1; SSX1 protein [Homo sapiens] | 111 |
| AA962236 | Hs.124005 | hypothetical protein MGC 19780 | 112 |
| AA969508 | Hs.10225 | HEYL protein; hairy-related transcription factor 3; hairy/enhancer-ofsplit related with YRPW motif-like | 113 |
| AA973494 | Hs.153003 | serine/threonine kinase; myristilated and palmitylated serine-threonine kinase MPSK; protein kinase expressed in day 12 fetal liver; F5-2; serine/threonine kinase KRCT; erine/threonine kinase 16 [Homo sapiens]; | 114 |
| AA976642 | Hs.42116 | axin 2 (conductin, axil) | 115 |
| AA977711 | Hs.128859 | null | 116 |
| AA987675 | Hs.176759 | null | 117 |
| AA989139 | Hs.16608 | candidate tumor suppressor protein; candidate tumor suppressor protein [Homo sapiens] | 118 |
| AA993736 | Hs.169838 | hypothetical protein; vesicle-associated membrane protein 4 [Homo sapiens]; Similar to vesicle-associated membrane protein 4 [Homo sapiens] | 119 |

TABLE 1-continued

Marker genes that can be used for prognosis of colorectal cancer

| GenBank ID | UNIGENE ID | Description | SEQ ID NO |
|---|---|---|---|
| AI000612 | Hs.819 | homeobox protein; homeobox c1 protein; TATAA binding protein; homeo box B7 protein; Unknown (protein for MGC:2 1362) [Homo sapiens]; homeo box B7; homeo box 2C; homeobox protein Hox-B7; homeo box ci protein [Homo sapiens] | 120 |
| AI002566 | Hs.81234 | immunoglobin superfamily, member 3 | 121 |
| AI081269 | Hs.184108 | Alu subfamily SX sequence contamination warning entry. | 122 |
| AI139498 | Hs.151899 | delta sarcoglycan; delta-sarcoglycan isoform 2; Sarcoglyan, delta (35 kD dystrophin-associated glycoprotein); dystrophin associated glycoprotein, delta sarcoglycan; 35 kD dystrophin-associated glycoprotein [Homo sapiens] | 123 |
| AI149393 | Hs.9302 | phosducin-like protein; phosducin-like protein; phosducin-like protein; phosducin-like protein; hypothetical protein; phosducin-like; Unknown (proteinfor MGC: 14088) [Homo sapiens] | 124 |
| AI203139 | Hs.180370 | hypothetical protein FLJ30934 | 125 |
| AI240881 | Hs.89688 | complement receptor type 1-like protein {Homo sapiens} | 126 |
| AI253017 | Hs.183438 | U4/U6 snRNP-associated 61 kDa protein {Homo sapiens} | 127 |
| AI261561 | Hs.182577 | Alu subfamily SQ sequence contamination warning entry. | 128 |
| AI288845 | Hs.105938 | putative chemokine receptor; putative chemokine receptor; chemokine receptor X; C-C chemokine receptor 6. (CCR6) (Evidence is not experimental); chemokine (C-C motit) receptor-like 2 [Homo sapiens] | 129 |
| AI299969 | Hs.255798 | unnamed protein product; HN1 like; Unknown (protein for MGC:22947) | 130 |
| AI362799 | Hs.110757 | hypothetical protein; NNP3 [Homo sapiens] | 131 |
| AI394426 | Hs.57732 | acid phosphatase {Homo sapiens} | 132 |
| H15267 | Hs.210863 | null | 133 |
| H17364 | Hs.80285 | CRE-BP1 family member; cyclic AMP response element DNA-binding protein isoform 1 family; cAMP response element binding protein (AA1-505); cyclic AMP response element-binding protein (HB 16); Similar to activating transcription factor 2 [Homo sapiens]; act | 134 |
| H17543 | Hs.92580 | Alu subfamily J sequence contamination warning entry. | 135 |
| H17627 | Hs.83869 | unnamed protein | 136 |

TABLE 1-continued

Marker genes that can be used for prognosis of colorectal cancer

| GenBank ID | UNIGENE ID | Description | SEQ ID NO |
|---|---|---|---|
| H17638 | Hs.17930 | dJ1033B10.2.2(chromosome 6 open reading frame 11 BING4), isoform 2) [Homo sapiens] | 137 |
| H18953 | Hs.15232 | Null | 138 |
| H18956 | Hs.21035 | unnamed protein product [Homo sapiens] | 139 |
| H19822 | Hs.2450 | KIAA0028; leucyl-tRNA synthetase, mitochondrial [Homo sapiens]; leucyl-tRNA synthetase, mitochondrial [Homo sapiens]; leucine-tRNA ligase precursor; leucine translase [Homo sapiens] | 140 |
| H23551 | Hs.30974 | NAD11 dehydrogenase subunit 4 {Deirochelys reticularia} | 141 |
| H29032 | Hs.7094 | null | 142 |
| H45391 | Hs.31793 | null | 143 |
| H51549 | Hs.21899 | UDP-galactose translocator; UDP-galactose transporter 1 [Homo sapiens] | 144 |
| H62801 | Hs.125059 | Unknown (protein for IMAGE:4309224) [Homo sapiens]; hypothetical protein [Homo sapiens] | 145 |
| H73608 | Hs.94903 | null | 146 |
| H81024 | Hs.180655 | Aik2; aurora-related kinase 2; serine/threonine kinase 12; Unknown (protein for MGC: 11031) [Homo sapiens]; Unknown (protein for MGC:4243) [Homo sapiens] | 147 |
| H85015 | Hs.138614 | null | 148 |
| H87795 | Hs.233502 | N/A | 149 |
| H94627 | Hs.255852 | N-ras protein (39 AA) (1 is 2nd base in codon) (115 is 2nd base in codon); neuroblastoma RAS viral (v-ras) oncogene homolog [Homo sapiens]; | 150 |
| H99544 | Hs.153445 | unknown; endothelial and smooth muscle cell-derived neuropilin-like protein [Homo sapiens]; endothelial and smooth muscle cell-derived neuropilin-like protein; coagulation factor V/VIII-homology domains protein 1 [Homo sapiens] | 151 |
| N21630 | Hs.143039 | hypothetical protein PR01942 | 152 |
| N36176 | Hs.108636 | membrane protein CHL; membrane protein CH1 [Homo sapiens]; membrane protein CH1 [Homo sapiens]; membrane protein CH1 [Homo sapiens] | 153 |
| N39584 | Hs.17404 | Null | 154 |
| N41021 | Hs.114408 | Toll/interleukin-1 receptor-like protein 3; Toll-like receptor 5; Toll-like receptor S [Homo sapiens]; toll-like receptor 5; Toll/interleukin- 1 receptor-like protein 3 [Homo sapiens] | 155 |

TABLE 1-continued

Marker genes that can be used for prognosis of colorectal cancer

| GenBank ID | UNIGENE ID | Description | SEQ ID NO |
|---|---|---|---|
| N45100 | Hs.34871 | HRIHFB2411; KIAA0569 gene product; Smad interacting protein 1 [Homo sapiens]; smad-interacting protein-i [Homo sapiens] | 156 |
| N45282 | Hs.201591 | calcitonin receptor-like | 157 |
| N46845 | Hs.144287 | hairy/enhancer-of-split related with YRPW motif 2; basic helix-loop-helix factor 1; HES-related repressor protein 1 HERP1; GRIDLOCK; basichelix-loop-helix protein; hairy-related transcription factor 2; hairy/enhancer-of-split related with YRPW motif 2 [H | 158 |
| N48270 | Hs.45114 | Similar to golgi autoantigen, golgin subfamily a, member 6 [Homo sapiens] | 159 |
| N50073 | Hs.84926 | hypothetical protein | 160 |
| N51543 | Hs.47292 | null | 161 |
| N51632 | Hs.75353 | The KIAA0123 gene product is related to rat general mitochondrial matrix processing protease (MPP).; Unknown (protein for IMAGE:3632957) [Homo sapiens]; Unknown (protein for IMAGE:3857242) [Homo sapiens]; inositol polyphosphate-5-phosphatase, 72 kDa; KIAA0 | 162 |
| N53172 | Hs.23016 | orphan receptor; orphan G protein-coupled receptor RDC 1 | 163 |
| N59451 | Hs.48389 | null | 164 |
| N59721 | Hs.21858 | glia-derived nexin precursor; serine (or cysteine) proteinase inhibitor, clade E (nexin, plasminogen activator inhibitor type 1), member 2; protease inhibitor 7 (protease nexin I); glia-derived nexin [Homo sapiens]; similar to serine (or cysteine) protein | 165 |
| N59846 | Hs.177812 | Unknown (protein for MGC:41314) {Mus musculus} | 166 |
| N63366 | Hs.161488 | N/A | 167 |
| N70777 | Hs.49927 | BA103J18.1.2 (novel protein, isoform 2) [Homo sapiens] | 168 |
| N72847 | Hs.125221 | Alu subfamily SP sequence contamination warning entry. [Human] {Homo sapiens} | 169 |
| N74527 | Hs.5420 | unnamed protein product | 170 |
| N75004 | Hs.49265 | hypothetical protein {Plasmodium falciparum 3D7} | 171 |
| N77998 | Hs.48220 | oculorhombin; paired box gene 6, isoform a; Similar to paired box gene 6 (aniridia, keratitis) [Homo sapiens]; paired box protein PAX6 [Homo sapiens] | 172 |
| N92519 | Hs.1189 | Unknown (protein for MGC:10231) [Homo sapiens] | 173 |
| N95226 | Hs.22039 | KIAA0758 protein; | 174 |

TABLE 1-continued

Marker genes that can be used for prognosis of colorectal cancer

| GenBank ID | UNIGENE ID | Description | SEQ ID NO |
|---|---|---|---|
| R06568 | Hs.187556 | null | 175 |
| R10545 | Hs.148877 | dJ425C14.2 (Placental protein | 176 |
| R16760 | Hs.20509 | HBV pX associated protein-8 | 177 |
| R17811 | Hs.77897 | splicing factor SF3a60; pre-mRNA splicing factor SF3a (60 kD), similar to *S. cerevisiae* PRP9 (spliceosome-associated protein 61); splicing factor 3a, subunit 3, 60 kD [*Homo sapiens*]; Similar to splicing factor 3a, subunit 3, 60 kD [*Homo sapiens*] | 178 |
| R22340 | null | unnamed protein product; chr2 synaptotagmin KIAA 1228 protein | 179 |
| R27767 | Hs.79946 | thyroid hormone receptor-associated protein, 150 kDa subunit; Similar to thyroid hormone receptor-associated protein, 150 kDa subunit [*Homo sapiens*];; | 180 |
| R30941 | Hs.24064 | signal transducer and activator of transcription Stat5B; transcription factorStat5b; STAT5B_CDS [*Homo sapiens*]; signal transducer and activator of transcription 5B; signal transducer and activator of transcription 5; transcription factor STAT5B [*Homo sapiens*] | 181 |
| R34578 | Hs.111314 | null | 182 |
| R37028 | Hs.20956 | cytochrome bd-type quinol oxidase subunit I related protein {Thermoplasma acidophilum} | 183 |
| R38266 | Hs.12431 | Unknown (protein for MGC:30132) | 184 |
| R38360 | Hs.145567 | unknown {*Homo sapiens*} | 185 |
| R38640 | Hs.89584 | insulinoma-associated 1; bA470C13.2 (insulinoma-associated protein 1) | 186 |
| R42984 | Hs.4863 | null | 187 |
| R43597 | Hs.137149 | trehalase homolog T19F6.30-*Arabidopsis thaliana* | 188 |
| R43684 | Hs.165575 | dJ402GL1.5 (novel protein similar to yeast and bacterial predicted proteins) | 189 |
| R43713 | Hs.22945 | null | 190 |
| R44546 | Hs.82563 | dJ526I14.2 (KIAA0153 (similar | 191 |
| R45595 | Hs.23892 | Null | 192 |
| R59314 | Hs.170056 | null | 193 |
| R59360 | Hs.12533 | null | 194 |
| R60193 | Hs.11637 | null | 195 |
| R63816 | Hs.28445 | unnamed protein product | 196 |
| R66605 | Hs.182485 | Unknown (protein for IMAGE:4843317) {*Homo sapiens*} | 197 |
| R68106 | Hs.233450 | Fc-gamma-RIIb2; precursor polypeptide (AA -42 to 249); IgG Fc | 198 |

TABLE 1-continued

Marker genes that can be used for prognosis of colorectal cancer

| GenBank ID | UNIGENE ID | Description | SEQ ID NO |
|---|---|---|---|
| | | receptor; IgG Fc receptor; IgG Fc receptor beta-Fc-gamma-RII; IgG Fc fragment receptor precursor; Fc gamma RIIB [Homo sapiens]; Fc gamma RIIB [Ho | |
| R91710 | Hs.15617 | Alu subfamily SQ sequence contamination warning entry. [Human] {Homo sapiens} | 199 |
| R92717 | Hs.170129 | choroideremia-like Rab escort protein 2; dJ317G22.3 (choroideremia-like (Rab escort protein 2)) | 200 |
| R92994 | Hs.1695 | metalloelastase; metalloelastase; matrix metalloproteinase 12 (macrophage elastase) | 201 |
| T49061 | Hs.8934 | HA-70 {Clostridium botulinum} | 202 |
| T51004 | Hs.167847 | null | 203 |
| T51316 | null | null | 204 |
| T56281 | Hs.8765 | metallothionein I-F; RNA helicase-related protein [Homo sapiens]; metallothionein 1F [Homo sapiens] | 205 |
| T64924 | Hs.220619 | null | 206 |
| T70321 | Hs.247129 | G3a protein; Apo M; apolipoprotein M; Unknown (protein for MGC:22400) [Homo sapiens]; apolipoprotein M; NG20-like protein [Homo sapiens] | 207 |
| T72535 | Hs.189825 | null | 208 |
| T81317 | Hs.189846 | Alu subfamily J sequence contamination warning entry. | 209 |
| T86932 | Hs.131924 | T-cell death-associated gene 8; similar to G protein-coupled receptor [Homo sapiens] | 210 |
| T90789 | Hs.121586 | ray; small GTP binding protein RAB35 [Homo sapiens]; RAB35, member RAS oncogene family; ras related protein rab-1c (GTP-binding protein ray) [Homo sapiens] | 211 |
| W45025 | Hs.170268 | Alu subfamily SX sequence contamination warning entry. [Human] {Homo sapiens} | 212 |
| W72103 | Hs.236443 | beta-spectrin 2 isoform 2 | 213 |
| W73732 | Hs.83634 | Null | 214 |
| W93370 | Hs.174219 | NKG2E; type II integral membrane protein; killer cell lectin-like receptor subfamily C, member 3; killer cell lectin-like receptor subfamily C, member 3 isoform NKG2-H; NKG2E [Homo sapiens]; NKG2E [Homo sapiens]; NKG2E [Homo sapiens] | 215 |
| W93592 | Hs.47343 | hWNT5A; wingless-type MMTV integration site family, member 5A precursor; proto-oncogene Wnt-5A precursor; WNT-5A protein precursor [Homo sapiens] | 216 |

TABLE 1-continued

Marker genes that can be used for prognosis of colorectal cancer

| GenBank ID | UNIGENE ID | Description | SEQ ID NO |
|---|---|---|---|
| W93980 | Hs.59511 | null | 217 |
| W96216 | Hs.110196 | NICE-1 protein | 218 |

Genes that are not listed in Table 1 or any of Tables 2-5, 7, and 8 (see Section 6, infra) but which are functional equivalents of any gene listed in Table 1 or any one of Tables 2-5, 7, and 8 can also be used with or in place of the gene listed in the table. A functional equivalent of a gene A refers to a gene that encodes a protein or mRNA that at least partially overlaps in physiological function in the cell to that of the protein or mRNA of gene A.

In various specific embodiments, different numbers and subcombinations of the genes listed in Table 1 are selected as the marker set, whose profile is used in the prognostic methods of the invention, as described in Section 5, supra. In various embodiments, such subcombinations include but are not limited to those genes listed in Table 2, 3, 4, 5, 7, or 8 infra in Section 6, or at least 5, 10, 15, 20, 25, 30, 40, 50, 60 or 70, or in the range of 8 to 19, in the range of 21 to 25, in the range of 27 to 42, in the range of 44 to 52, or in the range of 54 to 130 of the genes listed in Table 2, 3, 4, 5, 7, or 8, as applicable, or their respective functional equivalents.

In one embodiment, one or more genes that cluster together with one or more genes listed in a table can be selected to represent the cluster such that the marker set contains genes representing a plurality of different clusters. For example, among the 53 SAM-identified genes listed in Table 2, one gene can be selected from each cluster (see FIG. 1A) to constitute a marker set.

In a specific embodiment, measurements of gene products of the genes, respectively, shown in Table 2 (which is a subset of the genes listed in Table 1), or the + marked subset thereof, or their respective functional equivalents, are used for prognosis according to the invention. In a particular embodiment, measurements of gene products of all or at least 5, 10, 15, 20, 25, 30, 40, or 50, or in the range of 8 to 52 of the genes listed in Table 2, or the + marked subset thereof, are used.

In another specific embodiment, measurments of gene products of the genes shown in Table 3 (which is a subset of the genes listed in Table 1) or their respective functional equivalents are used for prognosis according to the invention. In a particular embodiment, measurement of gene products of all or at least 5 of the genes listed in Table 3, or their respective functional equivalents, are used.

In another embodiment, measurements of the gene products of the genes, respectively, shown in Table 4 (which is a subset of the genes listed in Table 1) or their respective functional equivalents are used for prognosis according to the invention. In a particular embodiment, measurements of gene products of all or at least 5, 10, 15, 20, 25, 30, 40, 50, 60, 70, 80, 90, or 100 of the genes listed in Table 4, or the asterisk (*) marked subset thereof, or the genes marked by M, are used. In another particular embodiment, measurements of gene products of all or in the range of 8 to 42 or in the range of 44 to 130 of the genes listed in Table 4 are used. In another particular embodiment, genes selected in at least a given number of iterations, e.g., at least 20, 30, 40, 50, 60, or 70 iterations as provided in the table, or selected in at least a given percentage of iterations, e.g., 20%, 40%, 50%, 75% or 90% of iterations, are used. Genes appearing in both the cDNA classifier and U133A-limited cDNA classifier are marked by * in Table 4. In another particular embodiment, measurements of the gene products of the genes, respectively, shown in Table 4 or their respective functional equivalents are measured using a cDNA microarray and used for prognosis according to the invention.

In another specific embodiment, measurements of gene products of the set of 43 genes shown in Table 5 (which is a subset of the genes listed in Table 1) or their respective functional equivalents are used for prognosis according to the invention. In another specific embodiment, measurements of the gene products of the 26 genes (identified by an asterisk in Table 5), which are mapped to the U133A Affymetrix® GeneChip® oligonucleotide-array based platform, are used. In a particular embodiment, measurements of gene products of all or at least 5, 10, 15, 20, 25, 30, or 40 of the genes listed in Table 5, or the asterisk marked subset thereof, are used. In another particular embodiment, measurements of gene products of all or in the range of 5 to 25 or in the range of 27 to 42 of the genes listed in Table 5 are used.

In another specific embodiment, measurements of gene products of the genes shown in Table 7 (which is a subset of the genes listed in Table 1) or their respective functional equivalents are used for prognosis according to the invention. In a particular embodiment, measurements of gene products of all or at least 5, 10, or 15 of the genes listed in Table 7, or their respective functional equivalents, are used.

In still another embodiment, measurements of the gene products of the genes, respectively, shown in Table 8 (which is a subset of the genes listed in Table 1) or their respective functional equivalents are used for prognosis according to the invention. In a particular embodiment, measurements of gene products of all or at least 5, 10, 15, 20, 25, 30, 40, 50, 60, 70, 80, 90, or 100 of the genes listed in Table 8, or the asterisk marked subset thereof, or the genes marked by M, are used. In another particular embodiment, measurements of gene products of all or in the range of 5 to 25 or in the range of 27 to 130 of the genes listed in Table 8 are used. In another particular embodiment, genes selected in at least a given number of iterations, e.g., at least 20, 30, 40, 50, 60, or 70 iterations as provided in the table, or selected in at least a given percentage of iterations, e.g., 20%, 40%, 50%, 75% or 90% of iterations, are used. Genes appearing in both the cDNA classifier and U133A-limited cDNA classifier are marked by * in Table 8. In another particular embodiment, measurements of the gene products of the genes, respectively, shown in Table 8 or their respective functional equivalents are measured using an Affymetrix® GeneChip® oligonucleotide-array and used for prognosis according to the invention.

In a specific embodiment, one or more of the genes listed in Table 3 can be used to subdivide a patient population into subgroups according to the expression levels of such genes, with the prognostic methods of the invention then applied to such a patient subgroup. For example, in a specific embodiment, the prognostic methods of the invention are applied to patients that have an osteopontin level higher than a predetermined threshold, e.g., the average level in subjects not having colorectal cancer or the average level in colorectal cancer patients.

In another specific embodiment, the prognostic methods of the invention are applied to patients that have a neuregulin 2 isoform 4 level higher than a predetermined threshold, e.g., the average level in subjects not having colorectal cancer or the average level in colorectal cancer patients.

In yet another embodiment, the pregnostic methods are applied to patients that have both osteopontin and neuregulin 2 isoform 4 levels higher than predetermined thresholds.

In one embodiment, a leave-one-out cross-validation method (LOOCV) (see Section 5.3., infra) is used to obtain a marker set using cDNA data of a training population of patients at 36 months of follow-up. By way of example, Table 4 lists genes selected by the LOOCV approach via t-test as discussed in Section 5.3. and Section 6.

In another specific embodiment, measurements of products of a set of genes that are selected in about 75% of the training population in a leave-one-out cross-validation (LOOCV) (see Section 5.3., infra) or their respective functional equivalents are used for prognosis according to the invention.

In a specific embodiment, cross-platform mapping of marker genes can also be carried out. For example, translation of cDNA gene signature into available Affymetrix® probe sets is carried out using the Resourcerer program (WWW.TIGR.org).

In another embodiment, SAM is used to identify a set of genes most correlated with censored survival time.

5.2. Methods of Predicting Cancer Outcome

The invention provides methods for predicting prognosis of colorectal cancer in a colorectal cancer patient using a measured marker profile comprising measurements of the gene products of genes, e.g., the sets of genes described in Section 5.1., supra. The prognosis indicates the patient's predicted survival at a predetermined time after surgery, e.g., at 2, 3, 4 or 5 years.

In preferred embodiments, the methods of the invention use a prognosis predictor, also called a classifier, for predicting prognosis. The prognosis predictor can be based on any appropriate pattern recognition method that receives an input comprising a marker profile and provides an output comprising data indicating a good prognosis or a poor prognosis. The prognosis predictor is trained with training data from a training population of colorectal cancer patients. Typically, the training data comprise for each of the colorectal cancer patients in the training population a marker profile comprising measurements of respective gene products of a plurality of genes in a tumor cell sample taken from the patient and prognosis outcome information. In a preferred embodiment, the training population comprises patients from each of the different stages of colorectal cancer, e.g., from adenomas (precancerous polyps), and Dukes stages A, B, C, and D. In another preferred embodiment, the training population comprises patients from each of the different TNM stages of colorectal cancer.

In a preferred embodiment, the prognosis predictor is an artificial neural network (ANN). An ANN can be trained with the training population using any suitable method known in the art, e.g., a method described in Section 5.4.1., infra. In a specific embodiment, the ANN is a feed-forward back-propagation neural network with a single hidden layer of 10 units, a learning rate of 0.05, and a momentum of 0.2.

In another embodiment, the prognosis predictor is a support vector machine (SVM). In a specific embodiment, the SVM is a linear SVM having a dot product kernel. In still another specific embodiment, the SVM is a nonlinear SVM having a nonlinear kernel, e.g., a d-degree dot product kernel or a Gaussian kernel. An SVM can be trained with the training population using any suitable method known in the art, e.g., a method described in Section 5.4.2., infra. Kernels that can be used in conjunction with the present invention are also described in Section 5.4.2., infra.

In still other embodiments, the prognosis predictor can also be based on other classification (pattern recognition) methods, e.g., logic regression (Section 5.4.3., infra), linear or quadratic discriminant analysis (Section 5.4.4., infra), decision trees (Section 5.4.5., infra), clustering (Section 5.4.6., infra), principal component analysis (Section 5.4.7., infra), nearest neighbor classifer analysis (Section 5.4.8., infra). Such prognosis predictors can be trained with the training population using methods described in the relevant sections, infra.

The marker profile can be obtained by measuring the plurality of gene products in a tumor cell sample from the patient using a method known in the art, e.g., a method described in Section 5.5., infra.

In a specific embodiment, the prognosis method of the invention can be used for evaluating whether a colorectal cancer patient may benefit from chemotherapy. The benefit of adjuvant chemotherapy for colorectal cancer appears limited to patients with Dukes stage C disease where the cancer has metastasized to lymph nodes at the time of diagnosis. For this reason, the clinicopathological Dukes' staging system is critical for determining how adjuvant therapy is administered. Unfortunately, as noted above, Dukes' staging is not very accurate in predicting overall survival and thus its application likely results in the treatment of a large number of patients to benefit an unknown few. Alternatively, there are a number of patients who would benefit from therapy that do not receive it based on the Dukes' staging system. Accordingly, an important use of the prognosis/survival classifier of the present invention is the ability to identify those Dukes' stage B and C cases for which chemotherapy may be beneficial.

Thus, in one embodiment, the invention provides a method for evaluating whether a colorectal cancer patient should be treated with chemotherapy, comprising (a) classifying said patient as having a good prognosis or a poor prognosis using a method described above; and (b) determining that said patient's predicted survival time favors treatment of the patient with chemotherapy if said patient is classified as having a poor prognosis. In one embodiment, the patient is further staged using Dukes staging.

The prognosis method of the invention can also be used in selecting patients for enrollment for a clinical trial of a chemotherapeutic agent for colorectal cancer. In one embodiment, this can be achieved using a method comprising (a) classifying each patient as having a good prognosis or a poor prognosis using a method described above; and (b) selecting patients having a poor prognosis for the clinical trial. By only enrolling patients having a poor prognosis, the efficacy of the chemotherapeutic agent can be more reliably evaluated. In a specific embodiment, the invention provides a method for enrolling colorectal cancer patients for a clinical trial of a chemotherapeutic agent for colorectal cancer, comprising (a) classifying each patient as having a good prognosis or a poor prognosis using a method described above; and (b) assigning each patient having a good prognosis to one patient group and each patient having a poor prognosis to another patient group, at least one of said patient group being enrolled in said clinical trial.

The patient is preferably a mammal, e.g., a primate or a human, and can be a non-human animal such as a dog, cat, horse, cow, mouse, rat, rabbit, etc.

5.3. Methods for Identifying Marker Sets

The invention provides methods for identifying a set of genes for prognosis of colorectal cancer. The methods make use of measured expression profiles of a plurality of genes (e.g., measurements of abundance levels of the corresponding gene products) in tumor samples from a plurality of patients whose prognosis outcomes are known. As used herein, a patient is animal inflicted with colorectal cancer. The patient can be but is not limited to a human, or, in a veterinary context, from non-human animals such as ruminants, horses, swine or sheep, or from domestic companion animals such as felines and canines. The prognosis outcomes are preferably those at a predetermined time after surgery. In one embodiment, for each of the plurality of genes a metric of correlation between expression level of the gene and survival outcome in the plurality of colorectal cancer patients is determined. One or more genes are then selected based on their metrics of correlation. The predetermined time can be any convenient time period, e.g., 2, 3, 4, or 5 years.

Prognosis markers can be obtained by identifying genes whose expression levels in good prognosis patients group are significantly different from those in poor prognosis patients. In preferred embodiments, the tumor samples from the plurality of patients are separated into a good prognosis group and a poor prognosis group for the predetermined time period. Genes whose expression levels exhibit differences between the good and poor prognosis groups to at least a predetermined level are selected as the genes whose expression levels correlate with patient survival, i.e., patient prognosis. In one embodiment, the metric of correlation of a gene with survival is an absolute t-value of a t-test. The absolute t-value can be calculated using expression levels of the gene in tumor samples from patients in the good prognosis group and expression levels of the gene in tumor samples from patients in the poor prognosis group. Genes whose t-value is higher than a certain threshold value can be selected as markers. In one embodiment, a gene is selected if the p-value of the gene corresponds to a predetermined significance level, e.g., a p-value less than 0.05.

In another embodiment, the metric of correlation of a gene is a relative difference in expression levels between the good and poor prognosis patients obtained using significance analysis of microarray (SAM). The relative difference can be calculated using expression levels of the gene in tumor samples in the good prognosis group and expression levels of the gene in tumor samples from patients in the poor prognosis group according to Tusher (Tusher et al., 2001, *Proc. Natl. Acad. Sci.* 98:5116-5121, which is incorporated by reference herein in its entirety). In SAM, the relative difference d(i) for gene i is defined based on the ratio of change in gene expression and standard deviation in the data for that gene. The relative difference d(i) in gene expression is a t-value between expression levels in the two sample groups. Relative differences $d_p(i)$'s from permutations of the hybridizations for the samples in one prognosis group and samples in the other prognosis group can be calculated to generate a large number of controls. To find significant changes in gene expression, genes are ranked by magnitude of their d(i) values so that d(1) is the largest relative difference, d(2) is the second largest relative difference, and d(i) is the ith largest relative difference. For each of the permutations, the genes are again ranked such that $d_p(i)$ is the ith largest relative difference for permutation p. The expected relative difference, $d_E(i)$, is defined as the average over the permutations. To identify potentially significant changes in expression, a scatter plot of the observed relative difference d(i) vs. the expected relative difference $d_E(i)$ can be used. For the vast majority of genes, $d(i) > d_E(i)$, but some genes are represented by points displaced from the $d(i) = d_E(i)$ line by a distance greater than a threshold Δ. Genes that are within a threshold Δ are "called significant." To determine the number of falsely significant genes generated by SAM, horizontal cutoffs are defined as the smallest d(i) among the genes called significantly induced and the least negative d(i) among the genes called significantly repressed. The number of falsely significant genes corresponding to each permutation is computed by counting the number of genes that exceeded the horizontal cutoffs for induced and repressed genes. The estimated number of falsely significant genes is the average of the number of genes called significant from all permutations. In one embodiment, a gene is selected such that a median false detection rate is less than 40%, 28%, or 15%.

In still another embodiment, difference in expression levels of a gene in good prognosis patients versus poor prognosis patients is determined using ANOVA. A gene is selected if the difference in expression levels of the gene between the good and poor prognosis groups corresponds to a predetermined significance level.

A set of genes for prognosis of colorectal cancer can also be identified using an iterative approach. In one embodiment, a subset of patients is created by leaving out one or more patients in a plurality of patients having known outcomes after obtaining tumor samples. A metric of correlation between expression level of each gene and survival outcome in the subset of colorectal cancer patients can then be determined using a method described above. One or more genes are then selected based on the metric of correlation. The process is repeated for a plurality of iterations, each with a different subset of patients by leaving out one or more patients who are different from the one or more patients left out in any other iteration. Genes that are selected in at least a predetermined percentage of all iterations are included for the marker set.

In one embodiment, for each iteration, the plurality of genes is ranked according to the correlation metric. A given number of genes that are ranked with the highest correlation are selected. In preferred embodiments, a set of 20, 50, 70 or 100 genes are selected from the rank list. The sets of genes obtained in different iterations are then compared to identify one or more genes that are selected in at least a predetermined percentage of all iterations. In one embodiment, the predetermined percentage is 50%, 75% or 90%.

In a preferred embodiment, the subset of patients is created by leaving out one of the plurality of patients. The embodiment is also termed a "leave-one-out" method.

In one embodiment, a total of T tumor samples from patients having known prognosis (the training population of patients) is used to identify marker genes that can be used for prognosis of colorectal cancer. Preferably, T is at least 50, 100, 200 or 500. In one embodiment, the samples are frozen colorectal cancer samples selected from based on evidence for good (survival>a predetermined number of months) or poor (survival<the predetermined number of months) prognosis. Among the T samples of the training population, M samples are poor prognosis and N samples are good prognosis cases. In one embodiment, the training population comprises samples in all different Dukes' stages, i.e., A, B, C, and D cases. Dukes' stage A cases are very rare. Thus, in one embodiment, P samples of adenomas are included in the T samples to represent very good prognosis cases. In other embodiment, the training population consists of samples from patients belonging to one or more specific Dukes stages, e.g., Dukes stage B, Dukes stage C, or Dukes stages B and C. Such training population can be used to identify genes that can be used for prognosis of colorectal cancer in patients belonging to the respective one or more Dukes stages. Survival is measured as last contact minus collection date for living patients, or date of death minus collection date for patients who had died. Samples are microdissected (>80% tumor cells) by frozen section guidance and RNA was extracted using Trizol followed by secondary purification on RNAEasy columns.

In one embodiment, identification of marker genes can be combined with construction and validation of a prognosis predictor. In one embodiment, after selecting a set of genes in each iteration, a prognosis predictor that receives an input comprising a marker profile comprising expression levels of the one or more selected genes and provides an output comprising data indicating a good prognosis or a poor prognosis is trained with training data from the subset of patients. The training data comprise for each patient a marker profile comprising measurements of the one or more selected genes in a tumor cell sample taken from the patient and prognosis information. The prognosis predictor is then used to determine a prognosis for at least one of the one or more patients who are left out. Thus, the accuracy of the prognosis predictor can be determined based on rate of true or false predictions from the plurality of iterations. In one embodiment, after the interations have been completed, another prognosis predictor is constructed using the one or more genes that are selected in at least a predetermined percentage of all iterations. This prognosis predictor can be trained with training data from the subset of patients or all patients and used as the prognosis predictor for predicting prognosis for new patients.

In a preferred embodiment, the prognosis predictor is an artificial neural network (ANN). In a specific embodiment, the ANN is a feed-forward back-propagation neural network with a single hidden layer of 10 units, a learning rate of 0.05, and a momentum of 0.2.

In another preferred embodiment, the prognosis predictor is a support vector machine (SVM). In another specific embodiment, the SVM is a linear SVM having a dot product kernel. In still another specific embodiment, the SVM is a nonlinear SVM having a nonlinear kernel, e.g., a d-degree dot product kernel or a Gaussian kernel. Exemplary kernels are described in Section 5.3.2.

In a specific embodiment, a leave-one-out cross-validation (LOOCV) technique is used for constructing and validating a neural network-based classifier. The test samples are classified as having "good" or "poor" prognosis based on survival for more or less than 36 months, respectively. Using the leave-one-out cross-validation approach also provides the ability to rank the selected genes. The number of times a particular gene is chosen can be an indicator of the usefulness of that gene for general classification and may imply biological significance. Therefore, genes that are consistently selected by the t-test are selected for the marker set. In one embodiment, a set of 43 core genes is identified in about 75% of the LOOCV iterations. The set of 43 genes is listed in Table 5, infra.

In another specific embodiment, a leave-one-out cross-validation (LOOCV) technique is used for constructing and validating a SVM-based classifier. The test samples are classified as having "good" or "poor" prognosis based on survival for more or less than 24 months, respectively. The SVM classifier is a linear SVM classifier. A set of 20 genes is identified in 14% of the LOOCV iterations. The set of 20 genes is listed in Table 7, infra.

In one embodiment, the molecular classifier is obtained using an iterative approach using iterations of two distinct steps: gene selection using an appropriate statistical method, e.g., a t-test, and classification using an appropriate prognosis predictor, e.g., a neural network. Both steps are taken after the one or more test samples are left out, e.g., from the leave-one-out cross-validation, to avoid bias from the gene selection step. A predetermined number of the top genes as ranked by absolute value of the t statistic using a t test are selected for each cross-validation step. In a specific embodiment, a feed-forward back-propagation neural network with a single hidden layer of 10 units, learning rate of 0.05, and momentum of 0.2 is constructed. Training occurred for a maximum of 500 epochs or until a zero misclassification error is achieved on the training set.

The obtained prognosis predictor can be evaluated for its accuracy. In one embodiment, differences between Kaplan-Meier curves are evaluated using the log-rank test, which is well known to a skilled person in the art. This can be performed both for the initial survival analysis and for the classifier results. In accordance with the present invention, the classifier can split the samples into two groups: those predicted as having good or poor prognosis. Classifier accuracy can then be reported to the user both as overall accuracy and as specificity/sensitivity. In one embodiment, a McNemar's Chi-Square test is used to compare the molecular classifier with the use of a Dukes' staging classifier. In a related embodiment, several permutations of the dataset (i.e., 1,000 permutations) are used to measure the significance of the classifier results as compared to chance.

Thus, the invention provides a method for identifying a set of genes for prognosis of colorectal cancer, comprising: (a) generating a subset of patients by leaving out one or more patients in a plurality of patients having known outcomes at a predetermined time after obtaining tumor samples; (b) determining for each of a plurality of genes a metric of correlation between abundance level of said gene and survival outcome in said subset of colorectal cancer patients having known outcomes at a predetermined time after obtaining tumor samples; (c) selecting one or more genes based on said metric of correlation; (d) repeating steps (a)-(c) for a plurality of iterations, each with a different subset of patients by leaving out one or more patients in said plurality, wherein said one or more patients are different from any previous iteration; and (e) selecting one or more genes that are selected in at least a predetermined percentage of all iterations.

In one embodiment, said step (c) is carried out by a method comprising (c1) ranking said plurality of genes according to said metric; and (c2) selecting a given number of genes that ranked with the highest correlation. In a specific embodiment, said given number is 50 and said predetermined percentage is about 75%.

In one embodiment, said step (b) is carried out by a method comprising (b1) dividing said plurality of colorectal cancer patients into a first group consisting of one or more patients who are living at said predetermined time and a second group consisting of one or more patients who are not living at said predetermined time; and (b2) determining a difference in expression levels between said first group and said second group, wherein said difference represents said metric of correlation, and wherein said difference for each of said plurality of genes is a t-value of a t-test of expression levels of said gene between said first group and said second group. In a specific embodiment, said selecting is carried out by a method comprising selecting a given number of top-ranked genes according to the absolute t-value of the genes. In another specific embodiment, said selecting is carried out by a method comprising selecting a gene if the p-value of said gene corresponds to a predetermined significance level, e.g., a p-value less than 0.05. In one embodiment, said predetermined time is 3 years.

The invention also provides a method for constructing prognosis predictor for prognosis of colorectal cancer, comprising: (a) generating a subset of patients by leaving out one or more patients in a plurality of patients having known outcomes at a predetermined time after obtaining tumor samples; (b) determining for each of a plurality of genes a metric of correlation between expression level of said gene and survival outcome in a plurality of colorectal cancer patients having known outcomes at a predetermined time after obtaining tumor samples from a plurality of colorectal cancer patients having known outcomes at a predetermined time after obtaining tumor samples; (c) selecting one or more genes based on said metric of correlation; (d) training a prognosis predictor, wherein said prognosis predictor receives an input comprising a marker profile comprising expression levels of said one or more genes selected in step (c) and provides an output comprising data indicating a good prognosis or a poor prognosis, with training data from said subset of patients, wherein said training data comprise for each of said subset of patients a marker profile comprising measurements of said one or more genes in a tumor cell sample taken from said patient and prognosis information; (e) determining a prognosis for at least one of said one or more patients who are left out in step (a); (f) repeating steps (a)-(e) for a plurality of iteractions, each with a different subset of patients by leaving out one or more patients in said plurality, wherein said one or more patients are different from any previous iteration; (g) selecting one or more genes that are selected in at least a predetermined percentage of all iterations; and (h) training a prognosis predictor, wherein said prognosis predictor receives an input comprising a marker profile comprising expression levels of said one or more genes selected in step (g) and provides an output comprising data indicating a good prognosis or a poor prognosis, with training data from said subset of patients, wherein said training data comprise for each of said plurality of patients a marker profile comprising measurements of said one or more genes in a tumor cell sample taken from said patient and prognosis information.

In one embodiment, said step (c) is carried out by a method comprising (c1) ranking said plurality of genes according to said metric; and (c2) selecting a given number of genes that ranked with the highest correlation.

In a preferred embodiment, said prognosis predictor is an artificial neural network (ANN).

In one embodiment, said step (b) is carried out by a method comprising (b1) dividing said plurality of colorectal cancer patients into a first group consisting of one or more patients who are living at said predetermined time and a second group consisting of one or more patients who are not living at said predetermined time; and (b2) determining a difference in expression levels between said first group and said second group, wherein said difference represents said metric of correlation. In a specific embodiment, said selecting is carried out by a method comprising selecting a given number of top-ranked genes according to the absolute t-value of the genes. In another specific embodiment, said selecting is carried out by a method comprising selecting a gene if the p-value of said gene corresponds to a predetermined significance level, e.g., a p-value less than 0.05. In one embodiment, said predetermined time is 3 years.

The invention also provides a computer system comprising a processor, and a memory coupled to said processor and encoding one or more programs, wherein said one or more programs cause the processor to carry out a method described above.

The invention also provides a computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method described above.

5.4. Statistical Methods

Various known statistical pattern recognition methods can be used in conjunction with the present invention. A prognosis predictor based on any of such methods can be constructed using the marker profiles and prognosis data of training patients. Such a prognosis predictor can then be used to predict prognosis of a colorectal patient based on the patient's marker profile. The methods can also be used to identify markers that discriminate between a good and poor prognosis using a marker profile and prognosis data of training patients.

5.4.1. Artificial Neural Network

In some embodiments, a neural network is used. A neural network can be constructed for a selected set of molecular markers of the invention. A neural network is a two-stage regression or classification model. A neural network has a layered structure that includes a layer of input units (and the bias) connected by a layer of weights to a layer of output units. For regression, the layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification*, Second Edition, John Wiley & Sons, Inc., New York; and Hastie et al., 2001, *The Elements of Statistical Learning*, Springer-Verlag, New York.

The basic approach to the use of neural networks is to start with an untrained network, present a training pattern, e.g., marker profiles from training patients, to the input layer, and to pass signals through the net and determine the output, e.g., the prognosis of the training patients, at the output layer. These outputs are then compared to the target values; any difference corresponds to an error. This error or criterion function is some scalar function of the weights and is minimized when the network outputs match the desired outputs. Thus, the weights are adjusted to reduce this measure of error. For regression, this error can be sum-of-squared errors. For classification, this error can be either squared error or cross-entropy (deviation). See, e.g., Hastie et al., 2001, *The Elements of Statistical Learning*, Springer-Verlag, New York.

Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the model defined by the network topology. In batch training, all patterns are presented to the network before learning takes place. Typically, in batch training, several passes are made through the training data. In online training, each pattern is presented once and only once to the net.

In some embodiments, consideration is given to starting values for weights. If the weights are near zero, then the operative part of the sigmoid commonly used in the hidden layer of a neural network (see, e.g., Hastie et al., 2001, *The Elements of Statistical Learning*, Springer-Verlag, New York) is roughly linear, and hence the neural network collapses into an approximately linear model. In some embodiments, starting values for weights are chosen to be random values near zero. Hence the model starts out nearly linear, and becomes nonlinear as the weights increase. Individual units localize to directions and introduce nonlinearities where needed. Use of exact zero weights leads to zero derivatives and perfect symmetry, and the algorithm never moves. Alternatively, starting with large weights often leads to poor solutions.

Since the scaling of inputs determines the effective scaling of weights in the bottom layer, it can have a large effect on the quality of the final solution. Thus, in some embodiments, at the outset all expression values are standardized to have mean zero and a standard deviation of one. This ensures all inputs are treated equally in the regularization process, and allows one to choose a meaningful range for the random starting weights. With standardization inputs, it is typical to take random uniform weights over the range [−0.7, +0.7].

A recurrent problem in the use of networks having a hidden layer is the optimal number of hidden units to use in the network. The number of inputs and outputs of a network are determined by the problem to be solved. In the present invention, the number of inputs for a given neural network can be the number of molecular markers in the selected set of molecular markers of the invention. The number of output for the neural network will typically be just one. However, in some embodiment more than one output is used so that more than just two states can be defined by the network. If too many hidden units are used in a neural network, the network will have too many degrees of freedom and is trained too long, there is a danger that the network will overfit the data. If there are too few hidden units, the training set cannot be learned. Generally speaking, however, it is better to have too many hidden units than too few. With too few hidden units, the model might not have enough flexibility to capture the nonlinearities in the data; with too many hidden units, the extra weight can be shrunk towards zero if appropriate regularization or pruning, as described below, is used. In typical embodiments, the number of hidden units is somewhere in the range of 5 to 100, with the number increasing with the number of inputs and number of training cases.

One general approach to determining the number of hidden units to use is to apply a regularization approach. In the regularization approach, a new criterion function is constructed that depends not only on the classical training error, but also on classifier complexity. Specifically, the new criterion function penalizes highly complex models; searching for the minimum in this criterion is to balance error on the training set with error on the training set plus a regularization term, which expresses constraints or desirable properties of solutions:

$$J=J_{pat}+\lambda J_{reg}.$$

The parameter $\lambda$ is adjusted to impose the regularization more or less strongly. In other words, larger values for $\lambda$ will tend to shrink weights towards zero: typically cross-validation with a validation set is used to estimate $\lambda$. This validation set can be obtained by setting aside a random subset of the training population. Other forms of penalty can also be used, for example the weight elimination penalty (see, e.g., Hastie et al., 2001, *The Elements of Statistical Learning*, Springer-Verlag, New York).

Another approach to determine the number of hidden units to use is to eliminate—prune—weights that are least needed. In one approach, the weights with the smallest magnitude are eliminated (set to zero). Such magnitude-based pruning can work, but is nonoptimal; sometimes weights with small magnitudes are important for learning and training data. In some embodiments, rather than using a magnitude-based pruning approach, Wald statistics are computed. The fundamental idea in Wald Statistics is that they can be used to estimate the importance of a hidden unit (weight) in a model. Then, hidden units having the least importance are eliminated (by setting their input and output weights to zero). Two algorithms in this regard are the Optimal Brain Damage (OBD) and the Optimal Brain Surgeon (OBS) algorithms that use second-order approximation to predict how the training error depends upon a weight, and eliminate the weight that leads to the smallest increase in training error.

Optimal Brain Damage and Optimal Brain Surgeon share the same basic approach of training a network to local minimum error at weight w, and then pruning a weight that leads to the smallest increase in the training error. The predicted functional increase in the error for a change in full weight vector $\delta w$ is:

$$\delta J = \left(\frac{\partial J}{\partial w}\right)^t \cdot \delta w + \frac{1}{2}\delta w^t \cdot \frac{\partial^2 J}{\partial w^2} \cdot \delta w + O(\|\delta w\|^3)$$

where $$\frac{\partial^2 J}{\partial w^2}$$

is the Hessian matrix. The first term vanishes because we are at a local minimum in error; third and higher order terms are ignored. The general solution for minimizing this function given the constraint of deleting one weight is:

$$\delta w = -\frac{w_q}{[\mathbb{H}^{-1}]_{qq}} \mathbb{H}^{-1} \cdot u_q \text{ and}$$

$$L_q = \frac{1}{2} \frac{w_q^2}{[\mathbb{H}^{-1}]_{qq}}$$

Here, $u_q$ is the unit vector along the qth direction in weight space and $L_q$ is approximation to the saliency of the weight q—the increase in training error if weight q is pruned and the other weights updated $\delta w$. These equations require the inverse of $\mathbb{H}$. One method to calculate this inverse matrix is to start with a small value, $H_0^{-1} = \alpha^{-1} I$, where $\alpha$ is a small parameter—effectively a weight constant. Next the matrix is updated with each pattern according to $$\mathbb{H}_{m+}^{-1} = \mathbb{H}_m^{-1} - \frac{\mathbb{H}_m^{-1} \mathbb{X}_{m+1} \mathbb{X}_{m+1}^T \mathbb{H}_m^{-1}}{\frac{n}{a_m} + \mathbb{X}_{m+1}^T \mathbb{H}_m^{-1} \mathbb{X}_{m+1}}$$

where the subscripts correspond to the pattern being presented and $a_m$ decreases with m. After the full training set has been presented, the inverse Hessian matrix is given by $H^{-1} = H_n^{-1}$. In algorithmic form, the Optimal Brain Surgeon method is:

began initialize $n_H, w, \theta$
   train a reasonable large network to minimum error
   do computer $H^{-1}$ by Eqn.1

$$q^* \leftarrow \arg\min_q w_q^2/(2[H^{-1}]_{qq})(\text{saliency } L_q)$$

$$w \leftarrow w - \frac{w_{q^*}}{[H^{-1}]_{q^*q^*}} H^{-1} e_{q^*} (\text{saliency } L_q)$$

until $J(w) > \theta$
   return w
end

The Optimal Brain Damage method is computationally simpler because the calculation of the inverse Hessian matrix in line 3 is particularly simple for a diagonal matrix. The above algorithm terminates when the error is greater than a criterion initialized to be $\theta$. Another approach is to change line 6 to terminate when the change in $J(w)$ due to elimination of a weight is greater than some criterion value.

In some embodiments, a back-propagation neural network (see, for example Abdi, 1994, "A neural network primer", J. Biol System. 2, 247-283) containing a single hidden layer of ten neurons (ten hidden units) found in EasyNN-Plus version 4.0g software package (Neural Planner Software Inc.) is used. In a specific example, parameter values within the EasyNN-Plus program are set as follows: a learning rate of 0.05, and a momentum of 0.2. In some embodiments in which the EasyNN-Plus version 4.0g software package is used, "outlier" samples are identified by performing twenty independently-seeded trials involving 20,000 learning cycles each.

5.4.2. Support Vector Machine

In some embodiments of the present invention, support vector machines (SVMs) are used to classify subjects using expression profiles of marker genes described in the present invention. General description of SVM can be found in, for example, Cristianini and Shawe-Taylor, 2000, *An Introduction to Support Vector Machines*, Cambridge University Press, Cambridge, Boser et al., 1992, "A training algorithm for optimal margin classifiers, in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York; Duda, *Pattern Classification*, Second Edition, 2001, John Wiley & Sons, Inc.; Hastie, 2001, *The Elements of Statistical Learning*, Springer, New York; and Furey et al., 2000, Bioinformatics 16, 906-914. Applications of SVM in biological applications are described in Jaakkola et al., *Proceedings of the 7th International Conference on Intelligent Systems for Molecular Biology*, AAAI Press, Menlo Park, Calif. (1999); Brown et al., *Proc. Natl. Acad. Sci.* 97(1):262-67 (2000); Zien et al., *Bioinformatics*, 16(9):799-807 (2000); Furey et al., *Bioinformatics*, 16(10):906-914 (2000)

In one approach, when a SVM is used, the gene expression data is standardized to have mean zero and unit variance and the members of a training population are randomly divided into a training set and a test set. For example, in one embodiment, two thirds of the members of the training population are placed in the training set and one third of the members of the training population are placed in the test set. The expression values for a selected set of genes of the present invention is used to train the SVM. Then the ability for the trained SVM to correctly classify members in the test set is determined. In some embodiments, this computation is performed several times for a given selected set of molecular markers. In each iteration of the computation, the members of the training population are randomly assigned to the training set and the test set. Then, the quality of the combination of molecular markers is taken as the average of each such iteration of the SVM computation.

Support vector machines map a given set of binary labeled training data to a high-dimensional feature space and separate the two classes of data with a maximum margin hyperplane. In general, this hyperplane corresponds to a nonlinear decision boundary in the input space. Let $X \in R_0 \subseteq \mathfrak{R}$ be the input vectors, $y \in \{-1, +1\}$ be the labels, and $\phi: R_0 \to F$ be the mapping from input space to feature space. Then the SVM learning algorithm finds a hyperplane (w,b) such that the quantity $$\gamma = \min_i y_i \{\langle w, \phi(\mathbb{X}_i) \rangle - b\}$$

is maximized, where the vector w has the same dimensionality as F, b is a real number, and $\gamma$ is called the margin. The corresponding decision function is then $$f(X) = \text{sign}(\langle w, \phi(X) \rangle - b)$$

This minimum occurs when $$w = \sum_i \alpha_i y_i \phi(X_i)$$

where $\{\alpha_i\}$ are positive real numbers that maximize $$\sum_i \alpha_i - \sum_{ij} \alpha_i \alpha_j y_i y_j \langle \phi(X_i), \phi(X_j) \rangle$$

subject to $$\sum_i \alpha_i y_i = 0, \alpha_i > 0$$

The decision function can equivalently be expressed as $$f(\mathbb{X}) = \text{sign}(\sum_i \alpha_i y_i \langle \phi(X_i), \phi(\mathbb{X}) \rangle - b)$$

From this equation it can be seen that the $\alpha_i$ associated with the training point $\mathbb{X}_i$ expresses the strength with which that point is embedded in the final decision function. A remarkable property of this alternative representation is that only a subset of the points will be associated with a non-zero $\alpha_i$. These points are called support vectors and are the points that lie closest to the separating hyperplane. The sparseness of the $\alpha$ vector has several computational and learning theoretic consequences. It is important to note that neither the learning algorithm nor the decision function needs to represent explicitly the image of points in the feature space, $\phi(\mathbb{X})$, since both use only the dot products between such images, $\langle \phi(X_i), \phi(X_j) \rangle$. Hence, if one were given a function $K(\mathbb{X}, \mathbb{Y}) = \langle \phi(\mathbb{X}), \phi(\mathbb{X}) \rangle$, one could learn and use the maximum margin hyperplane in the feature space without ever explicitly performing the mapping. For each continuous positive definite function $K(\mathbb{X}, \mathbb{Y})$ there exists a mapping $\phi$ such that $K(\mathbb{X}, \mathbb{Y}) = \langle \phi(\mathbb{X}), \phi(\mathbb{X}) \rangle$ for all $\mathbb{X}, \mathbb{Y} \in R_0$ (Mercer's Theorem). The function $K(\mathbb{X}, \mathbb{Y})$ is called the kernel function. The use of a kernel function allows the support vector machine to operate efficiently in a nonlinear high-dimensional feature spaces without being adversely affected by the dimensionality of that space. Indeed, it is possible to work with feature spaces of infinite dimension. Moreover, Mercer's theorem makes it possible to learn in the feature space without even knowing $\phi$ and F. The matrix $K_{ij} = \langle \phi(\mathbb{X}_i), \phi(\mathbb{X}_j) \rangle$ is called the kernel matrix. Finally, note that the learning algorithm is a quadratic optimization problem that has only a global optimum. The absence of local minima is a significant difference from standard pattern recognition techniques such as neural networks. For moderate sample sizes, the optimization problem can be solved with simple gradient descent techniques. In the presence of noise, the standard maximum margin algorithm described above can be subject to overfitting, and more sophisticated techniques should be used. This problem arises because the maximum margin algorithm always finds a perfectly consistent hypothesis and does not tolerate training error. Sometimes, however, it is necessary to trade some training accuracy for better predictive power. The need for tolerating training error has led to the development the soft-margin and the margin-distribution classifiers. One of these techniques replaces the kernel matrix in the training phase as follows:

$$K \leftarrow K + \lambda I$$

while still using the standard kernel function in the decision phase. By tuning $\lambda$, one can control the training error, and it is possible to prove that the risk of misclassifying unseen points can be decreased with a suitable choice of $\lambda$.

If instead of controlling the overall training error one wants to control the trade-off between false positives and false negatives, it is possible to modify K as follows:

$$K \leftarrow K + \lambda D$$

where D is a diagonal matrix whose entries are either $d^+$ or $d_-$, in locations corresponding to positive and negative examples. It is possible to prove that this technique is equivalent to controlling the size of the $\alpha_i$ in a way that depends on the size of the class, introducing a bias for larger $\alpha_i$ in the class with smaller d. This in turn corresponds to an asymmetric margin; i.e., the class with smaller d will be kept further away from the decision boundary. In some cases, the extreme imbalance of the two classes, along with the presence of noise, creates a situation in which points from the minority class can be easily mistaken for mislabelled points. Enforcing a strong bias against training errors in the minority class provides protection agaist such errors and forces the SVM to make the positive examples support vectors. Thus, choosing $$d^+ = \frac{1}{n^+} \text{ and}$$

$$d^- = \frac{1}{n^-}$$

provides a heuristic way to automatically adjust the relative importance of the two classes, based on their respective cardinalities. This technique effectively controls the trade-off between sensitivity and specificity.

In the present invention, a linear kernel can be used. The similarity between two marker profiles $\mathbb{X}$ and $\mathbb{Y}$ can be the dot product $\mathbb{X} \cdot \mathbb{Y}$. In one embodiment, the kernel is $$K(\mathbb{X} \cdot \mathbb{Y}) = \mathbb{X} \cdot \mathbb{Y} + 1$$

In another embodiment, a kernel of degree d is used $$K(\mathbb{X}, \mathbb{Y}) = (\mathbb{X} \cdot \mathbb{Y} + 1)^d, \text{ where d can be either 2, 3, } \ldots$$

In still another embodiment, a Gaussian kernel is used $$K(X, Y) = \exp\left(\frac{-|X-Y|^2}{2\sigma^2}\right)$$

where $\sigma$ is the width of the Gaussian.

5.4.3. Logistic Regression

In some embodiments, the prognosis predictor is based on a regression model, preferably a logistic regression model. Such a regression model includes a coefficient for each of the molecular markers in a selected set of molecular markers of the invention. In such embodiments, the coefficients for the regression model are computed using, for example, a maximum likelihood approach. In particular embodiments, molecular marker data from the two prognosis groups is used and the dependent variable is the prognosis of the patient for which molecular marker characteristic data are from.

Some embodiments of the present invention provide generalizations of the logistic regression model that handle multicategory (polychotomous) responses. Such embodiments can be used to discriminate an organism into one or three or more prognosis groups. Such regression models use multicategory logit models that simultaneously refer to all pairs of categories, and describe the odds of response in one category instead of another. Once the model specifies logits for a certain (J−1) pairs of categories, the rest are redundant. See, for example, Agresti, *An Introduction to Categorical Data Analysis*, John Wiley & Sons, Inc., 1996, New York, Chapter 8, which is hereby incorporated by reference.

5.4.4. Discriminant Analysis

Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the expression values for the selected set of molecular markers of the invention across a subset of the training population serve as the requisite continuous independent variables. The prognosis group classification of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how the expression of a molecular marker across the training set separates in the two groups (e.g., a group that has osteoarthritis and a group that does not have osteoarthritis) and how this gene expression correlates with the expression of other genes. In some embodiments, LDA is applied to the data matrix of the N members in the training sample by K genes in a combination of genes described in the present invention. Then, the linear discriminant of each member of the training population is plotted. Ideally, those members of the training population representing a first subgroup (e.g. those subjects that do not have osteoarthritis) will cluster into one range of linear discriminant values (e.g., negative) and those member of the training population representing a second subgroup (e.g. those subjects that have osteoarthritis) will cluster into a second range of linear discriminant values (e.g., positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, New York; Venables & Ripley, 1997, *Modern Applied Statistics with s-plus*, Springer, New York.

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

5.4.5. Decision Trees

In some embodiments of the present invention, decision trees are used to classify patients using expression data for a selected set of molecular markers of the invention. Decision tree algorithms belong to the class of supervised learning algorithms. The aim of a decision tree is to induce a classifier (a tree) from real-world example data. This tree can be used to classify unseen examples which have not been used to derive the decision tree.

A decision tree is derived from training data. An example contains values for the different attributes and what class the example belongs. In one embodiment, the training data is expression data for a combination of genes described in the present invention across the training population.

The following algorithm describes a decision tree derivation:

```
Tree(Examples,Class,Attributes)
  Create a root node
  If all Examples have the same Class value, give the root this label
  Else if Attributes is empty label the root according to the most
     common value
  Else begin
    Calculate the information gain for each attribute
    Select the attribute A with highest information gain and make
this the root attribute
    For each possible value, v, of this attribute
      Add a new branch below the root, corresponding to A = v
      Let Examples(v) be those examples with A = v
      If Examples(v) is empty, make the new branch a leaf node labeled
with the     most common value among Examples
      Else let the new branch be the tree created by
          Tree(Examples(v),Class,Attributes - {A})
  end
```

A more detailed description of the calculation of information gain is shown in the following. If the possible classes $v_i$ of the examples have probabilities $P(v_i)$ then the information content I of the actual answer is given by:

$$I(P(v_1), \ldots, P(v_n)) = \sum_{i=1}^{n} -P(v_i)\log_2 P(v_i)$$

The I-value shows how much information we need in order to be able to describe the outcome of a classification for the specific dataset used. Supposing that the dataset contains p positive (e.g. has osteoarthritis) and n negative (e.g. healthy) examples (e.g. individuals), the information contained in a correct answer is:

$$I\left(\frac{p}{p+n}, \frac{n}{p+n}\right) = -\frac{p}{p+n}\log_2 \frac{p}{p+n} - \frac{n}{p+n}\log_2 \frac{n}{p+n}$$

where $\log_2$ is the logarithm using base two. By testing single attributes the amount of information needed to make a correct classification can be reduced. The remainder for a specific attribute A (e.g. a gene) shows how much the information that is needed can be reduced.

$$\text{Remainder}(A) = \sum_{i=1}^{v} \frac{p_i + n_i}{p+n} I\left(\frac{p_i}{p_i + n_i}, \frac{n_i}{p_i + n_i}\right)$$

"v" is the number of unique attribute values for attribute A in a certain dataset, "i" is a certain attribute value, "$p_i$" is the number of examples for attribute A where the classification is positive (e.g. cancer), "$n_i$" is the number of examples for attribute A where the classification is negative (e.g. healthy).

The information gain of a specific attribute A is calculated as the difference between the information content for the classes and the remainder of attribute A:

$$\text{Gain}(A) = I\left(\frac{p}{p+n}, \frac{n}{p+n}\right) - \text{Remainder}(A)$$

The information gain is used to evaluate how important the different attributes are for the classification (how well they split up the examples), and the attribute with the highest information.

In general there are a number of different decision tree algorithms, many of which are described in Duda, *Pattern Classification*, Second Edition, 2001, John Wiley & Sons, Inc. Decision tree algorithms often require consideration of feature processing, impurity measure, stopping criterion, and pruning. Specific decision tree algorithms include, cut are not limited to classification and regression trees (CART), multivariate decision trees, ID3, and C4.5.

In one approach, when an exemplary embodiment of a decision tree is used, the gene expression data for a selected set of molecular markers of the invention across a training population is standardized to have mean zero and unit variance. The members of the training population are randomly divided into a training set and a test set. For example, in one embodiment, two thirds of the members of the training population are placed in the training set and one third of the members of the training population are placed in the test set. The expression values for a select combination of genes described in the present invention is used to construct the decision tree. Then, the ability for the decision tree to correctly classify members in the test set is determined. In some embodiments, this computation is performed several times for a given combination of molecular markers. In each iteration of the computation, the members of the training population are randomly assigned to the training set and the test set. Then, the quality of the combination of molecular markers is taken as the average of each such iteration of the decision tree computation.

5.4.6. Clustering

In some embodiments, the expression values for a selected set of molecular markers of the invention are used to cluster a training set. For example, consider the case in which ten genes described in the present invention are used. Each member m of the training population will have expression values for each of the ten genes. Such values from a member m in the training population define the vector:

| $X_{1m}$ | $X_{2m}$ | $X_{3m}$ | $X_{4m}$ | $X_{5m}$ | $X_{6m}$ | $X_{7m}$ | $X_{8m}$ | $X_{9m}$ | $X_{10m}$ | where $X_{im}$ is the expression level of the $i^{th}$ gene in organism m. If there are m organisms in the training set, selection of i genes will define m vectors. Note that the methods of the present invention do not require that each the expression value of every single gene used in the vectors be represented in every single vector m. In other words, data from a subject in which one of the $i^{th}$ genes is not found can still be used for clustering. In such instances, the missing expression value is assigned either a "zero" or some other normalized value. In some embodiments, prior to clustering, the gene expression values are normalized to have a mean value of zero and unit variance.

Those members of the training population that exhibit similar expression patterns across the training group will tend to cluster together. A particular combination of genes of the present invention is considered to be a good classifier in this aspect of the invention when the vectors cluster into the trait groups found in the training population. For instance, if the training population includes patients with good or poor prognosis, a clustering classifier will cluster the population into two groups, with each group uniquely representing either good or poor prognosis.

Clustering is described on pages 211-256 of Duda and Hart, *Pattern Classification and Scene Analysis*, 1973, John Wiley & Sons, Inc., New York. As described in Section 6.7 of Duda, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda. Criterion functions are discussed in Section 6.8 of Duda.

More recently, Duda et al., Pattern Classification, $2^{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

5.4.7. Principal Component Analysis

Principal component analysis (PCA) has been proposed to analyze gene expression data. Principal component analysis is a classical technique to reduce the dimensionality of a data set by transforming the data to a new set of variable (principal components) that summarize the features of the data. See, for example, Jolliffe, 1986, *Principal Component Analysis*, Springer, New York. Principal components (PCs) are uncorrelate and are ordered such that the $k^{th}$ PC has the kth largest variance among PCs. The $k^{th}$ PC can be interpreted as the direction that maximizes the variation of the projections of the data points such that it is orthogonal to the first k−1 PCs. The first few PCs capture most of the variation in the data set. In contrast, the last few PCs are often assumed to capture only the residual 'noise' in the data.

PCA can also be used to create a prognosis predictor in accordance with the present invention. In such an approach, vectors for a selected set of molecular markers of the invention can be constructed in the same manner described for clustering above. In fact, the set of vectors, where each vector represents the expression values for the select genes from a particular member of the training population, can be considered a matrix. In some embodiments, this matrix is represented in a Free-Wilson method of qualitative binary description of monomers (Kubinyi, 1990, 3D QSAR in drug design theory methods and applications, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been accounted for.

Then, each of the vectors (where each vector represents a member of the training population) is plotted. Many different types of plots are possible. In some embodiments, a one-dimensional plot is made. In this one-dimensional plot, the value for the first principal component from each of the members of the training population is plotted. In this form of plot, the expectation is that members of a first group (e.g. good prognosis patients) will cluster in one range of first principal component values and members of a second group (e.g., poor prognosis patients) will cluster in a second range of first principal component values.

In one example, the training population comprises two groups: good prognosis patients and poor prognosis patients. The first principal component is computed using the molecular marker expression values for the select genes of the present invention across the entire training population data set. Then, each member of the training set is plotted as a function of the value for the first principal component. In this example, those members of the training population in which the first principal component is positive are the good prognosis patients and those members of the training population in which the first principal component is negative are poor prognosis patients.

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects with mild osteoarthritis, a second cluster of members in the two-dimensional plot will represent subjects with moderate osteoarthritis, and so forth.

In some embodiments, the members of the training population are plotted against more than two principal components and a determination is made as to whether the members of the training population are clustering into groups that each uniquely represents a subgroup found in the training population. In some embodiments, principal component analysis is performed by using the R mva package (Anderson, 1973, Cluster Analysis for applications, Academic Press, New York 1973; Gordon, Classification, Second Edition, Chapman and Hall, CRC, 1999.). Principal component analysis is further described in Duda, Pattern Classification, Second Edition, 2001, John Wiley & Sons, Inc.

5.4.8. Nearest Neighbor Classifier Analysis

Nearest neighbor classifiers are memory-based and require no model to be fit. Given a query point $x_0$, the k training points $x_{(r)}$, r, . . . , k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_0\|.$$

Typically, when the nearest neighbor algorithm is used, the expression data used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. Profiles of a selected set of molecular markers of the invention represents the feature space into which members of the test set are plotted. Next, the ability of the training set to correctly characterize the members of the test set is computed. In some embodiments, nearest neighbor computation is performed several times for a given combination of genes of the present invention. In each iteration of the computation, the members of the training population are randomly assigned to the training set and the test set. Then, the quality of the combination of genes is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, Pattern Classification, Second Edition, 2001, John Wiley & Sons, Inc; and Hastie, 2001, The Elements of Statistical Learning, Springer, New York.

5.4.9. Evolutionary Methods

Inspired by the process of biological evolution, evolutionary methods of classifier design employ a stochastic search for an optimal classifier. In broad overview, such methods create several classifiers—a population—from measurements of gene products of the present invention. Each classifier varies somewhat from the other. Next, the classifiers are scored on expression data across the training population. In keeping with the analogy with biological evolution, the resulting (scalar) score is sometimes called the fitness. The classifiers are ranked according to their score and the best classifiers are retained (some portion of the total population of classifiers). Again, in keeping with biological terminology, this is called survival of the fittest. The classifiers are stochastically altered in the next generation—the children or offspring. Some offspring classifiers will have higher scores than their parent in the previous generation, some will have lower scores. The overall process is then repeated for the subsequent generation: The classifiers are scored and the best ones are retained, randomly altered to give yet another generation, and so on. In part, because of the ranking, each generation has, on average, a slightly higher score than the previous one. The process is halted when the single best classifier in a generation has a score that exceeds a desired criterion value. More information on evolutionary methods is found in, for example, Duda, *Pattern Classification*, Second Edition, 2001, John Wiley & Sons, Inc.

5.4.10. Bagging, Boosting and the Random Subspace Method

Bagging, boosting and the random subspace method are combining techniques that can be used to improve weak classifiers. These techniques are designed for, and usually applied to, decision trees. In addition, Skurichina and Duin provide evidence to suggest that such techniques can also be useful in linear discriminant analysis.

In bagging, one samples the training set, generating random independent bootstrap replicates, constructs the classifier on each of these, and aggregates them by a simple majority vote in the final decision rule. See, for example, Breiman, 1996, Machine Learning 24, 123-140; and Efron & Tibshirani, *An Introduction to Bootstrap*, Chapman & Hall, New York, 1993.

In boosting, classifiers are constructed on weighted versions of the training set, which are dependent on previous classification results. Initially, all objects have equal weights, and the first classifier is constructed on this data set. Then, weights are changed according to the performance of the classifier. Erroneously classified objects (molecular markers in the data set) get larger weights, and the next classifier is boosted on the reweighted training set. In this way, a sequence of training sets and classifiers is obtained, which is then combined by simple majority voting or by weighted majority voting in the final decision. See, for example, Freund & Schapire, "Experiments with a new boosting algorithm," Proceedings 13$^{th}$ International Conference on Machine Learning, 1996, 148-156.

To illustrate boosting, consider the case where there are two phenotypic groups exhibited by the population under study, phenotype 1 (e.g., poor prognosis patients), and phenotype 2 (e.g., good prognosis patients). Given a vector of molecular markers X, a classifier G(X) produces a prediction taking one of the type values in the two value set: {phenotype 1, phenotype 2}. The error rate on the training sample is $$\overline{err} = \frac{1}{N}\sum_{i=1}^{N} I(y_i \neq G(x_i))$$

where N is the number of subjects in the training set (the sum total of the subjects that have either phenotype 1 or phenotype 2). For example, if there are 30 good prognosis patients and 48 good prognosis patients, N is 78.

A weak classifier is one whose error rate is only slightly better than random guessing. In the boosting algorithm, the weak classification algorithm is repeatedly applied to modified versions of the data, thereby producing a sequence of weak classifiers $G_m(x)$, m,=1, 2, . . . , M. The predictions from all of the classifiers in this sequence are then combined through a weighted majority vote to produce the final prediction:

$$G(x) = \text{sign}\left[\sum_{m=1}^{M} \alpha_m G_m(x)\right]$$

Here $\alpha_1, \alpha_2, \ldots, \alpha_M$ are computed by the boosting algorithm and their purpose is to weigh the contribution of each respective $G_m(x)$. Their effect is to give higher influence to the more accurate classifiers in the sequence.

The data modifications at each boosting step consist of applying weights $w_1, w_2, \ldots, w_n$ to each of the training observations $(x_i, y_i)$, i=1, 2, . . . , N. Initially all the weights are set to $w_i=1/N$, so that the first step simply trains the classifier on the data in the usual manner. For each successive iteration m=2, 3, . . . , M the observation weights are individually modified and the classification algorithm is reapplied to the weighted observations. At stem m, those observations that were misclassified by the classifier $G_{m-1}$ (x) induced at the previous step have their weights increased, whereas the weights are decreased for those that were classified correctly. Thus as iterations proceed, observations that are difficult to correctly classify receive ever-increasing influence. Each successive classifier is thereby forced to concentrate on those training observations that are missed by previous ones in the sequence.

The exemplary boosting algorithm is summarized as follows:

1. Initialize the observation weights $w_i=1/N$, i=1, 2, . . . , N.
2. For m=1 to M:
   (a) Fit a classifier $G_m(x)$ to the training set using weights $w_i$.
   (b) Compute $$err_m = \frac{\sum_{i=1}^{N} w_i I(y_i \neq G_m(x_i))}{\sum_{i=1}^{N} w_i}$$

(c) Compute $\alpha_m = \log((1-err_m)/err_m)$.
   (d) Set $w_i \leftarrow w_i \cdot \exp[\alpha_m \cdot I(y_i \neq G_m(x_i))]$, i=1, 2, . . . , N.
3. Output $$G(x) = \text{sign}\left[\sum_{m=1}^{M} \alpha_m G_m(x)\right]$$

In the algorithm, the current classifier $G_m(x)$ is induced on the weighted observations at line 2a. The resulting weighted error rate is computed at line 2b. Line 2c calculates the weight $\alpha_m$ given to $G_m(x)$ in producing the final classifier $G_m(x)$ (line 3). The individual weights of each of the observations are updated for the next iteration at line 2d. Observations misclassified by $G_m(x)$ have their weights scaled by a factor $\exp(\alpha_m)$, increasing their relative influence for inducing the next classifier $G_{m+1}(x)$ in the sequence. In some embodiments, modifications of the Freund and Schapire, 1997, Journal of Computer and System Sciences 55, pp. 119-139, boosting method are used. See, for example, Hasti et al., *The Elements of Statistical Learning*, 2001, Springer, New York, Chapter 10. In some embodiments, boosting or adaptive boosting methods are used.

In some embodiments, modifications of Freund and Schapire, 1997, Journal of Computer and System Sciences 55, pp. 119-139, are used. For example, in some embodiments, feature preselection is performed using a technique such as the nonparametric scoring methods of Park et al., 2002, Pac. Symp. Biocomput. 6, 52-63. Feature preselection is a form of dimensionality reduction in which the genes that discriminate between classifications the best are selected for use in the classifier. Then, the LogitBoost procedure introduced by Friedman et al., 2000, Ann Stat 28, 337-407 is used rather than the boosting procedure of Freund and Schapire. In some embodiments, the boosting and other classification methods of Ben-Dor et al., 2000, Journal of Computational Biology 7, 559-583 are used in the present invention. In some embodiments, the boosting and other classification methods of Freund and Schapire, 1997, Journal of Computer and System Sciences 55, 119-139, are used.

In the random subspace method, classifiers are constructed in random subspaces of the data feature space. These classifiers are usually combined by simple majority voting in the final decision rule. See, for example, Ho, "The Random subspace method for constructing decision forests," IEEE Trans Pattern Analysis and Machine Intelligence, 1998; 20(8): 832-844.

5.4.11. Other Algorithms

The pattern classification and statistical techniques described above are merely examples of the types of models that can be used to construct a model for classification. Moreover, combinations of the techniques described above can be used. Some combinations, such as the use of the combination of decision trees and boosting, have been described. However, many other combinations are possible. In addition, in other techniques in the art such as Projection Pursuit and Weighted Voting can be used to construct a prognosis predictor.

5.5. Sample Collection

In the present invention, gene products, such as target polynucleotide molecules or proteins, are extracted from a sample taken from an individual afflicted with colorectal cancer. The sample may be collected in any clinically acceptable manner, but must be collected such that marker-derived polynucleotides (i.e., RNA) are preserved (if gene expression is to be measured) or proteins are preserved (if encoded proteins are to be measured). In one embodiment, samples can be microdissected (>80% tumor cells) by frozen section guidance and RNA extraction performed using Trizol followed by secondary purification on RNAEasy columns. In another embodiment, samples can be paraffin-embedded tissue sections (see, e.g., U.S. Patent Application Publication No. 2005/0048542A1, which is incorporated by reference herein in its entirety). The mRNA profiles of paraffin-embedded tissue samples are preferably obtained using quantitative reverse transcriptase polymerase chain reaction qRT-PCR (see Section 5.6.7., infra).

In a specific embodiment, mRNA or nucleic acids derived therefrom (i.e., cDNA or amplified RNA or amplied DNA) are preferably labeled distinguishably from polynucleotide molecules of a reference sample, and both are simultaneously or independently hybridized to a microarray comprising some or all of the markers or marker sets or subsets described above. Alternatively, mRNA or nucleic acids derived therefrom may be labeled with the same label as the reference polynucleotide molecules, wherein the intensity of hybridization of each at a particular probe is compared.

A sample may comprise any clinically relevant tissue sample, such as a tumor biopsy or fine needle aspirate, or a sample of body fluid, such as blood, plasma, serum, lymph, ascitic fluid, cystic fluid, or urine. The sample may be taken from a human, or, in a veterinary context, from non-human animals such as ruminants, horses, swine or sheep, or from domestic companion animals such as felines and canines.

Methods for preparing total and poly(A)+ RNA are well known and are described generally in Sambrook et al., MOLECULAR CLONING—A LABORATORY MANUAL (2ND ED.), Vols. 1-3, Cold Spring Harbor Laboratory, Cold Spring Harbor, N.Y. (1989)) and Ausubel et al., CURRENT PROTOCOLS IN MOLECULAR BIOLOGY, vol. 2, Current Protocols Publishing, New York (1994)). Preferably, total RNA, or total mRNA (poly(A)+ RNA) is meausured in the methods of the invention directly or indirectly (e.g., via measuring cDNA or cRNA).

RNA may be isolated from eukaryotic cells by procedures that involve lysis of the cells and denaturation of the proteins contained therein. Cells of interest include wild-type cells (i.e., non-cancerous), drug-exposed wild-type cells, tumor- or tumor-derived cells, modified cells, normal or tumor cell line cells, and drug-exposed modified cells. Preferably, the cells are breast cancer tumor cells.

Additional steps may be employed to remove DNA. Cell lysis may be accomplished with a nonionic detergent, followed by microcentrifugation to remove the nuclei and hence the bulk of the cellular DNA. In one embodiment, RNA is extracted from cells of the various types of interest using guanidinium thiocyanate lysis followed by CsCl centrifugation to separate the RNA from DNA (Chirgwin et al., *Biochemistry* 18:5294-5299 (1979)). Poly(A)+ RNA is selected by selection with oligo-dT cellulose (see Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, separation of RNA from DNA can be accomplished by organic extraction, for example, with hot phenol or phenol/chloroform/isoamyl alcohol.

If desired, RNase inhibitors may be added to the lysis buffer. Likewise, for certain cell types, it may be desirable to add a protein denaturation/digestion step to the protocol.

For many applications, it is desirable to preferentially enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or Sephadex™ (see Ausubel et al., CURRENT PROTOCOLS IN MOLECULAR BIOLOGY, vol. 2, Current Protocols Publishing, New York (1994). Once bound, poly (A)+ mRNA is eluted from the affinity column using 2 mM EDTA/0.1% SDS.

In a specific embodiment, total RNA or total mRNA from cells is used in the methods of the invention. The source of the RNA can be cells of an animal, e.g., human, mammal, primate, non-human animal, dog, cat, mouse, rat, bird, etc. In specific embodiments, the method of the invention is used with a sample containing total mRNA or total RNA from $1 \times 10^6$ cells or less. In another embodiment, proteins can be isolated from the foregoing sources, by methods known in the art, for use in expression analysis at the protein level.

Probes to the homologs of the marker sequences disclosed herein can be employed preferably when non-human nucleic acid is being assayed.

5.6. Determination of Abundance Levels of Gene Products

The abundance levels of the gene products of the genes in a sample may be determined by any means known in the art. The levels may be determined by isolating and determining the level (i.e., amount) of nucleic acid transcribed from each marker gene. Alternatively, or additionally, the level of specific proteins encoded by a marker gene may be determined.

The levels of transcripts of specific marker genes can be accomplished by determining the amount of mRNA, or polynucleotides derived therefrom, present in a sample. Any method for determining RNA levels can be used. For example, RNA is isolated from a sample and separated on an agarose gel. The separated RNA is then transferred to a solid support, such as a filter. Nucleic acid probes representing one or more markers are then hybridized to the filter by northern hybridization, and the amount of marker-derived RNA is determined. Such determination can be visual, or machine-aided, for example, by use of a densitometer. Another method of determining RNA levels is by use of a dot-blot or a slot-blot. In this method, RNA, or nucleic acid derived therefrom, from a sample is labeled. The RNA or nucleic acid derived therefrom is then hybridized to a filter containing oligonucleotides derived from one or more marker genes, wherein the oligonucleotides are placed upon the filter at discrete, easily-identifiable locations. Hybridization, or lack thereof, of the labeled RNA to the filter-bound oligonucleotides is determined visually or by densitometer. Polynucleotides can be labeled using a radiolabel or a fluorescent (i.e., visible) label.

These examples are not intended to be limiting; other methods of determining RNA abundance are known in the art.

The levels of transcripts of particular marker genes may also be assessed by determining the level of the specific protein expressed from the marker genes. This can be accomplished, for example, by separation of proteins from a sample on a polyacrylamide gel, followed by identification of specific marker-derived proteins using antibodies in a western blot. Alternatively, proteins can be separated by two-dimensional gel electrophoresis systems. Two-dimensional gel electrophoresis is well-known in the art and typically involves isoelectric focusing along a first dimension followed by SDS-PAGE electrophoresis along a second dimension. See, e.g., Hames et al, 1990, GEL ELECTROPHORESIS OF PROTEINS: A PRACTICAL APPROACH, IRL Press, New York; Shevchenko et al., *Proc. Nat'l Acad. Sci. USA* 93:1440-1445 (1996); Sagliocco et al., *Yeast* 12:1519-1533 (1996); Lander, *Science* 274:536-539 (1996). The resulting electropherograms can be analyzed by numerous techniques, including mass spectrometric techniques, western blotting and immunoblot analysis using polyclonal and monoclonal antibodies.

Alternatively, marker-derived protein levels can be determined by constructing an antibody microarray in which binding sites comprise immobilized, preferably monoclonal, antibodies specific to a plurality of protein species encoded by the cell genome. Preferably, antibodies are present for a substantial fraction of the marker-derived proteins of interest. Methods for making monoclonal antibodies are well known (see, e.g., Harlow and Lane, 1988, ANTIBODIES: A LABORATORY MANUAL, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array, and their binding is assayed with assays known in the art. Generally, the expression, and the level of expression, of proteins of diagnostic or prognostic interest can be detected through immunohistochemical staining of tissue slices or sections.

Finally, levels of transcripts of marker genes in a number of tissue specimens may be characterized using a "tissue array" (Kononen et al., *Nat. Med* 4(7):844-7 (1998)). In a tissue array, multiple tissue samples are assessed on the same microarray. The arrays allow in situ detection of RNA and protein levels; consecutive sections allow the analysis of multiple samples simultaneously.

5.6.1. Microarrays

In preferred embodiments, polynucleotide microarrays are used to measure expression so that the expression status of each of the markers above is assessed simultaneously. Generally, microarrays according to the invention comprise a plurality of markers informative for prognosis, or outcome determination, for a particular disease or condition, and, in particular, for individuals having specific combinations of genotypic or phenotypic characteristics of the disease or condition (i.e., that are prognosis-informative for a particular patient subset).

The invention also provides a microarray comprising for each of a plurality of genes, said genes being all or at least 5, 10, 20, 30, 40, 50 or 70 of the genes listed in Table 1 or any of Tables 2-5, 7 and 8, one or more polynucleotide probes complementary and hybridizable to a sequence in said gene, wherein polynucleotide probes complementary and hybridizable to said genes constitute at least 50%, 60%, 70%, 80%, 90%, 95%, or 98% of the probes on said microarray. In a particular embodiment, the invention provides such a microarray wherein the plurality of genes comprises the 43 genes listed in Table 5 or the 53 genes listed in Table 2 or the 7 genes listed in Table 3. The microarray can be in a sealed container.

The microarrays of the invention preferably comprise at least 2, 3, 4, 5, 7, 10, 15, 20, 25, 30, 35, 40, 45, 50, 75, 100, 150, 200 or more of markers, or all of the markers, or any combination of markers, identified as prognosis-informative within a patient subset, e.g., within Table 1 or any of Tables 2-5, 7 and 8. The actual number of informative markers the microarray comprises will vary depending upon the particular condition of interest.

In specific embodiments, the invention provides polynucleotide arrays in which the prognosis markers identified for a particular patient subset comprise at least 50%, 60%, 70%, 80%, 85%, 90%, 95% or 98% of the probes on the array. In another specific embodiment, the microarray comprises a plurality of probes, wherein said plurality of probes comprise probes complementary and hybridizable to at least 75% of the prognosis-informative markers identified for a particular patient subset. Microarrays of the invention, of course, may comprise probes complementary and hybridizable to prognosis-informative markers for a plurality of the patient subsets, or for each patient subset, identified for a particular condition. In another embodiment, therefore, the microarray of the invention comprises a plurality of probes complementary and hybridizable to at least 75% of the prognosis-informative markers identified for each patient subset identified for the condition of interest, and wherein the probes, in total, are at least 50% of the probes on said microarray.

In yet another specific embodiment, the microarray is a commercially-available cDNA microarray that comprises probes to at least five markers identified by the methods described herein. Preferably, a commercially-available cDNA microarray comprises probes to all of the markers identified by the methods described herein as being informative for a patient subset for a particular condition. However, such a microarray may comprise at least 5, 10, 15 or 25 of such markers, up to the maximum number of markers identified.

In one embodiment, the invention provides oligonucleotide or cDNA arrays comprising probes hybridizable to the genes corresponding to each of the marker sets described above, e.g., as shown in Table 1 or any one of Tables 2-5, 7 and 8. In another embodiment, a whole-genome cDNA array can be used. Any of the microarrays described herein may be provided in a sealed container in a kit.

The invention provides microarrays containing probes useful for the prognosis of colon cancer patients. In particular, the invention provides polynucleotide arrays comprising probes to a subset or subsets of at least 5, 10, 15, 20, 25 or more of the genetic markers, or up to the full set of markers, in Table 1, which distinguish between patients with good and poor prognosis. In certain embodiments, therefore, the invention provides microarrays comprising probes for a plurality of the genes for which markers are listed in Table 1. In a specific embodiment, the microarray of the invention comprises 1, 2, 3, 4, 5 or 10 of the markers in Table 1. In other embodiments, the microarray of the invention contains each of the markers in Table 1. In another embodiment, the microarray contains all of the markers shown in Table 1.

In specific embodiments, the invention provides polynucleotide arrays in which the colon cancer prognosis markers described herein in Table 1 comprise at least 50%, 60%, 70%, 80%, 85%, 90%, 95% or 98% of the probes on said array. In another specific embodiment, the microarray comprises a plurality of probes, wherein said plurality of probes comprise probes complementary and hybridizable to transcripts of at least 75% of the genes for which markers are listed in Table 1.

In yet another specific embodiment, the microarray is a commercially-available cDNA microarray that comprises probes to at least five of the markers listed in Table 1. Preferably, a commercially-available cDNA microarray comprises all of the markers listed in Table 1. However, such a microarray may comprise probes to at least 5, 10, 15 or 25 of the markers in Table 1, up to the maximum number of markers in Table 1, and may comprise probes to all of the markers in Table 1. In a specific embodiment of the microarrays used in the methods disclosed herein comprise probes to the markers that are all or a portion of Table 1 make up at least 50%, 60%, 70%, 80%, 90%, 95% or 98% of the probes on the microarray.

General methods pertaining to the construction of microarrays comprising the marker sets and/or subsets above are described in the following sections.

In a specific embodiment, the Affymetrix® Human Genome U133 (HG-U133) Set, consisting of two GeneChip® arrays, is used in accordance with known methods. The Human Genome U133 (HG-U133) Set contains almost 45,000 probe sets representing more than 39,000 transcripts derived from approximately 33,000 well-substantiated human genes. This set design uses sequences selected from GenBank®, dbEST, and RefSeq. The sequence clusters were created from the UniGene database (Build 133, Apr. 20, 2001). They were then refined by analysis and comparison with a number of other publicly available databases including the Washington University EST trace repository and the University of California, Santa Cruz Golden Path human genome database (April 2001 release).

In another embodiment, the HG-U133A array is used in accordance with the methods of the invention. The HG-U133A array includes representation of the RefSeq database sequences and probe sets related to sequences previously represented on the Human Genome U95Av2 array. The HG-U133B array contains primarily probe sets representing EST clusters. In another embodiment, the U133 Plus 2.0 GeneChip® is used in the invention. The U133 Plus 2.0 GeneChip® represents over 47,000 transcripts.

In another embodiment, a cDNA based microarray is used. In one embodiment, TIGR's 32,488-element spotted cDNA arrays is used. The TIGR cDNA array contains 31,872 human cDNAs representing 30,849 distinct transcripts: 23,936 unique TIGR TCs and 6,913 ESTs, 10 exogenous controls printed 36 times, and 4 negative controls printed 36-72 times.

5.6.2. Construction of Microarrays

Microarrays are prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic DNA. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support which may be either porous or non-porous. For example, the probes of the invention may be polynucleotide sequences which are attached to a nitrocellulose or nylon membrane or filter covalently at either the 3' or the 5' end of the polynucleotide. Such hybridization probes are well known in the art (see, e.g., Sambrook et al., MOLECULAR CLONING—A LABORATORY MANUAL (2ND ED.), Vols. 1-3, Cold Spring Harbor Laboratory, Cold Spring Harbor, N.Y. (1989). Alternatively, the solid support or surface may be a glass or plastic surface. In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel.

In preferred embodiments, a microarray comprises a support or surface with an ordered array of binding (e.g., hybridization) sites or "probes" each representing one of the markers described herein. Preferably the microarrays are addressable arrays, and more preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics. The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 1 cm² and 25 cm², between 12 cm² and 13 cm², or 3 cm². However, larger arrays are also contemplated and may be preferable, e.g., for use in screening arrays. Preferably, a given binding site or unique set of binding sites in the microarray will specifically bind (e.g., hybridize) to the product of a single gene in a cell (e.g., to a specific mRNA, or to a specific cDNA derived therefrom). However, in general, other related or similar sequences will cross hybridize to a given binding site.

The microarrays of the present invention include one or more test probes, each of which has a polynucleotide sequence that is complementary to a subsequence of RNA or DNA to be detected. Preferably, the position of each probe on the solid surface is known. Indeed, the microarrays are preferably positionally addressable arrays. Specifically, each probe of the array is preferably located at a known, predetermined position on the solid support such that the identity (i.e., the sequence) of each probe can be determined from its position on the array (i.e., on the support or surface).

According to the invention, the microarray is an array (i.e., a matrix) in which each position represents one of the markers described herein. For example, each position can contain a DNA or DNA analogue based on genomic DNA to which a particular RNA or cDNA transcribed from that genetic marker can specifically hybridize. The DNA or DNA analogue can be, e.g., a synthetic oligomer or a gene fragment. In one embodiment, probes representing each of the markers is present on the array. In a preferred embodiment, the array comprises probes for each of the markers listed in Table 1 or any one of Tables 2-5, 7 and 8.

5.6.3. Preparing Probes for Microarrays

As noted above, the "probe" to which a particular polynucleotide molecule specifically hybridizes according to the invention contains a complementary genomic polynucleotide sequence. The probes of the microarray preferably consist of nucleotide sequences of no more than 1,000 nucleotides. In some embodiments, the probes of the array consist of nucleotide sequences of 10 to 1,000 nucleotides. In a preferred embodiment, the nucleotide sequences of the probes are in the range of 10-200 nucleotides in length and are genomic sequences of a species of organism, such that a plurality of different probes is present, with sequences complementary and thus capable of hybridizing to the genome of such a species of organism, sequentially tiled across all or a portion of such genome. In other specific embodiments, the probes are in the range of 10-30 nucleotides in length, in the range of 10-40 nucleotides in length, in the range of 20-50 nucleotides in length, in the range of 40-80 nucleotides in length, in the range of 50-150 nucleotides in length, in the range of 80-120 nucleotides in length, and most preferably are 60 nucleotides in length.

The probes may comprise DNA or DNA "mimics" (e.g., derivatives and analogues) corresponding to a portion of an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates.

DNA can be obtained, e.g., by polymerase chain reaction (PCR) amplification of genomic DNA or cloned sequences. PCR primers are preferably chosen based on a known sequence of the genome that will result in amplification of specific fragments of genomic DNA. Computer programs that are well known in the art are useful in the design of primers with the required specificity and optimal amplification properties, such as Oligo version 5.0 (National Biosciences). Typically each probe on the microarray will be between 10 bases and 50,000 bases, usually between 300 bases and 1,000 bases in length. PCR methods are well known in the art, and are described, for example, in Innis et al., eds., PCR PROTOCOLS: A GUIDE TO METHODS AND APPLICATIONS, Academic Press Inc., San Diego, Calif. (1990). It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., *Nucleic Acid Res.* 14:5399-5407 (1986); McBride et al., *Tetrahedron Lett.* 24:246-248 (1983)). Synthetic sequences are typically between about 10 and about 500 bases in length, more typically between about 20 and about 100 bases, and most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., *Nature* 363:566-568 (1993); U.S. Pat. No. 5,539,083).

Probes are preferably selected using an algorithm that takes into account binding energies, base composition, sequence complexity, cross-hybridization binding energies, and secondary structure. See Friend et al., International Patent Publication WO 01/05935, published Jan. 25, 2001; Hughes et al., *Nat. Biotech.* 19:342-7 (2001).

A skilled artisan will also appreciate that positive control probes, e.g., probes known to be complementary and hybridizable to sequences in the target polynucleotide molecules, and negative control probes, e.g., probes known to not be complementary and hybridizable to sequences in the target polynucleotide molecules, should be included on the array. In one embodiment, positive controls are synthesized along the perimeter of the array. In another embodiment, positive controls are synthesized in diagonal stripes across the array. In still another embodiment, the reverse complement for each probe is synthesized next to the position of the probe to serve as a negative control. In yet another embodiment, sequences from other species of organism are used as negative controls or as "spike-in" controls.

5.6.4. Attaching Probes to the Solid Surface

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena et al, *Science* 270:467-470 (1995). This method is especially useful for preparing microarrays of cDNA (See also, DeRisi et al, *Nature Genetics* 14:457-460 (1996); Shalon et al., *Genome Res.* 6:639-645 (1996); and Schena et al., *Proc. Natl. Acad. Sci. U.S.A.* 93:10539-11286 (1995)).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251: 767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510, 270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. Usually, the array produced is redundant, with several oligonucleotide molecules per RNA.

Other methods for making microarrays, e.g., by masking (Maskos and Southern, 1992, *Nuc. Acids. Res.* 20:1679-1684), may also be used. In principle, and as noted supra, any type of array, for example, dot blots on a nylon hybridization membrane (see Sambrook et al., MOLECULAR CLONING—A LABORATORY MANUAL (2ND ED.), Vols. 1-3, Cold Spring Harbor Laboratory, Cold Spring Harbor, N.Y. (1989)) could be used. However, as will be recognized by those skilled in the art, very small arrays will frequently be preferred because hybridization volumes will be smaller.

In one embodiment, the arrays of the present invention are prepared by synthesizing polynucleotide probes on a support. In such an embodiment, polynucleotide probes are attached to the support covalently at either the 3' or the 5' end of the polynucleotide.

In a particularly preferred embodiment, microarrays of the invention are manufactured by means of an ink jet printing device for oligonucleotide synthesis, e.g., using the methods and systems described by Blanchard in U.S. Pat. No. 6,028,189; Blanchard et al., 1996, *Biosensors and Bioelectronics* 11:687-690; Blanchard, 1998, in Synthetic DNA Arrays in Genetic Engineering, Vol. 20, J. K. Setlow, Ed., Plenum Press, New York at pages 111-123. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Microarrays manufactured by this ink-jet method are typically of high density, preferably having a density of at least about 2,500 different probes per 1 cm². The polynucleotide probes are attached to the support covalently at either the 3' or the 5' end of the polynucleotide.

5.6.5. Target Labeling and Hybridization to Microarrays

The polynucleotide molecules which may be analyzed by the present invention (the "target polynucleotide molecules") may be from any clinically relevant source, but are expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. In one embodiment, the target polynucleotide molecules comprise RNA, including, but by no means limited to, total cellular RNA, poly(A)$^+$ messenger RNA (mRNA) or fraction thereof, cytoplasmic mRNA, or RNA transcribed from cDNA (i.e., cRNA; see, e.g., Linsley & Schelter, U.S. patent application Ser. No. 09/411,074, filed Oct. 4, 1999, or U.S. Pat. No. 5,545,522, 5,891,636, or 5,716,785). Methods for preparing total and poly(A)$^+$ RNA are well known in the art, and are described generally, e.g., in Sambrook et al., MOLECULAR CLONING—A LABORATORY MANUAL (2ND ED.), Vols. 1-3, Cold Spring Harbor Laboratory, Cold Spring Harbor, N.Y. (1989). In one embodiment, RNA is extracted from cells of the various types of interest in this invention using guanidinium thiocyanate lysis followed by CsCl centrifugation (Chirgwin et al., 1979, *Biochemistry* 18:5294-5299). In another embodiment, total RNA is extracted using a silica gel-based column, commercially available examples of which include RNeasy (Qiagen, Valencia, Calif.) and StrataPrep (Stratagene, La Jolla, Calif.). In an alternative embodiment, which is preferred for *S. cerevisiae*, RNA is extracted from cells using phenol and chloroform, as described in Ausubel et al., eds., 1989, CURRENT PROTOCOLS IN MOLECULAR BIOLOGY, Vol. III, Green Publishing Associates, Inc., John Wiley & Sons, Inc., New York, at pp. 13.12.1-13.12.5). Poly(A)$^+$ RNA can be selected, e.g., by selection with oligo-dT cellulose or, alternatively, by oligo-dT primed reverse transcription of total cellular RNA. In one embodiment, RNA can be fragmented by methods known in the art, e.g., by incubation with $ZnCl_2$, to generate fragments of RNA. In another embodiment, the polynucleotide molecules analyzed by the invention comprise cDNA, or PCR products of amplified RNA or cDNA.

In one embodiment, total RNA, mRNA, or nucleic acids derived therefrom, is isolated from a sample taken from a colorectal cancer patient. Target polynucleotide molecules that are poorly expressed in particular cells may be enriched using normalization techniques (Bonaldo et al., 1996, *Genome Res.* 6:791-806).

As described above, the target polynucleotides are detectably labeled at one or more nucleotides. Any method known in the art may be used to detectably label the target polynucleotides. Preferably, this labeling incorporates the label uniformly along the length of the RNA, and more preferably, the labeling is carried out at a high degree of efficiency. One embodiment for this labeling uses oligo-dT primed reverse transcription to incorporate the label; however, conventional methods of this method are biased toward generating 3' end fragments. Thus, in a preferred embodiment, random primers (e.g., 9-mers) are used in reverse transcription to uniformly incorporate labeled nucleotides over the full length of the target polynucleotides. Alternatively, random primers may be used in conjunction with PCR methods or T7 promoter-based in vitro transcription methods in order to amplify the target polynucleotides.

In a preferred embodiment, the detectable label is a luminescent label. For example, fluorescent labels, bioluminescent labels, chemiluminescent labels, and colorimetric labels may be used in the present invention. In a highly preferred embodiment, the label is a fluorescent label, such as a fluorescein, a phosphor, a rhodamine, or a polymethine dye derivative. Examples of commercially available fluorescent labels include, for example, fluorescent phosphoramidites such as FluorePrime (Amersham Pharmacia, Piscataway, N.J.), Fluoredite (Millipore, Bedford, Mass.), FAM (ABI, Foster City, Calif.), and Cy3 or Cy5 (Amersham Pharmacia, Piscataway, N.J.). In another embodiment, the detectable label is a radiolabeled nucleotide.

In a further preferred embodiment, target polynucleotide molecules from a patient sample are labeled differentially from target polynucleotide molecules of a reference sample. The reference can comprise target polynucleotide molecules from normal tissue samples (i.e., tissues from those not afflicted with colorectal cancer).

Nucleic acid hybridization and wash conditions are chosen so that the target polynucleotide molecules specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. One of skill in the art will appreciate that as the oligonucleotides become shorter, it may become necessary to adjust their length to achieve a relatively uniform melting temperature for satisfactory hybridization results. General parameters for specific (i.e., stringent) hybridization conditions for nucleic acids are described in Sambrook et al., MOLECULAR CLONING—A LABORATORY MANUAL (2ND ED.), Vols. 1-3, Cold Spring Harbor Laboratory, Cold Spring Harbor, N.Y. (1989), and in Ausubel et al., CURRENT PROTOCOLS IN MOLECULAR BIOLOGY, vol. 2, Current Protocols Publishing, New York (1994). Typical hybridization conditions for the cDNA microarrays of Schena et al. are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., *Proc. Natl. Acad. Sci. U.S.A.* 93:10614 (1993)). Useful hybridization conditions are also provided in, e.g., Tijessen, 1993, HYBRIDIZATION WITH NUCLEIC ACID PROBES, Elsevier Science Publishers B.V.; and Kricka, 1992, NONISOTOPIC DNA PROBE TECHNIQUES, Academic Press, San Diego, Calif.

Particularly preferred hybridization conditions include hybridization at a temperature at or near the mean melting temperature of the probes (e.g., within 51° C., more preferably within 21° C.) in 1 M NaCl, 50 mM MES buffer (pH 6.5), 0.5% sodium sarcosine and 30% formamide.

5.6.6. Signal Detection and Data Analysis

When fluorescently labeled gene products are used, the fluorescence emissions at each site of a microarray may be, preferably, detected by scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (see Shalon et al., 1996, "A DNA microarray system for analyzing complex DNA samples using two-color fluorescent probe hybridization," *Genome Research* 6:639-645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., *Genome Res.* 6:639-645 (1996), and in other references cited herein. Alternatively, the fiber-optic bundle described by Ferguson et al., *Nature Biotech.* 14:1681-1684 (1996), may be used to monitor mRNA abundance levels at a large number of sites simultaneously.

5.6.7. Other Assays for Detecting and Quantifying RNA

In addition to microarrays such as those described above any technique known to one of skill for detecting and measuring RNA can be used in accordance with the methods of the invention. Non-limiting examples of techniques include Northern blotting, nuclease protection assays, RNA fingerprinting, polymerase chain reaction, ligase chain reaction, Qbeta replicase, isothermal amplification method, strand displacement amplification, transcription based amplification systems, nuclease protection (SI nuclease or RNAse protection assays), SAGE as well as methods disclosed in International Publication Nos. WO 88/10315 and WO 89/06700, and International Applications Nos. PCT/US87/00880 and PCT/US89/01025.

A standard Northern blot assay can be used to ascertain an RNA transcript size, identify alternatively spliced RNA transcripts, and the relative amounts of mRNA in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Non-limiting examples of isotopes include $^3$H, $^{14}$C, $^{32}$P, $^{35}$S, $^{36}$Ci, $^{51}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Nuclease protection assays (including both ribonuclease protection assays and S1 nuclease assays) can be used to detect and quantitate specific mRNAs. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Serial Analysis Gene Expression (SAGE), which is described in e.g., Velculescu et al., 1995, *Science* 270:484-7; Carulli, et al., 1998, *Journal of Cellular Biochemistry Supplements* 30/31:286-96, can also be used to determine RNA abundances in a cell sample.

Quantitative reverse transcriptase PCR (qRT-PCR) can also be used to determine the expression profiles of marker genes (see, e.g., U.S. Patent Application Publication No. 2005/0048542A1). The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™. Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system includes software for running the instrument and for analyzing the data.

5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

5.6.8. Detection and Quantification of Protein

Measurement of the translational state may be performed according to several methods. For example, whole genome monitoring of protein (e.g., the "proteome,") can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array and their binding is assayed with assays known in the art.

Immunoassays known to one of skill in the art can be used to detect and quantify protein levels. For example, ELISAs can be used to detect and quantify protein levels. ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. In a preferred embodiment, an ELISA may be performed by coating a high binding 96-well microtiter plate (Costar) with 2 µg/ml of rhu-IL-9 in PBS overnight. Following three washes with PBS, the plate is incubated with three-fold serial dilutions of Fab at 25° C. for 1 hour. Following another three washes of PBS, 1 µg/ml anti-human kappa-alkaline phosphatase-conjugate is added and the plate is incubated for 1 hour at 25° C. Following three washes with PBST, the alkaline phosphatase activity is determined in 50 µl/AMP/PPMP substrate. The reactions are stopped and the absorbance at 560 nm is determined with a VMAX microplate reader. For further discussion regarding ELISAs see, e.g., Ausubel et al, eds, 1994, Current Protocols in Molecular Biology, Vol. 1, John Wiley & Sons, Inc., New York at 11.2.1.

Protein levels may be determined by Western blot analysis. Further, protein levels as well as the phosphorylation of proteins can be determined by immunoprecitation followed by Western blot analysis. Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, incubating the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

Protein expression levels can also be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274:536-539. The resulting electropherograms can be analyzed by numerous techniques, including mass spectrometric techniques, Western blotting and immunoblot analysis using polyclonal and monoclonal antibodies, and internal and N-terminal micro-sequencing.

5.7. Determining Therapeutic Regimens for Patients

The benefit of adjuvant chemotherapy for colorectal cancer appears limited to patients with Dukes stage C disease where the cancer has metastasized to lymph nodes at the time of diagnosis. For this reason, the clinicopathological Dukes' staging system is critical for determining how adjuvant therapy is administered. Unfortunately, as noted above, Dukes' staging is not very accurate in predicting overall survival and thus its application likely results in the treatment of a large number of patients to benefit an unknown few. Alternatively, there are a number of patients who would benefit from therapy that do not receive it based on the Dukes' staging system.

Thus, the methods of the prognosis prediction can be used for determining whether a colorectal cancer patient may benefit from chemotherapy. In one embodiment, the invention provides a method for determining whether a colorectal cancer patient should be treated with chemotherapy, comprising (a) classifying the patient as having a good prognosis or a poor prognosis using a method as described in Section 5.2.; and (b) determining that said patient's predicted survival time favors treatment of the patient with chemotherapy if said patient is classified as having a poor prognosis. In another embodiment, the methods are used in conjunction with Dukes staging. For example, the prognosis methods of the invention can be used to identify those Dukes' stage B and C cases for which chemotherapy may be beneficial.

If a patient is determined to be one likely to benefit from chemotherapy, a suitable chemotherapy may be prescribed for the patient. Chemotherapy can be performed using any one or a combination of the anti-cancer drugs known in the art, including but not limited to any topoisomerase inhibitor, DNA binding agent, anti-metabolite, ionizing radiation, or a combination of two or more of such known DNA damaging agents.

A topoisomerase inhibitor that can be used in conjunction with the invention can be, for example, a topoisomerase I (Topo I) inhibitor, a topoisomerase II (Topo II) inhibitor, or a dual topoisomerase I and II inhibitor. A topo I inhibitor can be from any of the following classes of compounds: camptothecin analogue (e.g., karenitecin, aminocamptothecin, lurtotecan, topotecan, irinotecan, BAY 56-3722, rubitecan, GI14721, exatecan mesylate), rebeccamycin analogue, PNU 166148, rebeccamycin, TAS-103, camptothecin (e.g., camptothecin polyglutamate, camptothecin sodium), intoplicine, ecteinascidin 743, J-107088, pibenzimol. Examples of preferred topo I inhibitors include but are not limited to camptothecin, topotecan (hycaptamine), irinotecan (irinotecan hydrochloride), belotecan, or an analogue or derivative thereof.

A topo II inhibitor that can be used in conjunction with the invention can be, for example, from any of the following classes of compounds: anthracycline antibiotics (e.g., carubicin, pirarubicin, daunorubicin citrate liposomal, daunomycin, 4-iodo-4-doxydoxorubicin, doxorubicin, n,n-dibenzyl daunomycin, morpholinodoxorubicin, aclacinomycin antibiotics, duborimycin, menogaril, nogalamycin, zorubicin, epirubicin, marcellomycin, detorubicin, annamycin, 7-cyanoquinocarcinol, deoxydoxorubicin, idarubicin, GPX-100, MEN-10755, valrubicin, KRN5500), epipodophyllotoxin compound (e.g., podophyllin, teniposide, etoposide, GL331, 2-ethylhydrazide), anthraquinone compound (e.g., ametantrone, bisantrene, mitoxantrone, anthraquinone), ciprofloxacin, acridine carboxamide, amonafide, anthrapyrazole antibiotics (e.g., teloxantrone, sedoxantrone trihydrochloride, piroxantrone, anthrapyrazole, losoxantrone), TAS-103, fostriecin, razoxane, XK469R, XK469, chloroquinoxaline sulfonamide, merbarone, intoplicine, elsamitrucin, CI-921, pyrazoloacridine, elliptinium, amsacrine. Examples of preferred topo II inhibitors include but are not limited to doxorubicin (Adriamycin), etoposide phosphate (etopofos), teniposide, sobuzoxane, or an analogue or derivative thereof.

DNA binding agents that can be used in conjunction with the invention include but are not limited to DNA groove binding agent, e.g., DNA minor groove binding agent; DNA crosslinking agent; intercalating agent; and DNA adduct forming agent. A DNA minor groove binding agent can be an anthracycline antibiotic, mitomycin antibiotic (e.g., porfiromycin, KW-2149, mitomycin B, mitomycin A, mitomycin C), chromomycin A3, carzelesin, actinomycin antibiotic (e.g., cactinomycin, dactinomycin, actinomycin F1), brostallicin, echinomycin, bizelesin, duocarmycin antibiotic (e.g., KW 2189), adozelesin, olivomycin antibiotic, plicamycin, zinostatin, distamycin, MS-247, ecteinascidin 743, amsacrine, anthramycin, and pibenzimol, or an analogue or derivative thereof.

DNA crosslinking agents include but are not limited to antineoplastic alkylating agent, methoxsalen, mitomycin antibiotic, psoralen. An antineoplastic alkylating agent can be a nitrosourea compound (e.g., cystemustine, tauromustine, semustine, PCNU, streptozocin, SarCNU, CGP-6809, carmustine, fotemustine, methylnitrosourea, nimustine, ranimustine, ethylnitrosourea, lomustine, chlorozotocin), mustard agent (e.g., nitrogen mustard compound, such as spiromustine, trofosfamide, chlorambucil, estramustine, 2,2, 2-trichlorotriethylamine, prednimustine, novembichin, phenamet, glufosfamide, peptichemio, ifosfamide, defosfamide, nitrogen mustard, phenesterin, mannomustine, cyclophosphamide, melphalan, perfosfamide, mechlorethamine oxide hydrochloride, uracil mustard, bestrabucil, DHEA mustard, tallimustine, mafosfamide, aniline mustard, chlomaphazine; sulfur mustard compound, such as bischloroethylsulfide; mustard prodrug, such as TLK286 and ZD2767), ethylenimine compound (e.g., mitomycin antibiotic, ethylenimine, uredepa, thiotepa, diaziquone, hexamethylene bisacetamide, pentamethylmelamine, altretamine, carzinophilin, triaziquone, meturedepa, benzodepa, carboquone), alkylsulfonate compound (e.g., dimethylbusulfan, Yoshi-864, improsulfan, piposulfan, treosulfan, busulfan, hepsulfam), epoxide compound (e.g., anaxirone, mitolactol, dianhydrogalactitol, teroxirone), miscellaneous alkylating agent (e.g., ipomeanol, carzelesin, methylene dimethane sulfonate, mitobronitol, bizelesin, adozelesin, piperazinedione, VNP40101M, asaley, 6-hydroxymethylacylfulvene, EO9, etoglucid, ecteinascidin 743, pipobroman), platinum compound (e.g., ZD0473, liposomal-cisplatin analogue, satraplatin, BBR 3464, spiroplatin, ormaplatin, cisplatin, oxaliplatin, carboplatin, lobaplatin, zeniplatin, iproplatin), triazene compound (e.g., imidazole mustard, CB 10-277, mitozolomide, temozolomide, procarbazine, dacarbazine), picoline compound (e.g., penclomedine), or an analogue or derivative thereof. Examples of preferred alkylating agents include but are not limited to cisplatin, dibromodulcitol, fotemustine, ifosfamide (ifosfamid), ranimustine (ranomustine), nedaplatin (latoplatin), bendamustine (bendamustine hydrochloride), eptaplatin, temozolomide (methazolastone), carboplatin, altretamine (hexamethylmelamine), prednimustine, oxaliplatin (oxalaplatinum), carmustine, thiotepa, leusulfon (busulfan), lobaplatin, cyclophosphamide, bisulfan, melphalan, and chlorambucil, or analogues or derivatives thereof.

Intercalating agents can be an anthraquinone compound, bleomycin antibiotic, rebeccamycin analogue, acridine, acridine carboxamide, amonafide, rebeccamycin, anthrapyrazole antibiotic, echinomycin, psoralen, LU 79553, BW A773U, crisnatol mesylate, benzo(a)pyrene-7,8-diol-9,10-epoxide, acodazole, elliptinium, pixantrone, or an analogue or derivative thereof, etc.

DNA adduct forming agents include but are not limited to enediyne antitumor antibiotic (e.g., dynemicin A, esperamicin A1, zinostatin, dynemicin, calicheamicin gamma 1I), platinum compound, carmustine, tamoxifen (e.g., 4-hydroxy-tamoxifen), psoralen, pyrazine diazohydroxide, benzo(a)pyrene-7,8-diol-9,10-epoxide, or an analogue or derivative thereof.

Anti-metabolites include but are not limited to cytosine, arabinoside, floxuridine, fluorouracil, mercaptopurine, Gemcitabine, and methotrexate (MTX).

In addition to identifying those patients for whom therapy is most beneficial, the classifier of the subject invention can identify those genes that are most biologically significant based on their frequency of appearance in the classification set. In one embodiment, those genes that are most biologically significant to colorectal cancer were identified using the classifier provided in the Example (Section 6). Specifically, osteopontin and neuregulin reported biological significance in the context of colorectal cancer.

5.8. Kits

The invention provides kits that are useful in predicting prognosis of colorectal cancer in a colorectal caner patient. The kits of the present invention comprise one or more probes and/or primers for each of at least 5, 10, 20, 30, 40, 50, 60, 70, 80, or 100 gene products that are encoded by the respectively marker genes listed in Table 1 or funtional equivalents of such genes. The probes of marker genes may be part of an array, or the biomarker(s) may be packaged separately and/or individually.

In one embodiment, the invention provides kits comprising probes that are immobilized at an addressable position on a substrate, e.g., in a microarray. In a particular embodiment, the invention provides such a microarray.

The kits of the present invention may also contain probes that can be used to detect protein products of the marker genes of the invention. In a specific embodiment, the invention provides a kit comprises a plurality of antibodies that specifically bind a plurality of at least 5, 10, 20, 30, 40, 50, 60, 70, 80, or 100 protens that are encoded by the respectively marker genes listed in Table 1 or funtional equivalents of such genes. In accordance with this embodiment, the kit may comprise a set of antibodies or functional fragments or derivatives thereof (e.g., Fab, F(ab')$_2$, Fv, or scFv fragments). In accordance with this embodiment, the kit may include antibodies, fragments or derivatives thereof (e.g., Fab, F(ab')$_2$, Fv, or scFv fragments) that are specific for these proteins. In one embodiment, the antibodies may be detectably labeled.

The kits of the present invention may also include reagents such as buffers, or other reagents that can be used in obtaining the marker profile. Prevention of the action of microorganisms can be ensured by the inclusion of various antibacterial and antifungal agents, for example, paraben, chlorobutanol, phenol sorbic acid, and the like. It may also be desirable to include isotonic agents such as sugars, sodium chloride, and the like.

In some embodiments of the invention, the kits of the present invention comprise a microarray. The microarray can be any of the microarrays described above, e.g., in Section 5.6.1, optionally in a sealed container. In one embodiment this microarray comprises a plurality of probe spots, wherein at least 20%, 40%, 60%, 80%, or 90% of the probe spots in the plurality of probe spots correspond to marker genes listed in Table 1.

In still other embodiments, the kits of the invention may further comprise a computer program product for use in conjunction with a computer system, wherein the computer program product comprises a computer readable storage medium and a computer program mechanism embedded therein. In such kits, the computer program mechanism comprises instructions for prediction of prognosis using a marker profile obtained with the reagents of the kits.

In still other embodiments, the kits of the present invention comprise a computer having a central processing unit and a memory coupled to the central processing unit. The memory stores instructions for for prediction of prognosis using a marker profile obtained with the reagents of the kits.

5.9. Computer-Facilitated Analysis

The analytic methods described in the previous sections can be implemented by use of the following computer systems and according to the following programs and methods. A computer system comprises internal components linked to external components. The internal components of a typical computer system include a processor element interconnected with a main memory. For example, the computer system can be based on an Intel 8086-, 80386-, 80486-, Pentium™, or Pentium IV™-based processor with preferably 512 MB or more of main memory. The computer system may also be a Macintosh or a Macintosh-based system, but may also be a minicomputer or mainframe.

The external components preferably include mass storage. This mass storage can be one or more hard disks (which are typically packaged together with the processor and memory). Such hard disks are preferably of 10 GB or greater storage capacity. Other external components include a user interface device, which can be a monitor, together with an inputting device, which can be a "mouse", or other graphic input devices, and/or a keyboard. A printing device can also be attached to the computer.

Typically, a computer system is also linked to network link, which can be part of an Ethernet link to other local computer systems, remote computer systems, or wide area communication networks, such as the Internet. This network link allows the computer system to share data and processing tasks with other computer systems.

Loaded into memory during operation of this system are several software components, which are both standard in the art and special to the instant invention. These software components collectively cause the computer system to function according to the methods of this invention. These software components are typically stored on the mass storage device. A software component comprises the operating system, which is responsible for managing computer system and its network interconnections. This operating system can be, for example, of the Microsoft Windows® family, such as Windows 3.1, Windows 95, Windows 98, Windows 2000, Windows NT, or Windows XP, or may be of the Macintosh OS family, or may be UNIX, a UNIX derivative such as LINUX, or an operating system specific to a minicomputer or mainframe. The software component represents common languages and functions conveniently present on this system to assist programs implementing the methods specific to this invention. Many high or low level computer languages can be used to program the analytic methods of this invention. Instructions can be interpreted during run-time or compiled. Preferred languages include C/C++, FORTRAN and JAVA. Most preferably, the methods of this invention are programmed in mathematical software packages that allow symbolic entry of equations and high-level specification of processing, including some or all of the algorithms to be used, thereby freeing a user of the need to procedurally program individual equations or algorithms. Such packages include Mathlab from Mathworks (Natick, Mass.), Mathematica® from Wolfram Research (Champaign, Ill.), or S-Plus® from Math Soft (Cambridge, Mass.). Specifically, the software component includes the analytic methods of the invention as programmed in a procedural language or symbolic package.

The software to be included with the kit comprises the data analysis methods of the invention as disclosed herein. In particular, the software may include mathematical routines for marker discovery, including the calculation of similarity values between clinical categories (e.g., prognosis) and marker expression. The software may also include mathematical routines for calculating the similarity between sample marker expression and control marker expression, using array-generated fluorescence data, to determine the clinical classification of a sample.

Additionally, the software may also include mathematical routines for determining the prognostic outcome, and recommended therapeutic regimen, for an individual with a cancer. The mathematical routines determine the prognostic outcome and recommended therapeutic regimen for an individual. Such software can include instructions for the computer system's processor to receive data structures that include the levels of expression of at least 5, 10, 20, 30, 40, 50, 60, 70, 80, or 100 of the genes (as appropriate) listed in Table 1, or in any of Tables 2-5, 7, and 8 or any subset of these tables, or respective functional equivalents thereof, in a colorectal cancer tumor sample obtained from the patient. The software may additionally include mathematical routines for assigning the patient a prognosis using one or more classifiers of the invention.

The software preferably would include decisional routines that integrate the patient's clinical and marker gene expression data, and recommend a course of therapy. In one embodiment, for example, the software causes the processor unit to receive expression data for prognosis-related genes in the patient's tumor sample, assign the patient a prognosis, and, on the basis of the prognosis, assign a recommended therapeutic regimen.

Correlating genes to clinical outcomes in accordance with the subject invention can be performed using software on a computing means. The computing means can also be responsible for maintenance of acquired data as well as the maintenance of the classifier system itself. The computing means can also detect and act upon user input via user interface means known to the skilled artisan (i.e., keyboard, interactive graphical monitors) for entering data to the computing system.

In one embodiment, the computing means further comprises means for storing and means for outputting processed data. The computing means includes any digital instrumentation capable of processing data input from the user. Such digital instrumentation, as understood by the skilled artisan, can process communicated data by applying algorithm and filter operations of the subject invention. Preferably, the digital instrumentation is a microprocessor, a personal desktop computer, a laptop, and/or a portable digital device. The computing means can be general purpose or application specific.

The subject invention can be practiced in a variety of situations. The computing means can directly or remotely connect to a central office or health care center. In one embodiment, the subject invention is practiced directly in an office or hospital. In another embodiment, the subject invention is practiced in a remote setting, for example, personal residences, mobile clinics, vessels at sea, rural villages and towns without direct access to healthcare, and ambulances, wherein the patient is located some distance from the physician.

In a related embodiment, the computing means is a custom, portable design and can be carried or attached to the health care provider in a manner similar to other portable electronic devices such as a portable radio or computer.

The computing means used in accordance with the subject invention can contain at least one user-interface device including, but not limited to, a keyboard, stylus, microphone, mouse, speaker, monitor, and printer. Additional user-interface devices contemplated herein include touch screens, strip recorders, joysticks, and rollerballs.

Preferably, the computing means comprises a central processing unit (CPU) having sufficient processing power to perform algorithm operations in accordance with the subject invention. The algorithm operations, including the microarray analysis operations (such as SAM or binary classification), can be embodied in the form of computer processor usable media, such as floppy diskettes, CD-ROMS, zip drives, non-volatile memory, or any other computer-readable storage medium, wherein the computer program code is loaded into and executed by the computing means. Optionally, the operational algorithms of the subject invention can be programmed directly onto the CPU using any appropriate programming language, preferably using the C programming language.

In certain embodiments, the computing means comprises a memory capacity sufficiently large to perform algorithm operations in accordance with the subject invention. The memory capacity of the invention can support loading a computer program code via a computer-readable storage media, wherein the program contains the source code to perform the operational algorithms of the subject invention. Optionally, the memory capacity can support directly programming the CPU to perform the operational algorithms of the subject invention. A standard bus configuration can transmit data between the CPU, memory, ports and any communication devices.

In addition, as understood by the skilled artisan, the memory capacity of the computing means can be expanded with additional hardware and with saving data directly onto external mediums including, for example, without limitation, floppy diskettes, zip drives, non-volatile memory and CD-ROMs.

Further, the computing means can also include the necessary software and hardware to receive, route and transfer data to a remote location.

In one embodiment, the patient is hospitalized, and clinical data generated by a computing means is transmitted to a central location, for example, a monitoring station or to a specialized physician located in a different locale.

In another embodiment, the patient is in remote communication with the health care provider. For example, patients can be located at personal residences, mobile clinics, vessels at sea, rural villages and towns without direct access to healthcare, and ambulances. An expression profile of the patient can be measured on-site, and communicated to the health care provider. By using the classifier of the invention, the health care provider can carry out prognosis remotely. Advantageously, mobile stations, such as ambulances, and mobile clinics, can monitor patient health by using a portable computing means of the subject invention when transporting and/or treating a patient.

To ensure patient privacy, security measures, such as encryption software and firewalls, can be employed. Optionally, clinical data can be transmitted as unprocessed or "raw" signal(s) and/or as processed signal(s). Advantageously, transmitting raw signals allows any software upgrades to occur at the remote location where a computing means is located. In addition, both historical clinical data and real-time clinical data can be transmitted.

Communication devices such as wireless interfaces, cable modems, satellite links, microwave relays, and traditional telephonic modems can transfer clinical data from a computing means to a healthcare provider via a network. Networks available for transmission of clinical data include, but are not limited to, local area networks, intranets and the open internet. A browser interface, for example, NETSCAPE NAVIGATOR or INTERNET EXPLORER, can be incorporated into communications software to view the transmitted data.

Advantageously, a browser or network interface is incorporated into the processing device to allow the user to view the processed data in a graphical user interface device, for example, a monitor. The results of algorithm operations of the subject invention can be displayed in the form of interactive graphics.

An exemplary computer system is shown in FIG. 5. The exemplary system is a computer system 10 having: a central processing unit 22; a main non-volatile storage unit 14, for example, a hard disk drive, for storing software and data, the storage unit 14 controlled by storage controller 12; a system memory 36, preferably high speed random-access memory (RAM), for storing system control programs, data, and application programs, comprising programs and data loaded from non-volatile storage unit 14; system memory 36 may also include read-only memory (ROM); a user interface 32, comprising one or more input devices (e.g., keyboard 28) and a display 26 or other output device; a network interface card 20 for connecting to any wired or wireless communication network 34 (e.g., a wide area network such as the Internet); an internal bus 30 for interconnecting the aforementioned elements of the system; and a power source 24 to power the aforementioned elements. Operation of computer 10 is controlled primarily by operating system 40, which is executed by central processing unit 22. Operating system 40 can be stored in system memory 36. In addition to operating system 40, in a typical implementation system memory 36 includes: file system 42 for controlling access to the various files and data structures used by the present invention.

6. EXAMPLE

The following example is presented by way of illustration of the present invention, and is not intended to limit the present invention in any way.

6.1. Tumor Samples and Measurement of Expression Profiles

A set of 78 tumor samples, including 3 adenomas and 75 cancers were used for the development of the cDNA classifiers. These were informative frozen colorectal cancer samples selected from the Moffitt Cancer Center Tumor Bank (Tampa, Fla.) based on evidence for good (survival>36 mo) or poor prognosis (survival<36 mo) from the Tumor Registry (the "Moffitt set"). Dukes' stages can include B, C, and D. Survival was measured as last contact minus collection date for living patients, or date of death minus collection date for patients who have died.

The 75 cancer samples in the Moffitt set include 23 Dukes stage B samples, 22 Dukes stage C samples, and 30 Dukes stage D samples. Just as adenomas can be included to help train the classifier to recognize good prognosis patients, Dukes D patients with synchronous metastatic disease can be used to train the classifier to recognize poor prognosis patients.

All samples in the Moffitt set were selected to have at least 36 months of follow-up. The follow-up results in this embodiment showed that thirty-two of the patients survived more than 36 months, while 46 patients died within 36 months. The median follow-up time for all 78 patients was 27.9 months. The median follow-up for the poor prognosis cases (<36 months survival) was 11.7 months, and for the good prognosis cases (>36 months survival) was 64.2 months.

Since the NIH consensus conference in 1990, chemotherapeutic application in the United States has been relatively homogeneous, with nearly all Dukes stage B avoiding chemotherapy, and nearly all Dukes stage C receiving 6 months of adjuvant 5-fluorouracil (5-FU) and leucovorin.

Samples in the Moffitt set were microdissected (>80% tumor cells) by frozen section guidance and RNA extraction performed using Trizol followed by secondary purification on RNAEasy columns. The samples were profiled on cDNA arrays (i.e., TIGR's 32,488-element spotted cDNA arrays, containing 31,872 human cDNAs representing 30,849 distinct transcripts—23,936 unique TIGR TCs and 6,913 ESTs, 10 exogenous controls printed 36 times, and 4 negative controls printed 36-72 times).

Tumor samples were co-hybridized with a common reference pool in the Cy5 channel for normalization purposes. The reference pool contained a mixture of RNAs derived from multiple cell lines. cDNA synthesis, aminoallyl labeling and hybridizations were performed according to previously published protocols (see Hegde, P. et al., "A concise guide to cDNA microarray analysis," *Biotechniques;* 29:552-562 (2000) and Yang, I. V, et al., "Within the fold: assessing differential expression measures and reproducibility in microarray assays," *Genome Biol;* 3:research0062 (2002)). For example, labeled first-strand cDNA was prepared, and co-hybridized with labeled samples are prepared, from a universal reference RNA consisting of equimolar quantities of total RNA derived from three cell lines, CaCO2 (colon), KM12L4A (colon), and U118MG (brain). Detailed protocols and description of the array are available at the website for the Institute for Genomic Research, Cancer Microarray Research at TIGR Array probes were identified and local background were subtracted in Spotfinder (Saeed, A. I. et al., "TM4: a free, open-source system for microarray data management and analysis," *Biotechniques;* 34:374-8 (2003)). Individual arrays can be normalized in MIDAS (see Saeed, A. I. ibid.) using LOWESS (an algorithm known to the skilled artisan for use in normalizing data) with smoothing parameter set to 0.33.

In addition to the 78-sample Moffitt training set, a set of eighty-eight patients with Dukes' stage B and C colorectal cancer and a minimum follow-up time of 60 months were used for the development of the U133 classifiers. This set of samples is also referred to as the "Denmark set" of samples.

In the Denmark set, there were 28 patients with stage B and 60 patients with stage C colorectal cancers. All Dukes' stage B patients were treated by surgical resection alone whereas all C patients received 5-FU/leucovorin adjuvant chemotherapy in addition to surgery. Colorectal tumor samples were obtained fresh from surgery and were immediately snap-frozen in fluid nitrogen but were not microdissected, with the potential for inclusion of samples with <80% purity. Total RNA was isolated from 50-150 mg tumor sample using RNAzol (WAK-Chemie Medical) or using spin column technology (Sigma) according to the manufacturer's instructions. Results were noted (i.e., fifty-seven of the patients survived more than 36 months, while 31 died within 36 months).

Ten micrograms of total RNA were used as starting material for the cDNA preparation and hybridized to Affymetrix® U133A GeneChips® (Santa Clara, Calif.) by standard protocols supplied by the manufacturer. The U133A gene chip is disclosed in U.S. Pat. Nos. 5,445,934; 5,700,637; 5,744,305; 5,945,334; 6,054,270; 6,140,044; 6,261,776; 6,291,183; 6,346,413; 6,399,365; 6,420,169; 6,551,817; 6,610,482; and 6,733,977; and in European Patent Nos. 619,321 and 373,203, all of which are hereby incorporated in their entirety. The first and second strand cDNA synthesis was performed using the SuperScript II System (Invitrogen) according to the manufacturer's instructions except using an oligodT primer containing a T7 RNA polymerase promoter site. Labeled cRNA was prepared using the BioArray High Yield RNA Transcript Labeling Kit (Enzo). Biotin labeled CTP and UTP (Enzo) were used in the reaction together with unlabeled NTP's. Following the IVT reaction, the unincorporated nucleotides were removed using RNeasy columns (Qiagen). Fifteen micrograms of cRNA were fragmented at 94° C. for 35 min in a fragmentation buffer containing 40 mM Tris-acetate pH 8.1, 100 mM KOAc, 30 mM MgOAc. Prior to hybridization, the fragmented cRNA in a 6×SSPE-T hybridization buffer (1 M NaCl, 10 mM Tris pH 7.6, 0.005% Triton) was heated to 95° C. for 5 min and subsequently to 45° C. for 5 min before loading onto the Affymetrix® HG_U133A probe array cartridge. The probe array was then incubated for 16 h at 45° C. at constant rotation (60 rpm). The washing and staining procedure were performed in an Affymetrix® Fluidics Station.

The probe array was exposed to several washes (i.e., 10 washes in 6×SSPE-T at 25° C. followed by 4 washes in 0.5×SSPE-T at 50° C.). The biotinylated cRNA was stained with a streptavidinphycoerythrin conjugate, final concentration 2 mg/ml (Molecular Probes, Eugene, Oreg.) in 6×SSPE-T for 30 min at 25° C. followed by 10 washes in 6×SSPE-T at 25° C. An antibody amplification step followed, using normal goat IgG as blocking reagent, final concentration 0.1 mg/ml (Sigma) and biotinylated anti-streptavidin antibody (goat), final concentration 3 mg/ml (Vector Laboratories). This was followed by a staining step with a streptavidin-phycoerythrin conjugate, final concentration 2 mg/ml (Molecular Probes, Eugene, Oreg.) in 6×SSPE-T for 30 min at 25° C. and 10 washes in 6×SSPE-T at 25° C. The probe arrays were scanned (i.e., at 560 nm using a confocal laser-scanning microscope (Hewlett Packard GeneArray Scanner G2500A)). The readings from the quantitative scanning were analyzed by the Affymetrix® Gene Expression Analysis Software (MAS 5.0) and normalized to a common mean expression value of 150.

6.2. Identification of Prognosis-Related Genes Using SAM

The first analysis of the colon cancer survival data was performed using censored survival time (in months) and 500 permutations. Significance analysis of microarrays (SAM) was used to select genes most closely correlated to survival. The subset of genes that correspond to an empirically derived, estimated false discovery rate (FDR) was then chosen. This subset of genes was used in subsequent cluster analyses. Cluster 3.0 and Java TreeView 1.03 were used to cluster and visualize the SAM-selected genes.

SAM survival analysis was used to identify a set of genes most correlated with censored survival time using the training set tumor samples. A set of 53 genes was found, corresponding to a median expected false discovery rate (FDR) of 28%. These genes are listed in the following Table 2, wherein genes denoted with (+) indicate a positive correlation to survival time and genes without the (+) notation indicate a negative correlation in survival time (over expression in poor prognosis cases). Included in this list of genes in Table 2 are several genes believed to be biologically significant, such as osteopontin and neuregulin. Table 3 illustrates seven genes selected by SAM survival analysis with a FDR of 13.5%, where osteopontin and neuregulin are noted to be present and in common with the gene lists for all classifiers. In Table 3, genes denoted with (+) indicate a positive correlation to survival time and genes without the (+) notation indicate a negative correlation in survival time (over expression in poor prognosis cases).

Table 2-Censored Survival Analysis Using SAM, Resultant 53 Genes Selected with Median 28% FDR

| GENBANK ID | UniGene UniGene | Description | SEQ ID NO |
|---|---|---|---|
| N36176 | Hs.108636 | membrane protein CH1 | 153 |
| AA149253 | Hs.107987 | N/A | 17 |
| AA425320 | Hs.250461 | hypothetical protein; MDG1; similar to putative microvascular endothelial differentiation gene 1; similar to X98993 (PID:g1771560) | 29 |
| AA775616 | Hs.313 | OPN-b; osteopontin; secreted phosphoprotein 1 (osteopontin, bone sialoprotein I, early T-lymphocyte activation 1) | 92 |
| N72847 | Hs.125221 | Alu subfamily SP sequence contamination warning entry. [Human] {Homo sapiens} | 169 |
| AA706226 | Hs.113264 | neuregulin 2 isoform 4 | 87 |
| AA976642 | Hs.42116 | axin 2 (conductin, axil) | 115 |
| AA133215 | Hs.32989 | Receptor activity-modifying protein 1 precursor (CRLR activity- modifyingprotein 1) | 15 |
| AA457267 | Hs.70669 | P19 protein; HMP19 protein | 41 |
| N50073 | Hs.84926 | hypothetical protein | 160 |
| R38360 | Hs.145567 | Unknown {Homo sapients} | 185 |
| AA450205 | Hs.8146 | translocation protein-1; Sec62; Dtrp1 protein; membrane protein SEC62, S. cerevisiae, homolog of [Homo sapiens]; | 36 |
| AA148578 | Hs.110956 | KOX 13 protein (56 AA) | 16 |
| R38640 | Hs.89584 | insulinoma-associated 1; bA470C13.2 (insulinoma-associated protein 1) | 186 |
| AA487274 | Hs.48950 | heptacellular carcinoma novel gene-3 protein; DAPPER 1 | 57 |

-continued

| GENBANK ID | UniGene | Description | SEQ ID NO |
|---|---|---|---|
| N53172 | Hs.23016 | orphan receptor; orphan G protein-coupled receptor RDC1 | 163 |
| AA045308 | Hs.7089 | insulin induced protein 2; INSIG-2 membrane protein | 7 |
| AA045075 | Hs.62751 | syntaxin 7 | 6 |
| N63366 | Hs.161488 | N/A | 167 |
| R22340 | null | chr2 synaptotagmin; KIAA1228 protein | 179 |
| AA437223 | Hs.46640 | Adult retina protein | 32 |
| AA481250 | Hs.154138 | chitinase precursor; chitinase 3-like 2; chondrocyte protein 39 | 50 |
| AA045793 | Hs.6790 | hypothetical protein; MDG1; similar to putative microvascular endothelial differentiation gene 1; similar to X98993 (PID:g1771560); microvascular endothelial differentiation gene 1 product; microvascular endothelial differentiation gene 1; DKFZP564F1862 p | 8 |
| H87795 | Hs.233502 | N/A | 149 |
| AA121806 | Hs.84564 | Rab3c; hypothetical protein BC013033 | 12 |
| AA284172 | Hs.89385 | NPAT; predicted amino acids have three regions which share similarity to annotated domains of transcriptional factor oct-1, nucleolus-cytoplasm shuttle phosphoprotein and protein kinases; NPAT; nuclear protein, ataxiatelangiectasia locus; Similar to nuc | 24 |
| R68106 | Hs.233450 | Fc-gamma-RIIb2; precursor polypeptide (AA -42 to 249); IgG Fc receptor; IgG Fc receptor; IgG Fc receptor beta-Fc-gamma-RII; IgG Fc fragment receptor precursor; Fc gamma RIIB [Homo sapiens]; Fc gamma RIIB [Ho | 198 |
| AA479270 | Hs.250802 | Diff33 protein homolog; KIAA1253 protein [Homo sapiens]; KIAA1 253protein [Homo sapiens] | 48 |
| AA432030 | Hs.179972 | Interferon-induced protein 6-16 precursor (ffi-6-16). [Human] {Homo sapiens} | 31 |
| R10545 | Hs.148877 | dJ425C 14.2 (Placental protein | 176 |
| AA453508 | Hs.168075 | transportin; karyopherin (importin) beta 2 [Homo sapiens]; karyopherin beta 2; importin beta 2; transportin; M9 region interaction protein [Homo sapiens] | 39 |
| AI149393 | Hs.9302 | phosducin-like protein; phosducin-like protein; phosducin-like protein; phosducin-like protein; hypothetical protein; phosducin-like; Unknown (proteinfor MGC:14088) [Homo sapiens] | 124 |

-continued

| GENBANK ID | UniGene UniGene | Description | SEQ ID NO |
|---|---|---|---|
| AA883496 | Hs.125778 | Null | 103 |
| AA167823 | Hs.112058 | CD27BP [Homo sapiens] | 18 |
| A1203139 | Hs.180370 | hypothetical protein FLJ30934 [Homo sapiens] | 125 |
| +H19822 | Hs.2450 | KIAA0028; leucyl-tRNA synthetase, mitochondrial [Homo sapiens]; leucyltRNA synthetase, mitochondrial [Homo sapiens]; leucine-tRNA ligase precursor; leucine translase [Homo sapiens] | 140 |
| +W73732 | Hs.83634 | Null | 214 |
| +AA777892 | Hs.121939 | Null | 98 |
| +AA885478 | Hs.125741 | unnamed protein product [Homo sapiens]; hypothetical protein FLJ12505 [Homo sapiens]; Unknown (protein for MGC:39884) [Homo sapiens] | 105 |
| +AA932696 | Hs.8022 | TU3A protein; TU3A protein [Homo sapiens] | 109 |
| +AA481507 | Hs.159492 | unnamed protein product [Homo sapiens] | 51 |
| +H18953 | Hs.15232 | Null | 138 |
| +AA709158 | Hs.42853 | put. DNA binding protein; put. DNA binding protein; cAMP responsive element binding protein-like 1; Creb-related protein [Homo sapiens] | 88 |
| +AA488652 | Hs.4209 | HSPC235; ribosomal protein L2; Similar to ribosomal protein, mitochondrial, L2 [Homo sapiens]; mitochondrial ribosomal protein L37; ribosomal protein, mitochondrial, L2 [Homo sapiens] | 58 |
| +N39584 | Hs.17404 | Null | 154 |
| +H62801 | Hs.125059 | Unknown (protein for IMAGE:4309224) [Homo sapiens]; hypothetical protein [Homo sapiens] | 145 |
| +H17638 | Hs.17930 | dJ1033BL0.2.2 (chromosome 6 open reading frame 11 (BING4), isoform 2) [Homo sapiens] | 137 |
| +R43684 | Hs.165575 | dJ402G11.5 (novel protein similar to yeast and bacterial predicted proteins) [Homo sapiens] | 189 |
| +N21630 | Hs.143039 | hypothetical protein PRO1942 | 152 |
| +T81317 | Hs.189846 | Alu subfamily J sequence contamination warning entry. [Human] [Homo sapiens] | 209 |
| +R45595 | Hs.23892 | Null | 192 |
| +T90789 | Hs.121586 | ray; small GTP binding protein RAB35 [Homo sapiens]; RAB35, member RAS oncogene family; ras-related protein rab-1c (GTP-binding protein ray) [Homo sapiens] | 211 |

-continued

| GENBANK ID | UniGene UniGene | Description | SEQ ID NO |
|---|---|---|---|
| +AA283062 | Hs.73986 | Similar to CDC-like kinase 2 {Homo sapiens} | 23 |

TABLE 3

Censored survival analysis using SAM; seven genes selected with median estimated FDR of 13.5%

| GenBank ID | UniGene ID | Description | SEQ ID NO |
|---|---|---|---|
| N36176 | Hs.108636 | membrane protein CH1 | 153 |
| AA149253 | Hs.107987 | N/A | 17 |
| AA425320 | Hs.250461 | hypothetical protein; MDGL; similar to putative microvascular endothelial differentiation gene 1; similar to X98993 (PID:g1771560) | 29 |
| AA775616 | Hs.313 | OPN-b; osteopontin; secreted phosphoprotein 1 (osteopontin, bone sialoprotein I, early T lymphocyte activation 1) | 92 |
| N72847 | Hs.125221 | N/A | 169 |
| AA706226 | Hs.113264 | neuregulin 2 isoform 4 | 87 |
| +AA883496 | Hs.125778 | N/A | 103 |

A hierarchical clustering algorithm was used to analyze the expression profiles of the 53 genes, with complete linkage and the correlation coefficient (i.e., Pearson correlation coefficient) as the similarity metric. Dukes' staging clusters were manually created in the appropriate format. Clustering software produced heatmap (see FIGS. 1A and 1B) and dendrograms. The highest level partition of the SAM-selected genes was chosen as a survival grouping. Given two clusters of survival times, Kaplan-Meier curves were plotted (see FIGS. 2A and 2B).

Figure 1:
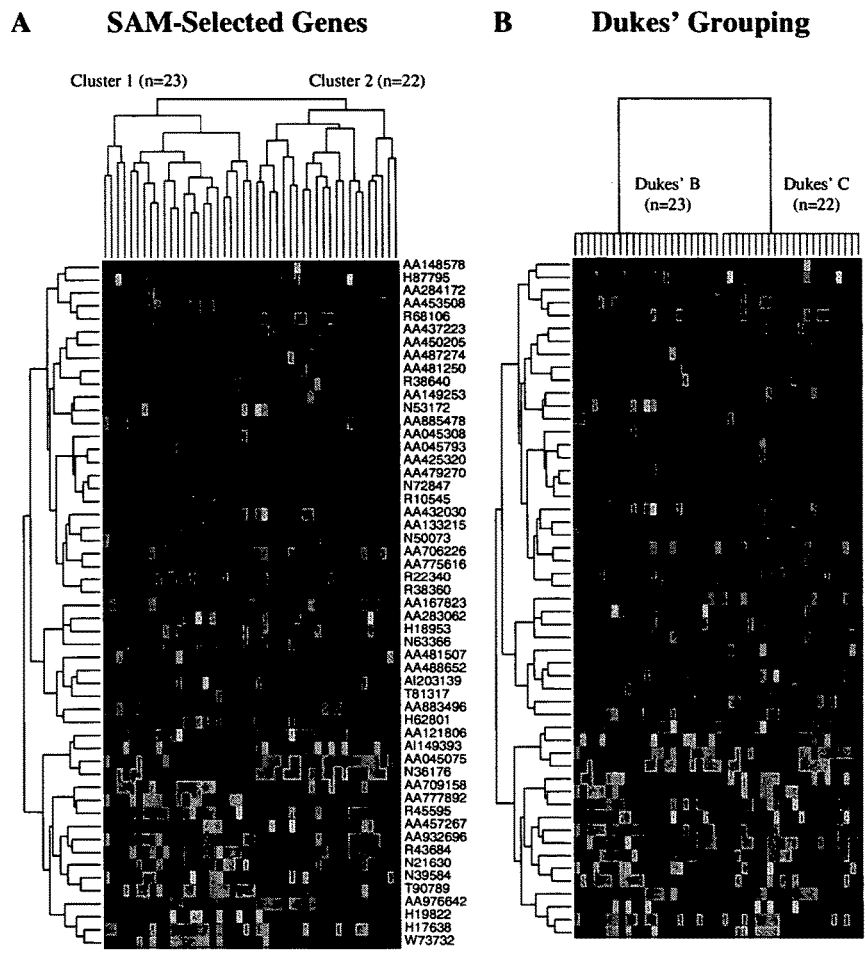

FIG. 1A presents a graphical representation of the 53 SAM-selected genes (as described above) as a clustered heat map. Darker areas represent over-expressed genes whereas lighter areas represent under-expressed genes. FIG. 1A shows only the Dukes' stage B and C cases, whose outcome Dukes' staging predicts poorly. Since only genes correlated with survival were used in clustering, the distinctly illustrated clusters in the heatmap correspond to very different prognosis groups.

The 53 SAM-selected genes were also arranged by annotated Dukes' stage in FIG. 1B. Unlike FIG. 1A, where two gene groups were apparent, there was no discernible gene expression grouping when arranged by Dukes' stage.

Figure 2:
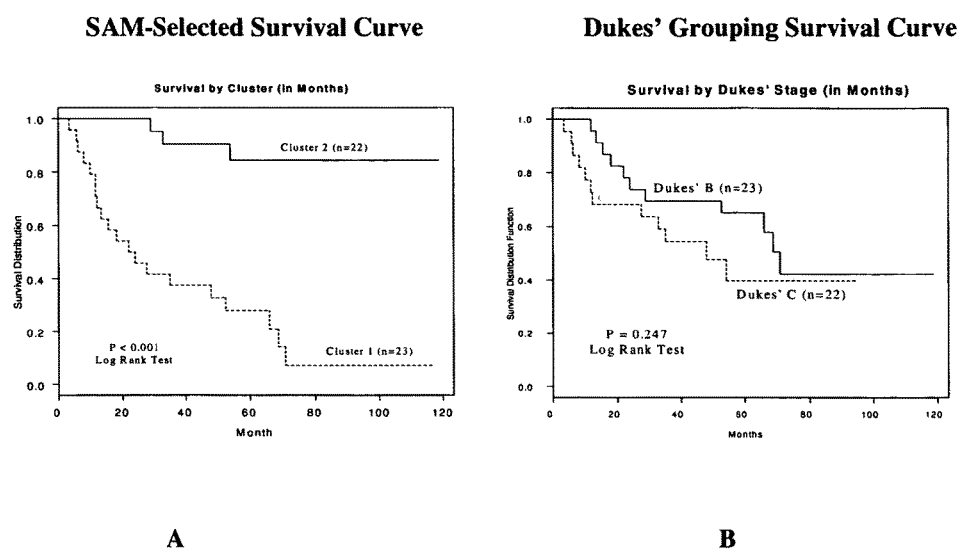
FIG. 2A shows Kaplan-Meier survival curves corresponding to gene clusters.
FIG. 2B shows Kaplan-Meier survival curves for Dukes' B and C patients.

FIG. 2A shows the Kaplan-Meier plot for two dominant clusters of genes correlated with stage B and C test set tumor samples. These genes separated the cases into two distinct clusters of patients with good prognosis (cluster 2) and poor prognosis (cluster 1) (P<0.001 using a log rank test). FIG. 2B presents a Kaplan-Meier plot of the survival times of Dukes' stage B and C tumors grouped by stage, showing no statistically significant difference.

As noted above, Dukes' staging provides only a probability of survival for each member of a population of patients, based on historical statistics. Accordingly, the prognosis of an individual patient can be predicted based on historical outcome probabilities of the associated Dukes' stage. For example, if a Dukes° C. survival rate was 55% at 36 months of follow up, any individual Dukes° C. patient would be classified as having a good prognosis since more than 50% of patients would be predicted to be alive.

As illustrated in FIGS. 1A, 1B, 2A, and 2B, gene expression profiles separate good and poor prognosis cases better than Dukes' staging. This suggests that a gene-expression based classifier described in this example may be used for more accurate prediction of patient prognosis than the traditional Dukes' staging.

The identified genes may also have biological significance. For example, osteopontin, a secreted glycoprotein and ligand for CD44 and $\alpha v \beta 3$, appears to have a number of biological functions associated with cellular adhesion, invasion, angiogenesis and apoptosis (see Fedarko N S et al., "Elevated serum bone sialoprotein and osteopontin in colon, breast, prostate, and lung cancer," *Clin Cancer Res*, 7:4060-6 (2001); Yeatman T J and Chambers A F, "Osteopontin and colon cancer progression," *Clin Exp Metastasis*, 20:85-90 (2003)). Using an oligonucleotide microarray platform, osteopontin was identified as a gene whose expression was strongly associated with colorectal cancer stage progression (Agrawal D et al., "Osteopontin identified as lead marker of colon cancer progression, using pooled sample expression profiling," *J Natl Cancer Inst*, 94:513-21(2002)). INSIG-2, one of the 43 core classifier genes provided in Example 1, was recently identified as an osteopontin signature gene, suggesting that an osteopontin pathway may be prominent in regulating colon cancer survival.

Similarly, neuregulin appeared to have biological significance in the context of colorectal cancer based on frequency of appearance in the classification set of the present invention. Neuregulin, a ligand for tyrosine kinase receptors (ERBB receptors), may have biological significance in the context of colorectal cancer where current data suggest a strong relationship between colon cancer growth and the ERBB family of receptors (Carraway K L, 3rd, et al., "Neuregulin-2, a new ligand of ErbB3/ErbB4-receptor tyrosine kinases," *Nature*, 387:512-6 (1997)). Neuregulin was recently identified as a prognostic gene whose expression correlated with bladder cancer recurrence (Dyrskjot L, et al., "Identifying distinct classes of bladder carcinoma using microarrays," Nat Genet, 33:90-6 (2003)).

Accordingly, the identification of such genes may be significant in terms of gene therapy. For example, a therapeutic gene may be identified, which when reintroduced into tumor cells, may arrest or even prevent growth in cancer cells. Additionally, using the classifier of the present invention, a therapeutic gene may be identified that enables increased responsiveness to interventions such as radiation or chemotherapy.

6.3. Construction of Colorectal Cancer Classifiers Using cDNA Array Data

A leave-one-out cross-validation (LOOCV) technique was used for constructing and validating a neural network-based classifier using the Moffitt set of 78 tumor samples (see Section 6.1). The samples were classified as having "good" or "poor" prognosis based on survival for more or less than 36 months, respectively. Using the leave-one-out cross-validation approach also provided the ability to rank the selected genes. The number of times a particular gene was chosen was used as an indicator of the usefulness of that gene for general classification and may imply biological significance. Table 4 lists genes used in a cDNA classifier (selected by t-test) and ranked by selection frequency using LOOCV. A set of 43 core genes were identified in 75% of the LOOCV iterations. Table 5 lists the set of 43 genes.

TABLE 4

Genes used in a cDNA classifier (selected by t-test) and ranked by selection frequency using LOOCV

| Number of Times Occurred | Genbank ID | UNIGENE ID | Description | SEQ ID NO |
|---|---|---|---|---|
| M*78 | AA045075 | Hs.62751 | syntaxin7 | 6 |
| M *78 | AA425320 | Hs.250461 | hypothetical protein; MDG1; similar to putative microvascular endothelial differentiation gene 1; similar to X98993 (PID:g1771560); microvascular endothelial differentiation gene 1 product; microvascularendothelial differentiation gene 1; DKFZP564F1862 p | 29 |
| M 78 | AA437223 | Hs.46640 | adult retina protein | 32 |
| M *78 | AA479270 | Hs.250802 | Diff33 protein homolog; KIAA1253 protein | 48 |
| M *78 | AA486233 | Hs.2707 | G1 to S phase transition 1 | 56 |
| M *78 | AA487274 | Hs.48950 | heptacellular carcinoma novel gene-3 protein; DAPPER 1 | 57 |
| M78 | AA488652 | Hs.4209 | H5PC235; ribosomal protein L2; Similar to ribosomal protein, mitochondrial, L2 [Homo sapiens]; mitochondrial ribosomal protein L37; ribosomal protein, mitochondrial, L2 [Homo sapiens] | 58 |
| M78 | AA694500 | Hs.116328 | hypothetical protein MGC33414; Similar to PR domain containing 1, with ZNF domain | 77 |
| M 78 | AA704270 | Hs.189002 | Null | 83 |
| M *78 | AA706226 | Hs.113264 | neuregulin 2 isofonn 4 | 87 |
| M *78 | AA709158 | Hs.42853 | put. DNA binding protein; put. DNA binding protein; cAMP responsive element binding protein-like 1; Creb-related protein | 88 |
| M *78 | AA775616 | Hs.313 | OPN-b; osteopontin; secreted phosphoprotein 1 (osteopontin, bone sialoprotein I, early T-lymphocyte activation 1) | 92 |

TABLE 4-continued

Genes used in a cDNA classifier (selected by t-test) and ranked by selection frequency using LOOCV

| Number of Times Occurred | Genbank ID | UNIGENE ID | Description | SEQ ID NO |
|---|---|---|---|---|
| M 78 | AA777892 | Hs.121939 | Null | 98 |
| M *78 | AA873159 | Hs.182778 | apolipoprotein CI; apolipoprotein C-I variant II; apolipoprotein C-I variant I | 102 |
| M *78 | AA969508 | Hs.10225 | HEYL protein; hairy-related transcription factor 3; hairy/enhancer-ofsplit related with YRPW motif-like | 113 |
| M 78 | AI203139 | Hs.180370 | hypothetical protein FLJ30934 | 125 |
| M *78 | AI299969 | Hs.255798 | unnamed protein product; HN1 like; Unknown (protein for MGC:22947) | 130 |
| M *78 | H17364 | Hs.80285 | CRE-BP1 family member; cyclic AMP response element DNA-binding protein isoform 1 family; cAMP response element binding protein (AA1-505); cyclic AMP response element-binding protein (HB 16); Similar to activating transcription factor 2 [Homo sapiens]; act | 134 |
| M 78 | H17627 | Hs.83869 | unnamed protein | 136 |
| M *78 | H19822 | Hs.2450 | KIAA0028; leucyl-tRNA synthetase, mitochondrial [Homo sapiens]; leucyl-tRNA synthetase, mitochondrial [Homo sapiens]; leucine-tRNA ligase precursor; leucine translase [Homo sapiens] | 140 |
| M*78 | H23551 | Hs.30974 | NADH dehydrogenase subunit 4 {Deirochelys reticularia} | 141 |
| M 78 | H62801 | Hs.125059 | Unknown (protein for IMAGE:4309224) [Homo sapiens]; hypothetical protein [Homo sapiens] | 145 |
| M78 | H85015 | Hs.138614 | null | 148 |
| M 78 | N21630 | Hs.143039 | hypothetical protein PRO1942 | 152 |
| M *78 | N36176 | Hs.108636 | membrane protein CH1; membrane protein CH1 [Homo sapiens]; membrane protein CH1 [Homo sapiens]; membrane protein CH1 [Homo sapiens] | 153 |
| M *78 | N72847 | Hs.125221 | Alu subfamily SP sequence contamination warning entry. [Human] {Homo sapiens} | 169 |
| M 78 | N92519 | Hs.1189 | Unknown (protein for MGC:10231) [Homo sapiens] | 173 |
| M *78 | R27767 | Hs.79946 | thyroid hormone receptor-associated protein, 150 kDa subunit; Similar to thyroid hormone receptor-associated protein, 150 kDa subunit [Homo sapiens];; | 180 |
| M*78 | R34578 | Hs.111314 | null | 182 |
| M 78 | R38360 | Hs.145567 | unknown {Homo sapiens} | 185 |
| M 78 | R43597 | Hs.137149 | trehalase homolog T19F6.30-Arabidopsis thaliana | 188 |

TABLE 4-continued

Genes used in a cDNA classifier (selected by t-test) and ranked by selection frequency using LOOCV

| Number of Times Occurred | Genbank ID | UNIGENE ID | Description | SEQ ID NO |
|---|---|---|---|---|
| M 78 | R43684 | Hs.165575 | dJ402GL1.5 (novel protein similar to yeast and bacterial predicted proteins) | 189 |
| M *78 | W73732 | Hs.83634 | Null | 214 |
| M *77 | AA450205 | Hs.8146 | translocation protein-1; Sec62; translocation protein 1; Dtrp1 protein; membrane protein SEC62, S. cerevisiae, homolog of [Homo sapiens]; | 36 |
| M 77 | AI081269 | Hs.184108 | Alu subfamily SX sequence contamination warning entry. | 122 |
| M*77 | R59314 | Hs.170056 | null | 193 |
| M *72 | AA702174 | Hs.75263 | pRb-interacting protein RbBP-36 | 80 |
| M *70 | AI002566 | Hs.81234 | immunoglobin superfamily, member 3 | 121 |
| M *63 | AA676797 | Hs.1973 | cyclin F | 72 |
| M *62 | AA453508 | Hs.168075 | transportin; karyopherin (importin) beta 2; M9 region interaction protein | 39 |
| M 62 | W93980 | Hs.59511 | null | 217 |
| M *58 | AA045308 | Hs.7089 | insulin induced protein 2; INSIG-2 membrane protein | 7 |
| M 58 | AA953396 | Hs.127557 | null | 110 |
| M 52 | AA962236 | Hs.124005 | hypothetical protein MGC19780 | 112 |
| M *50 | AA418726 | Hs.4764 | null | 28 |
| M 50 | R43713 | Hs.22945 | null | 190 |
| M *41 | AA664240 | Hs.8454 | artifact-warning sequence (translated ALU class C) - human | 71 |
| M *38 | AA477404 | Hs.125262 | hypothetical protein; unnamed protein product; GL003; AAAS protein; adracalin; aladin | 46 |
| M *37 | AA826237 | Hs.3426 | Era GTPase A protein; conserved ERA-like GTPase [Homo sapiens]; ERA-W [Homo sapiens]; Era G-protein-like 1; GTPase, human homolog of E. coli essential cell cycle protein Era; era (E. coli Gprotein homolog)-like 1 [Homo sapiens] | 99 |
| M *30 | AA007421 | Hs.113992 | candidate tumor suppressor protein {Homo sapiens} | 2 |
| M *30 | AA478952 | Hs.91753 | unnamed protein product; hypothetical protein [Homo sapiens];unnamed protein product [Homo sapiens]; hypothetical protein [Homo sapiens] | 47 |
| 30 | AA885096 | Hs.43948 | Alu subfamily SQ sequence contamination warning entry. | 104 |
| 28 | H29032 | Hs.7094 | null 142 | |
| *24 | R10545 | Hs.148877 | dJ425C14.2 (Placental protein | 176 |

TABLE 4-continued

Genes used in a cDNA classifier (selected by t-test) and ranked by selection frequency using LOOCV

| Number of Times Occurred | Genbank ID | UNIGENE ID | Description | SEQ ID NO |
|---|---|---|---|---|
| *22 | AA448641 | Hs.108371 | transcription factor; E2F transcription factor 4; p107/p130-binding protein | 34 |
| 20 | R38266 | Hs.12431 | Unknown (protein for MGC:30132) | 184 |
| 19 | H17543 | Hs.92580 | Alu subfamily J sequence contamination warning entry. | 135 |
| 11 | T81317 | Hs.189846 | Alu subfamily J sequence contamination warning entry. | 209 |
| *9 | AA453790 | Hs.255585 | null | 40 |
| 9 | R22340 | null | unnamed protein product; chr2 synaptotagmin KIAA1228 protein | 179 |
| 7 | AA987675 | Hs.176759 | null | 117 |
| 7 | N51543 | Hs.47292 | null | 161 |
| *7 | N74527 | Hs.5420 | unnamed protein product | 170 |
| *6 | AA121778 | Hs.95685 | null | 11 |
| *6 | AA258031 | Hs.125104 | unnamed protein product; MUS81 endonuclease | 21 |
| *6 | AA702422 | Hs.66521 | josephin MJD1; super cysteine rich protein; SCRP | 81 |
| 6 | T64924 | Hs.220619 | null | 206 |
| *5 | R42984 | Hs.4863 | null | 187 |
| *5 | R59360 | Hs.12533 | null | 194 |
| *5 | R63816 | Hs.28445 | unnamed protein product | 196 |
| 5 | T49061 | Hs.8934 | HA-70 {*Clostridium botulinum*} | 202 |
| 4 | AA016210 | Hs.24920 | null | 3 |
| 4 | AA682585 | Hs.193822 | null | 75 |
| 4 | AA705040 | Hs.119646 | Alu subfamily J sequence [Human] {*Homo sapiens*} | 85 |
| 4 | AA909959 | Hs.130719 | NESH; hypothetical protein; NESH protein [*Homo sapiens*]; NESH protein; new molecule including SH3 [*Homo sapiens*] | 106 |
| 4 | A1240881 | Hs.89688 | complement receptor type 1-like protein {*Homo sapiens*} | 126 |
| *3 | AA133215 | Hs.32989 | Receptor activity-modifying protein 1 precursor (CRLR activity-modifying-protein 1) | 15 |
| 3 | AA699408 | Hs.168103 | prp28, US snRNP 100 kd protein; prp28, US snRNP 100 kd protein [*Homo sapiens*] | 78 |
| 3 | AA910771 | Hs.130421 | null | 107 |
| *3 | AI362799 | Hs.110757 | hypothetical protein; NNP3 [*Homo sapiens*] | 131 |
| *3 | H51549 | Hs.21899 | UDP-galactose translocator; UDP-galactose transporter 1 [*Homo sapiens*] | 144 |

TABLE 4-continued

Genes used in a cDNA classifier (selected by t-test) and ranked by selection frequency using LOOCV

| Number of Times Occurred | Genbank ID | UNIGENE ID | Description | SEQ ID NO |
|---|---|---|---|---|
| 3 | R06568 | Hs.187556 | null | 175 |
| 2 | AA001604 | Hs.204840 | null | 1 |
| *2 | AA132065 | Hs.109144 | unknown; SMAP-5; Similar to hypothetical protein AF140225 | 14 |
| *2 | AA490493 | Hs.24340 | null | 59 |
| 2 | AA633845 | Hs.192156 | null | 69 |
| *2 | AI261561 | Hs.182577 | Alu subfamily SQ sequence contamination warning entry. | 128 |
| *2 | H81024 | Hs.180655 | Aik2; aurora-related kinase 2; serine/threonine kinase 12; Unknown (protein for MGC: 11031) [Homo sapiens]; Unknown (protein for MGC:4243) [Homo sapiens] | 147 |
| 2 | N75004 | Hs.49265 | hypothetical protein {Plasmodium falciparum 3D7 } | 171 |
| 2 | W96216 | Hs.110196 | NICE-1 protein | 218 |
| 1 | AA045793 | Hs.6790 | hypothetical protein; MDG1; similar to putative microvascular endothelial differentiation gene 1; similar to X98993 (PID:g1771560); microvascular endothelial differentiation gene 1 product; microvascular endothelial differentiation gene 1; DKFZP564F1862 p | 8 |
| *1 | AA284172 | Hs.89385 | NPAT; predicted amino acids have three regions which share similarity to annotated domains of transcriptional factor oct-1, nucleoluscytoplasm shuttle phosphoprotein and protein kinases; NPAT; nuclear protein, ataxia-telangiectasia locus; Similar to nuc | 24 |
| *1 | AA411324 | Hs.67878 | interleukin-13 receptor; interleukin-13 receptor; interleukin 13 receptor,alpha 1 [Homo sapiens]; Similar to interleukin 13 receptor, alpha 1 [Homo sapiens]; bB12804.2.1 (interleukin 13 receptor, alpha 1) [Homo sapiens]; interleukin 13 receptor, alpha 1 | 25 |
| *1 | AA448261 | Hs.139800 | high mobility group AT-hook 1 isoform b; nonhistone chromosomal high-mobility group protein HMG-I/HMG-Y [Homo sapiens] | 33 |
| *1 | AA479952 | Hs.154145 | Alu subfamily SX sequence contamination warning entry. [Human] {Homo sapiens} | 49 |
| * 1 | AA485752 | Hs.9573 | ATP-binding cassette, sub-family F, member 1; ATP-binding cassette 50; ATP-binding cassette, sub-family F (GCN20), member 1 [Homo sapiens]; | 54 |

TABLE 4-continued

Genes used in a cDNA classifier (selected by t-test) and ranked by selection frequency using LOOCV

| Number of Times Occurred | Genbank ID | UNIGENE ID | Description | SEQ ID NO |
|---|---|---|---|---|
| *1 | AA504266 | Hs.8217 | nuclear protein SA-2; bA517O1.1 (similar to SA2 nuclear protein); hypothetical protein [Homo sapiens]; stromal antigen 2 [Homo sapiens] | 61 |
| *1 | AA630376 | Hs.8121 | null | 68 |
| *1 | AA634261 | Hs.25035 | null | 70 |
| 1 | AA701167 | Hs.191919 | Alu subfamily SB sequence contamination warning entry. [Human] {Homo sapiens} | 79 |
| *1 | AA703019 | Hs.114159 | small GTP-binding protein; RAB-8b protein; Unknown (protein for MGC:22321) [Homo sapiens] | 82 |
| *1 | AA706041 | Hs.170253 | unnamed protein product [Homo sapiens]; hypothetical protein FLJ23282 [Homo sapiens];; | 86 |
| 1 | AA773139 | Hs.66103 | null | 91 |
| 1 | AA776813 | Hs.191987 | hypothetical protein {Macaca fascicularis} | 95 |
| *1 | AA862465 | Hs.71 | zinc-alpha2-glycoprotein precursor; Zn-alpha2-glycoprotein; Znalpha2-glycoprotein; alpha-2-glycoprotein 1, zinc; alpha-2-glycoprotein 1, zinc [Homo sapiens];; | 101 |
| *1 | AA977711 | Hs.128859 | null | 116 |
| 1 | AI288845 | Hs.105938 | putative chemokine receptor; putative chemokine receptor; chemokine receptor X; C-C chemokine receptor 6. (CCR6) (Evidence is not experimental); chemokine (C-C motif) receptor-like 2 [Homo sapiens] | 129 |
| *1 | H15267 | Hs.210863 | null | 133 |
| 1 | H18956 | Hs.21035 | unnamed protein product [Homo sapiens] | 138 |
| 1 | H73608 | Hs.94903 | null | 146 |
| *1 | H99544 | Hs.153445 | unknown; endothelial and smooth muscle cell-derived neuropilin-like protein [Homo sapiens]; endothelial and smooth muscle cell-derived neuropilin-like protein; coagulation factor V/VIII-homology domains protein 1 [Homo sapiens] | 151 |
| *1 | N45282 | Hs.201591 | calcitonin receptor-like | 157 |
| *1 | N48270 | Hs.45114 | Similar to golgi autoantigen, golgin subfamily a, member 6 [Homo sapiens] | 159 |
| 1 | N59451 | Hs.48389 | null | 164 |
| *1 | N95226 | Hs.22039 | KIAA0758 protein; | 174 |
| 1 | R37028 | Hs.20956 | cytochrome bd-type quinol oxidase subunit I related protein Thermoplasma acidophilum | 183 |

TABLE 4-continued

Genes used in a cDNA classifier (selected by t-test) and ranked by selection frequency using LOOCV

| Number of Times Occurred | Genbank ID | UNIGENE ID | Description | SEQ ID NO |
|---|---|---|---|---|
| 1 | R66605 | Hs.182485 | Unknown (protein for IMAGE:4843317) {Homo sapiens} | 197 |
| *1 | T51004 | Hs.167847 | null | 203 |
| 1 | T51316 | null | null | 204 |
| 1 | T72535 | Hs.189825 | null | 208 |
| *1 | W72103 | Hs.236443 | beta-spectrin 2 isoform 2 | 213 |

M denotes genes that were used to classify 75% of all tumors, and genes appearing in both the cDNA classifier and the U133A-limited cDNA classifier are marked by *

TABLE 5

The 43 genes

| Number of Times Occurred | GenBank ID | UNIGENE ID | Description | SEQ ID NO |
|---|---|---|---|---|
| M*78 | AA045075 | Hs.62751 | syntaxin 7 | 6 |
| M *78 | AA425320 | Hs.250461 | hypothetical protein; MDG1; similar to putative microvascular endothelial differentiation gene 1; similar to X98993 (PID:g1771560); microvascular endothelial differentiation gene 1 product; microvascularendothelial differentiation gene 1; DKFZP564F1862 p | 29 |
| M 78 | AA437223 | Hs.46640 | adult retina protein | 32 |
| M *78 | AA479270 | Hs.250802 | Diff33 protein homolog; KIAA1253 protein | 48 |
| M *78 | AA486233 | Hs.2707 | G1 to S phase transition 1 | 56 |
| M *78 | AA487274 | Hs.48950 | heptacellular carcinoma novel gene-3 protein; DAPPER1 | 57 |
| M78 | AA488652 | Hs.4209 | HSPC235; ribosomal protein L2; Similar to ribosomal protein, mitochondrial, L2 [Homo sapiens]; mitochondrial ribosomal protein L37; ribosomal protein, mitochondrial, L2 [Homo sapiens] | 58 |
| M78 | AA694500 | Hs.116328 | hypothetical protein MGC33414; Similar to PR domain containing 1, with ZNF domain | 77 |
| M 78 | AA704270 | Hs.189002 | Null | 83 |
| M *78 | AA706226 | Hs.113264 | neuregulin 2 isoform 4 | 87 |
| M *78 | AA709158 | Hs.42853 | put. DNA binding protein; put. DNA binding protein; cAMP responsive element binding protein-like 1; Creb-related protein | 88 |
| M *78 | AA775616 | Hs.313 | OPN-b; osteopontin; secreted phosphoprotein 1 (osteopontin, bone sialoprotein I, early T-lymphocyte activation 1) | 92 |
| M 78 | AA777892 | Hs.121939 | Null | 98 |

TABLE 5-continued

The 43 genes

| Number of Times Occurred | GenBank ID | UNIGENE ID | Description | SEQ ID NO |
|---|---|---|---|---|
| M *78 | AA873159 | Hs.182778 | apolipoprotein CI; apolipoprotein C-I variant II; apolipoprotein C-I variant I | 102 |
| M *78 | AA969508 | Hs.10225 | HEYL protein; hairy-related transcription factor 3; hairy/enhancer-ofsplit related with YRPW motif-like | 113 |
| M 78 | AI203139 | Hs.180370 | hypothetical protein FLJ30934 | 125 |
| M *78 | AI299969 | Hs.255798 | unnamed protein product; HN1 like; Unknown (protein for MGC:22947) | 130 |
| M *78 | H17364 | Hs.80285 | CRE-BP1 family member; cyclic AMP response element DNA-binding protein isoform 1 family; cAMP response element binding protein (AA1-505); cyclic AMP response element-binding protein (HB 16); Similar to activating transcription factor 2 [Homo sapiens]; act | 134 |
| M 78 | H17627 | Hs.83869 | unnamed protein | 136 |
| M *78 | H19822 | Hs.2450 | KIAA0028; leucyl-tRNA synthetase, mitochondrial [Homo sapiens]; leucyl-tRNA synthetase; mitochondrial [Homo sapiens]; leucine-tRNA ligase precursor; leucine translase [Homo sapiens] | 140 |
| M *78 | H23551 | Hs.30974 | NADH dehydrogenase subunit 4 {Deirochelys reticularia} | 141 |
| M 78 | H62801 | Hs.125059 | Unknown (protein for IMAGE:4309224) [Homo sapiens]; hypothetical protein [Homo sapiens] | 145 |
| M78 | H85015 | Hs.138614 | null | 148 |
| M 78 | N21630 | Hs.143039 | hypothetical protein PRO1942 | 152 |
| M *78 | N36176 | Hs.108636 | membrane protein CH1; membrane protein CH1 [Homo sapiens]; membrane protein CH1 [Homo sapiens]; membrane protein CH1 [Homo sapiens] | 153 |
| M *78 | N72847 | Hs.125221 | Alu subfamily SP sequence contamination warning entry. [Human]{Homo sapiens} | 169 |
| M 78 | N92519 | Hs.1189 | Unknown (protein for MGC:10231) [Homo sapiens] | 173 |
| M *78 | R27767 | Hs.79946 | thyroid hormone receptor-associated protein, 150 kDa subunit; Similar to thyroid hormone receptor-associated protein, 150 kDa subunit [Homo sapiens]; | 180 |
| M *78 | R34578 | Hs.111314 | null | 182 |
| M 78 | R38360 | Hs.145567 | unknown {Homo sapiens} | 185 |
| M 78 | R43597 | Hs.137149 | trehalasehomologT19F6.30-Arabidopsis thaliana | 188 |
| M 78 | R43684 | Hs.165575 | dJ402GLL.5 (novel protein similar to yeast and bacterial predicted proteins) | 189 |

TABLE 5-continued

The 43 genes

| Number of Times Occurred | GenBank ID | UNIGENE ID | Description | SEQ ID NO |
|---|---|---|---|---|
| M *78 | W73732 | Hs.83634 | Null | 214 |
| M *77 | AA450205 | Hs.8146 | translocation protein-1; Sec62; trans location protein 1; Dtrp1 protein; membrane protein SEC62, S. cerevisiae, homolog of [Homo sapiens]; | 36 |
| M 77 | AI081269 | Hs.184108 | Alu subfamily SX sequence contamination warning entry. | 122 |
| M *77 | R59314 | Hs.170056 | null | 193 |
| M *72 | AA702174 | Hs.75263 | pRb-interacting protein RbBP-36 | 80 |
| M *70 | AI002566 | Hs.81234 | immunoglobin superfamily, member 3 | 121 |
| M *63 | AA676797 | Hs.1973 | cyclinF | 72 |
| M *62 | AA453508 | Hs.168075 | transportin; karyopherin (importin) beta 2; M9 region interaction protein | 39 |
| M 62 | W93980 | Hs.59511 | null | 217 |
| M *58 | AA045308 | Hs.7089 | insulin induced protein 2; INSIG-2 membrane protein | 7 |
| M 58 | AA953396 | Hs.127557 | null | 110 |

The molecular classifier was obtained using a procedure of two distinct steps: gene selection using a t-test and classification using a neural network. Both steps were taken after the test sample was left out (from the leave-one-out cross-validation) to avoid bias from the gene selection step. The top 50 genes as ranked by absolute value of the t statistic using a t test were retained for each cross-validation step. A feed-forward back-propagation neural network with a single hidden layer of 10 units, learning rate of 0.05, and momentum of 0.2 was constructed. Training occurred for a maximum of 500 epochs or until a zero misclassification error was achieved on the training set. It was found that neural networks were extremely robust to both the number of genes selected and the level of noise in these genes.

Using LOOCV, the classifier was evaluated in predicting prognosis for each patient at 36 months follow-up as compared to Dukes' staging predictions. The results of LOOCV demonstrated that the cDNA classifier was 90% accurate (93% sensitivity/84% specificity) in predicting the correct prognosis for each patient at 36 month of follow-up. A log-rank test of the two predicted groups (good and poor prognosis) was significant (P<0.001), demonstrating the ability of the cDNA classifier to distinguish the two outcomes (FIG. 2A). Permutation analysis demonstrates the result is better than possible by chance (P<0.001-1000 permutations).

This result was also significantly higher than that observed using Dukes' staging as a classifier (77%) for the same group of patients (P=0.03878). The results for both Dukes' staging and molecular staging are summarized in Tables 6A-6C below. Table 6A shows the relative accuracies of Dukes' staging and the cDNA classifier (molecular staging) for all tumors and then a comparison by Dukes' stage. Table 6B shows that Dukes' staging was particularly inaccurate at predicting outcome for patients with poor prognosis (70% and 55% for all stages and B and C, respectively). In contrast, molecular staging, as provided by the present invention, identified the good prognosis cases (the "default" classification using Dukes' staging), but also identified poor prognosis cases with a high degree of accuracy. Table 6C shows the detailed confusion matrix for all samples in the dataset, showing the equivalent misclassification rate of both good and poor prognosis groups by the cDNA classifier.

TABLE 6A

LOOCV Accuracy of Dukes' vs. Molecular Staging for all tumors.

| Classification Method | Total Accuracy | Sensitivity | Specificity |
|---|---|---|---|
| Dukes' Staging | 77% | 63% | 97% |
| Molecular Staging | *90% | 93% | 84% |

TABLE 6B

Comparison of Molecular Staging and Dukes' Staging Accuracy.

| Dukes' Stage | Molecular Staging | Dukes' Staging |
|---|---|---|
| Adenoma | 100% | 100% |
| B | 87% | 70% |
| C | 91% | 55% |
| D | 90% | 97% |

TABLE 6C

Confusion Matrix of cDNA Classifier Results.

| Observed/Predicted | Poor | Good | Totals |
|---|---|---|---|
| Poor | 43 | 3 | 46 |
| Good | 5 | 27 | 32 |
| Total | 48 | 30 | 78 |

* Dukes' staging vs. cDNA Classifier, P = 0.03878, one-sided McNemar's test.

Leave-one-out cross-validation technique was also utilized to construct a SVM classifier using a set of 72 samples from Moffitt. The classifier was constructed in two steps: first a gene selection procedure was performed with SAM and then a support vector machine was constructed on each fold using all but one sample that was left out.

The gene selection approach used was a univariate selection. SAM (significance analysis of microarrays) was the method chosen for selecting genes. Since gene selected was to be based on two classes (good vs. poor prognosis), the two-class SAM method was used for selecting genes with the best d values. SAM calculates false discovery rates empirically through the use of permutation analysis. SAM provides an estimate of the false discovery rate (FDR) along with a list of genes considered significant relative to censored survival. This feature of SAM was used with this particular embodiment to select the number of genes that resulted in the smallest FDR possible, e.g., zero FDR.

Once the genes were selected using the SAM method, a linear support vector machine (SVM) was constructed. The software used for this approach was implemented in a weka machine learning toolkit. A linear SVM was then chosen to reduce the potential for overfitting the data, given the small sample sizes and large dimensionality. One further advantage of this approach is the transparency of the constructed model, which is of particular interest when comparing the classifier of the subject invention on two different platforms (see below).

A prognostic classifier was also constructed based on an analysis of 20 genes capable of determining survival that is significantly more accurate than Dukes staging. Methods: Seventy-two patients were selected from the Moffitt Cancer Center Tumor Bank and Registry who had been followed for greater than 24 months. Gene expression profiles were created using a 32,000 cDNA microarray and then subjected to Significance Analysis of Microarray (SAM) analysis to identify large sets of discriminating genes. Construction of a Support Vector Machine was then undertaken to develop a classifier capable of predicting outcome. The accuracy of this classifier was assessed by leave one out cross validation and compared to that of standard Dukes staging. Results: Hierarchical clustering and principal component analysis identified two populations of genes distinguishing the majority of patients that had survived greater than 24 months versus those that did not. These observations strongly suggested the potential for underlying gene expression information to drive a prognostic classifier. SVM analysis identified a set of approximately 20 genes whose expression discriminated good from bad survival with better accuracy than Dukes staging at a minimum of 24 months of follow-up (82% vs 77%). Interestingly, one of the 20 genes identified by the SVM as important in survival prediction was osteopontin, a gene we previously reported to be the gene most strongly correlated with advancing tumor stage in colorectal cancer. Conclusion: a molecular classifier was constructed which is capable of predicting outcome for colon cancer that exceeds the accuracy of Dukes staging, particularly in stages B and C where discrimination is critical. This classifier is based on a 20 gene set of which osteopontin, a known gene associated with colon cancer progression, plays a prominent role. The list of 20 genes is provided in the following Table 7.

TABLE 7

The 20 genes used in the SVM classifier

| GenBank ID | UniGene ID | Description | SEQ ID NO |
|---|---|---|---|
| AA626316 | Hs.90020 | unnamed protein product {Homo sapiens} | 67 |
| AA449359 | Hs.178100 | null | 35 |
| AA775616 | Hs.313 | OPN-b; osteopontin; secreted phosphoprotein 1 (osteopontin, bone sialoprotein I, early T-lymphocyte activation 1); secreted phosphoprotein 1 (osteopontin, bone sialoprotein I, early T-lymphocyte activation 1) [Homo sapiens]; secreted phosphoprotein 1 (ost | |
| AA479270 | Hs.250802 | Diff33 protein homolog; KIAA1253 protein [Homo sapiens]; KIAA1253 protein [Homo sapiens] | 48 |
| AA706226 | Hs.113264 | neuregulin 2 isoform 4; neuregulin 2 isoform 4 | 87 |
| AA911661 | Hs.2733 | Hox2H protein (AA 1-356); K8 homeo protein; HOX2.8 gene product; HOXB2 protein; HOX-2.8 protein (77 AA); homeo box B2; homeo box 2H; homeobox protein Hox-B2; K8 home protein [Homo sapiens]; | 108 |
| AA777050 | Hs.186566 | Unknown (protein for IMAGE:4154275) [Homo sapiens]; Unknown (protein for IMAGE:4421249) [Homo sapiens] | 96 |

TABLE 7-continued

The 20 genes used in the SVM classifier

| GenBank ID | UniGene ID | Description | SEQ ID NO |
|---|---|---|---|
| AA704613 | Hs.7647 | Similar to MYC-associated zinc finger protein (purine-binding transcription factor) [Homo sapiens] | 84 |
| AA130669 | Hs.16420 | SH3 domain-binding protein SNP70; Npw38-binding protein NpwBP; Npw38-binding protein NpwBP [Homo sapiens]; Unknown (protein for IMAGE:3448162) [Homo sapiens]; WW domain binding protein 11; SH3 domain-binding protein SNP70; Npw38-binding protein NpwBP [Hom | 13 |
| AA458926 | Hs.163724 | HSPC019 protein; Unknown (protein for MGC:27309) [Homo sapiens]; unnamed protein product [Homo sapiens]; grey-lethal osteopetrosis [Homo sapiens]; | 43 |
| AA490925 | Hs.22464 | LAFPTPase; laforin; epilepsy, progressive myoclonus type 2, Lafora disease (laforin); epilepsy, progressive myoclonic epilepsy, type 2 gene; Lafora disease gene (laforin); Laforin [Homo sapiens] | 60 |
| AA451865 | Hs.174139 | unnamed protein product {Homo sapiens} | 37 |
| N77998 | Hs.48220 | oculorhombin; paired box gene 6, isoform a; Similar to paired box gene 6 (aniridia, keratitis) [Homo sapiens]; paired box protein PAX6 [Homo sapiens] | 172 |
| H94627 | Hs.255852 | N-ras protein (39 AA) (1 is 2nd base in codon) (115 is 2nd base in codon); neuroblastoma RAS viral (v-ras) oncogene homolog [Homo sapiens]; | 150 |
| AI000612 | Hs.819 | homeobox protein; homeobox c1 protein; TATAA binding protein; homeo box B7 protein; Unknown (protein for MGC:21362) [Homo sapiens]; homeo box B7; homeo box 2C; homeobox protein Hox-B7; homeo box c1 protein [Homo sapiens] | 120 |
| AA181643 | Hs.167791 | reticulocalbin 1, EF-hand calcium binding domain; reticulocalbin 1, EF-hand calcium binding domain [Homo sapiens] | 19 |
| AA504785 | Hs.211608 | nuclear pore complex protein hnup 153; nucleoporin 153 kDa; nuclear pore complex protein hnup153 [Homo sapiens] | 63 |
| R91710 | Hs.15617 | Alu subfamily SQ sequence contamination warning entry. [Human]{Homo sapiens} | 199 |
| AA486228 | Hs.181271 | HSPCL81; CGI-120 protein; zetal-COP; CGI-120 protein [Homo sapiens] | 55 |
| AA521434 | Hs.155024 | B-cell lymphoma 6 protein; B-cell CLUlymphoma-6; cys-his2 zinc finger transcription factor BCL5; zinc finger protein 51; lymphoma-associated zinc finger gene on chromosome 3 [Homo sapiens] | 64 |

6.4. U133 Colorectal Cancer Classifier

A colorectal cancer survival classifier was obtained using U133A-limited genes selected by LOOCV via statistical analytic tools (i.e., t-test). The list of U133A-limited genes selected using LOOCV via t-test is provided in Table 8. The named genes common to both the original classifier (a set of 43 genes) and the U133A-limited classifier are marked with an asterisk in Table 5.

TABLE 8

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| M *78 | AA007421 | Hs.113992 | candidate tumor suppressor protein | 2 |
| M *78 | AA045075 | Hs.62751 | syntaxin 7 | 6 |
| M *78 | AA045308 | Hs.7089 | insulin induced protein 2, INSIG-2 membrane protein | 7 |
| M *78 | AA418726 | Hs.4764 | null | 28 |
| M *78 | AA425320 | Hs.250461 | hypothetical protein; MDG1; similar to putative microvascular endothelial differentiation gene 1; similar to X98993 (PID:g177 1560); microvascular endothelial differentiation gene 1 product; microvascular endothelial differentiation gene 1; DKFZP564F1862 p | 29 |
| M *78 | AA450205 | Hs.8146 | translocation protein-1; Sec62; translocation protein 1; Dtrp1 protein; membrane protein SEC62, *S. cerevisiae*, homolog of [*Homo sapiens*]; | 36 |
| M *78 | AA453508 | Hs.168075 | transportin; karyopherin (importin) beta 2; M9 region interaction protein | 39 |
| M *78 | AA453790 | Hs.255585 | null | 40 |
| M *78 | AA477404 | Hs.125262 | hypothetical protein; unnamed protein product; GL003; AAAS protein; adracalin; aladin; adracalin | 46 |
| M *78 | AA478952 | Hs.91753 | unnamed protein product | 47 |
| M *78 | AA479270 | Hs.250802 | Diff33 protein homolog; KIAA1253 protein | 48 |
| M *78 | AA486233 | Hs.2707 | G1 to S phase transition [*Homo sapiens*] | 156 |
| M *78 | AA487274 | Hs.48950 | heptacellular carcinoma novel gene-3 protein; DAPPER1 [*Homo sapiens*]; unnamed protein product [*Homo sapiens*] | 57 |
| M *78 | AA664240 | Hs.8454 | artifact-warning sequence (translated ALU class C) - human | 71 |
| M *78 | AA676797 | Hs.1973 | cyclin F | 72 |
| M *78 | AA702174 | Hs.75263 | pRb-interacting protein RbBP-36 | 80 |
| M *78 | AA706226 | Hs.113264 | neuregulin 2 isoform 4 | 87 |
| M *78 | AA709158 | Hs.42853 | put. DNA binding protein; put. DNA binding protein; cAMP responsive element binding protein-like 1; Creb-related protein [*Homo sapiens*] | 88 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| M *78 | AA775616 | Hs.313 | OPN-b; osteopontin; secreted phosphoprotein 1 (osteopontin, bone sialoprotein I, early T-lymphocyte activation 1); secreted phosphoprotein 1 (osteopontin, bone sialoprotein I, early T-lymphocyte activation 1) [Homo sapiens]; secreted phosphoprotein 1 (ost | 92 |
| M *78 | AA826237 | Hs.3426 | Era GTPase A protein; conserved ERA-like GTPase [Homo sapiens]; ERA-W [Homo sapiens]; Era G-protein-like 1; GTPase, human homolog of E. coli essential cell cycle protein Era; era (E. coli G-protein homolog)-like 1 [Homo sapiens] | 99 |
| M *78 | AA873159 | Hs.182778 | apolipoprotein CI; apolipoprotein CI; apolipoprotein C-I; apolipoprotein C-I precursor; apolipoprotein C-I variant II; apolipoprotein C-I variant I; Similar to apolipoprotein C-I [Homo sapiens] | 102 |
| M *78 | AA969508 | Hs.10225 | HEYL protein; hairy-related transcription factor 3; hairy/enhancer-of-split related with YRPW motif-like [Homo sapiens] | 113 |
| M *78 | AI002566 | Hs.81234 | immunoglobin superfamily, member 3 | 121 |
| M *78 | AI299969 | Hs.255798 | unnamed protein product [Homo sapiensi; HN1 like [Homo sapiens]; Unknown (protein for MGC:22947) [Homo sapiens]; HN1 like [Homo sapiens] | 130 |
| M *78 | H17364 | Hs.80285 | CRE-BP1 family member; cyclic AMP response element DNA-binding protein isoform 1 family; cAMP response element binding protein (AA 1-505); cyclic AMP response element-binding protein (HB16); Similar to activating transcription factor 2 [Homo sapiens]; act | 134 |
| M*78 | H19822 | Hs.2450 | K1AA0028; leucyl-tRNA synthetase, mitochondrial [Homo sapiens]; leucyl-tRNA synthetase, mitochondrial [Homo sapiens]; leucine-tRNA ligase precursor; leucine translase [Homo sapiens] | 140 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| M *78 | H23551 | Hs.30974 | NADH dehydrogenase subunit 4 {Deirochelys reticul aria} | 141 |
| M *78 | N36176 | Hs.108636 | membrane protein CH1; membrane protein CH1 [Homo sapiens]; membrane protein CH1 [Homo sapiens]; membrane protein CH1 [Homo sapiens] | 153 |
| M *78 | N72847 | Hs.125221 | Alu subfamily SP sequence contamination warning entry. [Human]{Homo sapiens} | 169 |
| M *78 | R10545 | Hs.148877 | dJ425C 14.2 (Placental protein | 176 |
| M *78 | R27767 | Hs.79946 | thyroid hormone receptor-associated protein, 150 kDa subunit; Similar to thyroid hormone receptor-associated protein, 150 kDa subunit [Homo sapiens];; | 180 |
| M *78 | R34578 | Hs.111314 | null | 182 |
| M *78 | R59314 | Hs.170056 | null | 193 |
| M *78 | W73732 | Hs.83634 | null | 214 |
| M *74 | AA448641 | Hs.108371 | transcription factor; E2F transcription factor 4, p107/p130-binding protein [Homo sapiens]; E2F transcription factor 4, p107/p130-binding [Homo sapiens]; E2F transcription factor 4, p107/p130-binding [Homo sapiens]; | 34 |
| M *68 | R59360 | Hs.12533 | null | 194 |
| M *63 | AA121778 | Hs.95685 | null | 11 |
| M *59 | H51549 | Hs.21899 | UDP-galactose translocator; UDP-galactose transporter 1 [Homo sapiens] | 144 |
| *57 | H81024 | Hs.180655 | Aik2; aurora-related kinase 2; serine/threonine kinase 12; serine/threonine kinase 12 [Homo sapiens]; Unknown (protein for MGC:11031) [Homo sapiens]; Unknown (protein for MGC:4243) [Homo sapiens] | 147 |
| *56 | AA490493 | Hs.24340 | 0 | 59 |
| *56 | R42984 | Hs.4863 | null | 187 |
| *53 | AA258031 | Hs.125104 | unnamed protein product [Homo sapiens]; MUS81 endonuclease [Homo sapiens]; MUS81 endonuclease [Homo sapiens] | 21 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| *52 | AA133215 | Hs.32989 | Receptor activity-modifying protein 1 precursor (CRLR activity-modifying-protein 1) | 15 |
| *52 | R63816 | Hs.28445 | unnamed protein product [Homo sapiens] | 196 |
| *51 | N95226 | Hs.22039 | KIAA0758 protein | 174 |
| *45 | N74527 | Hs.5420 | unnamed protein product {Homo sapiens} | 170 |
| *36 | AA702422 | Hs.66521 | josephin MJD1; super cysteine rich protein; SCRP | 81 |
| *29 | AI261561 | Hs.182577 | Alu subfamily SQ sequence contamination warning entry. [Human]{Homo sapiens} | 128 |
| *28 | AA132065 | Hs.109144 | unknown; SMAP-5; Similar to hypothetical protein AF140225 [Homo sapiens]; Similar to hypothetical protein AF140225 [Homo sapiens]; unnamed protein product [Homo sapiens]; unknown [Homo sapiens]; hypothetical protein AF140225 [Homo sapiens] | 14 |
| *28 | A1362799 | Hs.110757 | hypothetical protein; NNP3 [Homo sapiens] | 131 |
| *27 | AA045793 | Hs.6790 | hypothetical protein; MDG1; similar to putative microvascular endothelial differentiation gene 1; similar to X98993 (PID:g1771560); microvascular endothelial differentiation gene 1 product; microvascular endothelial differentiation gene 1; DKFZP564F1862 p | 8 |
| *27 | AA284172 | Hs.89385 | NPAT; predicted amino acids have three regions which share similarity to annotated domains of transcriptional factor oct-1, nucleolus-cytoplasm shuttle phosphoprotein and protein kinases; NPAT; nuclear protein, ataxia-telangiectasia locus; Similar to nuc | 24 |
| 24 | N51632 | Hs.75353 | The KIAO123 gene product is related to rat general mitochondrial matnx processing protease (MPP).; Unknown (protein for IMAGE:3632957) [Homo sapiens]; Unknown (protein for IMAGE:3857242) [Homo sapiens]; inositol polyphosphate-5-phosphatase, 72 kDa; KIAA0 | 162 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| 23 | AA482110 | Hs.4900 | Unknown gene product; PRO0915; CUA001; hypothetical protein [Homo sapiens]; hypothetical protein [Homo sapiens] | 52 |
| 22 | AA485450 | Hs.132821 | flavin containing monooxygenase 2; flavin containing monooxygenase 2 [Homo sapiens] | 53 |
| *19 | AA699408 | Hs.168103 | prp28, U5 snRNP 100 kd protein; prp28, U5 snRNP 100 kd protein [Homo sapiens] | 78 |
| 18 | N70777 | Hs.49927 | BA103JL8.1.2 (novel protein, isoform 2) [Homo sapiens] | 168 |
| 16 | AA993736 | Hs.169838 | hypothetical protein; vesicle-associated membrane protein 4 [Homo sapiens]; Similar to vesicle-associated membrane protein 4 [Homo sapiens] | 119 |
| 15 | A1139498 | Hs.151899 | delta sarcoglycan; delta-sarcoglycan isoform 2; Sarcoglyan, delta (35 kD dystrophin-associated glycoprotein); dystrophin associated glycoprotein, delta sarcoglycan; 35 kD dystrophin-associated glycoprotein [Homo sapiens] | 123 |
| 15 | N59721 | Hs.21858 | glia-derived nexin precursor; serine (or cysteine) proteinase inhibitor, clade E (nexin, plasmmogen activator inhibitor type 1), member 2; protease inhibitor 7 (protease nexin I); glia-derived nexin [Homo sapiens]; similar to serine (or cysteine) protein | 165 |
| 14 | AA431885 | Hs.5591 | MAP kinase-interacting serine/threonine kinase 1; MAP kinase interacting kinase 1 [Homo sapiens] | 30 |
| 14 | AA911661 | Hs.2733 | Hox2H protein (AA 1-356); K8 homeo protein; HOX2.8 gene product; HOXB2 protein; HOX-2.8 protein (77 AA); homeo box B2; homeo box 2H; homeobox protein Hox-B2; K8 home protein [Homo sapiens]; | 108 |
| 13 | AA775865 | Hs.7579 | KIAA1192 protein; HSPC273; unnamed protein product; hypothetical protein FLJ10402 [Homo sapiens]; unnamed protein product [Homo sapiens]; hypothetical protein FLJ10402 [Homo sapiens]; | 93 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| | | | hypothetical protein [Homo sapiens]; unnamed protein product [Homo sapiens] | |
| 13 | R30941 | Hs.24064 | signal transducer and activator of transcription Stat5B; transcription factorStat5b; STAT5B_CDS [Homo sapiens]; signal transducer and activator of transcription 5B; signal transducer and activator of transcription 5; transcription factor STAT5B [Homo sapiens] | 181 |
| *11 | AA703019 | Hs.114159 | small GTP-binding protein; RAB-8b protein; Unknown (protein for MGC:22321) [Homo sapiens] | 82 |
| 11 | AA777192 | Hs.47062 | RNA Polymerase II subunit 14.5 kD; DNA directed RNA polymerase II polypeptide I; DNA directed RNA polymerase II 14.5 kda polypeptide [Homo sapiens]; polymerase (RNA) II (DNA directed) polypeptide I (14.5 kD) [Homo sapiens] | 97 |
| *10 | W72103 | Hs.236443 | beta-spectrin 2 isoform 2 [Homo sapiens] | 213 |
| *9 | H15267 | Hs.210863 | null | 133 |
| 8 | H17638 | Hs.17930 | dJ1033B10.2.2 (chromosome 6 open reading frame 11 BING4), isoform 2) [Homo sapiens] | 137 |
| 8 | R60193 | Hs.11637 | null | 195 |
| 7 | R92717 | Hs.170129 | choroideremia-like Rab escort protein 2; dJ3 17G22.3 (choroideremia-like (Rab escort protein 2)) | 200 |
| *6 | AA706041 | Hs.170253 | unnamed protein product [Homo sapiens]; hypothetical protein FLJ23282 [Homo sapiens]; | 86 |
| *5 | AA411324 | Hs.67878 | interleukin-13 receptor; interleukin- 13 receptor; interleukin 13 receptor, alpha 1 [Homo sapiens]; Similar to interleukin 13 receptor, alpha 1 [Homo sapiens]; bB128O4.2.1 (interleukin 13 receptor, alpha 1) [Homo sapiens]; interleukin 13 receptor, alpha 1 | 25 |
| *5 | AA504266 | Hs.8217 | nuclear protein SA-2; bA517O1.1 (similar to SA2 nuclear protein); hypothetical protein [Homo | 61 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| | | | *sapiens*]; stromal antigen 2 [*Homo sapiens*] | |
| 5 | AA932696 | Hs.8022 | TU3A protein; TU3A protein [*Homo sapiens*] | 109 |
| 5 | AA973494 | Hs.153003 | serine/threonine kinase; myristilated and palmitylated serine-threonine kinase MPSK; protein kinase expressed in day 12 fetal liver; F5-2; serine/threonine kinase KRCT; erine/threonine kinase 16 [*Homo sapiens*]; | 114 |
| 5 | N45100 | Hs.34871 | HRIHFB2411; KIAA0569 gene product; Smad interacting protein 1 [*Homo sapiens*]; smad-interacting protein-i [*Homo sapiens*] | 156 |
| 4 | AA418410 | Hs.9880 | cyclophilin; U-snRNP-associated cyclophilin; peptidyl prolyl isomerase H (cyclophilin H) [*Homo sapiens*] | 27 |
| 4 | AA725641 | Hs.154397 | WD-repeat protein | 89 |
| 4 | AA954482 | Hs.222677 | SSX1; synovial sarcoma, X breakpoint 1 [*Homo sapiens*]; synovial sarcoma, X breakpoint 8 [*Homo sapiens*]; synovial sarcoma, X breakpoint 1; sarcoma, synovial, X-chromosome-related 1; SSX1 protein [*Homo sapiens*] | 111 |
| 4 | H45391 | Hs.31793 | null | 143 |
| 4 | T86932 | Hs.131924 | T-cell death-associated gene 8; similar to G protein-coupled receptor [*Homo sapiens*] | 210 |
| 3 | AA279188 | Hs.86947 | disintegrin and metalloprotease domain 8 precursor | 22 |
| *3 | AA485752 | Hs.9573 | ATP-binding cassette, sub-family F, member 1; ATP binding cassette 50; ATP binding cassette, sub-family F (GCN20), member 1 [*Homo sapiens*] | 54 |
| 3 | AA680132 | Hs.55235 | sphingomyelin phosphodiesterase 2, neutral membrane (neutral sphingomyelinase); Unknown (protein for MGC:1617) [*Homo sapiens*] | 74 |
| *3 | AA977711 | Hs.128859 | null | 116 |
| 3 | W93370 | Hs.174219 | NKG2E; type II integral membrane protein; killer cell lectin-like receptor subfamily C, member 3; killer cell lectin-like | 215 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| | | | receptor subfamily C, member 3 isoform NKG2-H; NKG2E [Homo sapiens]; NKG2E [Homo sapiens]; NKG2E [Homo sapiens] | |
| 2 | AA036727 | Hs.180236 | null | 5 |
| 2 | AA071075 | Hs.25523 | Alu subfamily SP sequence contamination warning entry. [Human]{Homo sapiens} | 10 |
| 2 | AA464612 | Hs.190161 | PTD017; HSPC183; PTD017 protein [Homo sapiens]; mitochondrial ribosomal protein S18B; mitochondrial ribosomal protein S18-2; mitochondrial 28S ribosomal protein S18-2 [Homo sapiens] | 45 |
| 2 | AA481250 | Hs.154138 | chitinase precursor; chitinase 3-like 2; chondrocyte protein 39; chitinase 3-like 2 [Homo sapiens] | 50 |
| 2 | AA598659 | Hs.168516 | NuMA protein {Homo sapiens} | 65 |
| 2 | AA682905 | Hs.8004 | huntingtin-associated protein interacting protein | 76 |
| 2 | R17811 | Hs.77897 | splicing factor SF3a60; pre-mRNA splicing factor SF3a (60 kD), similar to S. cerevisiae PRP9 (spliceosome-associated protein 61); splicing factor 3a, subunit 3, 60 kD [Homo sapiens]; Similar to splicing factor 3a, subunit 3, 60 kD [Homo sapiens] | 178 |
| 2 | W93592 | Hs.47343 | hWNT5A; wingless-type MMTV integration site family, member 5A precursor; proto-oncogene Wnt-5A precursor; WNT-5A protein precursor [Homo sapiens] | 216 |
| 1 | AA017301 | Hs.60796 | artifact-warning sequence (translated ALU class C)-human | 4 |
| 1 | AA046406 | Hs.100134 | unnamed protein product [Homo sapiens]; hypothetical protein FLJ12787 [Homo sapiens] | 9 |
| 1 | AA256304 | Hs.172648 | Unknown (protein for MGC:9448) [Homo sapiens]; distal-less homeo box 7 [Homo sapiens]; distal-less homeobox 4, isoform a; beta protein 1 [Homo sapiens] | 20 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| 1 | AA416759 | Hs.239760 | Unknown (protein for MGC:2503) [Homo sapiens]; unnamed protein product [Homo sapiens] | 26 |
| *1 | AA448261 | Hs.139800 | high mobility group AT-hook 1 isoform b; nonhistone chromosomal higlimobility group protein HMG-I/HMG-Y [Homo sapiens] | 33 |
| 1 | AA452130 | Hs.28219 | Alu subfamily SX sequence contamination warning entry. [Human]{Homo sapiens} | 38 |
| 1 | AA457528 | Hs.22979 | unnamed protein product [Homo sapiens]; hypothetical protein FLJ13993 [Homo sapiens]; FLJ00167 protein [Homo sapiens] | 42 |
| 1 | AA460542 | Hs.121849 | microtubule-associated proteins 1A/1B light chain 3; microtubuleassociated proteins 1A/1B light chain 3; microtubule-associated proteins 1A/1B light chain 3 [Homo sapiens]; microtubule-associated proteins 1A/1B light chain 3 [Homo sapiens] | 44 |
| *1 | AA479952 | Hs.154145 | Alu subfamily SX sequence contamination warning entry. [Human]{Homo sapiens} | 49 |
| 1 | AA481507 | Hs.159492 | unnamed protein product [Homo sapiens] | 51 |
| 1 | AA504342 | Hs.7763 | null | 62 |
| 1 | AA598970 | Hs.7918 | unnamed protein product; hypothetical protein; dJ453C12.6.2 (uncharacterized hypothalamus protein (isoform 2)); hypothetical protein [Homo sapiens]; uncharacterized hypothalamus protein HSMNP1 [Homo sapiens] | 66 |
| *1 | AA630376 | Hs.8121 | null | 68 |
| *1 | AA634261 | Hs.25035 | null | 70 |
| 1 | AA677254 | Hs.52002 | CT-2; CD5 antigen-like (scavenger receptor cysteine rich family); bA120D12.1 (CD5 antigen-like (scavenger receptor cysteine rich family)) [Homo sapiens]; CD5 antigen-like (scavenger receptor cysteine rich family) [Homo sapiens] | 73 |
| 1 | AA757564 | Hs.13214 | Probable G protein-coupled receptor GPR27 (Super | 90 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| | | | conserved receptor expressed in brain 1). [Human] | |
| 1 | AA775888 | Hs.163151 | null | 94 |
| 1 | AA844864 | Hs.4158 | regenerating protein I beta; regenerating islet-derived 1 beta precursor; lithostathine 1 beta; regenerating protein I beta; secretory pancreatic stone protein 2 [Homo sapiens] | 100 |
| *1 | AA862465 | Hs.71 | zinc-alpha2-glycoprotein precursor; Zn-alpha2-glycoprotein; Zn-alpha2-glycoprotein; alpha-2-glycoprotein 1, zinc; alpha-2-glycoprotein 1, zinc [Homo sapiens];; | 101 |
| 1 | AA989139 | Hs.16608 | candidate tumor suppressor protein; candidate tumor suppressor protein [Homo sapiens] | 118 |
| 1 | AI253017 | Hs.183438 | U4/U6 snRNP-associated 61 kDa protein {Homo sapiens} | 127 |
| 1 | AI394426 | Hs.57732 | acid phosphatase {Homo sapiens} | 132 |
| *1 | H99544 | Hs.153445 | unknown; endothelial and smooth muscle cell-derived neuropilin-like protein [Homo sapiens]; endothelial and smooth muscle cell-derived neuropilin-like protein; coagulation factor V/VIII-homology domains protein 1 [Homo sapiens] | 151 |
| 1 | N41021 | Hs.114408 | Toll/interleukin-1 receptor-like protein 3; Toll-like receptor 5; Toll-like receptor 5 [Homo sapiens]; toll-like receptor 5; Toll/interleukin-1 receptor-like protein 3 [Homo sapiens] | 155 |
| *1 | N45282 | Hs.201591 | calcitonin receptor-like | 157 |
| 1 | N46845 | Hs.144287 | hairy/enhancer-of-split related with YRPW motif 2; basic helix-loop-helix factor 1; HES-related repressor protein 1 HERP1; GRIDLOCK; basichelix-loop-helix protein; hairy-related transcription factor 2; hairy/enhancer-of-split related with YRPW motif 2 [H | 158 |
| *1 | N48270 | Hs.45114 | Similar to golgi autoantigen, golgin subfamily a, member 6 [Homo sapiens] | 159 |

TABLE 8-continued

Genes used in U133A-limited cDNA classifier (selected by t-test) and ranked by selection frequency using LOOCV

| Number Times Occurred | GenBank ID | UNIGENE ID | DESCRIPTION | SEQ ID NO |
|---|---|---|---|---|
| 1 | N59846 | Hs.177812 | Unknown (protein for MGC:41314) {Mus musculus} | 166 |
| 1 | R16760 | Hs.20509 | HBV pX associated protein-8 | 177 |
| 1 | R44546 | Hs.82563 | dJ526I14.2(KIAA0153 (similar | 191 |
| 1 | R92994 | Hs.1695 | metalloelastase; metalloelastase; matrix metalloproteinase 12 (macrophage elastase) | 201 |
| *1 | T51004 | Hs.167847 | null | 203 |
| 1 | T56281 | Hs.8765 | metallothionein I-F; RNA helicase-related protein [Homo sapiens]; metallothionein iF [Homo sapiens] | 205 |
| 1 | T70321 | Hs.247129 | G3a protein; Apo M; apolipoprotein M; Unknown (protein for MGC:22400) [Homo sapiens]; apolipoprotein M; NG20-like protein [Homo sapiens] | 207 |
| 1 | W45025 | Hs.170268 | Alu subfamily SX sequence contamination warning entry. [Human]{Homo sapiens} | 212 |

M denotes genes used to classify 75% of all tumors, and genes appearing in both the cDNA classifier and U133A-limited cDNA classifier are marked by *.

The cDNA classifier was tested by applying a classifier to an immediately available, well-annotated, independent test set of colon cancer tumor samples (Denmark set, as described in Section 6.1.) run on the Affymetrix® platform. Using database software such as the Resourcer software from TIGR (see also Tsai J et al., "RESOURCER: a database for annotating and linking microarray resources within and across species," Genome Biol, 2:software0002.1-0002.4 (2001)), genes were mapped out from the cDNA chip to a corresponding gene on the Affymetrix® platform. The linkage was done by common Unigene IDs.

12,951 genes (out of 32,000) were mapped to an Affymetrix® U133A GeneChip. In certain instances, probes on the cDNA chip were unknown expressed sequence tag markers (ESTs) which can reduce the number of usable genes identified. A U133A-limited cDNA classifier was constructed in accordance with the subject invention by using the identical approach on this reduced set of overlapping genes.

With the U133A-limited cDNA classifier, only those cDNA probes were chosen that (according to Resourcerer) mapped to an Affymetrix® probe set. This approach enabled cross-platform comparison. For example, the training set samples were used together with the test set tumor samples in a flip-dye design. The end expression value from a cDNA probe was then the log2 of the training set to test set sample ratio. This same reference RNA was used on two U133A Affymetrix® chips.

Once the U133A-limited cDNA classifier was constructed, a linear scaling factor based on the expression of a common training set (H. Lee Moffitt Cancer Center & Research Institute, Tampa, Fla.) sample applied to both the cDNA microarrays and the U133A GeneChips, was applied equally to all Affymetrix® samples (the Moffitt training set as well as the Denmark test set). Using this assumption, the U133A chip value corresponding to a cDNA probe was the ratio of training set to test set sample (on U133A chips). Each of the Affymetrix® U133A arrays (both the test set and the reference samples) was scaled to a constant average intensity (150) prior to taking the ratio and the test sample chip values were averaged.

The results of a full LOOCV for the U133A-limited classifier on the test set sample (Moffitt Cancer Center cDNA microarray data set; original 78 samples) are shown in Tables 9A-9C. The accuracy of the U133A-limited classifier was 72% (80% sensitivity/59% specificity), which contrasted from the original cDNA classifier results (90%, P=0.001154). Many ESTs were selected both in the SAM survival analysis and in the original cDNA-based classifier, indicating unknown genes (ESTs) may be very important to colorectal cancer outcome. The U133A-limited classifier was not significantly different, however, than the Dukes' staging (77%), P=0.4862 using a two-sided McNemar's test, and still significantly discriminated the two groups, as can be seen in FIG. 3B (P<0.001).

Figure 3A:
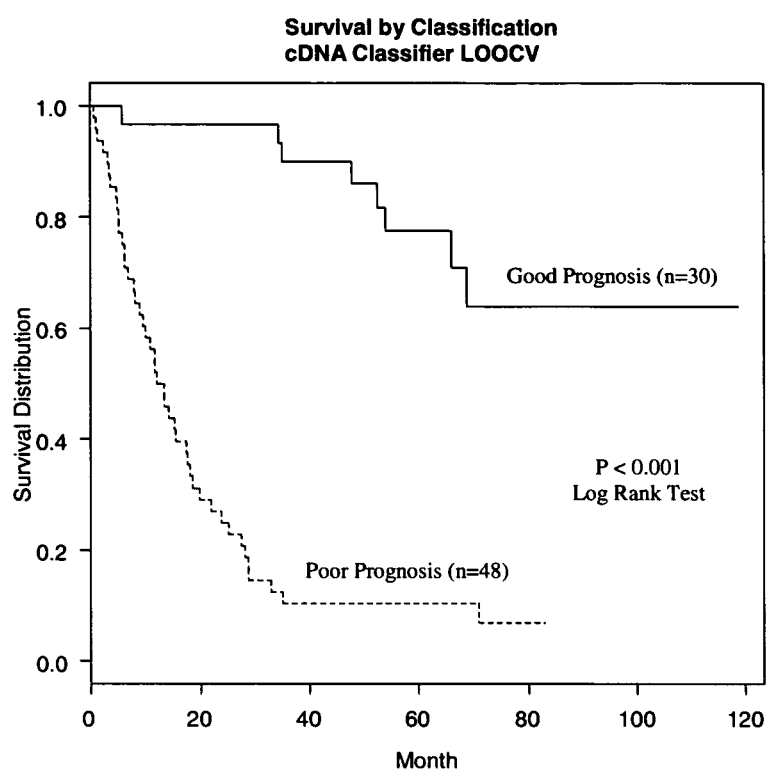
FIG. 3A shows survival curves for molecular classifiers using 78 samples tested by Leave-One-Out-Cross-Validation (LOOCV).
Figure 3B:
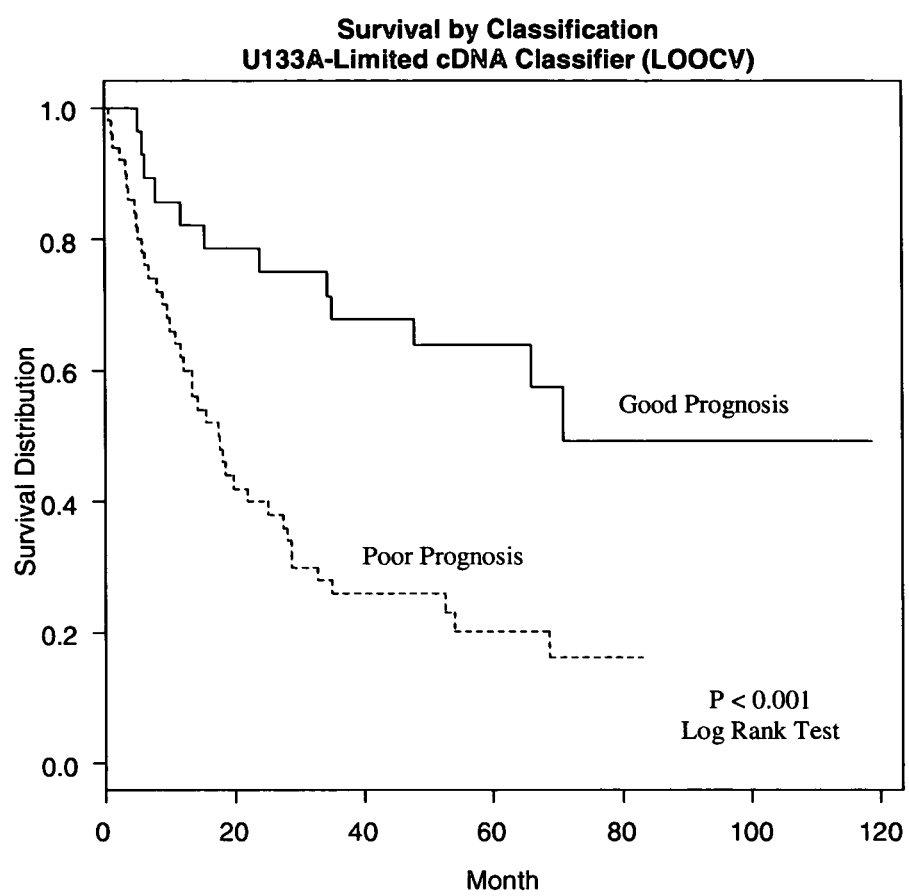
FIG. 3B illustrates the survival curve for the U133A-limited cDNA classifier (LOOCV).

FIG. 3A illustrates the survival curve for a cDNA classifier of the subject invention on the 78 training set samples (LOOCV). FIG. 3B illustrates the survival curve for the U133A-limited cDNA classifier (LOOCV). FIGS. 4A-C illustrate the survival curves for an independent test set classification (Denmark test set sample). A large difference in sensitivity can be seen between the Dukes' method and the classifier (Tables 9A-9C). The confusion matrix and accuracy rates by Dukes' stage are also presented in Tables 9A-9C.

TABLE 9A

LOOCV Accuracy of Dukes' vs. Molecular Staging for all tumors.

| Classification Method | Total Accuracy | Sensitivity | Specificity |
| --- | --- | --- | --- |
| Dukes' Staging | 76.9% | 63% | 97% |
| Molecular Staging | 71.8% | 80% | 59% |

TABLE 9B

Comparison of Molecular Staging and Dukes' Staging Accuracy

| Dukes' Stage | Molecular Staging | Dukes' Staging |
| --- | --- | --- |
| Adenoma | 67% | 100% |
| B | 70% | 70% |
| C | 64% | 55% |
| D | 80% | 97% |

TABLE 9C

Confusion Matrix of cDNA Classifier Results

| Observed/Predicted | Poor | Good | Totals |
| --- | --- | --- | --- |
| Poor | 38 | 8 | 46 |
| Good | 14 | 18 | 32 |
| Total | 52 | 26 | 78 |

With respect to comparing the predictive power of a classifier of the subject invention to Dukes' staging, the U133A-limited classifier was tested on the test set of colorectal cancer samples from Denmark that were profiled on the Affymetrix® U133A platform. The normalized and scaled test-set data were evaluated with the U133A-limited cDNA classifier. Because the Denmark cases included only Dukes' stages B and C, classification of outcome by Dukes' staging would predict all samples to be of good prognosis. The accuracy of the cDNA classifier was reduced from 72% in LOOCV of the training set (Tables 9A-9C) to 68% in the Denmark cross-platform test set (Tables 10A-10C). A reduction in accuracy (4%) was expected due to the limitations imposed by cross-platform analyses, however this reduction was very small compared to that caused by limiting the classifier gene set to U133A content. This result is not significantly different from that achieved by classification using Dukes' staging (64%, P=0.7194 using a two sided McNemar's test) and is better than other reported results (47%) (see Sorlie T et al., "Repeated observation of breast tumor subtypes in independent gene expression data sets," Proc Natl Acad Sci USA, 100:8418-23 (2003)) for cross-platform analyses where scaling was required. Moreover, the classifier of the subject invention was able to predict the outcome for poor prognosis patients (sensitivity) with an accuracy of 55% whereas 0% would be predicted correctly by Dukes' staging.

FIGS. 4A-4C show results from the independent Test Set Evaluation (Denmark Test Set) using the U133A data set. A) Survival curves generated using probe sets corresponding to 26 of the Molecular Classifier genes. Using these translated probe sets, 95 tumors were clustered and censored survivorship was evaluated (P<0.001). B) Survival curves using Dukes' staging criteria show no significant difference in outcome. C) Survival curves grouped by both Dukes' stage and molecular signature shows that both Dukes' B and C cases can be further subdivided into good and poor prognosis groups.

TABLE 10A

Accuracy of U133A limited Molecular Staging on Cross-Platform Denmark Independent Test Set.

| Classification Method | Total Accuracy | Sensitivity | Specificity |
| --- | --- | --- | --- |
| Dukes' Staging | 64% | 0% | 100% |
| Molecular Staging | 68.5% | 55% | 75% |

TABLE 10B

Comparison of Dukes' Staging and U133A limited Molecular Staging Accuracy on Cross-Platform Denmark Independent Test Set.

| Dukes' Stage | Molecular Staging | Dukes' Staging |
| --- | --- | --- |
| B | 64% | 79% |
| C | 70% | 58% |

TABLE 10C

Confusion Matrix of U133A limited Molecular Staging Results on Cross-Platform Denmark Independent Test Set

| Observed/Predicted | Poor | Good | Totals |
| --- | --- | --- | --- |
| Poor | 17 | 14 | 31 |
| Good | 14 | 43 | 57 |
| Total | 31 | 57 | 88 |

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for treating colorectal cancer in a human colorectal cancer patient, comprising:
obtaining a colorectal sample from the human patient;
measuring RNA transcripts corresponding to 7 genes having GenBank ID numbers N36176, AA149253, AA425320, AA775616, N72847, AA706226, and AA883496 in the sample; and
classifying said patient as having a poor prognosis by inputting the measurements to a prognosis predictor within a computer system comprising a processor coupled to memory, wherein the prognosis predictor comprises a neural network resident in the computer system, the neural network having been generated by
obtaining a training set of data from a population of colorectal cancer patients for whom marker profiles for the RNA transcripts corresponding to the 7 genes and prognosis outcomes are known,
determining, using the processor, one or more correlations between the marker profiles and a known prognosis of colorectal cancer in a human colorectal cancer patient, wherein determining a correlation comprises calculating a t-value,
weighting, using the processor, a correlation of the marker profiles based upon a value of the at least one marker profile within the population of colorectal cancer patients, wherein the weighting includes having the neural network start with a set of random weights, and
training the neural network with the training set of data to provide outputs indicative of a prognosis of colorectal cancer and adjust the weights to minimize error between the outputs to the known prognosis outcomes, wherein training the neural network comprises stochastic training, batch training, or online training;
providing, using the computer system, an output that includes the poor prognosis, wherein said poor prognosis predicts non-survival of a patient within said time period; and
treating the subject with a chemotherapy suitable for the poor prognosis.

2. The method of claim 1, wherein said time period is 5 years.

3. The method of claim 1, wherein measurement of each of said RNA transcript is obtained by a method comprising contacting a positionally-addressable microarray with nucleic acids from said cell sample or nucleic acids derived therefrom under hybridization conditions, and detecting the amount of hybridization that occurs, said microarray comprising one or more polynucleotide probes complementary to a hybridizable sequence of each said gene transcript.

4. The method of claim 3, wherein said microarray is selected from the group consisting of cDNA microarray, ink-jet synthesized microarray, and oligonucleotide microarray.

5. The method of claim 1, wherein said patient has an increased level of an RNA transcript of osteopontin or neuregulin 2 isoform 4 relative to the average level of said RNA transcript in patients without colorectal cancer.

6. The method of claim 1, wherein said plurality of RNA transcripts comprises RNA transcripts of osteopontin and neuregulin 2 isoform 4, respectively.

* * * * *